US008852937B2

(12) United States Patent
Baxter et al.

(10) Patent No.: US 8,852,937 B2
(45) Date of Patent: *Oct. 7, 2014

(54) SMALL ORGANIC MOLECULE REGULATORS OF CELL PROLIFERATION

(75) Inventors: Anthony David Baxter, Abingdon (GB); Edward Andrew Boyd, Didcot (GB); Maria Frank-Kamenetsky, Brookline, MA (US); Oivin Guicherit, Belmont, MA (US); Jeffery Porter, Lexington, MA (US); Stephen Price, Hertford (GB); Lee Rubin, Wellesley, MA (US); John Harry Alexander Stibbard, Didcot (GB)

(73) Assignee: Curis, Inc., Cambridge, MA (US)

( * ) Notice: Subject to any disclaimer, the term of this patent is extended or adjusted under 35 U.S.C. 154(b) by 1977 days.

This patent is subject to a terminal disclaimer.

(21) Appl. No.: 11/894,557

(22) Filed: Aug. 20, 2007

(65) Prior Publication Data

US 2008/0207740 A1 Aug. 28, 2008

Related U.S. Application Data

(63) Continuation of application No. 11/412,424, filed on Apr. 27, 2006, now Pat. No. 8,129,425, which is a
(Continued)

(51) Int. Cl.
*C12N 5/00* (2006.01)
*A01N 43/12* (2006.01)
(Continued)

(52) U.S. Cl.
CPC ............ *A61K 31/381* (2013.01); *C07D 409/14* (2013.01); *C07D 333/70* (2013.01); *A61K 31/4436* (2013.01); *A61K 31/44* (2013.01); *A61K 31/517* (2013.01); *A61K 31/50* (2013.01); *A61K 31/422* (2013.01); *C07D 409/12* (2013.01)
USPC ............ 435/375; 514/443; 514/438; 514/243

(58) Field of Classification Search
USPC ......................................................... 435/375
See application file for complete search history.

(56) References Cited

U.S. PATENT DOCUMENTS

| 4,353,888 A | 10/1982 | Sefton |
| 4,391,909 A | 7/1983 | Lim |

(Continued)

FOREIGN PATENT DOCUMENTS

| EP | 0 426 021 A1 | 8/1991 |
| JP | 06025250 | 2/1994 |

(Continued)

OTHER PUBLICATIONS

Alcedo et al., 1996, "The *Drosophila* smoothened gene encodes a seven-pass membrane protein, a putative receptor for the hedgehog signal", Cell 86:221-232.

(Continued)

*Primary Examiner* — Sharmila G. Landau
*Assistant Examiner* — Sheridan Macauley
(74) *Attorney, Agent, or Firm* — Pabst Patent Group LLP

(57) ABSTRACT

The present invention makes available methods and reagents for modulating proliferation or differentiation in a cell or tissue comprising contacting the cell with a hedgehog agonist, such as the compounds depicted in FIGS. 32 and 33. In certain embodiments, the methods and reagents may be employed to correct or inhibit an aberrant or unwanted growth state, e.g., by antagonizing a normal ptc pathway or agonizing smoothened or hedgehog activity.

40 Claims, 62 Drawing Sheets

Related U.S. Application Data continuation of application No. 10/245,844, filed on Sep. 17, 2002, now Pat. No. 7,115,653, which is a continuation-in-part of application No. 09/964,276, filed on Sep. 26, 2001, now Pat. No. 6,683,192, which is a continuation-in-part of application No. 09/724,492, filed on Nov. 28, 2000, now Pat. No. 6,683,108.

(60) Provisional application No. 60/193,279, filed on Mar. 30, 2000.

(51) Int. Cl.
| | | |
|---|---|---|
| A01N 43/06 | (2006.01) | |
| A01N 43/64 | (2006.01) | |
| C07D 409/14 | (2006.01) | |
| C07D 333/70 | (2006.01) | |
| A61K 31/4436 | (2006.01) | |
| A61K 31/44 | (2006.01) | |
| A61K 31/517 | (2006.01) | |
| A61K 31/50 | (2006.01) | |
| A61K 31/422 | (2006.01) | |
| A61K 31/381 | (2006.01) | |
| C07D 409/12 | (2006.01) | |

(56) References Cited

U.S. PATENT DOCUMENTS

| | | |
|---|---|---|
| 4,892,538 A | 1/1990 | Aebischer et al. |
| 4,955,892 A | 9/1990 | Daniloff |
| 5,041,138 A | 8/1991 | Vacanti et al. |
| 5,092,871 A | 3/1992 | Aebischer et al. |
| 5,106,627 A | 4/1992 | Aebischer et al. |
| 5,244,893 A | 9/1993 | Elbe et al. |
| 5,288,514 A | 2/1994 | Ellman |
| 5,359,115 A | 10/1994 | Campbell et al. |
| 5,362,899 A | 11/1994 | Campbell |
| 5,557,002 A | 9/1996 | Urawa et al. |
| 5,712,171 A | 1/1998 | Zambias et al. |
| 5,736,412 A | 4/1998 | Zambias et al. |
| 5,756,502 A | 5/1998 | Padia |
| 5,869,665 A | 2/1999 | Padia |
| 6,022,708 A | 2/2000 | de Sauvage et al. |
| 6,114,311 A | 9/2000 | Parmacek et al. |
| 6,166,030 A | 12/2000 | MacDonald et al. |
| 6,218,426 B1 | 4/2001 | Anderson et al. |
| 6,683,108 B1 * | 1/2004 | Baxter et al. .......... 514/443 |
| 2002/0156281 A1 | 10/2002 | Booth et al. |

FOREIGN PATENT DOCUMENTS

| | | |
|---|---|---|
| WO | WO 91/07087 | 5/1991 |
| WO | WO 92/10092 | 6/1992 |
| WO | WO 93/01275 | 1/1993 |
| WO | WO 93/09668 | 5/1993 |
| WO | WO 93/20242 | 10/1993 |
| WO | WO 94/08051 | 4/1994 |
| WO | WO 94/09119 | 4/1994 |
| WO | WO 94/10292 | 5/1994 |
| WO | WO 94/16718 | 8/1994 |
| WO | WO 95/18856 | 7/1995 |
| WO | WO 95/19169 | 7/1995 |
| WO | WO 96/17924 | 6/1996 |
| WO | WO 99/10004 | 3/1999 |
| WO | WO 99/20298 | 4/1999 |
| WO | WO 00/27422 | 5/2000 |
| WO | WO00/69810 | 11/2000 |
| WO | WO 01/16114 | 3/2001 |
| WO | WO 01/19800 | 3/2001 |
| WO | WO 01/30768 | 5/2001 |

OTHER PUBLICATIONS

Apfel et al., 1992, "Nerve growth factor prevents experimental cisplatin neuropathy", Ann. Neurol. 31:76-80.
Bellusci et al., 1997, "Involvement of Sonic hedgehog (Shh) in mouse embryonic lung growth and morphogenesis", Development 124:53-63.
Berge et al., 1977, "Pharmaceutical salts", J. Pharm. Sci. 66:1-19.
Bitgood and McMahon, 1995, "Hedgehog and Bmp genes are coexpressed at many diverse sites of cell-cell interaction in the mouse embryo", Dev. Biol. 172:126-138.
Bitgood et al, 1996, "Sertoli cell signaling by Desert hedgehog regulates the male germline", Curr. Biol. 6:298-304.
Blondelle et al., 1995, "Soluble combinatorial libraries of organic, peptidomimetic and peptide diversities", Trends Anal. Chem. 14:83-92.
Bumcrot, 1995, "Proteolytic processing yields two secreted forms of sonic hedgehog", Mol. Cell. Biol. 15:2294-2303.
Chang et al., 1994, "Products, genetic linkage and limb patterning activity of a murine hedgehog gene", Development 120:3339-3353.
Chen and Sigel 1994, "Through-space polar -π effects on the acidity and hydrogen-bonding capacity of carboxylic acids", JACS 116:5959-5960.
Chen et al., 1996, "Dual roles for patched in sequestering and transducing Hedgehog", Cell 87:553.
Davidson, 1990, "How embryos work: a comparative view of diverse modes of cell fate specification", Development 108:365-389.
Dunnett et al., 1987, "Mechanisms of function of neural grafts in the adult mammalian brain", J. Exp. Biol. 123:265-289.
Echelard et al., 1993, "Sonic hedgehog, a member of a family of putative signaling molecules, is implicated in the regulation of CNS polarity", Cell 75:1417-1430.
Ekker et al., 1995, "Patterning activities of vertebrate hedgehog proteins in the developing eye and brain", Curr. Biol. 5:944-955.
Ekker et al., 1995, "Distinct expression and shared activities of members of the hedgehog gene family of *Xenopus laevis*", Development 121:2337-2347.
Ericson et al., 1995, "Sonic hedgehog induces the differentiation of ventral forebrain neurons: a common signal for ventral patterning within the neural tube", Cell 81:747-756.
Fan and Tessier-Lavigne, 1994, Cell 79:1175-1186.
Fan et al., 1995, "Long-range sclerotome induction by sonic hedgehog: direct role of the amino-terminal cleavage product and modulation by the cyclic AMP signaling pathway", Cell 81:457-465.
Fietz et al., 1995, "Secretion of the amino-terminal fragment of the hedgehog protein is necessary and sufficient for hedgehog signalling in *Drosophila*", Curr. Biol. 5:643-651.
First Declaration of Dr. Jeffrey Finer (Jun. 30, 2006).
Second Declaration of Dr. Jeffrey Finer (Jun. 30, 2006).
Forbes et al., 1996, "Hedgehog is required for the proliferation and specification of ovarian somatic cells prior to egg chamber formation in *Drosophila*", Development 122:1125-1135.
Francis et al., 1994, "Bone morphogenetic proteins and a signalling pathway that controls patterning in the developing chick limb", Development 120:209-218.
Franco, P. et al., 1999, "Functional association fo retinoic acid and hedgehog signaling in *Xenopus* primary neurogenesis", Development 128:4257-4265.
Freed et al., 1993, "Neocartilage formation in vitro and in vivo using cells cultured on synthetic biodegradable polymers", J. Biomed. Mater. Res. 27:11.
Freund et al., 1985, "Efferent synaptic connections of grafted dopaminergic neurons reinnervating the host neostriatum: a tyrosine hydroxylase immunocytochemical study", J. Neurosci. 5:603-616.
Gaffield, W. et al., 1999, "A Looking Glass Perspective: Thalidomide and Cyclopamine", Cellular and Molecular Biology 45(5):579-588.
Gailani, et al. 1996, "The role of the human homologue of *Drosophila* patched in sporadic basal cell carcinomas", Nat. Genetics 14:78-81.
Goodrich et al., 1996, "Conservation of the hedgehog/patched signaling pathway from flies to mice: induction of a mouse patched gene by Hedgehog", Genes Dev. 10:301-312.
Grande et al., 1989, "The repair of experimentally produced defects in rabbit articular cartilage by autologous chondrocyte transplantation", J. Orthop. Res. 7:208-218.

(56) References Cited

OTHER PUBLICATIONS

Gurdon, 1992, "The generation of diversity and pattern in animal development", Cell 68:185-199.
Hahn et al., 1996, "Mutations of the human homolog of *Drosophila* patched in the nevoid basal cell carcinoma syndrome", Cell 85:841.
Hammerschmidt et al., 1996, "Protein kinase A is a common negative regulator of Hedgehog signaling in the vertebrate embryo", Genes Dev. 10:647-658.
Hidalgo and Ingham, 1990, "ICell patterning in the *Drosophila* segment: spatial regulation of the segment polarity gene patched", Development 110:291-301.
Honig 1981, "Positional signal transmission in the developing chick limb", Nature 291:72-73.
Hooper et al., 1989, "The *Drosophila* patched gene encodes a putative membrane protein required for segmental patterning", Cell 59:751.
Hui et al., 1994, "Expression of three mouse homologs of the *Drosophila* segment polarity gene cubitus interruptus, Gli, Gli-2, and Gli-3, in ectoderm- and mesoderm-derived tissues suggests multiple roles during postimplantation development", Dev. Biol. 162:402-413.
Hynes et al., 1995, "Induction of midbrain dopaminergic neurons by Sonic hedgehog", Neuron 15:35-44.
Jensen et al., 1997, "Expression of Sonic hedgehog and its putative role as a precursor cell mitogen in the developing mouse retina", Development 124:363.
Jessell et al, 1992, "Diffusible factors in vertebrate embryonic induction", Cell 68:257-270.
Johnson et al., 1994, "Ectopic expression of Sonic hedgehog alters dorsal-ventral patterning of somites", Cell 79:1165-1173.
Johnson, et al. 1996, "Human homolog of patched, a candidate gene for the basal cell nevus syndrome", Science 272:1668.
Kerr et al., 1993, "The mechanism of photochemical smog formation", JACS 115:252.
Kinzler et al., 1988, "The GLI gene is a member of the Kruppel family of zinc finger proteins", Nature 332:371.
Kinzler et al., 1990, "The GLI gene encodes a nuclear protein which binds specific sequences in the human genome", Mol. Cell. Biol. 10:634-642.
Krauss et al., 1993, "A functionally conserved homolog of the *Drosophila* segment polarity gene hh is expressed in tissues with polarizing activity in zebrafish embryos", Cell 75:1431-1444.
Lai et al., 1995, "Patterning of the neural ectoderm of *Xenopus laevis* by the amino-terminal product of hedgehog autoproteolytic cleavage", Development 121:2349-2360.
Laufer, 1994, "Sonic hedgehog and Fgf-4 act through a signaling cascade and feedback loop to integrate growth and patterning of the developing limb bud", Cell 79:993-1003.
Lee et al., 1992, "Secretion and localized transcription suggest a role in positional signaling for products of the segmentation gene hedgehog", Cell 71:33-50.
Lee et al., 1994, "Autoproteolysis in hedgehog protein biogenesis", Science 266:1528-1537.
Legha, 1986, "Vincristine neurotoxicity. Pathophysiology and management", Med. Toxicol. 1:421-427.
Lench et al., 1997, "Characterisation of human patched germ line mutations in naevoid basal cell carcinoma syndrome", Hum. Genetics 100:497-502.
Levin et al., 1995, "A molecular pathway determining left-right asymmetry in chick embryogenesis", Cell 82:803-814.
Levine et al., 1997, "Sonic hedgehog promotes rod photoreceptor differentiation in mammalian retinal cells in vitro", J. Neurosci. 17:6277.
Lopez-Martinez et al., 1995, "Limb-patterning activity and restricted posterior localization of the amino-terminal product of Sonic hedgehog cleavage", Curr. Biol. 5:791-795.
Marigo et al., 1996, "Conservation in hedgehog signaling: induction of a chicken patched homolog by Sonic hedgehog in the developing limb", Development 122:1225-1233.
Marigo et al., 1996, "Biochemical evidence that patched is the Hedgehog receptor", Nature 384:176-179.
Marigo et al., 1996, "Regulation of patched by sonic hedgehog in the developing neural tube", PNAS 93:9346-9351.
Marti et al., 1995, "Distribution of Sonic hedgehog peptides in the developing chick and mouse embryo", Development 121:2537-2547.
Marti et al.,. 1995, "Requirement of 19K form of Sonic hedgehog for induction of distinct ventral cell types in CNS explants", Nature 375:322-325.
Mollman, 1990, "Cisplatin neurotoxicity", New Engl. J. Med. 322:126-127.
Munsterberg et al., 1995, "Combinatorial signaling by Sonic hedgehog and Wnt family members induces myogenic bHLH gene expression in the somite", Genes Dev. 9:2911-2922.
Nakano et al., 1989, "A protein with several possible membrane-spanning domains encoded by the *Drosophila* segment polarity gene patched", Nature 341:508.
Niswander et al., 1994, "A positive feedback loop coordinates growth and patterning in the vertebrate limb", Nature 371:609-612.
Nusse, 1996, "Patching up Hedgehog", Nature 384:119-120.
Nusslein-Volhard and Wieschaus, 1980, "Mutations affecting segment number and polarity in *Drosophila*", Nature 287:795-801.
Olesen et al., 1991, "Prevention and management of drug-induced peripheral neuropathy", Drug Safety 6:302-314.
Orenic et al., 1990, "Cloning and characterization of the segment polarity gene cubitus interruptus Dominant of *Drosophila*", Genes & Dev. 4:1053-1067.
Partridge, 1991,. "Invited review: myoblast transfer: a possible therapy for inherited myopathies?", Muscle & Nerve 14:197-212.
Pepinsky et al., 1998, "Identification of a palmitic acid-modified form of human Sonic hedgehog" J. Biol. Chem. 273:14037-14045.
Perrimon, 1995, "Hedgehog and beyond", Cell 80:517.
Perrimon, 1996, "Serpentine proteins slither into the wingless and hedgehog fields", Cell 86:513-516.
Placzek et al., 1993, "Induction of floor plate differentiation by contact-dependent, homeogenetic signals", Development 117:205-218.
Porter et al., 1996, "Hedgehog patterning activity: role of a lipophilic modification mediated by the carboxy-terminal autoprocessing domain", Cell 86:21-34.
Porter et al., 1995, The product of hedgehog autoproteolytic cleavage active in local and long-range signaling. Nature 374:363-366.
Reynolds et al., 1992, "Generation of neurons and astrocytes from isolated cells of the adult mammalian central nervous system", Science 255:1707-1710.
Riddle et al., 1993, "Sonic hedgehog mediates the polarizing activity of the ZPA", Cell 75:1401-1416.
Roberts et al., 1995, "Sonic hedgehog is an endodermal signal inducing Bmp-4 and Hox genes during induction and regionalization of the chick hindgut", Development 121:3163-3174.
Roelink et al., 1994, "Floor plate and motor neuron induction by vhh-1, a vertebrate homolog of hedgehog expressed by the notochord", Cell 76:761-775.
Roelink et al., 1995, "Floor plate and motor neuron induction by different concentrations of the amino-terminal cleavage product of sonic hedgehog autoproteolysis", Cell 81:445-455.
Ruiz I Ataba et al., 1995, "Restrictions to floor plate induction by hedgehog and winged-helix genes in the neural tube of frog embryos", Mol. Cell. Neurosci. 6:106-121.
Stone et al., 1990, "Future directions. Collagen-based prostheses for meniscal regeneration", Clin. Orthop. Relat. Red. 252:129.
Stone et al., 1996, "The tumour-suppressor gene patched encodes a candidate receptor for Sonic hedgehog", Nature 384:129-134.
Tabata et al., 1992, "The *Drosophila* hedgehog gene is expressed specifically in posterior compartment cells and is a target of engrailed regulation", Genes Dev. 6:2635-2645.
Takigawa et al., 1987, "Chondrocytes dedifferentiated by serial monolayer culture form cartilage nodules in nude mice", Bone Mineral. 2:449.
Tanabe et al., 1995, "Induction of motor neurons by Sonic hedgehog is independent of floor plate differentiation", Curr. Biol. 5:651-658.

(56) References Cited

OTHER PUBLICATIONS

Thornber, 1969, "Isosterism and Molecular Modification in Drug Design", C. Hansch, Accounts Chem. Res., 2:232.

Vacanti et al., 1991, "Synthetic polymers seeded with chondrocytes provide a template for new cartilage formation", Plast. Reconstruc. Surg. 88:753.

Von Schroeder et al., 1991, "The use of polylactic acid matrix and periosteal grafts for the reconstruction of rabbit knee articular defects", J. Biomed. Mater Res. 25:329.

Wakitani et al., 1989, "Repair of rabbit articular surfaces with allograft chondrocytes embedded in collagen gel", J. Bone Jt. Surg. 71B:74.

Wang et al., 1995, "Induction of dopaminergic neuron phenotype in the midbrain by Sonic hedgehog protein", Nat. Med.1:1184-1188.

Weinberg et al., 1996, "Developmental regulation of zebrafish MyoD in wild-type, no tail and spadetail embryos", Development 122:271-280.

Yamada et al., 1993, "Control of cell pattern in the neural tube: motor neuron induction by diffusible factors from notochord and floor plate", Cell 73:673-686.

\* cited by examiner

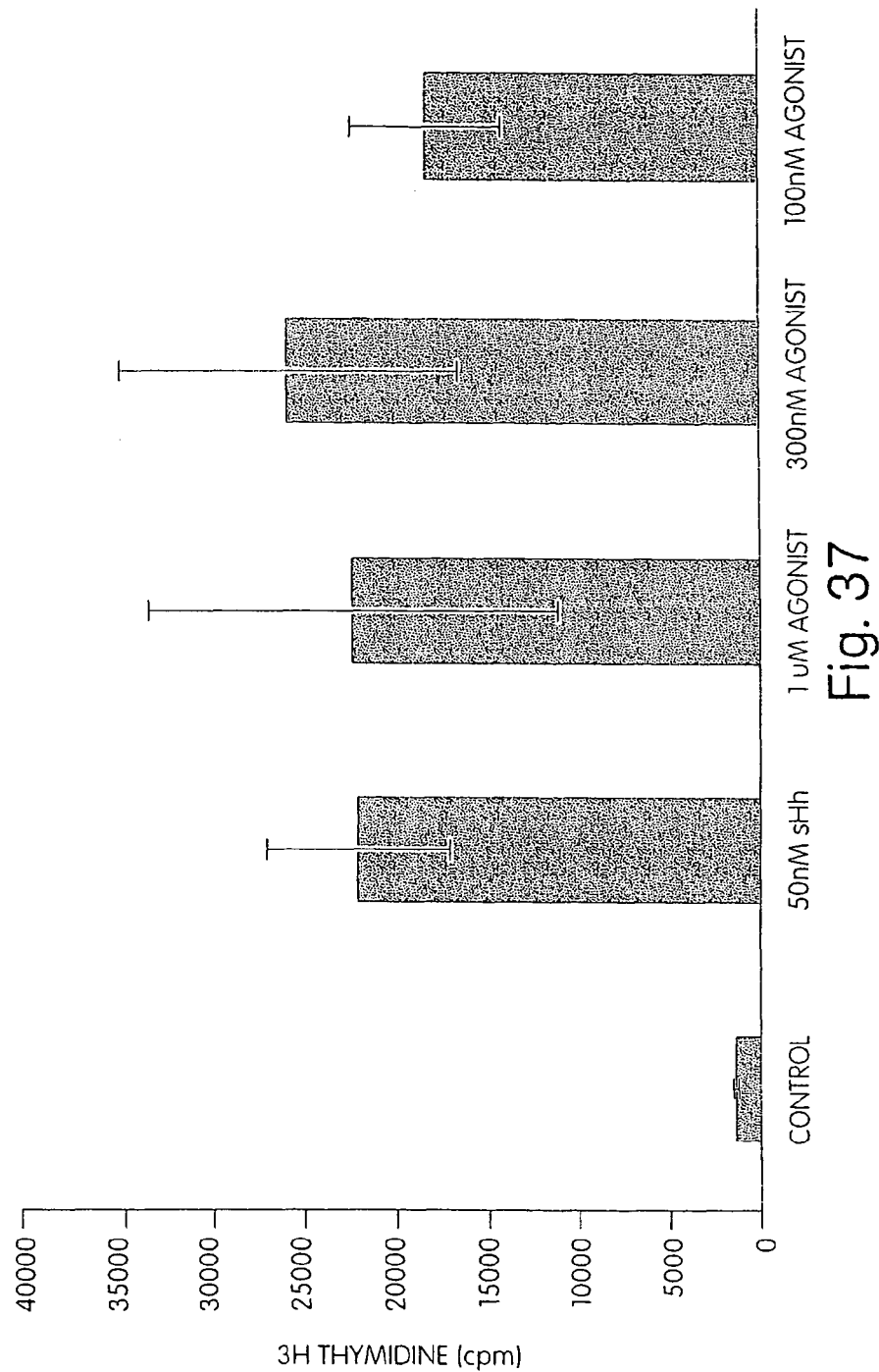

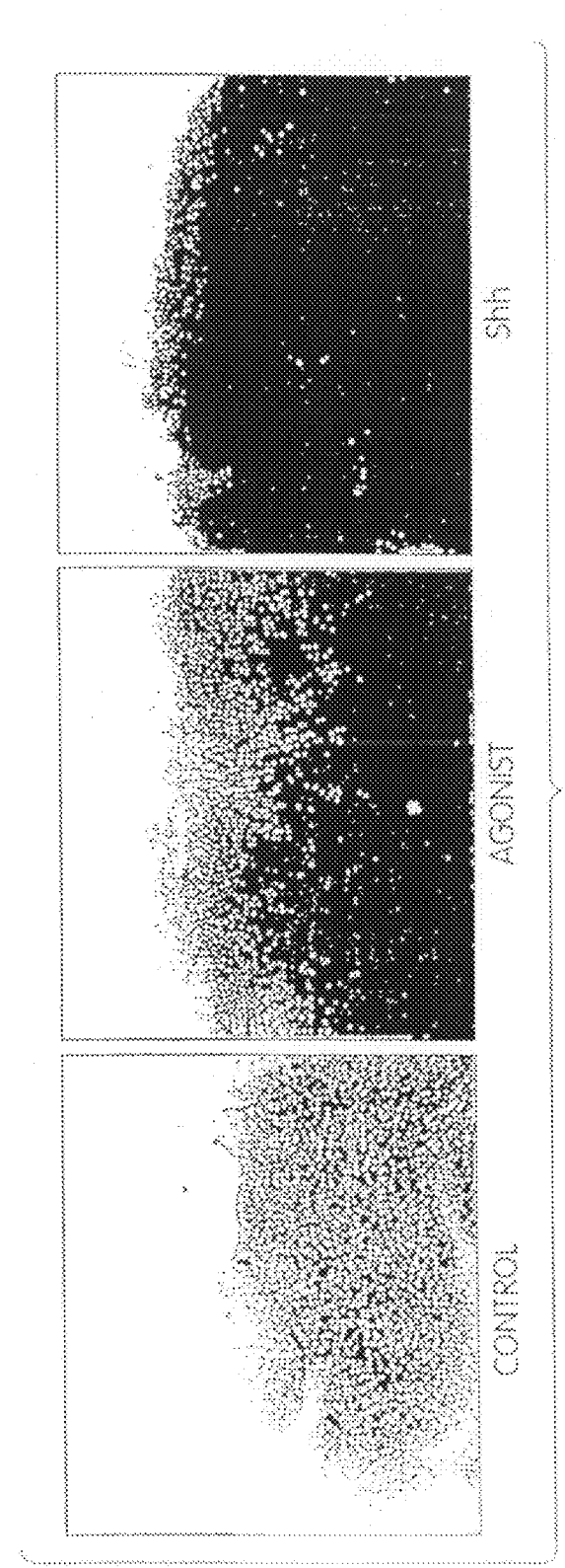

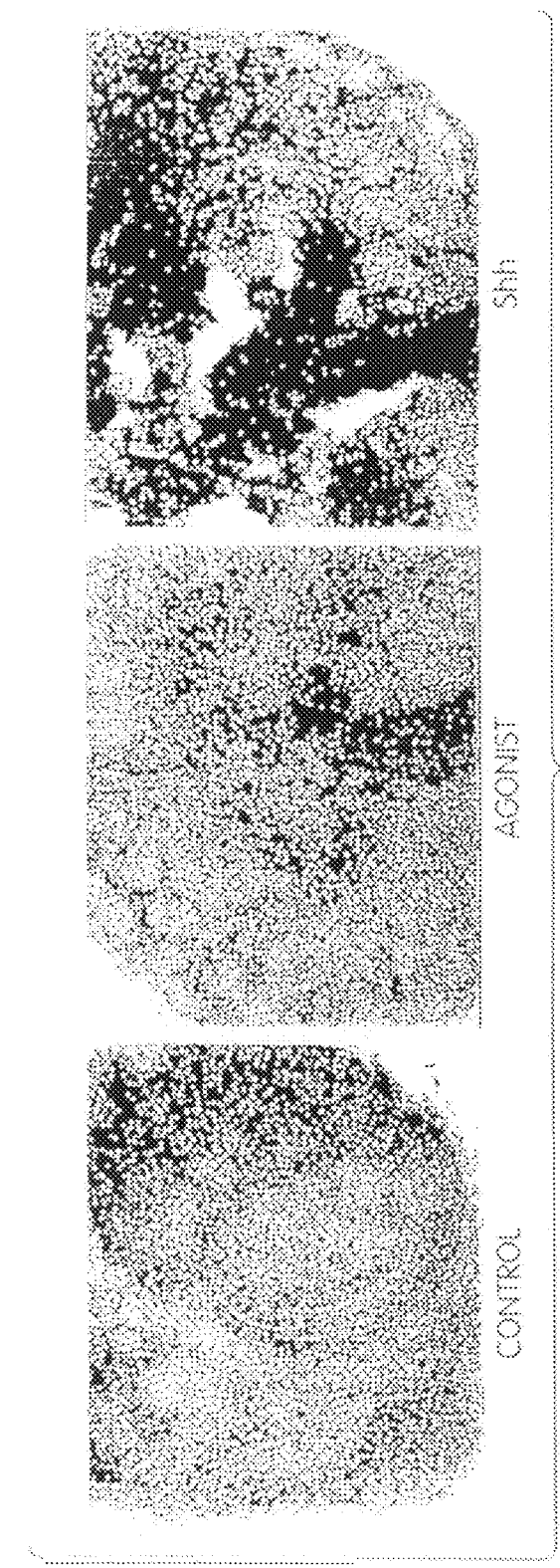

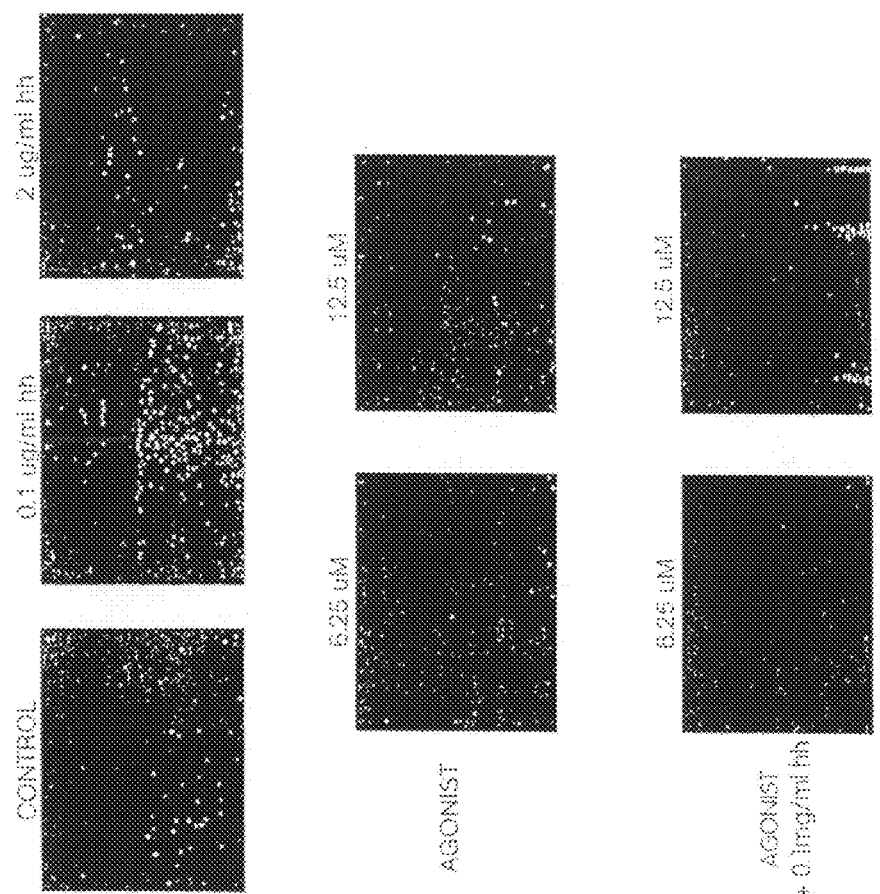

SMALL ORGANIC MOLECULE REGULATORS OF CELL PROLIFERATION

RELATED APPLICATIONS

This application is a continuation of U.S. application Ser. No. 11/412,424, filed Apr. 27, 2006, now U.S. Pat. No. 8,129,425 which is a continuation of U.S. application Ser. No. 10/245,844, filed Sep. 17, 2002, now issued U.S. Pat. No. 7,115,653, which is a continuation-in-part of U.S. application Ser. No. 09/964,276, filed Sep. 26, 2001, now issued U.S. Pat. No. 6,683,192, which is a continuation-in-part of U.S. application Ser. No. 09/724,492, filed Nov. 28, 2000, now issued U.S. Pat. No. 6,683,108, which claims benefit of U.S. Provisional Application No. 60/193,279, filed Mar. 30, 2000, the specifications of each of which are incorporated by reference herein.

BACKGROUND OF THE INVENTION

Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diverse cell types during tissue differentiation (Davidson, E., (1990) *Development* 108: 365-389; Gurdon, J. B., (1992) *Cell* 68: 185-199; Jessell, T. M. et al., (1992) *Cell* 68: 257-270). The effects of developmental cell interactions are varied. Typically, responding cells are diverted from one route of cell differentiation to another by inducing cells that differ from both the uninduced and induced states of the responding cells (inductions). Sometimes cells induce their neighbors to differentiate like themselves (homeogenetic induction); in other cases a cell inhibits its neighbors from differentiating like itself. Cell interactions in early development may be sequential, such that an initial induction between two cell types leads to a progressive amplification of diversity. Moreover, inductive interactions occur not only in embryos, but in adult cells as well, and can act to establish and maintain morphogenetic patterns as well as induce differentiation (J. B. Gurdon (1992) *Cell* 68:185-199).

Members of the Hedgehog family of signaling molecules mediate many important short- and long-range patterning processes during invertebrate and vertebrate development. In the fly, a single hedgehog gene regulates segmental and imaginal disc patterning. In contrast, in vertebrates, a hedgehog gene family is involved in the control of left-right asymmetry, polarity in the CNS, somites and limb, organogenesis, chondrogenesis and spermatogenesis.

The first hedgehog gene was identified by a genetic screen in the fruit fly *Drosophila melanogaster* (Nüsslein-Volhard, C. and Wieschaus, E. (1980) *Nature* 287, 795-801). This screen identified a number of mutations affecting embryonic and larval development. In 1992 and 1993, the molecular nature of the *Drosophila* hedgehog (hh) gene was reported (C. F., Lee et al. (1992) *Cell* 71, 33-50), and since then, several hedgehog homologues have been isolated from various vertebrate species. While only one hedgehog gene has been found in *Drosophila* and other invertebrates, multiple Hedgehog genes are present in vertebrates.

The vertebrate family of hedgehog genes includes at least four members, e.g., paralogs of the single *drosophila* hedgehog gene. Exemplary hedgehog genes and proteins are described in PCT publications WO 95/18856 and WO 96/17924. Three of these members, herein referred to as Desert hedgehog (Dhh), Sonic hedgehog (Shh) and Indian hedgehog (Ihh), apparently exist in all vertebrates, including fish, birds, and mammals. A fourth member, herein referred to as tiggie-winkle hedgehog (Thh), appears specific to fish. Desert hedgehog (Dhh) is expressed principally in the testes, both in mouse embryonic development and in the adult rodent and human; Indian hedgehog (Ihh) is involved in bone development during embryogenesis and in bone formation in the adult; and, Shh, which as described above, is primarily involved in morphogenic and neuroinductive activities. Given the critical inductive roles of hedgehog polypeptides in the development and maintenance of vertebrate organs, the identification of hedgehog interacting proteins is of paramount significance in both clinical and research contexts.

The various Hedgehog proteins consist of a signal peptide, a highly conserved N-terminal region, and a more divergent C-terminal domain. In addition to signal sequence cleavage in the secretory pathway (Lee, J. J. et al. (1992) *Cell* 71:33-50; Tabata, T. et al. (1992) *Genes Dev.* 2635-2645; Chang, D. E. et al. (1994) *Development* 120:3339-3353), Hedgehog precursor proteins undergo an internal autoproteolytic cleavage which depends on conserved sequences in the C-terminal portion (Lee et al. (1994) *Science* 266:1528-1537; Porter et al. (1995) *Nature* 374:363-366). This autocleavage leads to a 19 kD N-terminal peptide and a C-terminal peptide of 26-28 kD (Lee et al. (1992) supra; Tabata et al. (1992) supra; Chang et al. (1994) supra; Lee et al. (1994) supra; Bumcrot, D. A., et al. (1995) *Mol. Cell. Biol.* 15:2294-2303; Porter et al. (1995) supra; Ekker, S. C. et al. (1995) *Curr. Biol.* 5:944-955; Lai, C. J. et al. (1995) *Development* 121:2349-2360). The N-terminal peptide stays tightly associated with the surface of cells in which it was synthesized, while the C-terminal peptide is freely diffusible both in vitro and in vivo (Porter et al. (1995) *Nature* 374:363; Lee et al. (1994) supra; Bumcrot et al. (1995) supra; Mart', E. et al. (1995) *Development* 121:2537-2547; Roelink, H. et al. (1995) *Cell* 81:445-455). Interestingly, cell surface retention of the N-terminal peptide is dependent on autocleavage, as a truncated form of HH encoded by an RNA which terminates precisely at the normal position of internal cleavage is diffusible in vitro (Porter et al. (1995) supra) and in vivo (Porter, J. A. et al. (1996) *Cell* 86, 21-34). Biochemical studies have shown that the autoproteolytic cleavage of the HH precursor protein proceeds through an internal thioester intermediate which subsequently is cleaved in a nucleophilic substitution. It is likely that the nucleophile is a small lipophilic molecule which becomes covalently bound to the C-terminal end of the N-peptide (Porter et al. (1996) supra), tethering it to the cell surface. The biological implications are profound. As a result of the tethering, a high local concentration of N-terminal Hedgehog peptide is generated on the surface of the Hedgehog producing cells. It is this N-terminal peptide which is both necessary and sufficient for short- and long-range Hedgehog signaling activities in *Drosophila* and vertebrates (Porter et al. (1995) supra; Ekker et al. (1995) supra; Lai et al. (1995) supra; Roelink, H. et al. (1995) *Cell* 81:445-455; Porter et al. (1996) supra; Fietz, M. J. et al. (1995) *Curr. Biol.* 5:643-651; Fan, C.-M. et al. (1995) *Cell* 81:457-465; Mart', E., et al. (1995) *Nature* 375:322-325; Lopez-Martinez et al. (1995) *Curr. Biol* 5:791-795; Ekker, S. C. et al. (1995) *Development* 121:2337-2347; Forbes, A. J. et al. (1996) *Development* 122:1125-1135).

HH has been implicated in short- and long-range patterning processes at various sites during *Drosophila* development. In the establishment of segment polarity in early embryos, it has short-range effects which appear to be directly mediated, while in the patterning of the imaginal discs, it induces long-range effects via the induction of secondary signals.

In vertebrates, several hedgehog genes have been cloned in the past few years. Of these genes, Shh has received most of the experimental attention, as it is expressed in different organizing centers which are the sources of signals that pattern neighboring tissues. Recent evidence indicates that Shh is involved in these interactions.

The expression of Shh starts shortly after the onset of gastrulation in the presumptive midline mesoderm, the node in the mouse (Chang et al. (1994) supra; Echelard, Y. et al. (1993) Cell 75:1417-1430), the rat (Roelink, H. et al. (1994) Cell 76:761-775) and the chick (Riddle, R. D. et al. (1993) Cell 75:1401'-1416), and the shield in the zebrafish (Ekker et al. (1995) supra; Krauss, S. et al. (1993) Cell 75:1431-1444). In chick embryos, the Shh expression pattern in the node develops a left-right asymmetry, which appears to be responsible for the left-right situs of the heart (Levin, M. et al. (1995) Cell 82:803-814).

In the CNS, Shh from the notochord and the floorplate appears to induce ventral cell fates. When ectopically expressed, Shh leads to a ventralization of large regions of the mid- and hindbrain in mouse (Echelard et al. (1993) supra; Goodrich, L. V. et al. (1996) Genes Dev. 10:301-312), Xenopus (Roelink, H. et al. (1994) supra; Ruiz i Altaba, A. et al. (1995) Mol. Cell. Neurosci. 6:106-121), and zebrafish (Ekker et al. (1995) supra; Krauss et al. (1993) supra: Hammerschmidt, M., et al. (1996) Genes Dev. 10:647-658). In explants of intermediate neuroectoderm at spinal cord levels, Shh protein induces floorplate and motor neuron development with distinct concentration thresholds, floor plate at high and motor neurons at lower concentrations (Roelink et al. (1995) supra; Mart' et al. (1995) supra; Tanabe, Y. et al. (1995) Curr. Biol. 5:651-658). Moreover, antibody blocking suggests that Shh produced by the notochord is required for notochord-mediated induction of motor neuron fates (Mart' et al. (1995) supra). Thus, high concentration of Shh on the surface of Shh-producing midline cells appears to account for the contact-mediated induction of floorplate observed in vitro (Placzek, M. et al. (1993) Development 117:205-218), and the midline positioning of the floorplate immediately above the notochord in vivo. Lower concentrations of Shh released from the notochord and the floorplate presumably induce motor neurons at more distant ventrolateral regions in a process that has been shown to be contact-independent in vitro (Yamada, T. et al. (1993) Cell 73:673-686). In explants taken at midbrain and forebrain levels, Shh also induces the appropriate ventrolateral neuronal cell types, dopaminergic (Heynes, M. et al. (1995) Neuron 15:35-44; Wang, M. Z. et al. (1995) Nature Med. 1:1184-1188) and cholinergic (Ericson, J. et al. (1995) Cell 81:747-756) precursors, respectively, indicating that Shh is a common inducer of ventral specification over the entire length of the CNS. These observations raise a question as to how the differential response to Shh is regulated at particular anteroposterior positions.

Shh from the midline also patterns the paraxial regions of the vertebrate embryo, the somites in the trunk (Fan et al. (1995) supra) and the head mesenchyme rostral of the somites (Hammerschmidt et al. (1996) supra). In chick and mouse paraxial mesoderm explants, Shh promotes the expression of sclerotome-specific markers like Pax1 and Twist, at the expense of the dermamyotomal marker Pax3. Moreover, filter barrier experiments suggest that Shh mediates the induction of the sclerotome directly rather than by activation of a secondary signaling mechanism (Fan, C.-M. and Tessier-Lavigne, M. (1994) Cell 79, 1175-1186).

Shh also induces myotomal gene expression (Hammerschmidt et al. (1996) supra; Johnson, R. L. et al. (1994) Cell 79:1165-1173; Münsterberg, A. E. et al. (1995) Genes Dev. 9:2911-2922; Weinberg, E. S. et al. (1996) Development 122: 271-280), although recent experiments indicate that members of the WNT family, vertebrate homologues of Drosophila wingless, are required in concert (Münsterberg et al. (1995) supra). Puzzlingly, myotomal induction in chicks requires higher Shh concentrations than the induction of sclerotomal markers (Münsterberg et al. (1995) supra), although the sclerotome originates from somitic cells positioned much closer to the notochord. Similar results were obtained in the zebrafish, where high concentrations of Hedgehog induce myotomal and repress sclerotomal marker gene expression (Hammerschmidt et al. (1996) supra). In contrast to amniotes, however, these observations are consistent with the architecture of the fish embryo, as here, the myotome is the predominant and more axial component of the somites. Thus, modulation of Shh signaling and the acquisition of new signaling factors may have modified the somite structure during vertebrate evolution.

In the vertebrate limb buds, a subset of posterior mesenchymal cells, the "Zone of polarizing activity" (ZPA), regulates anteroposterior digit identity (reviewed in Honig, L. S. (1981) Nature 291:72-73). Ectopic expression of Shh or application of beads, soaked in Shh peptide mimics the effect of anterior ZPA grafts, generating a mirror image duplication of digits (Chang et al. (1994) supra; Lopez-Martinez et al. (1995) supra; Riddle et al. (1993) supra) (FIG. 2g). Thus, digit identity appears to depend primarily on Shh concentration, although it is possible that other signals may relay this information over the substantial distances that appear to be required for AP patterning (100-150 µm). Similar to the interaction of HH and DPP in the Drosophila imaginal discs, Shh in the vertebrate limb bud activates the expression of Bmp2 (Francis, P. H. et al. (1994) Development 120:209-218), a dpp homologue. However, unlike DPP in Drosophila, Bmp2 fails to mimic the polarizing effect of Shh upon ectopic application in the chick limb bud (Francis et al. (1994) supra). In addition to anteroposterior patterning, Shh also appears to be involved in the regulation of the proximodistal outgrowth of the limbs by inducing the synthesis of the fibroblast growth factor FGF4 in the posterior apical ectodermal ridge (Laufer, E. et al. (1994) Cell 79:993-1003; Niswander, L. et al. (1994) Nature 371:609-612).

The close relationship between Hedgehog proteins and BMPs is likely to have been conserved at many, but probably not all sites of vertebrate Hedgehog expression. For example, in the chick hindgut, Shh has been shown to induce the expression of Bmp4, another vertebrate dpp homologue (Roberts, D. J. et al. (1995) Development 121:3163-3174). Furthermore, Shh and Bmp2, 4, or 6 show a striking correlation in their expression in epithelial and mesenchymal cells of the stomach, the urogenital system, the lung, the tooth buds and the hair follicles (Bitgood, M. J. and McMahon, A. P. (1995) Dev. Biol. 172:126-138). Further, Ihh, one of the two other mouse Hedgehog genes, is expressed adjacent to Bmp expressing cells in the gut and developing cartilage (Bitgood and McMahon (1995) supra).

Recent evidence suggests a model in which Ihh plays a crucial role in the regulation of chondrogenic development (Roberts et al. (1995) supra). During cartilage formation, chondrocytes proceed from a proliferating state via an intermediate, prehypertrophic state to differentiated hypertrophic chondrocytes. Ihh is expressed in the prehypertrophic chondrocytes and initiates a signaling cascade that leads to the blockage of chondrocyte differentiation. Its direct target is the perichondrium around the Ihh expression domain, which responds by the expression of Gli and Patched (Ptc), conserved transcriptional targets of Hedgehog signals (see below). Most likely, this leads to secondary signaling resulting in the synthesis of parathyroid hormone-related protein (PTHrP) in the periarticular perichondrium. PTHrP itself signals back to the prehypertrophic chondrocytes, blocking their further differentiation. At the same time, PTHrP represses expression of Ihh, thereby forming a negative feedback loop that modulates the rate of chondrocyte differentiation.

Patched was originally identified in *Drosophila* as a segment polarity gene, one of a group of developmental genes that affect cell differentiation within the individual segments that occur in a homologous series along the anterior-posterior axis of the embryo. See Hooper, J. E. et al. (1989) *Cell* 59:751; and Nakano, Y. et al. (1989) *Nature* 341:508. Patterns of expression of the vertebrate homologue of patched suggest its involvement in the development of neural tube, skeleton, limbs, craniofacial structure, and skin.

Genetic and functional studies demonstrate that patched is part of the hedgehog signaling cascade, an evolutionarily conserved pathway that regulates expression of a number of downstream genes. See Perrimon, N. (1995) *Cell* 80:517; and Perrimon, N. (1996) *Cell* 86:513. Patched participates in the constitutive transcriptional repression of the target genes; its effect is opposed by a secreted glycoprotein, encoded by hedgehog, or a vertebrate homologue, which induces transcriptional activation. Genes under control of this pathway include members of the Wnt and TGF-beta families.

Patched proteins possess two large extracellular domains, twelve transmembrane segments, and several cytoplasmic segments. See Hooper, supra; Nakano, supra; Johnson, R. L. et al. (1996) *Science* 272:1668; and Hahn, H. et al. (1996) *Cell* 85:841. The biochemical role of patched in the hedgehog signalling pathway is unclear. Direct interaction with the hedgehog protein has, however, been reported (Chen, Y. et al. (1996) *Cell* 87:553), and patched may participate in a hedgehog receptor complex along with another transmembrane protein encoded by the smoothened gene. See Perrimon, supra; and Chen, supra.

The human homologue of patched was recently cloned and mapped to chromosome 9q22.3. See Johnson, supra; and Hahn, supra. This region has been implicated in basal cell nevus syndrome (BCNS), which is characterized by developmental abnormalities including rib and craniofacial alterations, abnormalities of the hands and feet, and spina bifida.

BCNS also predisposes to multiple tumor types, the most frequent being basal cell carcinomas (BCC) that occur in many locations on the body and appear within the first two decades of life. Most cases of BCC, however, are unrelated to the syndrome and arise sporadically in small numbers on sun-exposed sites of middle-aged or older people of northern European ancestry.

Recent studies in BCNS-related and sporadic BCC suggest that a functional loss of both alleles of patched leads to development of BCC. See Johnson, supra; Hahn, supra; and Gailani, M. R. et al. (1996) *Nature Genetics* 14:78. Single allele deletions of chromosome 9q22.3 occur frequently in both sporadic and hereditary BCC. Linkage analysis revealed that the defective inherited allele was retained and the normal allele was lost in tumors from BCNS patients.

Sporadic tumors also demonstrated a loss of both functional alleles of patched. Of twelve tumors in which patched mutations were identified with a single strand conformational polymorphism screening assay, nine had chromosomal deletion of the second allele and the other three had inactivating mutations in both alleles (Gailani, supra). The alterations did not occur in the corresponding germline DNA.

Most of the identified mutations resulted in premature stop codons or frame shifts. Lench, N. J., et al., *Hum. Genet.* 1997 October; 100(5-6): 497-502. Several, however, were point mutations leading to amino acid substitutions in either extracellular or cytoplasmic domains. These sites of mutation may indicate functional importance for interaction with extracellular proteins or with cytoplasmic members of the downstream signaling pathway.

The involvement of patched in the inhibition of gene expression and the occurrence of frequent allelic deletions of patched in BCC support a tumor suppressor function for this gene. Its role in the regulation of gene families known to be involved in cell signaling and intercellular communication provides a possible mechanism of tumor suppression.

SUMMARY OF THE INVENTION

The present invention makes available methods and compositions for modulating differentiation or proliferation of a cell. Compounds useful in such methods and compositions include those represented by general formula (I):

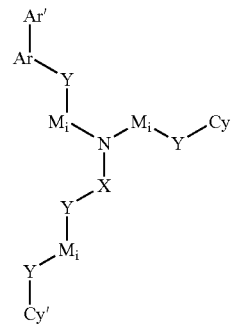

Formula I wherein, as valence and stability permit,

Ar and Ar' independently represent substituted or unsubstituted aryl or heteroaryl rings;

Y, independently for each occurrence, is absent or represents —N(R)—, —O—, —S—, or —Se—;

X is selected from —C(=O)—, —C(=S)—, —S(O$_2$)—, —S(O)—, —C(=NCN)—, —P(=O)(OR)—, and a methylene group optionally substituted with 1-2 groups such as lower alkyl, alkenyl, or alkynyl groups;

M represents, independently for each occurrence, a substituted or unsubstituted methylene group, such as —CH$_2$—, —CHF—, —CHOH—, —CH(Me)—, —C(=O)—, etc., or two M taken together represent substituted or unsubstituted ethene or ethyne;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

Cy and Cy' independently represent substituted or unsubstituted aryl, heterocyclyl, heteroaryl, or cycloalkyl, including polycyclic groups; and i represents, independently for each occurrence, an integer from 0 to 5, preferably from 0 to 2.

In certain embodiments, M represents, independently for each occurrence, a substituted or unsubstituted methylene group, such as —CH$_2$—, —CHF—, —CHOH—, —CH(Me)—C(=O)—, etc.

In certain embodiments, Ar and Ar' represent phenyl rings, e.g., unsubstituted or substituted with one or more groups including heteroatoms such as O, N, and S. In certain embodiments, at least one of Ar and Ar' represents a phenyl ring. In certain embodiments, at least one of Ar and Ar' represents a heteroaryl ring, e.g., a pyridyl, thiazolyl, thienyl, pyrimidyl, etc. In certain embodiments, Y and Ar' are attached to Ar in a meta and/or 1,3-relationship.

In certain embodiments, Y is absent from all positions. In embodiments wherein Y is present in a position, i preferably represents an integer from 1-2 in an adjacent M; if i=0 would result in two occurrences of Y being directly attached, or an occurrence of Y being directly attached to N.

In certain embodiments, Cy' is a substituted or unsubstituted aryl or heteroaryl. In certain embodiments, Cy' is directly attached to X. In certain embodiments, Cy' is a substituted or unsubstituted bicyclic or heteroaryl ring, preferably both bicyclic and heteroaryl, such as benzothiophene, benzofuran, benzopyrrole, benzopyridine, etc. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system.

In certain embodiments, X is selected from —C(=O)—, —C(=S)—, and —S(O$_2$)—.

In certain embodiments, R represents H or lower alkyl, e.g., H or Me.

In certain embodiments, Cy represents a substituted or unsubstituted non-aromatic carbocyclic or heterocyclic ring, i.e., including at least one sp$^3$ hybridized atom, and preferably a plurality of sp$^3$ hybridized atoms. In certain embodiments, Cy includes an amine within the atoms of the ring or on a substituent of the ring, e.g., Cy is pyridyl, imidazolyl, pyrrolyl, piperidyl, pyrrolidyl, piperazyl, etc., and/or bears an amino substituent. In certain embodiments, Cy is a 5- to 7-membered ring. In certain embodiments, Cy is directly attached to N. In embodiments wherein Cy is a six-membered ring directly attached to N and bears an amino substituent at the 4 position of the ring relative to N, the N and amine substituents may be disposed trans on the ring.

In certain embodiments, substituents on Ar or Ar' are selected from halogen, lower alkyl, lower alkenyl, aryl, heteroaryl, carbonyl, thiocarbonyl, ketone, aldehyde, amino, acylamino, cyano, nitro, hydroxyl, azido, sulfonyl, sulfoxido, sulfate, sulfonate, sulfamoyl, sulfonamido, phosphoryl, phosphonate, phosphinate, —(CH$_2$)$_p$alkyl, —(CH$_2$)$_p$alkenyl, —(CH$_2$)$_p$alkynyl, —(CH$_2$)$_p$aryl, —(CH$_2$)$_p$aralkyl, —(CH$_2$)$_p$OH, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$NR-lower alkenyl, —NR(CH$_2$)$_n$R, and protected forms of the above, wherein p and n, individually for each occurrence, represent integers from 0 to 10, preferably from 0 to 5.

In certain embodiments, compounds useful in the present invention may be represented by general formula (II):

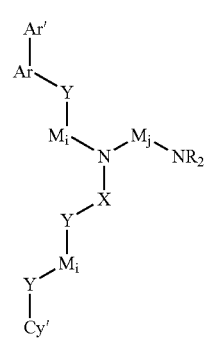

Formula II wherein, as valence and stability permit,

Ar and Ar' independently represent substituted or unsubstituted aryl or heteroaryl rings;

Y, independently for each occurrence, is absent or represents —N(R)—, —O—, —S—, or —Se—;

X is selected from —C(=O)—, —C(=S)—, —S(O2)-, —S(O)—, —C(=NCN)—, —P(=O)(OR)—, and a methylene group optionally substituted with 1-2 groups such as lower alkyl, alkenyl, or alkynyl groups;

M represents, independently for each occurrence, a substituted or unsubstituted methylene group, such as —CH2-, —CHF—, —CHOH—, —CH(Me)—, —C(=O)—, etc., or two M taken together represent substituted or unsubstituted ethene or ethyne, wherein some or all occurrences of M in M$_j$ form all or part of a cyclic structure;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

Cy' represents a substituted or unsubstituted aryl, heterocyclyl, heteroaryl, or cycloalkyl, including polycyclic groups;

j represents, independently for each occurrence, an integer from 0 to 10, preferably from 2 to 7; and i represents, independently for each occurrence, an integer from 0 to 5, preferably from 0 to 2.

In certain embodiments, M represents, independently for each occurrence, a substituted or unsubstituted methylene group, such as —CH$_2$—, —CHF—, —CHOH—, CH(Me)-, —C(=O)—, etc.

In certain embodiments, Ar and Ar' represent phenyl rings, e.g., unsubstituted or substituted with one or more groups including heteroatoms such as O, N, and S. In certain embodiments, at least one of Ar and Ar' represents a phenyl ring. In certain embodiments, at least one of Ar and Ar' represents a heteroaryl ring, e.g., a pyridyl, thiazolyl, thienyl, pyrimidyl, etc. In certain embodiments; Y and Ar' are attached to Ar in a meta and/or 1,3-relationship.

In certain embodiments, Y is absent from all positions. In embodiments wherein Y is present in a position, i preferably represents an integer from 1-2 in an adjacent M$_i$ if i=0 would result in two occurrences of Y being directly attached, or an occurrence of Y being directly attached to N or NR$_2$.

In certain embodiments, Cy' is a substituted or unsubstituted aryl or heteroaryl. In certain embodiments, Cy' is directly attached to X. In certain embodiments, Cy' is a substituted or unsubstituted bicyclic or heteroaryl ring, preferably both bicyclic and heteroaryl, such as benzothiophene, benzofuran, benzopyrrole, benzopyridine, etc. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system.

In certain embodiments, X is selected from —C(=O)—, —C(=S)—, and —S($O_2$)—.

In certain embodiments, R represents H or lower alkyl, e.g., H or Me.

In certain embodiments, $NR_2$ represents a primary amine or a secondary or tertiary amine substituted with one or two lower alkyl groups, aryl groups, or aralkyl groups, respectively, preferably a primary amine or secondary amine.

In certain embodiments, substituents on Ar or Ar' are selected from halogen, lower alkyl, lower alkenyl, aryl, heteroaryl, carbonyl, thiocarbonyl, ketone, aldehyde, amino, acylamino, cyano, nitro, hydroxyl, azido, sulfonyl, sulfoxido, sulfate, sulfonate, sulfamoyl, sulfonamido, phosphoryl, phosphonate, phosphinate, —$(CH_2)_p$alkyl, —$(CH_2)_p$alkenyl, —$(CH_2)_p$alkynyl, —$(CH_2)_p$aryl, —$(CH_2)_p$aralkyl, —$(CH_2)_p$OH, —$(CH_2)_p$O-lower alkyl, —$(CH_2)_p$O-lower alkenyl, —O$(CH_2)_n$R, —$(CH_2)_p$SH, —$(CH_2)_p$S-lower alkyl, —$(CH_2)_p$S-lower alkenyl, —S$(CH_2)_n$R; —$(CH_2)_p$N$(R)_2$, —$(CH_2)_p$NR-lower alkyl, —$(CH_2)_p$NR-lower alkenyl, —NR$(CH_2)_n$R, and protected forms of the above, wherein p and n, individually for each occurrence, represent integers from 0 to 10, preferably from 0 to 5.

In certain embodiments, compounds useful in the present invention may be represented by general formula (III):

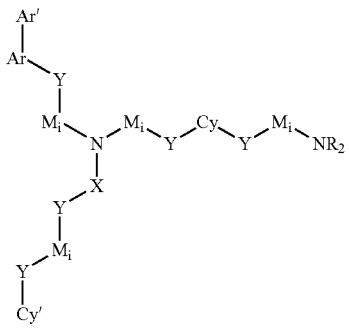

Formula III wherein, as valence and stability permit,

Ar and Ar' independently represent substituted or unsubstituted aryl or heteroaryl rings;

Y, independently for each occurrence, is absent or represents —N(R)—, —O—, —S—, or —Se—;

X is selected from —C(=O)—, —C(=S)—, —S($O_2$)—, —S(O)—, —C(=NCN)—, —P(=O)(OR)—, and a methylene group optionally substituted with 1-2 groups such as lower alkyl, alkenyl, or alkynyl groups;

M represents, independently for each occurrence, a substituted or unsubstituted methylene group, such as —$CH_2$—, —CHF—, —CHOH—, —CH(Me)—, —C(=O)—, etc., or two M taken together represent substituted or unsubstituted ethene or ethyne;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

Cy and Cy' independently represent substituted or unsubstituted aryl, heterocyclyl, heteroaryl, or cycloalkyl, including polycyclic groups; and i represents, independently for each occurrence, an integer from 0 to 5, preferably from 0 to 2.

In certain embodiments, M represents, independently for each occurrence, a substituted or unsubstituted methylene group, such as —$CH_2$—, —CHF—, —CHOH—, —CH(Me)-, —C(=O)—, etc.

In certain embodiments, Ar and Ar' represent phenyl rings, e.g., unsubstituted or substituted with one or more groups including heteroatoms such as O, N, and S. In certain embodiments, at least one of Ar and Ar' represents a phenyl ring. In certain embodiments, at least one of Ar and Ar' represents a heteroaryl ring, e.g., a pyridyl, thiazolyl, thienyl, pyrimidyl, etc. In certain embodiments, Y and Ar' are attached to Ar in a meta and/or 1,3-relationship.

In certain embodiments, Y is absent from all positions. In embodiments wherein Y is present in a position, i preferably represents an integer from 1-2 in an adjacent $M_i$ if i=0 would result in two occurrences of Y being directly attached, or an occurrence of Y being directly attached to N or $NR_2$.

In certain embodiments, Cy' is a substituted or unsubstituted aryl or heteroaryl. In certain embodiments, Cy' is directly attached to X. In certain embodiments, Cy' is a substituted or unsubstituted bicyclic or heteroaryl ring, preferably both bicyclic and heteroaryl, such as benzothiophene, benzofuran, benzopyrrole, benzopyridine, etc. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different directly connected by one or more bonds, e.g., to form a biaryl or bicyclic ring system.

In certain embodiments, X is selected from —C(=O)—, —C(=S)—, and —S($O_2$)—.

In certain embodiments, R represents H or lower alkyl, e.g., H or Me.

In certain embodiments, $NR_2$ represents a primary amine or a secondary or tertiary amine substituted with one or two lower alkyl groups, aryl groups, or aralkyl groups, respectively, preferably a primary amine or a secondary amine.

In certain embodiments, Cy represents a substituted or unsubstituted non-aromatic carbocyclic or heterocyclic ring, i.e., including at least one $sp^3$ hybridized atom, and preferably a plurality of $sp^3$ hybridized atoms. In certain embodiments, Cy is directly attached to N and/or to $NR_2$. In certain embodiments, Cy is a 5- to 7-membered ring. In embodiments wherein Cy is a six-membered ring directly attached to N and bears an amino substituent at the 4 position of the ring relative to N, the N and amine substituents may be disposed trans on the ring.

In certain embodiments, substituents on Ar or Ar' are selected from halogen, lower alkyl, lower alkenyl, aryl, heteroaryl, carbonyl, thiocarbonyl, ketone, aldehyde, amino, acylamino, cyano, nitro, hydroxyl, azido, sulfonyl, sulfoxido, sulfate, sulfonate, sulfamoyl, sulfonamido, phosphoryl, phosphonate, phosphinate, —$(CH_2)_p$alkyl, $(CH_2)_p$alkenyl, —$(CH_2)_p$alkynyl, —$(CH_2)_p$aryl, —$(CH_2)_p$aralkyl, —$(CH_2)_p$OH, —$(CH_2)_p$O-lower alkyl, —$(CH_2)_p$O-lower alkenyl, —O$(CH_2)_n$R, —$(CH_2)_p$SH, —$(CH_2)_p$S-lower alkyl, —$(CH_2)_p$S-lower alkenyl, —S$(CH_2)_n$R, —$(CH_2)_p$N$(R)_2$, —$(CH_2)_p$NR-lower alkyl, —$(CH_2)_p$NR-lower alkenyl, —NR$(CH_2)_n$R, and protected forms of the above, wherein n and p, individually for each occurrence, represent integers from 0 to 10, preferably from 0 to 5.

In certain embodiments, compounds useful in the subject methods include compounds represented by general formula (IV):

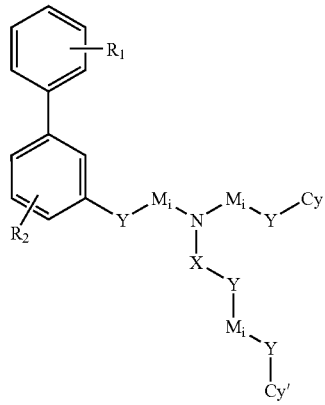

Formula IV wherein, as valence and stability permit,

Cy' represents a substituted or unsubstituted aryl or heteroaryl ring, including polycyclics;

Y, independently for each occurrence, is absent or represents —N(R)—, —O—, —S—, or —Se—;

X is selected from —C(=O)—, —C(=S)—, —S(O$_2$)—, —S(O)—, —C(=NCN)—, —P(=O)(OR)—, and a methylene group optionally substituted with 1-2 groups such as lower alkyl, alkenyl, or alkynyl groups;

M represents, independently for each occurrence, a substituted or unsubstituted methylene group, such as —CH$_2$—, —CHF—, —CHOH—, —CH(Me)—, —C(=O)—, etc., or two M taken together represent substituted or unsubstituted ethene or ethyne;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

R$_1$ and R$_2$ represent, independently and as valency permits, from 0-5 substituents on the ring to which it is attached, selected from halogen, lower alkyl, lower alkenyl, aryl, heteroaryl, carbonyl, thiocarbonyl, ketone, aldehyde, amino, acylamino, amido, amidino, cyano, nitro, hydroxyl, azido, sulfonyl, sulfoxido, sulfate, sulfonate, sulfamoyl, sulfonamido, phosphoryl, phosphonate, phosphinate, —(CH$_2$)$_p$alkyl, —(CH$_2$)$_p$alkenyl, —(CH$_2$)$_p$alkynyl, —(CH$_2$)$_p$aryl, —(CH$_2$)$_p$aralkyl, —(CH$_2$)$_p$OH, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$NR-lower alkenyl, —NR(CH$_2$)$_n$R, and protected forms of the above;

Cy represents substituted or unsubstituted aryl, heterocyclyl, heteroaryl, or cycloalkyl, including polycyclic groups;

i represents, independently for each occurrence, an integer from 0 to 5, preferably from 0 to 2; and p and n, individually for each occurrence, represent integers from 0 to 10, preferably from 0 to 5.

In certain embodiments, M represents, independently for each occurrence, a substituted or unsubstituted methylene group, such as —CH$_2$—, —CHF—, —CHOH—, —CH(Me)-, C(=O)—, etc.

In certain embodiments, Cy' represents a substituted or unsubstituted bicyclic or heterocyclic ring system, preferably both bicyclic and heteroaryl, such as benzothiophene, benzofuran, benzopyrrole, benzopyridine, etc. In certain embodiments, Cy' is directly attached to X. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system.

In certain embodiments, Y is absent from all positions. In embodiments wherein Y is present in a position, i preferably represents an integer from 1-2 in an adjacent M$_i$ if i=0 would result in two occurrences of Y being directly attached, or an occurrence of Y being directly attached to N.

In certain embodiments, X is selected from —C(=O)—, —C(=S)—, and —S(O$_2$)—.

In certain embodiments, R represents H or lower alkyl, e.g., H or Me.

In certain embodiments, Cy represents a substituted or unsubstituted non-aromatic carbocyclic or heterocyclic ring, i.e., including at least one sp$^3$ hybridized atom, and preferably a plurality of sp$^3$ hybridized atoms. In certain embodiments, Cy includes an amine within the atoms of the ring or on a substituent of the ring, e.g., Cy is pyridyl, imidazolyl, pyrrolyl, piperidyl, pyrrolidyl, piperazyl, etc., and/or bears an amino substituent. In certain embodiments, Cy is directly attached to N. In certain embodiments, Cy is a 5- to 7-membered ring. In embodiments wherein Cy is a six-membered ring directly attached to N and bears an amino substituent at the 4 position of the ring relative to N, the N and amine substituents may be disposed trans on the ring.

In certain embodiments, R$_1$ and R$_2$ represent, independently and as valency permits, from 0-5 substituents on the ring to which it is attached, selected from halogen, lower alkyl, lower alkenyl, carbonyl, thiocarbonyl, ketone, aldehyde, amino, acylamino, cyano, nitro, hydroxyl, sulfonyl, sulfoxido, sulfate, sulfonate, sulfamoyl, sulfonamido, —(CH$_2$)$_p$alkyl, —(CH$_2$)$_p$alkenyl, —(CH$_2$)$_p$alkynyl, —(CH$_2$)$_p$OH, —(CH$_2$)$_p$O-lower alkyl, —(CH$_2$)$_p$O-lower alkenyl, —(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$NR-lower alkenyl, —NR(CH$_2$)$_n$R, and protected forms of the above.

In certain embodiments, compounds useful in the present invention may be represented by general formula (V):

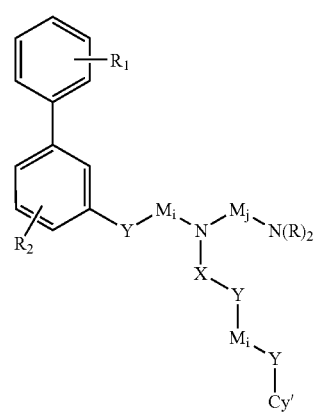

Formula V wherein, as valence and stability permit,

Cy' represents a substituted or unsubstituted aryl or heteroaryl ring, including polycyclics;

Y, independently for each occurrence, is absent or represents —N(R)—, —O—, —S—, or —Se—;

X is selected from —C(=O)—, —C(=S)—, —S(O$_2$)—, —S(O)—, —C(=NCN)—, —P(=O)(OR)—, and a methylene group optionally substituted with 1-2 groups such as lower alkyl, alkenyl, or alkynyl groups;

M represents, independently for each occurrence, a substituted or unsubstituted methylene group, such as —CH$_2$—, —CHF—, CHOH—, —CH(Me)—, —C(=O)—, etc., or two M taken together represent substituted or unsubstituted ethene or ethyne;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

$R_1$ and $R_2$ represent, independently and as valency permits, from 0-5 substituents on the ring to which it is attached, selected from halogen, lower alkyl, lower alkenyl, aryl, heteroaryl, carbonyl, thiocarbonyl, ketone, aldehyde, amino, acylamino, amido, amidino, cyano, nitro, hydroxyl, azido, sulfonyl, sulfoxido, sulfate, sulfonate, sulfamoyl, sulfonamido, phosphoryl, phosphonate, phosphinate, —(CH$_2$)$_p$alkyl, —(CH$_2$)$_p$alkenyl, —(CH$_2$)$_p$alkynyl, —(CH$_2$)$_p$aryl, —(CH$_2$)$_p$aralkyl, —(CH$_2$)$_p$OH, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$NR-lower alkenyl, —NR(CH$_2$)$_n$R, and protected forms of the above;

Cy' represents a substituted or unsubstituted aryl, heterocyclyl, heteroaryl, or cycloalkyl, including polycyclic groups;

j represents, independently for each occurrence, an integer from 0 to 10, preferably from 2 to 7;

i represents, independently for each occurrence, an integer from 0 to 5, preferably from 0 to 2; and p and n, individually for each occurrence, represent integers from 0 to 10, preferably from 0 to 5.

In certain embodiments, M represents, independently for each occurrence, a substituted or unsubstituted methylene group, such as —CH$_2$—, —CHF—, —CHOH—, —CH(Me)-, —C(=O)—, etc.

In certain embodiments, Cy' represents a substituted or unsubstituted bicyclic or heterocyclic ring system, preferably both bicyclic and heteroaryl, such as benzothiophene, benzofuran, benzopyrrole, benzopyridine, etc. In certain embodiments, Cy' is directly attached to X. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system.

In certain embodiments, Y is absent from all positions. In embodiments wherein Y is present in a position, i preferably represents an integer from 1-2 in an adjacent $M_i$ if i=0 would result in two occurrences of Y being directly attached, or an occurrence of Y being directly attached to N or NR$_2$.

In certain embodiments, X is selected from —C(=O)—, —C(=S)—, and —S(O$_2$)—.

In certain embodiments, NR$_2$ represents a primary amine or a secondary or tertiary amine substituted with one or two lower alkyl groups, aryl groups, or aralkyl groups, respectively, preferably a primary or secondary amine.

In certain embodiments, R represents H or lower alkyl, e.g., H or Me.

In certain embodiments, $R_1$ and $R_2$ represent, independently and as valency permits, from 0-5 substituents on the ring to which it is attached, selected from halogen, lower alkyl, lower alkenyl, carbonyl, thiocarbonyl, ketone, aldehyde, amino, acylamino, cyano, nitro, hydroxyl, sulfonyl, sulfoxido, sulfate, sulfonate, sulfamoyl, sulfonamido, —(CH$_2$)$_p$allyl, —(CH$_2$)$_p$alkenyl, —(CH$_2$)$_p$alkynyl, —(CH$_2$)$_p$OH, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$NR-lower alkenyl, —NR(CH$_2$)$_n$R, and protected forms of the above.

In certain embodiments, compounds useful in the present invention may be represented by general formula (VI):

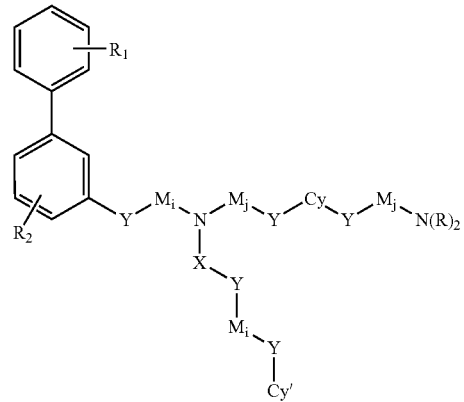

Formula VI wherein, as valence and stability permit,

Cy' represents a substituted or unsubstituted aryl or heteroaryl ring, including polycyclics;

Y, independently for each occurrence, is absent or represents —N(R)—, —O—, —S—, or —Se—;

X is selected from —C(=O)—, —C(=S)—, —S(O$_2$)—, —S(O)—, —C(=NCN)—, —P(=O)(OR)—, and a methylene group optionally substituted with 1-2 groups such as lower alkyl, alkenyl, or alkynyl groups;

M represents, independently for each occurrence, a substituted or unsubstituted methylene group, such as —CH$_2$—, —CHF—, —CHOH—, —CH(Me)—, —C(=O)—, etc., or two M taken together represent substituted or unsubstituted ethene or ethyne;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

Cy represents substituted or unsubstituted aryl, heterocyclyl, heteroaryl, or cycloalkyl, including polycyclic groups;

$R_1$ and $R_2$ represent, independently and as valency permits, from 0-5 substituents on the ring to which it is attached, selected from halogen, lower alkyl, lower alkenyl, aryl, heteroaryl, carbonyl, thiocarbonyl, ketone, aldehyde, amino, acylamino, amido, amidino, cyano, nitro, hydroxyl, azido, sulfonyl, sulfoxido, sulfate, sulfonate, sulfamoyl, sulfonamido, phosphoryl, phosphonate, phosphinate, —(CH$_2$)$_p$alkyl, —(CH$_2$)$_p$alkenyl, —(CH$_2$)$_p$alkynyl, —(CH$_2$)$_p$aryl, —(CH$_2$)$_p$aralkyl, —(CH$_2$)$_p$OH, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$—NR-lower alkyl, —(CH$_2$)$_p$NR-lower alkenyl, —NR(CH$_2$)$_n$R, and protected forms of the above;

i represents, independently for each occurrence, an integer from 0 to 5, preferably from 0 to 2; and n and p, individually for each occurrence, represent integers from 0 to 10, preferably from 0 to 5.

In certain embodiments, M represents, independently for each occurrence, a substituted or unsubstituted methylene group, such as —CH$_2$—, —CHF—, —CHOH—, —CH(Me)-, —C(=O)—, etc.

In certain embodiments, Cy' represents a substituted or unsubstituted bicyclic or heteroaryl ring system, preferably both bicyclic and heteroaryl, e.g., benzothiophene, benzofuran, benzopyrrole, benzopyridyl, etc. In certain embodiments, Cy' is directly attached to X. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system.

In certain embodiments, Y is absent from all positions. In embodiments wherein Y is present in a position, i preferably represents an integer from 1-2 in an adjacent M$_i$ if i=0 would result in two occurrences of Y being directly attached, or an occurrence of Y being directly attached to N or NR$_2$.

In certain embodiments, X is selected from —C(=O)—, —C(=S)—, and —S(O$_2$)—.

In certain embodiments, NR$_2$ represents a primary amine or a secondary or tertiary amine substituted with one or two lower alkyl groups, aryl groups, or aralkyl groups, respectively, preferably a primary amine.

In certain embodiments, R represents H or lower alkyl, e.g., H or Me.

In certain embodiments, Cy represents a substituted or unsubstituted non-aromatic carbocyclic or heterocyclic ring, i.e., including at least one sp$^3$ hybridized atom, and preferably a plurality of sp$^3$ hybridized atoms. In certain embodiments, Cy is directly attached to N and/or to NR$_2$. In certain embodiments, Cy is a 5- to 7-membered ring. In embodiments wherein Cy is a six-membered ring directly attached to N and bears an amino substituent at the 4 position of the ring relative to N, the N and amine substituents may be disposed trans on the ring.

In certain embodiments, R$_1$ and R$_2$ represent, independently and as valency permits, from 0-5 substituents on the ring to which it is attached, selected from halogen, lower alkyl, lower alkenyl, carbonyl, thiocarbonyl, ketone, aldehyde, amino, acylamino, cyano, nitro, hydroxyl, sulfonyl, sulfoxido, sulfate, sulfonate, sulfamoyl, sulfonamido, —(CH$_2$)$_p$alkyl, —(CH$_2$)$_p$alkenyl, —(CH$_2$)$_p$alkynyl, —(CH$_2$)$_p$OH, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$NR-lower alkenyl, —NR(CH$_2$)$_n$R, and protected forms of the above.

In certain embodiments, a subject compound has the structure of Formula VII:

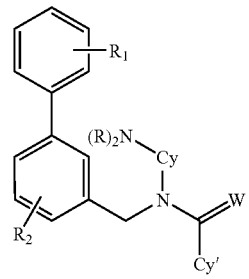

Formula VII wherein, as valence and stability permit,

Cy represents a substituted or unsubstituted heterocyclyl or cycloalkyl;

Cy' is a substituted or unsubstituted aryl or heteroaryl ring, including polycyclics;

W is O or S;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

R$_1$ and R$_2$ represent, independently and as valency permits, from 0-5 substituents on the ring to which it is attached, selected from halogen, lower alkyl, lower alkenyl, aryl, heteroaryl, carbonyl, thiocarbonyl, ketone, aldehyde, amino, acylamino, amido, amidino, cyano, nitro, hydroxyl, azido, sulfonyl, sulfoxido, sulfate, sulfonate, sulfamoyl, sulfonamido, phosphoryl, phosphonate, phosphinate, —(CH$_2$)$_p$alkyl, —(CH$_2$)$_p$alkenyl, —(CH$_2$)$_p$alkynyl, —(CH$_2$)$_p$aryl, —(CH$_2$)$_p$aralkyl, —(CH$_2$)$_p$OH, —(CH$_2$)$_p$O-lower alkyl, (CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$NR, —(CH$_2$)$_p$NR-lower alkyl, —(CH$_2$)$_p$NR-lower alkenyl, —NR(CH$_2$)$_n$R, and protected forms of the above;

n and p, individually for each occurrence, represent integers from 0 to 10, preferably from 0 to 5.

In certain embodiments, Cy' represents a substituted or unsubstituted bicyclic or heteroaryl ring system, preferably both bicyclic and heteroaryl, e.g., benzothiophene, benzofuran, benzopyrrole, benzopyridyl, etc. In certain other embodiments, Cy' represents an aryl or heteroaryl ring substituted at least with a substituted or unsubstituted aryl or heteroaryl ring, i.e., to form a biaryl ring system.

In certain embodiments, NR$_2$ represents a primary amine or a secondary or tertiary amine substituted with one or two lower alkyl groups, aryl groups, or aralkyl groups, respectively, preferably a primary or secondary amine.

In certain embodiments, Cy represents a substituted or unsubstituted saturated carbocyclic or heterocyclic ring, i.e., composed of a plurality of sp$^3$ hybridized atoms. In certain embodiments, Cy is a 5- to 7-membered ring. In embodiments wherein Cy is a six-membered ring directly attached to N and bears an amino substituent at the 4 position of the ring relative to N, the N and amine substituents may be disposed trans on the ring.

In certain embodiments, R$_1$ and R$_2$ represent, independently and as valency permits, from 0-5 substituents on the ring to which it is attached, selected from halogen, lower alkyl, lower alkenyl, carbonyl, thiocarbonyl, ketone, aldehyde, amino, acylamino, cyano, nitro, hydroxyl, sulfonyl, sulfoxido, sulfate, sulfonate, sulfamoyl, sulfonamido, —(CH$_2$)$_p$alkyl, —(CH$_2$)$_p$alkenyl, —(CH$_2$)$_p$alkynyl, —(CH$_2$)$_p$OH, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$R-lower alkenyl, —NR(CH$_2$)$_n$R, and protected forms of the above.

In certain embodiments, a subject compound has a structure of Formula VIII:

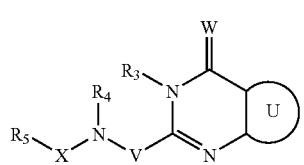

Formula VIII wherein, as valence and stability permit,

U represents a substituted or unsubstituted aryl or heteroaryl ring fused to the nitrogen-containing ring;

V represents a lower alkylene group, such as methylene, 1,2-ethylene, 1,1-ethylene, 1,1-propylene, 1,2-propylene, 1,3-propylene, etc.;

W represents S or O, preferably O;

X represents C=O, C=S, or SO$_2$;

R$_3$ represents substituted or unsubstituted aryl, heteroaryl, lower alkyl, lower alkenyl, lower alkynyl; carbocyclyl, carbocyclylalkyl, heterocyclyl, heterocyclylalkyl, aralkyl, or heteroaralkyl;

R$_4$ represents substituted or unsubstituted aralkyl or lower alkyl, such as phenethyl, benzyl, or aminoalkyl, etc.;

R$_5$ represents substituted or unsubstituted aryl, heteroaryl, aralkyl, or heteroaralkyl, including polycyclic aromatic or heteroaromatic groups.

In certain embodiments, U represents a phenyl ring fused to the nitrogen-containing ring.

In certain embodiments, R$_3$ is selected from substituted or unsubstituted aryl, heteroaryl, lower alkyl, lower alkenyl, aralkyl, and heteroaralkyl.

In certain embodiments, R$_4$ is an unsubstituted lower alkyl group, or is a lower alkyl group substituted with a secondary or tertiary amine.

In certain embodiments, R$_5$ is selected from substituted or unsubstituted phenyl or naphthyl, or is a diarylalkyl group, such as 2,2-diphenylethyl, diphenylmethyl, etc.

Additionally, compounds having structures of Formulae IX-XII may be useful in the compositions and methods of the present invention.

In certain embodiments, a hedgehog-independent compound useful in the present invention, such as described above, may have an EC$_{50}$ for inducing or augmenting one or more hedgehog activities (such as upregulation of gli expression) of less than about 1000 mm, less than about 100 nm, less than about 10 mm, or even less than about 1 nm. In certain embodiments, a hedgehog-dependent compound useful in the present invention, such as described above, augmenting one or more hedgehog activities (such as upregulation of gli expression) by at least one, two, or even three orders of magnitude. Compounds of the invention may be used in in vivo methods, e.g., for treating a disease or condition in an animal or patient, and in in vitro methods, e.g., for culturing cells (e.g., as a component of the culture medium), including stem or progenitor cells, such as to promote proliferation, survival, and/or differentiation of the cultured cells.

BRIEF DESCRIPTION OF THE DRAWINGS

FIGS. 36 and 37 portray the increased proliferation of cerebellar neuron precursors in the presence of subject agonists.

FIG. 44 portrays the effects of a subject agonist on developing lung tissue.

FIG. 45 shows the effects of a subject agonist on developing kidney tissue.

DETAILED DESCRIPTION OF THE INVENTION

I. Overview

Figure 1:
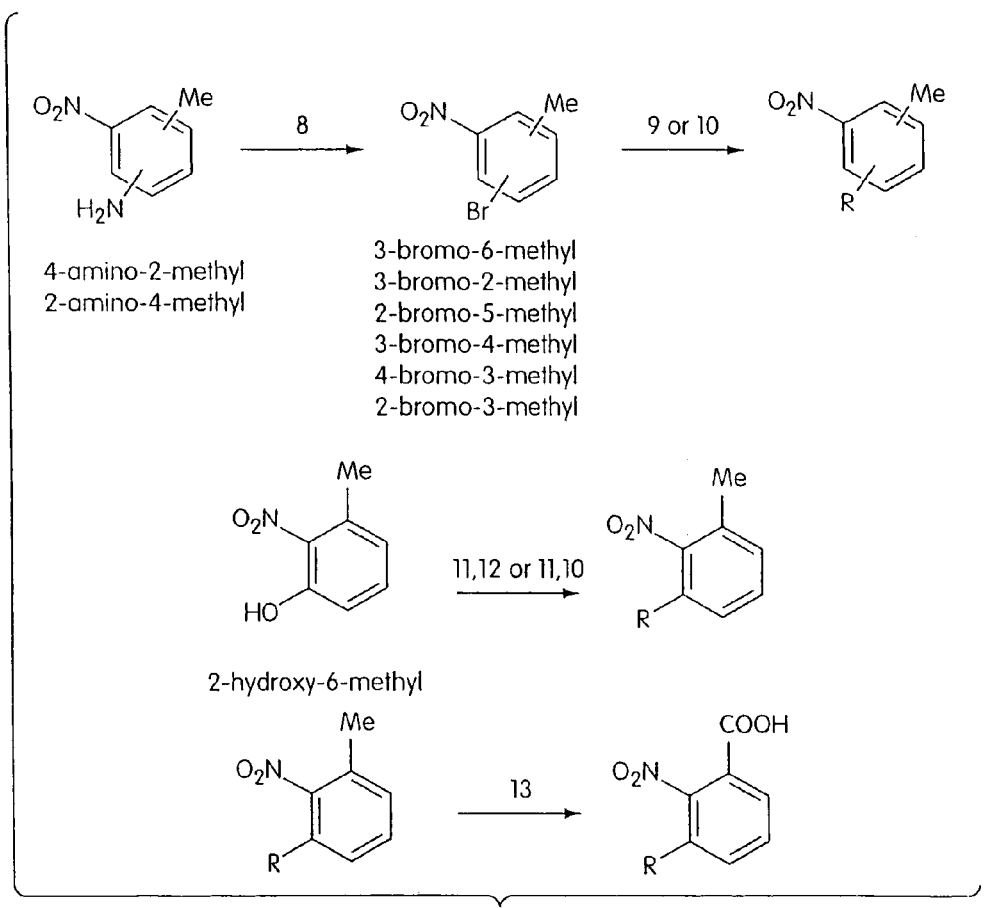
FIGS. 1-31 depict reactions useful for synthesizing compounds according to the present invention.
Figure 2:
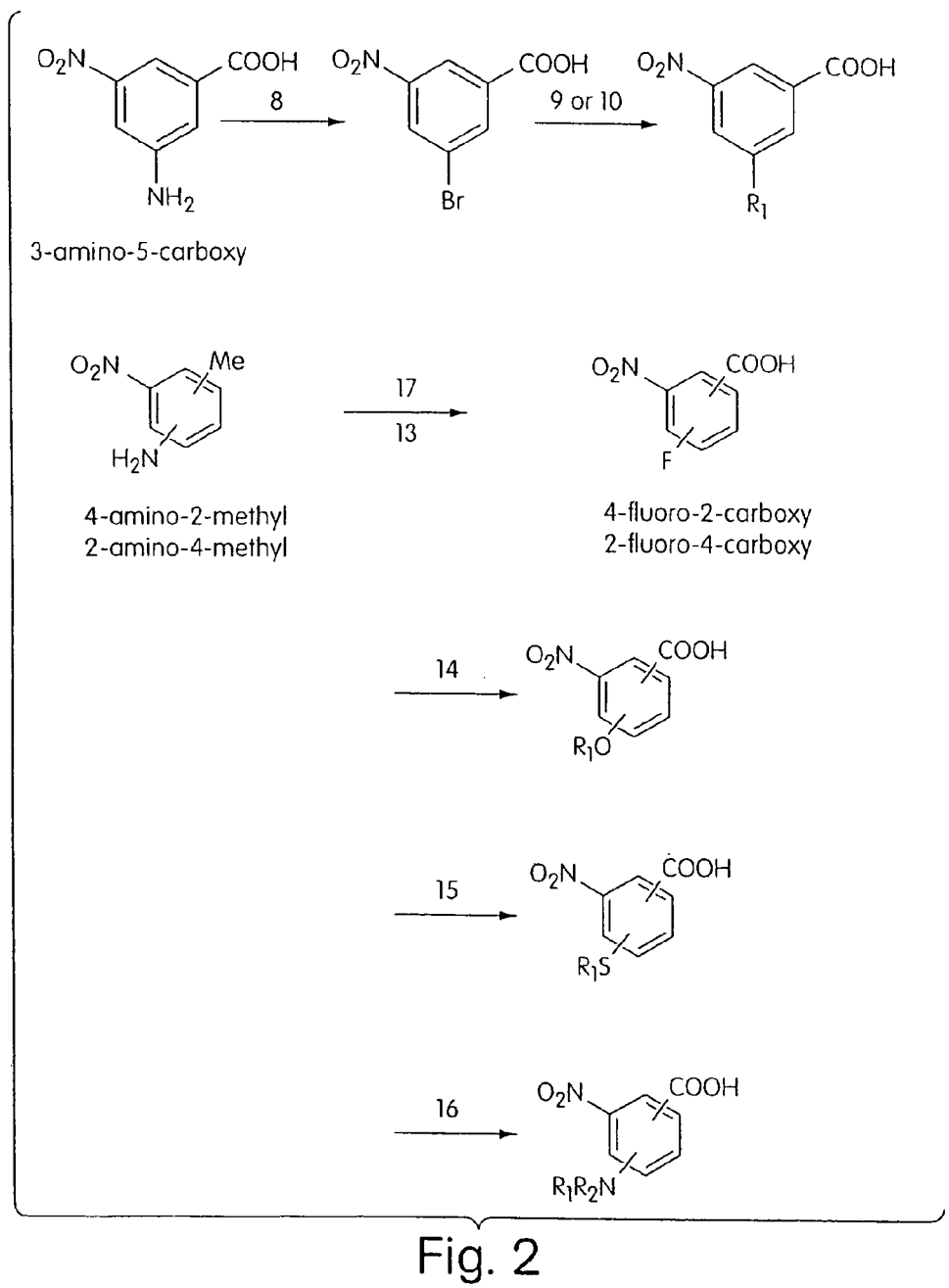
Figure 3:
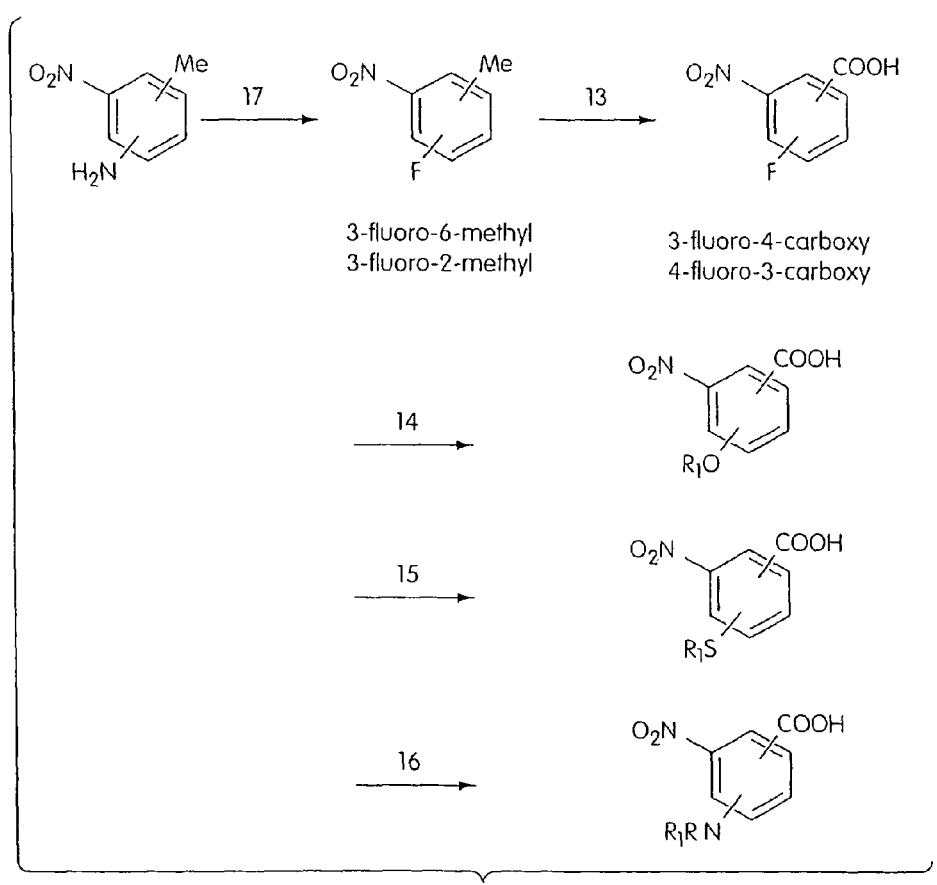
Figure 4:
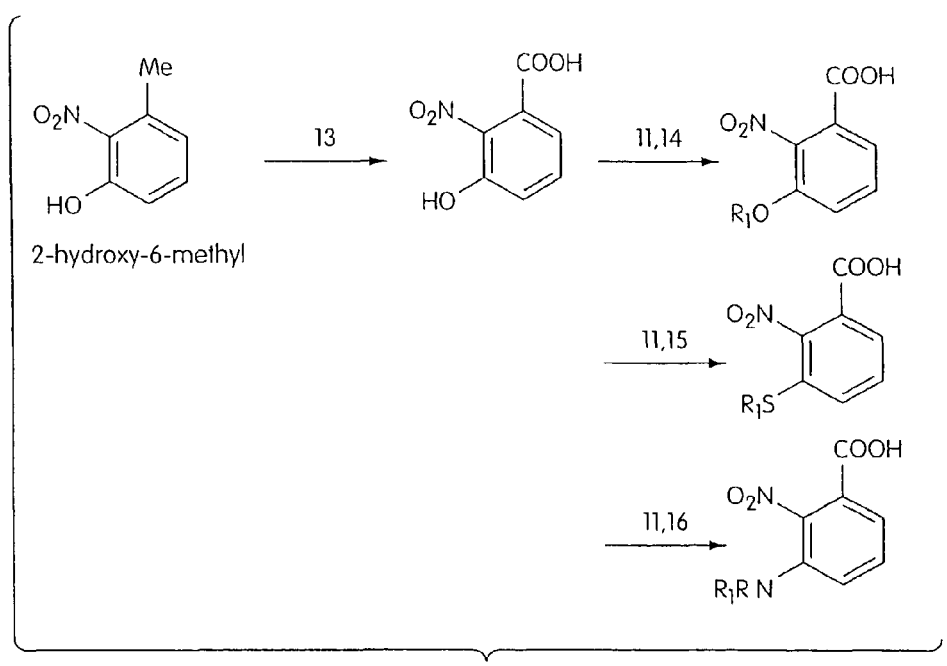
Figure 5:
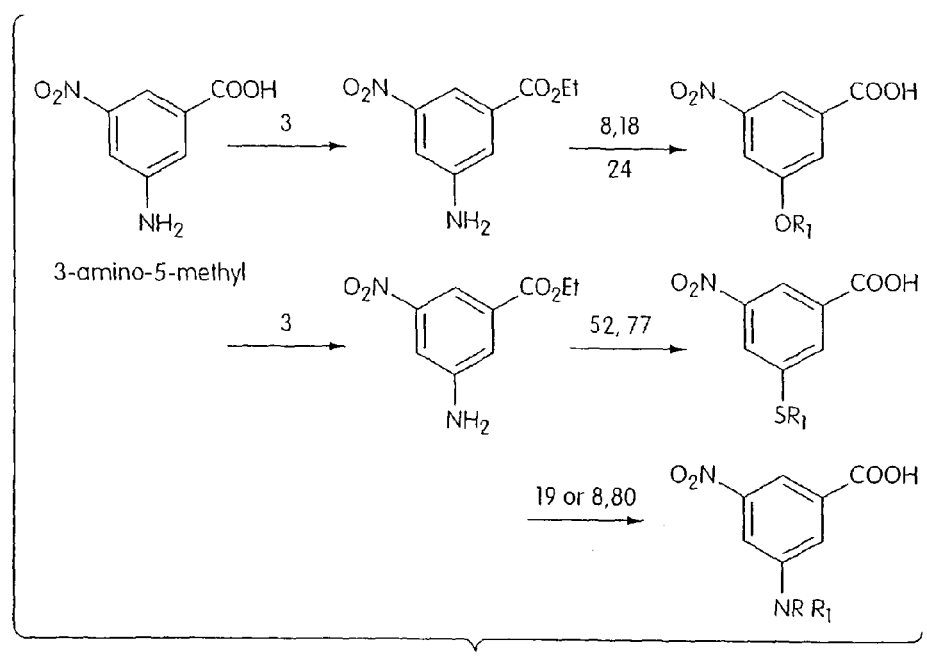
Figure 6:
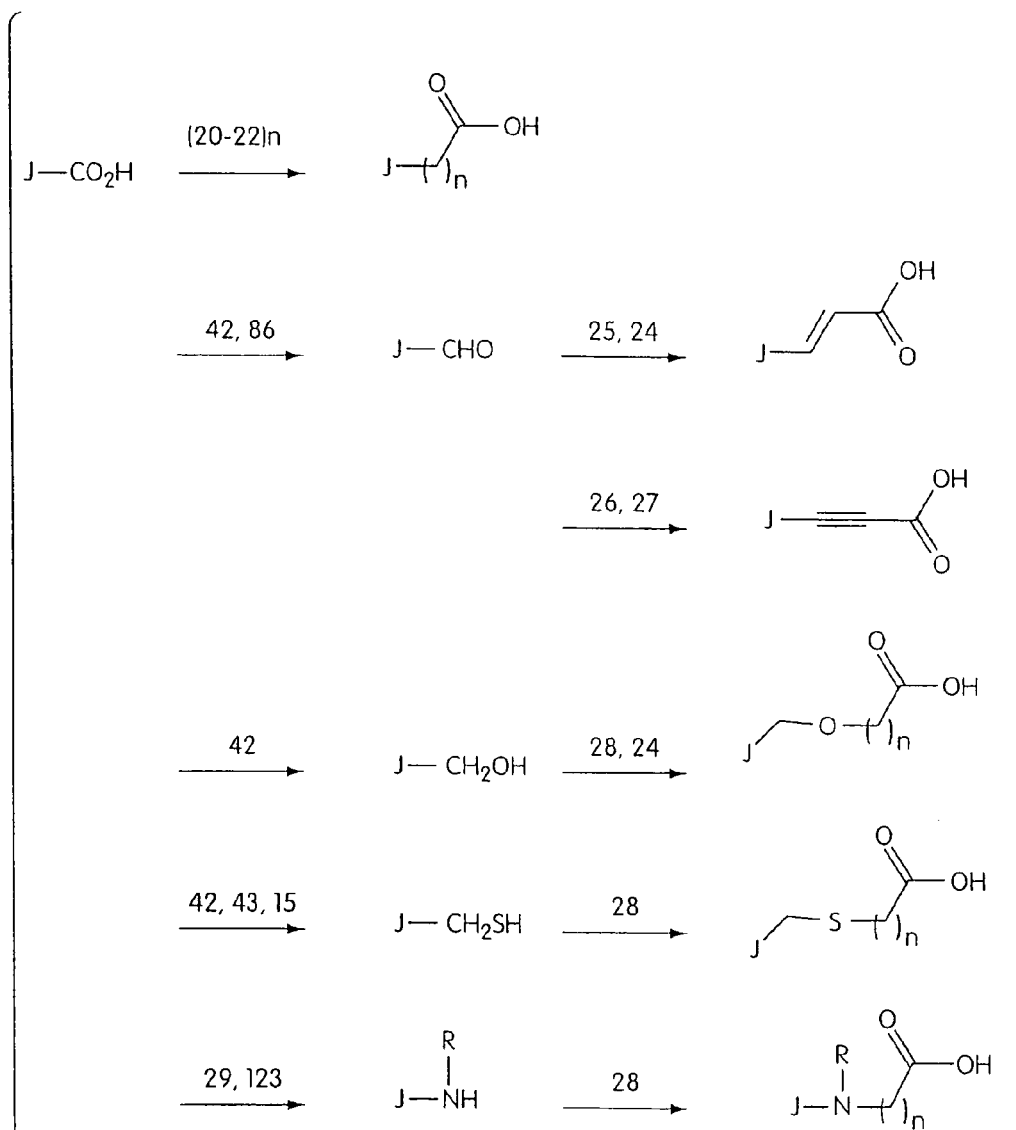
Figure 7:
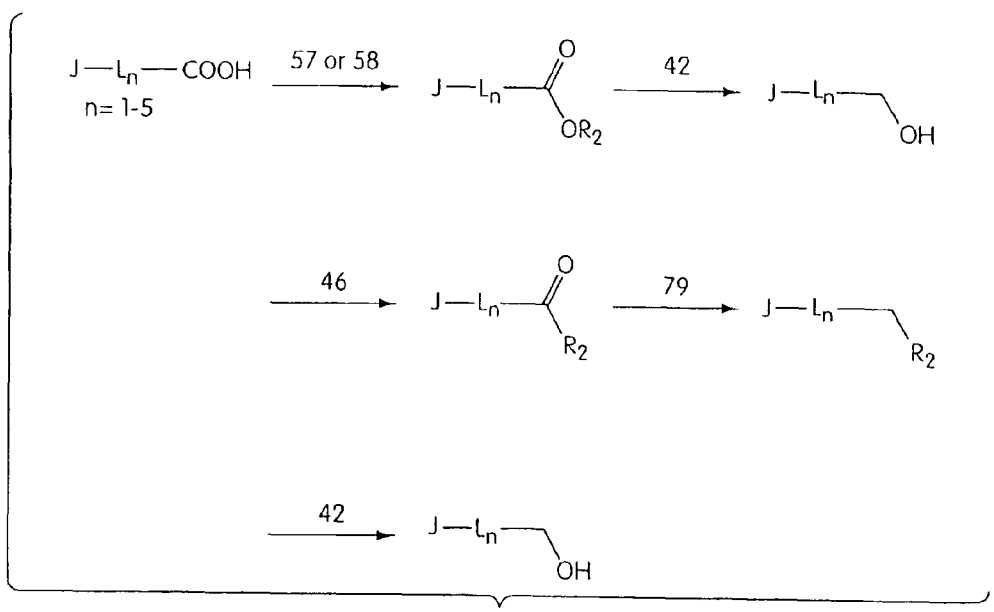
Figure 8:
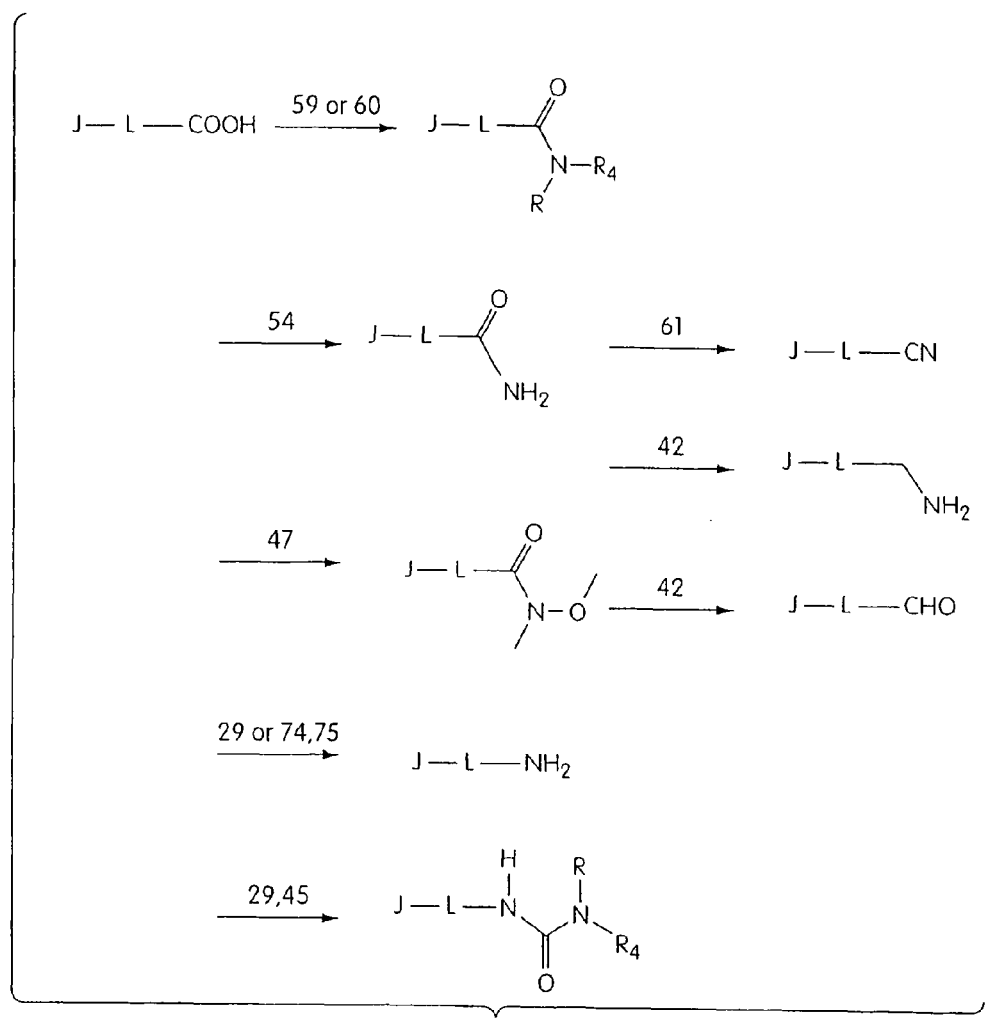
Figure 9:
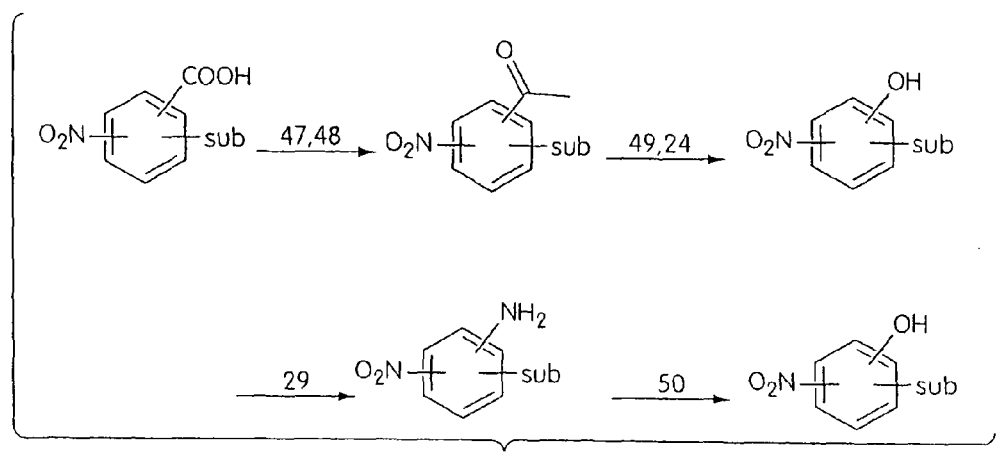
Figure 10:
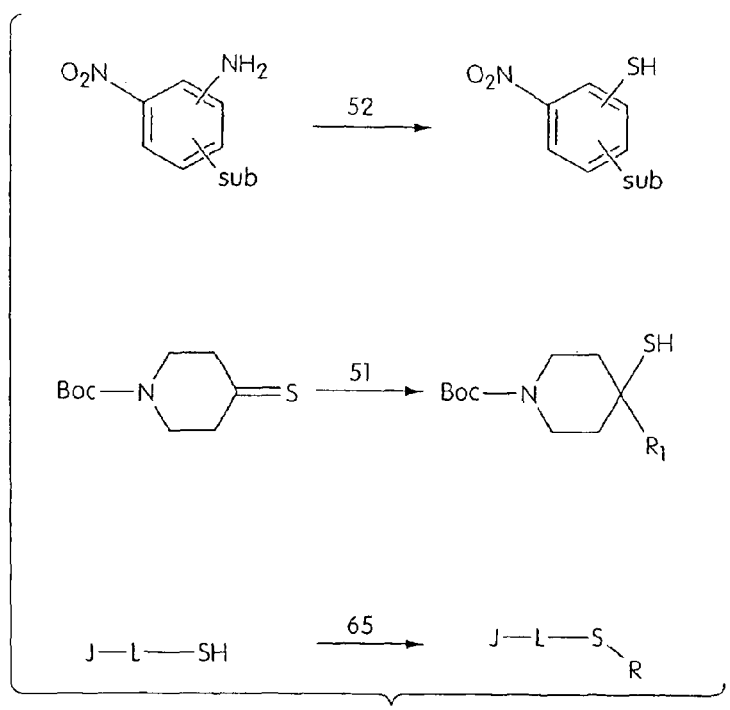
Figure 11:
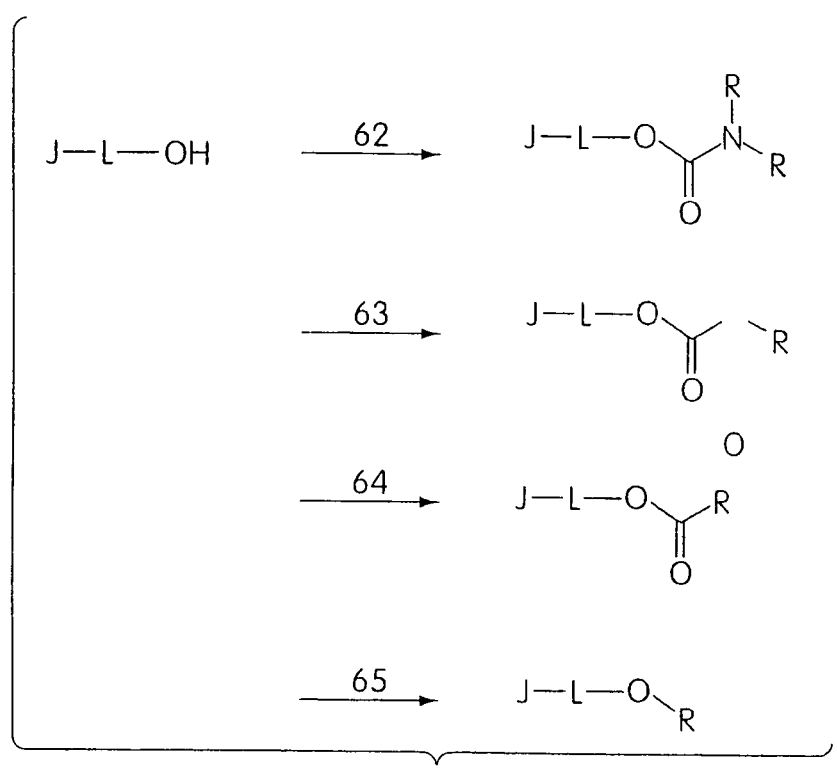
Figure 12:
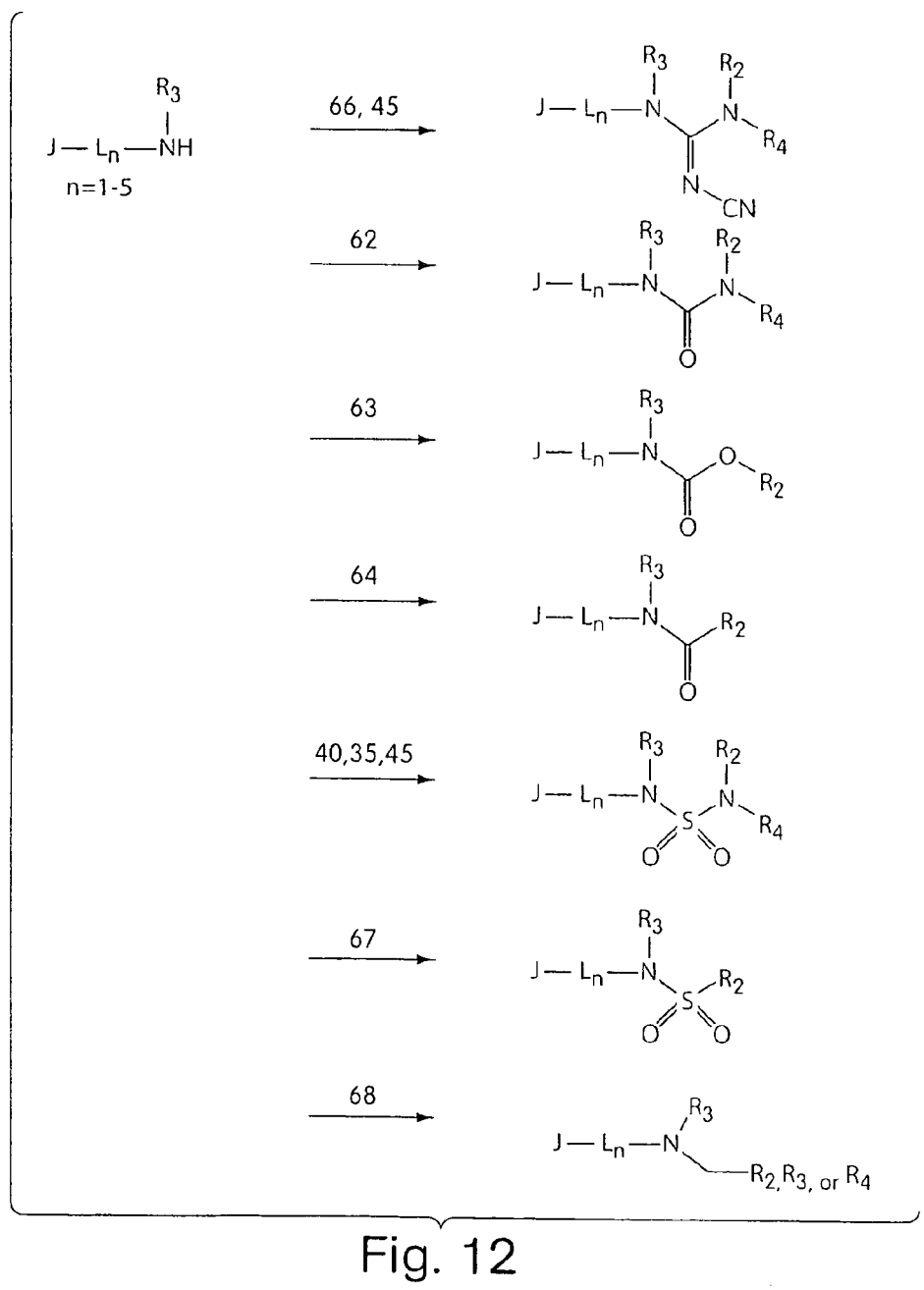
Figure 13:
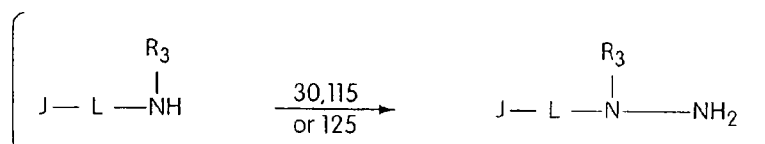
Figure 14:
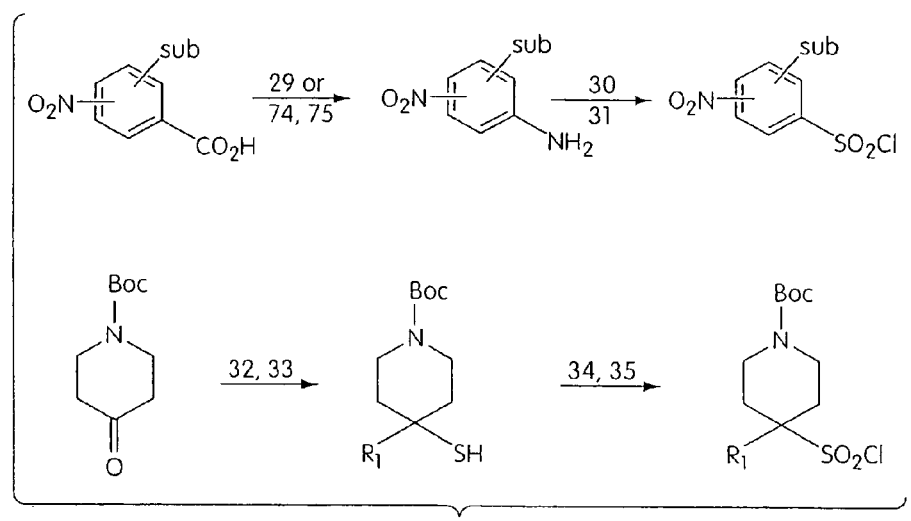
Figure 15:
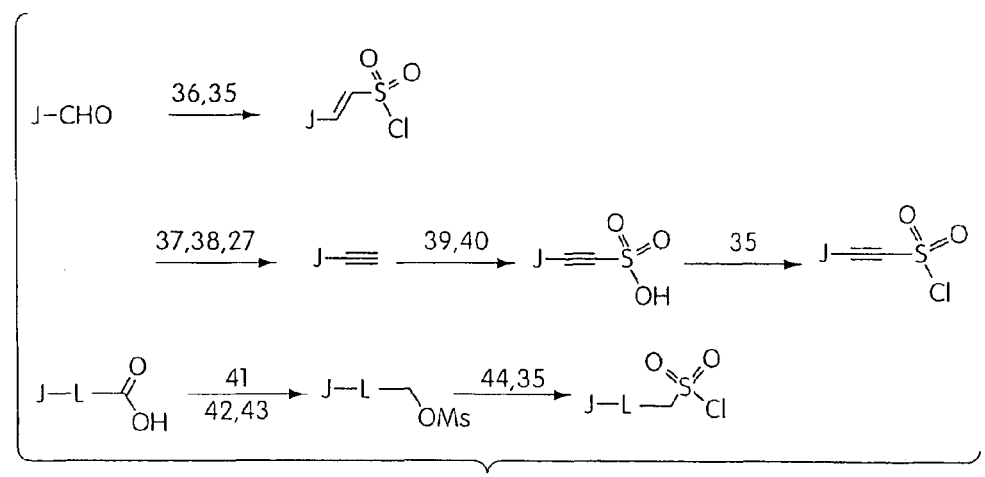
Figure 16:
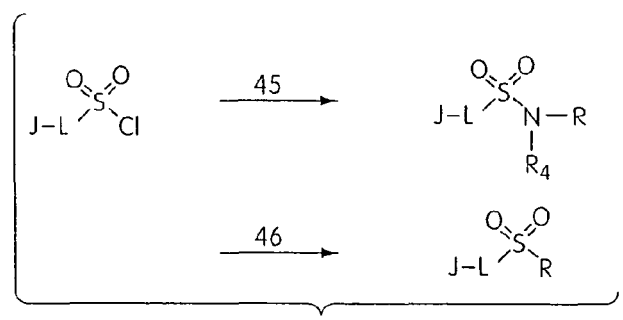
Figure 17:
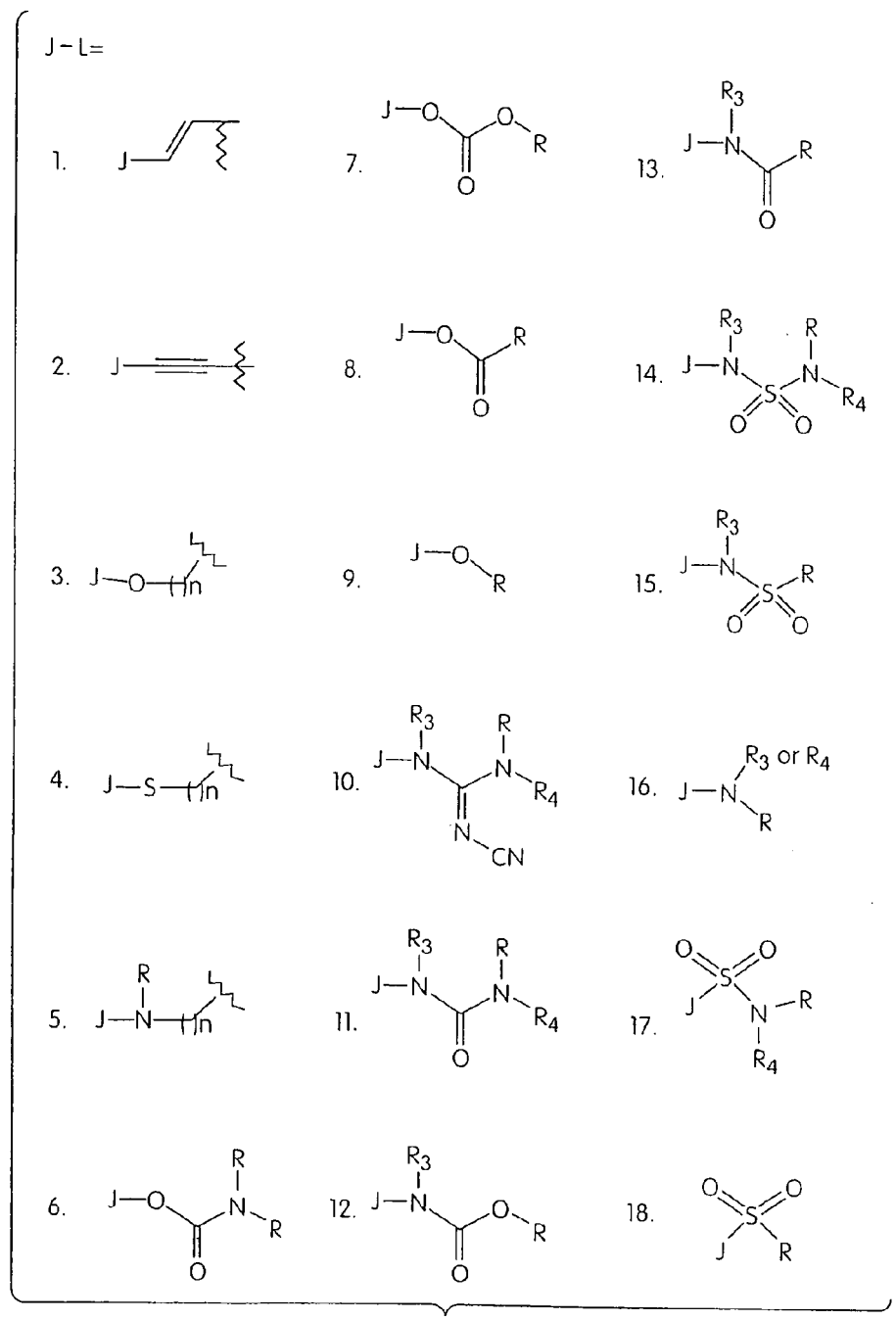
Figure 18:
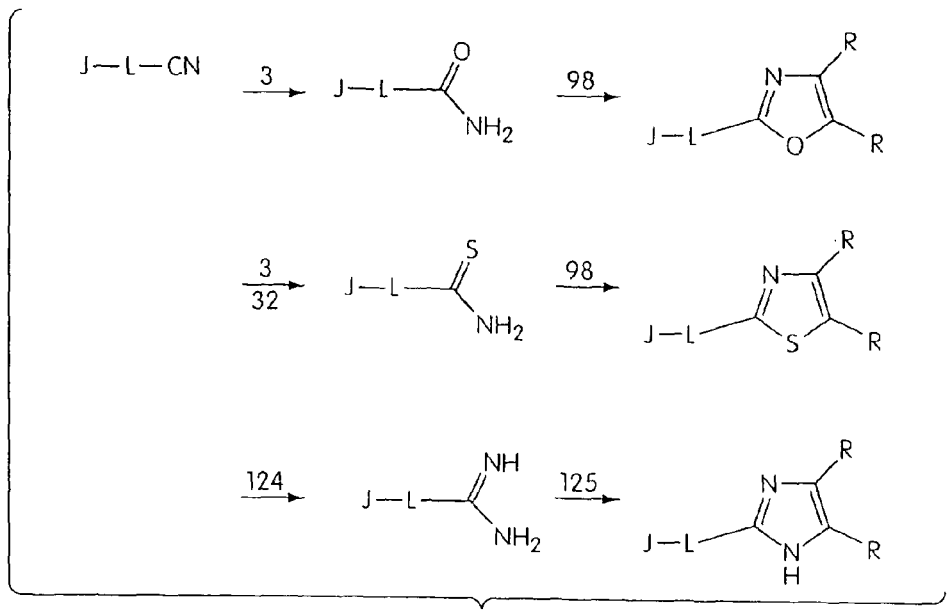
Figure 19:
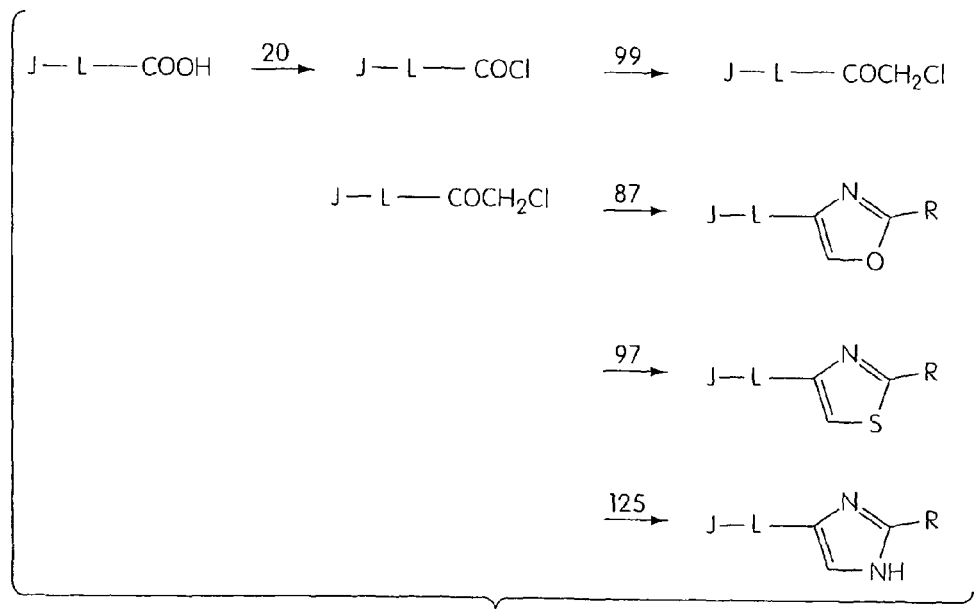
Figure 20:
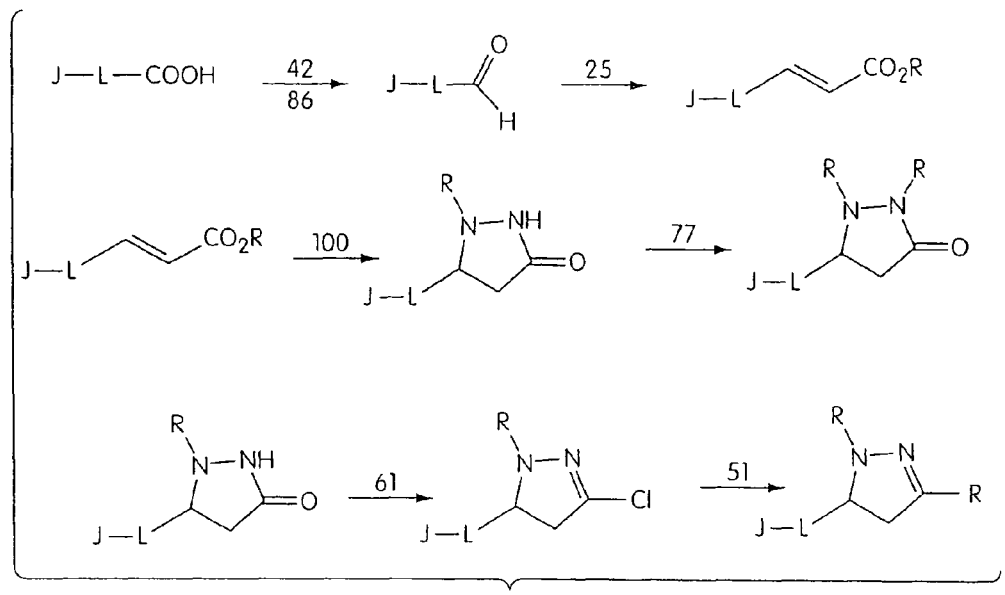
Figure 21:
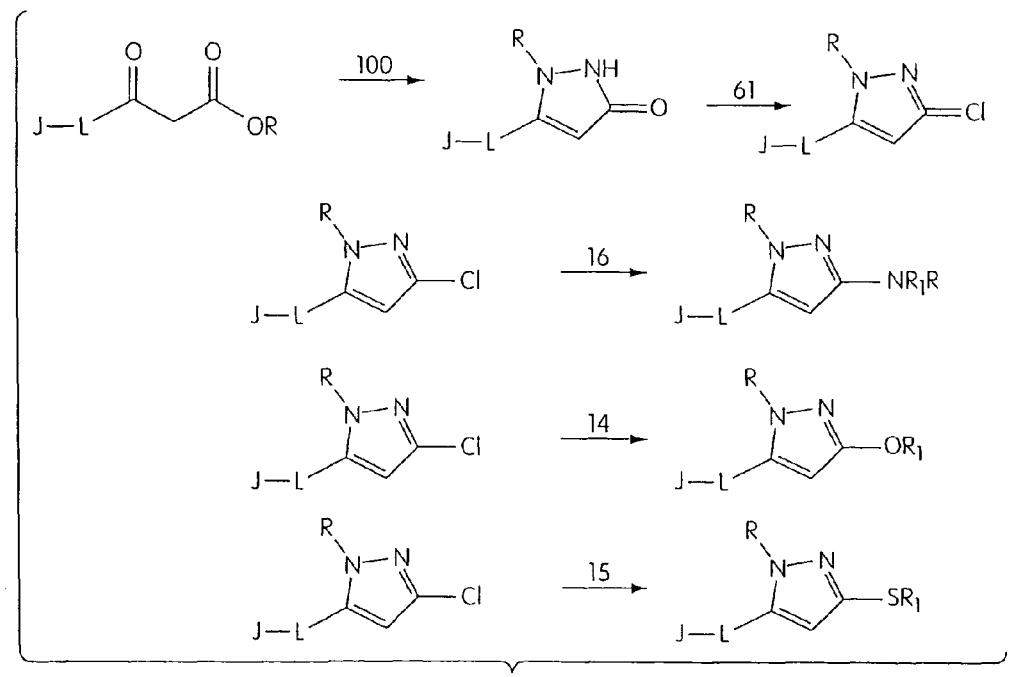
Figure 22:
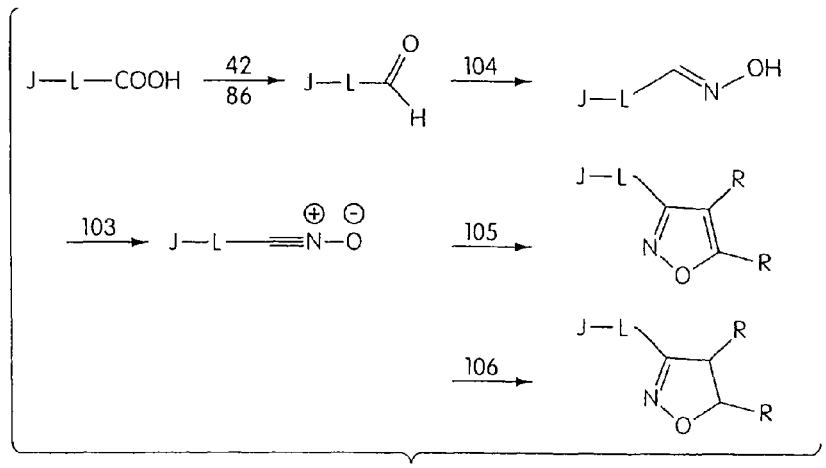
Figure 23:
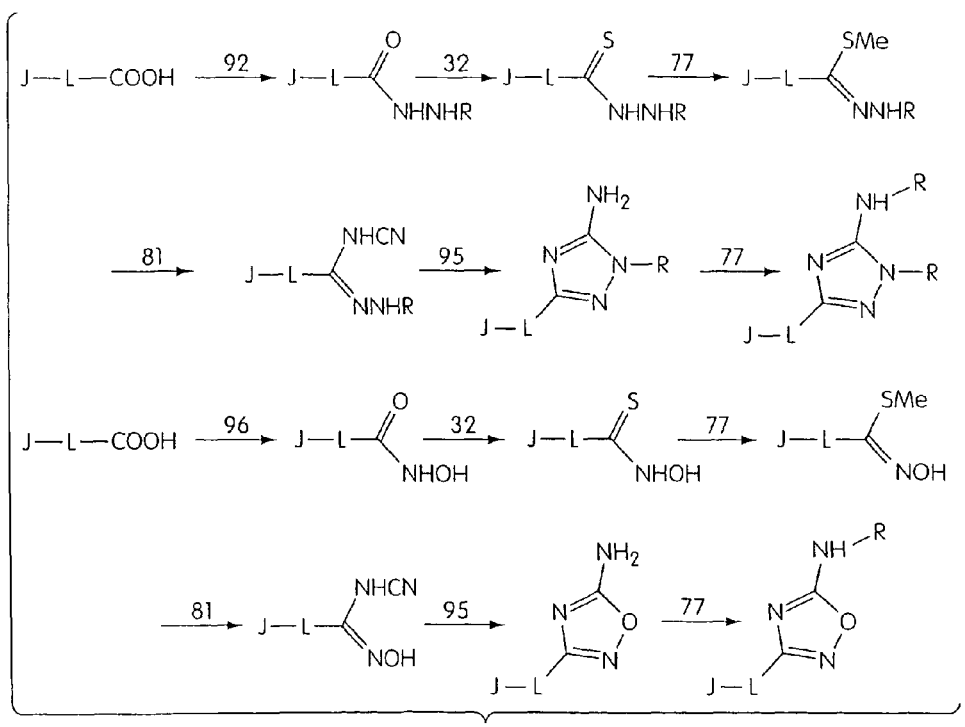
Figure 24:
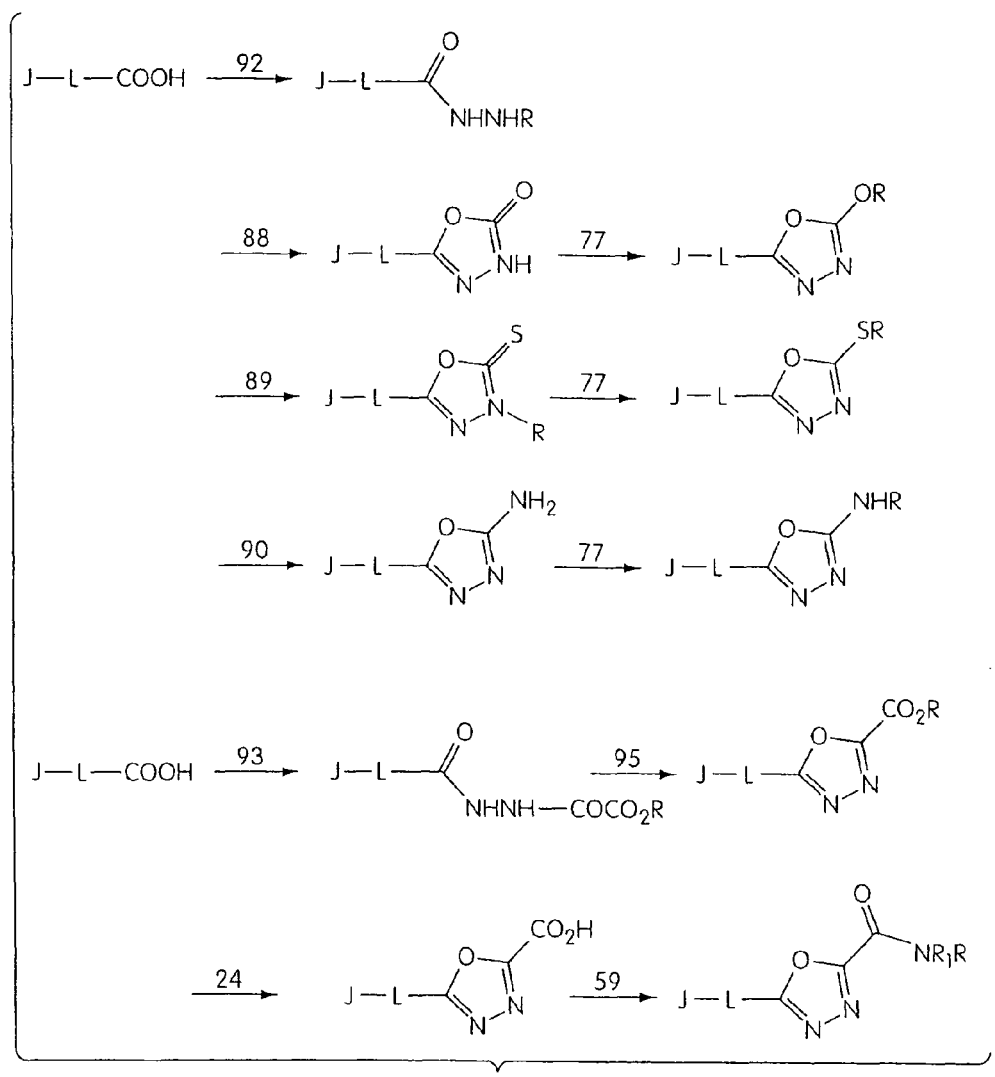
Figure 25:
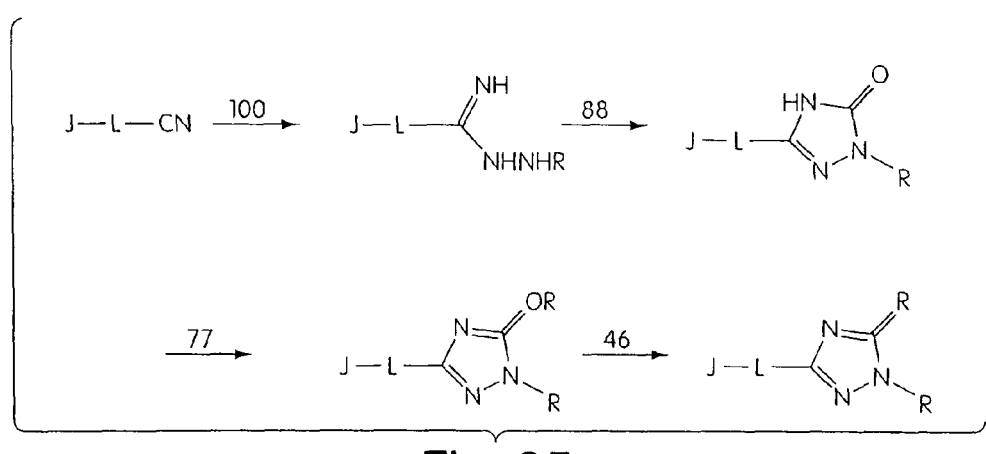
Figure 26:
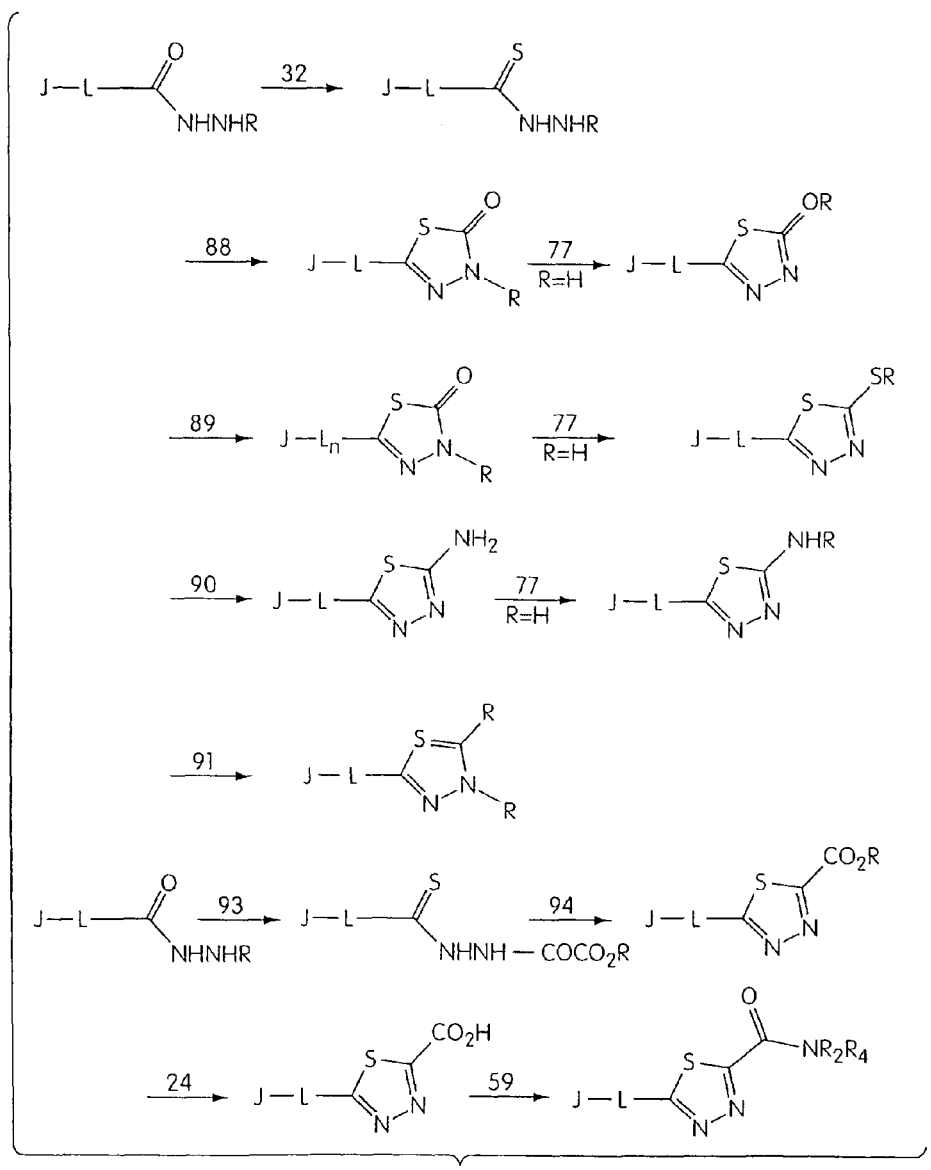
Figure 27:
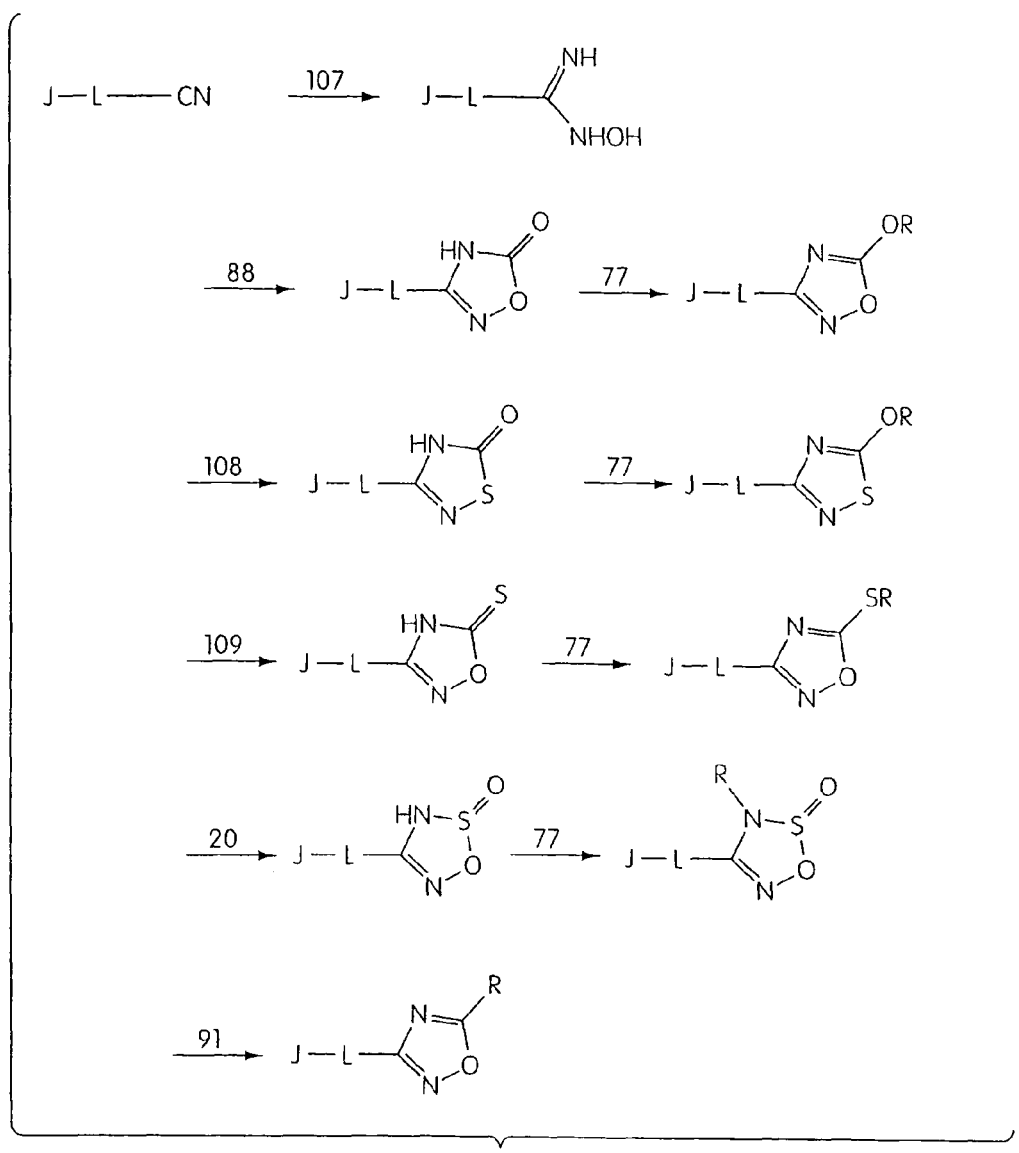
Figure 28:
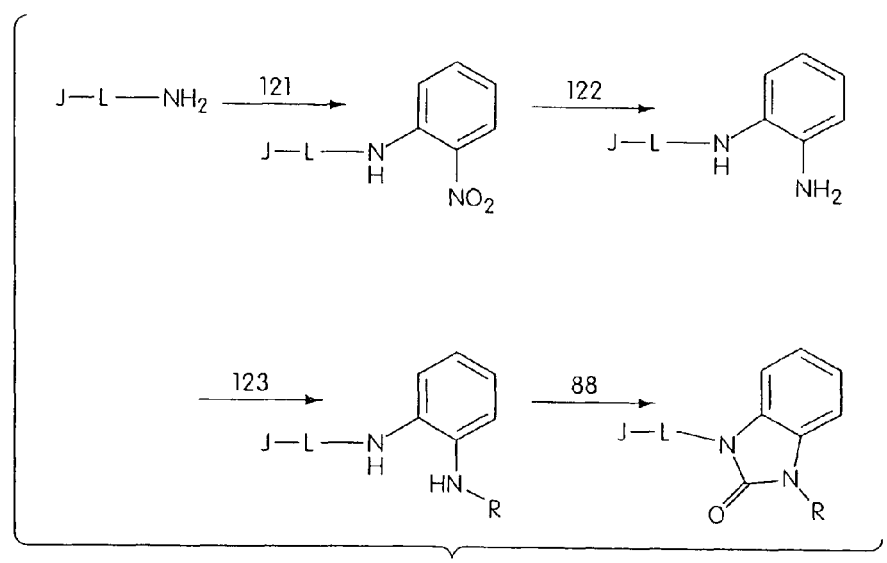
Figure 29:
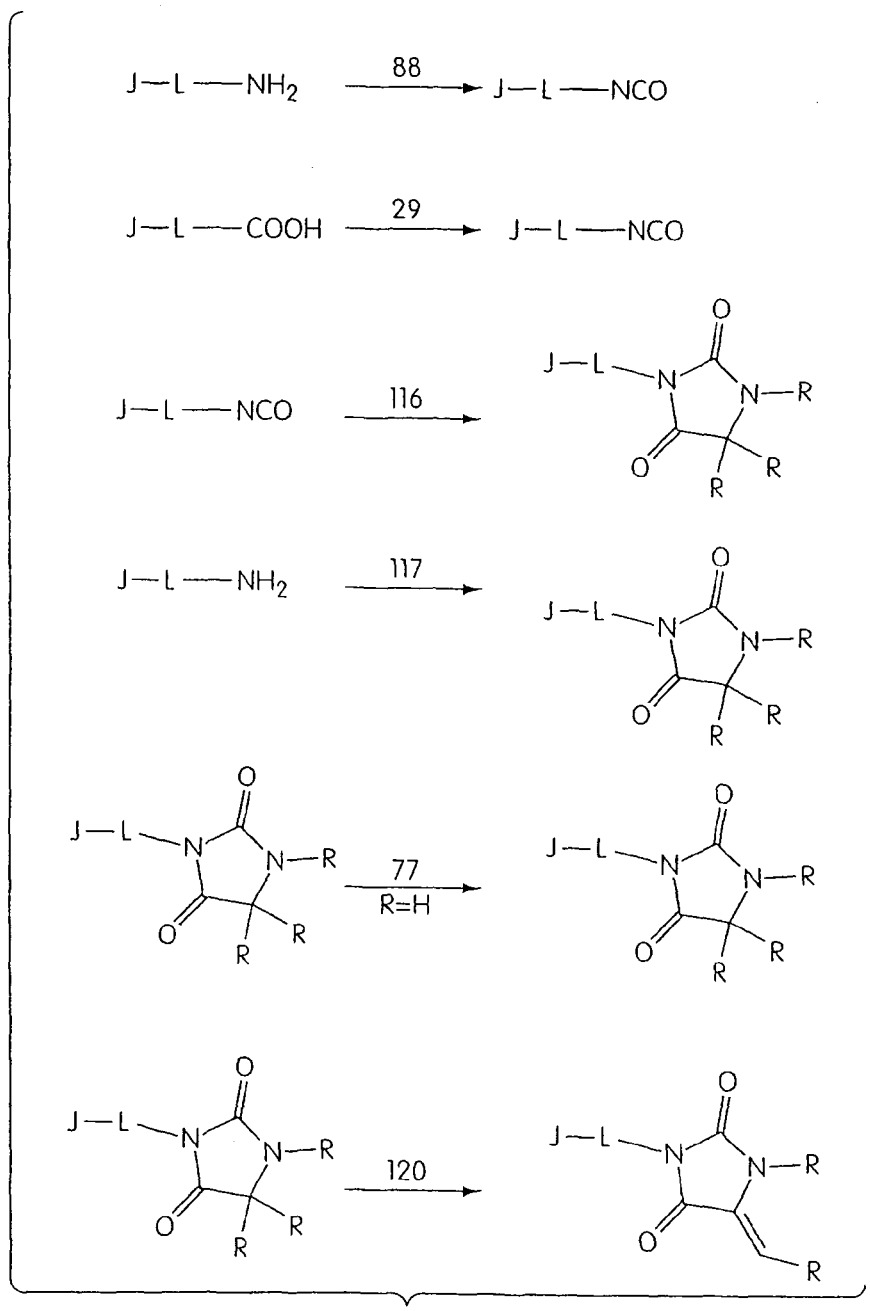
Figure 30:
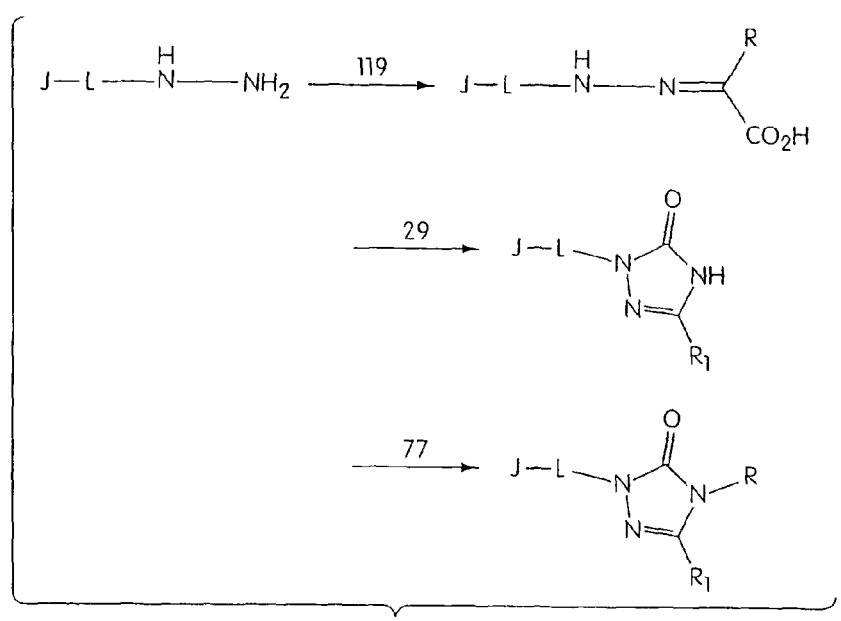
Figure 31:
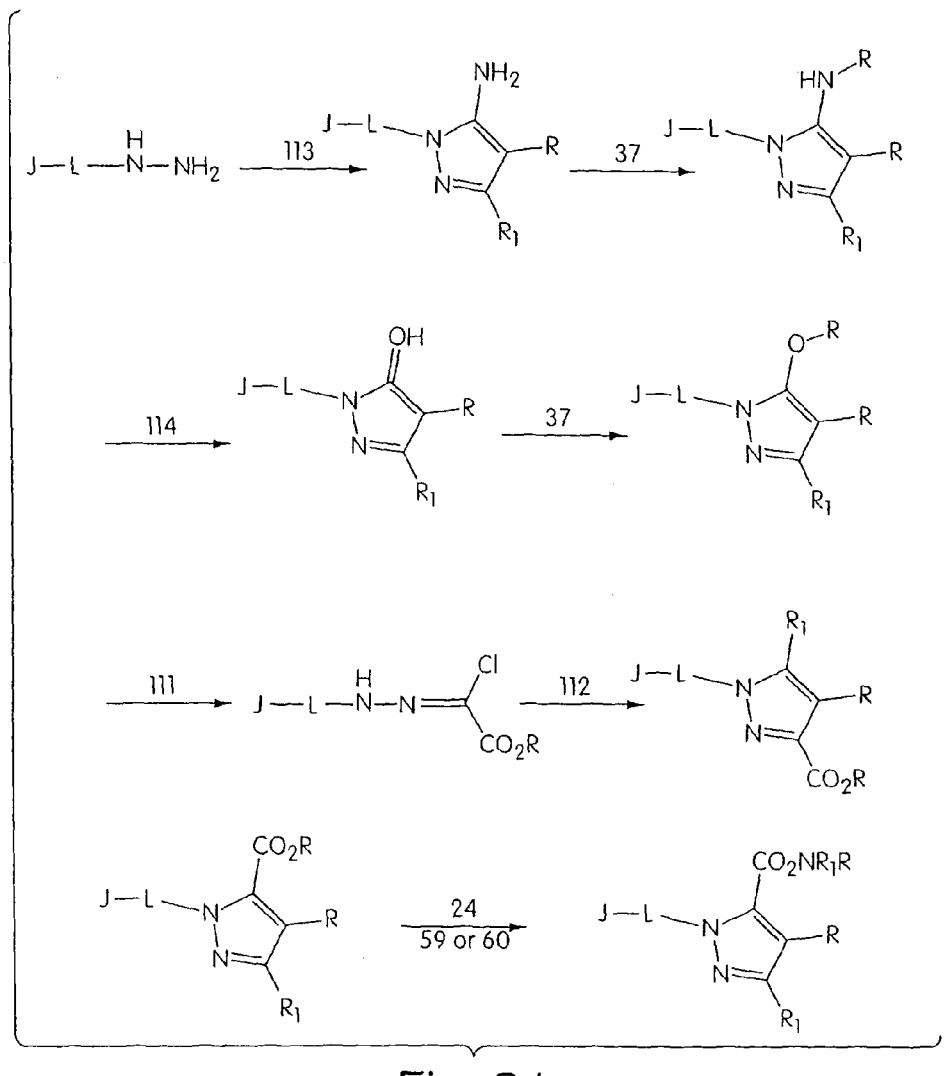

The present invention relates to the discovery that signal transduction pathways regulated by hedgehog, patched (ptc), gli and/or smoothened can be modulated, at least in part, by small molecules. While not wishing to be bound by any particular theory, the activation of a patched-smoothened pathway through alteration of cell-surface associations (such as complexes) may be the mechanism by which these agents act. The hedgehog pathway is believed to be negatively regulated by association of patched and smoothened, such as in the form of protein complexes, which association is disrupted by the binding of hedgehog to patched. Accordingly, the ability of these agents to activate the hedgehog pathway may be due to the ability of such molecules to interact with or bind to patched or smoothened, to otherwise disrupt the association of smoothened with patched, or at least to promote the ability of those proteins to activate a hedgehog, ptc, and/or smoothened-mediated signal transduction pathway. This mode of action, e.g., modulation of a smoothened-dependent pathway, is to be distinguished from compounds which modulate the hedgehog pathway by directly activating the cAMP pathway, e.g., by binding to or interacting with PKA, adenylate cyclase, cAMP phosphodiesterase, etc.

Certain hedgehog agonists disclosed herein modulate hedgehog activity in the absence of hedgehog protein itself, e.g., the compounds mimic the activity of hedgehog, rather than merely supplement or increase the activity of hedgehog protein, e.g., by promoting hedgehog binding to patched. These compounds are referred to herein as hedgehog-independent agonists and alone can mimic the phenotype or effect resulting from hedgehog treatment. Certain other compounds of the present invention enhance the activity of hedgehog protein, and require the presence or addition of hedgehog protein to observe the phenotype or effect resulting from hedgehog induction. Such hedgehog-dependent agonists may be used in therapeutic preparations or treatments which include hedgehog protein, or may be used to increase the activity of hedgehog protein naturally produced by the cells or tissue to be treated with the agonist. The hedgehog agonists disclosed herein may induce dissociation of a patched-smoothened complex or disrupt interactions between patched and smoothened, such as by binding to patched or to smoothened, thereby activating the hedgehog pathway. In certain embodiments, the compositions and methods of the present invention employ a compound which acts on one or more components of the extracellular membrane of a target cell.

In certain embodiments, hedgehog agonists useful in the present induce hedgehog-dependent transcriptional regulation, such as expression of the gli1 or ptc genes. Such agonists can thus induce or increase the hedgehog-dependent pathway activation resulting from, for example, increased levels of hedgehog protein.

It is, therefore, specifically contemplated that these small molecules which modulate aspects of hedgehog, ptc, or smoothened signal transduction activity will likewise be capable of promoting proliferation (or other biological consequences) in cells having a functional ptc-smo pathway. In preferred embodiments, the subject agonists are organic molecules having a molecular weight less than 2500 amu, more preferably less than 1500 amu, and even more preferably less than 750 amu, and are capable of inducing or augmenting at least some of the biological activities of hedgehog proteins, preferably specifically in target cells. Activation of the hedgehog pathway by a hedgehog agonist may be quantified, for example, by detecting the increase in ptc or gli-1 transcription in the presence of the agonist relative to a control in the absence of agonist. For example, an increase of at least 5%, at least 10%, at least 20%, or even at least 50% may be indicative of hedgehog pathway activation by a test compound. In certain embodiments, the agonist activity of the subject compounds is not inhibited by the hedgehog antibody 5E1, but is inhibited by jervine or an antagonist having the formula:

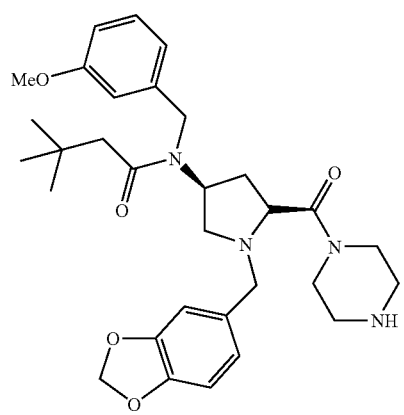

This quality can be quantified, for example, by determining whether the antibody or antagonist induces a decrease of more than 50%, more than 20%, more than 10%, or even more than 5% of the ptc or gli-1 upregulation induced by the agonist in the absence of the hedgehog antagonist, etc. In certain embodiments, a compound useful in the present invention, such as described above, may have an $EC_{50}$ for inducing or augmenting one or more hedgehog activities (such as upregulation of ptc or gli expression) of less than about 1000 nM, less than about 100 nM, less than about 10 nM, or even less than about 1 nM. The coding sequences for exemplary human Gli genes include, for example, the Gli-1 gene sequence of GenBank accession X07384 and the Gli-2 gene sequence of GenBank accession AB007298. See also Kinzler et al. *Nature* 1988, 332, 371. The level of gli or ptc expression can be determined, for example, by measuring the level of mRNA (transcription) or the level of protein (translation).

Thus, the methods of the present invention include the use of small molecules which antagonize ptc inhibition of hedgehog signalling, such as by activating smoothened or downstream components of the signal pathway, in the regulation of repair and/or functional performance of a wide range of cells, tissues and organs. For instance, the subject method has therapeutic and cosmetic applications ranging from regulation of neural tissues, bone and cartilage formation and repair, regulation of spermatogenesis, regulation of smooth muscle, regulation of lung, liver, urogenital organs (e.g., bladder), and other organs arising from the primitive gut, regulation of hematopoietic function, regulation of skin and hair growth, etc. Moreover, the subject methods can be performed on cells which are provided in culture (in vitro), or on cells in a whole animal (in vivo). See, for example, PCT publications WO 95/18856 and WO 96/17924 (the specifications of which are expressly incorporated by reference herein).

In one embodiment, the subject method can be to treat epithelial cells. In general, an epithelial cell may be contacted with an amount of a hedgehog agonist to induce epithelial tissue growth and/or formation. The subject method can be carried out on epithelial cells which may be either dispersed in culture or a part of an intact tissue or organ. Moreover, the method can be performed on cells which are provided in culture (in vitro), or on cells in a whole animal (in vivo).

The hedgehog agonists of the present invention may be used as part of regimens in the treatment of disorders of, or surgical or cosmetic repair of, such epithelial tissues as skin and skin organs; corneal, lens and other ocular tissue; mucosal membranes; and periodontal epithelium. The methods and compositions disclosed herein provide for the treatment or prevention of a variety of damaged epithelial and mucosal tissues. For instance, the subject method can be used to control wound healing processes, as for example may be desirable in connection with any surgery involving epithelial tissue, such as from dermatological or periodontal surgeries. Exemplary surgical repair for which hedgehog agonists may be useful include severe burn and skin regeneration, skin grafts, pressure sores, dermal ulcers, fissures, post surgery scar reduction, and ulcerative colitis.

In another aspect of the present invention, a hedgehog agonist can be used to effect the growth of hair, as for example in the treatment of alopecia whereby hair growth is potentiated.

In another preferred embodiment, the subject method can be used as part of a treatment regimen for malignant medulloblastoma and other primary CNS malignant neuroectodermal tumors.

In another aspect, the present invention provides pharmaceutical preparations comprising, as an active ingredient, a hedgehog agonist, ptc antagonist, or smoothened agonist such as described herein, formulated in an amount sufficient to promote, in vivo, proliferation or other biological consequences.

The subject treatments using hedgehog agonists, patched antagonists, or smoothened agonists can be effective for both human and animal subjects. Animal subjects to which the invention is applicable extend to both domestic animals and livestock, raised either as pets or for commercial purposes. Examples are dogs, cats, cattle, horses, sheep, hogs, and goats.

II. Definitions

For convenience, certain terms employed in the specification, examples, and appended claims are collected here.

The phrase "aberrant modification or mutation" of a gene refers to such genetic lesions as, for example, deletions, substitution or addition of nucleotides to a gene, as well as gross chromosomal rearrangements of the gene and/or abnormal methylation of the gene. Likewise, mis-expression of a gene refers to aberrant levels of transcription of the gene relative to those levels in a normal cell under similar conditions, as well as non-wild-type splicing of mRNA transcribed from the gene.

"Burn wounds" refer to cases where large surface areas of skin have been removed or lost from an individual due to heat and/or chemical agents.

The "corium" or "dermis" refers to the layer of the skin deep to the epidermis, consisting of a dense bed of vascular connective tissue, and containing the nerves and terminal organs of sensation. The hair roots, and sebaceous and sweat glands are structures of the epidermis which are deeply embedded in the dermis.

"Dental tissue" refers to tissue in the mouth which is similar to epithelial tissue, for example gum tissue. The method of the present invention is useful for treating periodontal disease.

"Dermal skin ulcers" refer to lesions on the skin caused by superficial loss of tissue, usually with inflammation. Dermal skin ulcers which can be treated by the method of the present invention include decubitus ulcers, diabetic ulcers, venous stasis ulcers and arterial ulcers. Decubitus wounds refer to chronic ulcers that result from pressure applied to areas of the skin for extended periods of time. Wounds of this type are often called bedsores or pressure sores. Venous stasis ulcers result from the stagnation of blood or other fluids from defective veins. Arterial ulcers refer to necrotic skin in the area around arteries having poor blood flow.

The term "$ED_{50}$" means the dose of a drug which produces 50% of its maximum response or effect.

An "effective amount" of, e.g., a hedgehog agonist, with respect to the subject method of treatment, refers to an amount of the agonist in a preparation which, when applied as part of a desired dosage regimen brings about, e.g., a change in the rate of cell proliferation and/or the state of differentiation of a cell and/or rate of survival of a cell according to clinically acceptable standards for the disorder to be treated or the cosmetic purpose.

The terms "epithelia", "epithelial" and "epithelium" refer to the cellular covering of internal and external body surfaces (cutaneous, mucous and serous), including the glands and other structures derived therefrom, e.g., corneal, esophageal, epidermal, and hair follicle epithelial cells. Other exemplary epithelial tissue includes: olfactory epithelium, which is the pseudostratified epithelium lining the olfactory region of the nasal cavity, and containing the receptors for the sense of smell; glandular epithelium, which refers to epithelium composed of secreting cells; squamous epithelium, which refers to epithelium composed of flattened plate-like cells. The term epithelium can also refer to transitional epithelium, like that which is characteristically found lining hollow organs that are subject to great mechanical change due to contraction and distention, e.g., tissue which represents a transition between stratified squamous and columnar epithelium.

The term "epithelialization" refers to healing by the growth of epithelial tissue over a denuded surface.

The term "epidermal gland" refers to an aggregation of cells associated with the epidermis and specialized to secrete or excrete materials not related to their ordinary metabolic needs. For example, "sebaceous glands" are holocrine glands in the corium that secrete an oily substance and sebum. The term "sweat glands" refers to glands that secrete sweat, situated in the corium or subcutaneous tissue, opening by a duct on the body surface.

The term "epidermis" refers to the outermost and nonvascular layer of the skin, derived from the embryonic ectoderm, varying in thickness front 0.07-1.4 mm. On the palmar and plantar surfaces it comprises, from within outward, five layers: basal layer composed of columnar cells arranged perpendicularly; prickle-cell or spinous layer composed of flattened polyhedral cells with short processes or spines; granular layer composed of flattened granular cells; clear layer composed of several layers of clear, transparent cells in which the nuclei are indistinct or absent; and horny layer composed of flattened, cornified non-nucleated cells. In the epidermis of the general body surface, the clear layer is usually absent.

"Excisional wounds" include tears, abrasions, cuts, punctures or lacerations in the epithelial layer of the skin and may extend into the dermal layer and even into subcutaneous fat and beyond. Excisional wounds can result from surgical procedures or from accidental penetration of the skin.

The "growth state" of a cell refers to the rate of proliferation of the cell and/or the state of differentiation of the cell. An "altered growth state" is a growth state characterized by an abnormal rate of proliferation, e.g., a cell exhibiting an increased or decreased rate of proliferation relative to a normal cell.

The term "hair" refers to a threadlike structure, especially the specialized epidermal structure composed of keratin and developing from a papilla sunk in the corium, produced only by mammals and characteristic of that group of animals. Also, "hair" may refer to the aggregate of such hairs. A "hair follicle" refers to one of the tubular-invaginations of the epidermis enclosing the hairs, and from which the hairs grow. "Hair follicle epithelial cells" refers to epithelial cells which surround the dermal papilla in the hair follicle, e.g., stem cells, outer root sheath cells, matrix cells, and inner root sheath cells. Such cells may be normal non-malignant cells, or transformed/immortalized cells.

The term "hedgehog agonist" refers to an agent which potentiates or recapitulates the bioactivity of hedgehog, such as to activate transcription of target genes. Preferred hedgehog agonists can be used to mimic or enhance the activity or effect of hedgehog protein in a smoothened-dependent manner. The term 'hedgehog agonist' as used herein refers not only to any agent that may act by directly activating the normal function of the hedgehog protein, but also to any agent that activates the hedgehog signalling pathway, and thus inhibits the function of ptc.

The term "hedgehog loss-of-function" refers to an aberrant modification or mutation of a ptc gene, hedgehog gene, or smoothened gene, or a decrease (or loss) in the level of expression of such a gene, which results in a phenotype which resembles contacting a cell with a hedgehog inhibitor, e.g., aberrant inhibition of a hedgehog pathway. The loss-of-function may include an increase in the ability of the ptc gene product to regulate the level of expression of Ci genes, e.g., Gli1, Gli2, and Gli3. The term 'hedgehog loss-of-function' is also used herein to refer to any similar cellular phenotype (e.g., exhibiting reduced proliferation) which occurs due to an alteration anywhere in the hedgehog signal transduction pathway, including, but not limited to, a modification or mutation of hedgehog itself. For example, a cell with an abnormally low proliferation rate due to inactivation of the hedgehog signalling pathway would have a 'hedgehog loss-of-function' phenotype, even if hedgehog is not mutated in that cell.

As used herein, "immortalized cells" refers to cells which have been altered via chemical and/or recombinant means such that the cells have the ability to grow through an indefinite number of divisions in culture.

"Internal epithelial tissue" refers to tissue inside the body which has characteristics similar to the epidermal layer in the skin. Examples include the lining of the intestine. The method of the present invention is useful for promoting the healing of certain internal wounds, for example wounds resulting from surgery.

The term "keratosis" refers to proliferative skin disorder characterized by hyperplasia of the horny layer of the epidermis. Exemplary keratotic disorders include keratosis follicularis, keratosis palmaris et plantaris, keratosis pharyngea, keratosis pilaris, and actinic keratosis.

The term "$LD_{50}$" means the dose of a drug which is lethal in 50% of test subjects.

The term "nail" refers to the horny cutaneous plate on the dorsal surface of the distal end of a finger or toe.

The term "patched gain-of-function" refers to an aberrant modification or mutation of a ptc gene, or an increased level of expression of the gene, which results in a phenotype which resembles contacting a cell with a hedgehog inhibitor, e.g., aberrant deactivation of a hedgehog pathway. The gain-of-function may include an increase of the ability of the ptc gene product to regulate the level of expression of Ci genes, e.g., Gli1, Gli2 and Gli3.

A "patient" or "subject" to be treated by the subject method can mean either a human or non-human animal.

The term "prodrug" is intended to encompass compounds which, under physiological conditions, are converted into the therapeutically active agents of the present invention. A common method for making a prodrug is to include selected moieties which are hydrolyzed under physiological conditions to reveal the desired molecule. In other embodiments, the prodrug is converted by an enzymatic activity of the host animal.

As used herein, "proliferating" and "proliferation" refer to cells undergoing mitosis.

Throughout this application, the term "proliferative skin disorder" refers to any disease/disorder of the skin marked by unwanted or aberrant proliferation of cutaneous tissue. These conditions are typically characterized by epidermal cell proliferation or incomplete cell differentiation, and include, for example, X-linked ichthyosis, psoriasis, atopic dermatitis, allergic contact dermatitis, epidermolytic hyperkeratosis, and seborrheic dermatitis. For example, epidermodysplasia is a form of faulty development of the epidermis. Another example is "epidermolysis", which refers to a loosened state of the epidermis with formation of blebs and bullae either spontaneously or at the site of trauma.

The term "skin" refers to the outer protective covering of the body, consisting of the corium and the epidermis, and is understood to include sweat and sebaceous glands, as well as hair follicle structures. Throughout the present application, the adjective "cutaneous" may be used, and should be understood to refer generally to attributes of the skin, as appropriate to the context in which they are used.

The term "small molecule" refers to a compound having a molecular weight less than about 2500 amu, preferably less than about 2000 amu, even more preferably less than about 1500 amu, still more preferably less than about 1000 amu, or most preferably less than about 750 amu.

The term "smoothened loss-of-function" refers to an aberrant modification or mutation of a smo gene, or a decreased level of expression of the gene, which results in a phenotype which resembles contacting a cell with a hedgehog inhibitor, e.g., aberrant deactivation of a hedgehog pathway. While not wishing to be bound by any particular theory, it is noted that ptc may not signal directly into the cell, but rather interact with smoothened, another membrane-bound protein located downstream of ptc in hedgehog signaling (Marigo et al., (1996) *Nature* 384: 177-179). The gene smo is a segment-polarity gene required for the correct patterning of every segment in *Drosophila* (Alcedo et al., (1996) *Cell* 86: 221-232). Human homologs of smo have been identified. See, for example, Stone et al. (1996) *Nature* 384:129-134, and GenBank accession U84401. The smoothened gene encodes an integral membrane protein with characteristics of heterotrimeric G-protein-coupled receptors; i.e., 7-transmembrane regions. This protein shows homology to the *Drosophila* Frizzled (Fz) protein, a member of the wingless pathway. It was originally thought that smo encodes a receptor of the Hh signal. However, this suggestion was subsequently disproved, as evidence for ptc being the Hh receptor was obtained. Cells that express Smo fail to bind Hh, indicating that smo does not interact directly with Hh (Nusse, (1996) *Nature* 384: 119-120). Rather, the binding of Sonic hedgehog (SHH) to its receptor, PTCH, is thought to prevent normal inhibition by PTCH of smoothened (SMO), a seven-span transmembrane protein.

The term "therapeutic index" refers to the therapeutic index of a drug defined as $LD_{50}/ED_{50}$.

The term "acylamino" is art-recognized and refers to a moiety that can be represented by the general formula:

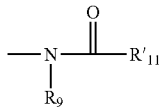

wherein $R_9$ is as defined above, and $R'_{11}$ represents a hydrogen, an alkyl, an alkenyl or —$(CH_2)_m$—$R_8$, where m and $R_8$ are as defined above.

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The terms "alkenyl" and "alkynyl" refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, preferred cycloalkyls have from 3-10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethylthio, and the like.

The terms "amine" and "amino" are art-recognized and refer to both unsubstituted and substituted amines, e.g., a moiety that can be represented by the general formula:

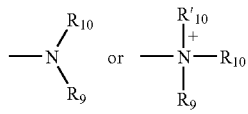

wherein $R_9$, $R_{10}$ and $R'_{10}$ each independently represent a hydrogen, an alkyl, an alkenyl, $(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In still more preferred embodiments, the term 'amine' does not encompass amides, e.g., wherein one of $R_9$ and $R_{10}$ represents a carbonyl. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "amido" is art-recognized as an amino-substituted carbonyl and includes a moiety that can be represented by the general formula:

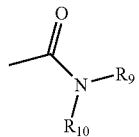

wherein $R_9$, $R_{10}$ are as defined above. Preferred embodiments of the amide will not include imides which, may be unstable.

The term "aralkyl", as used herein, refers to an alkyl group substituted with an aryl group (e.g., an aromatic or heteroaromatic group).

The term "aryl" as used herein includes 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like.

Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "carbocycle", as used herein, refers to an aromatic or non-aromatic ring in which each atom of the ring is carbon.

The term "carbonyl" is art-recognized and includes such moieties as can be represented by the general formula:

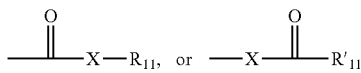

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R'_{11}$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "heteroatom" as used herein means an atom of any element other than carbon or hydrogen. Preferred heteroatoms are boron, nitrogen, oxygen, phosphorus, sulfur and selenium.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

A "phosphonamidite" can be represented in general formula:

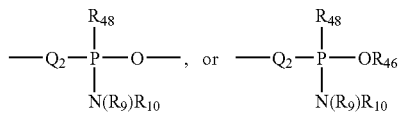

wherein $R_9$ and $R_{10}$ are as defined above, $Q_2$ represents O, S or N, and $R_{48}$ represents a lower alkyl or an aryl, $Q_2$ represents O, S or N.

A "phosphoramidite" can be represented in general formula:

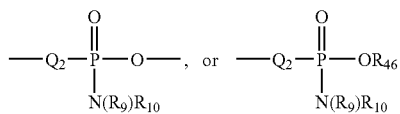

wherein $R_9$ and $R_{10}$ are as defined above, and $Q_2$ represents O, S or N.

A "phosphoryl" can in general be represented by the formula:

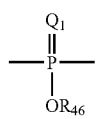

wherein $Q_1$ represented S or O, and $R_{46}$ represents hydrogen, a lower alkyl or an aryl. When used to substitute, for example, an alkyl, the phosphoryl group of the phosphorylalkyl can be represented by the general formula:

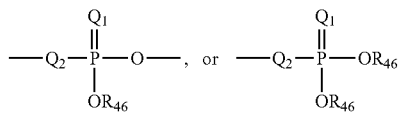

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis,* 2nd ed.; Wiley: New York, 1991).

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—(CH$_2$)$_m$—R$_8$, m and R$_8$ being defined above.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The term "sulfamoyl" is art-recognized and includes a moiety that can be represented by the general formula:

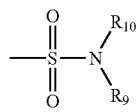

in which R$_9$ and R$_{10}$ are as defined above.

The term "sulfate" is art recognized and includes a moiety that can be represented by the general formula:

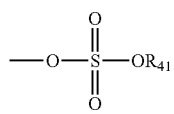

in which R$_{41}$ is as defined above.

The term "sulfonamido" is art recognized and includes a moiety that can be represented by the general formula:

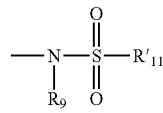

in which R$_9$ and R'$_{11}$ are as defined above.

The term "sulfonate" is art-recognized and includes a moiety that can be represented by the general formula:

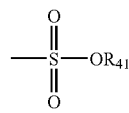

in which R$_{41}$ is an electron pair, hydrogen, alkyl, cycloalkyl, or aryl.

The terms "sulfoxido" or "sulfinyl", as used herein, refers to a moiety that can be represented by the general formula:

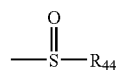

in which R$_{44}$ is selected from the group consisting of hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention.

Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., the ability to activate hedgehog signaling), wherein one or more simple variations of substituents are made which do not adversely affect the efficacy of the compound. In general, the compounds of the present invention may be prepared by the methods illustrated in general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds which can be substituted or unsubstituted.

III. Exemplary Compounds of the Invention

As described in further detail below, it is contemplated that the subject methods can be carried out using a variety of different small molecules which can be readily identified, for example, by such drug screening assays as described herein. For example, compounds useful in the subject methods include compounds represented by general formula (I):

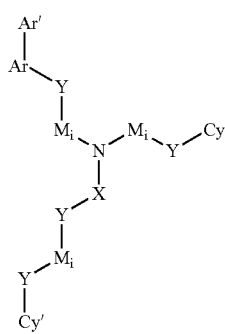

Formula I wherein, as valence and stability permit,

Ar and Ar' independently represent substituted or unsubstituted aryl or heteroaryl rings;

Y, independently for each occurrence, is absent or represents —N(R)—, —O—, —S—, or —Se—;

X is selected from —C(=O)—, —C(=S)—, —S(O$_2$)—, —S(O)—, —C(=NCN)—, —P(=O)(OR)—, and a methylene group optionally substituted with 1-2 groups such as lower alkyl, alkenyl, or alkynyl groups;

M represents, independently for each occurrence, a substituted or unsubstituted methylene group, such as —CH$_2$—, —CHF—, —CHOH—, —CH(Me)—, —C(=O)—, etc., or two M taken together represent substituted or unsubstituted ethene or ethyne;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

Cy and Cy' independently represent substituted or unsubstituted aryl, heterocyclyl, heteroaryl, or cycloalkyl, including polycyclic groups; and i represents, independently for each occurrence, an integer from 0 to 5, preferably from 0 to 2.

In certain embodiments, M represents, independently for each occurrence, a substituted or unsubstituted methylene group, such as —CH$_2$—, —CHF—, —CHOH—, —CH(Me)-, —C(=O)—, etc.

In certain embodiments, Ar and Ar' represent phenyl rings, e.g., unsubstituted or substituted with one or more groups including heteroatoms such as O, N, and S. In certain embodiments, at least one of Ar and Ar' represents a phenyl ring. In certain embodiments, at least one of Ar and Ar' represents a heteroaryl ring, e.g., a pyridyl, thiazolyl, thienyl, pyrimidyl, etc. In certain embodiments, Y and Ar' are attached to Ar in a meta and/or 1,3-relationship.

In certain embodiments, Y is absent from all positions. In embodiments wherein Y is present in a position, i preferably represents an integer from 1-2 in an adjacent M$_i$ if i=0 would result in two occurrences of Y being directly attached, or an occurrence of Y being directly attached to N.

In certain embodiments, Cy' is a substituted or unsubstituted aryl or heteroaryl. In certain embodiments, Cy' is directly attached to X. In certain embodiments, Cy' is a substituted or unsubstituted bicyclic or heteroaryl ring, preferably both bicyclic and heteroaryl, such as benzothiophene, benzofuran, benzopyrrole, benzopyridine, etc. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system. In certain embodiments, Cy' represents a benzo[b]thien-2-yl, preferably a 3-chloro-benzo[b]thien-2-yl, 3-fluoro-benzo[b]thien-2-yl, or 3-methyl-benzo[b]thien-2-yl, e.g., wherein the benzo ring is substituted with from 1-4 substituents selected from halogen, nitro, cyano, methyl (e.g., including halomethyl, such as CHCl$_2$ and CF$_3$), and ethyl (e.g., including haloethyl, such as, CH$_2$CCl$_3$, C$_2$F$_5$, etc.), preferably from halogen and methyl (e.g., including halomethyl, such as CHCl$_2$ and CF$_3$). In certain such embodiments Cy' represents a 3-chloro-benzo[b]thien-2-yl, 3-fluoro-benzo[b]thien-2-yl, or 3-methyl-benzo[b]thien-2-yl wherein the benzo ring is substituted with fluoro at the 4-position (peri to the 3-substituent on the thienyl ring) and; optionally, at the 7-position ('peri' to the S of the thienyl ring).

In certain embodiments, X is selected from —C(═O)—, —C(═S)—, and —S(O₂)—.

In certain embodiments, R represents H or lower alkyl, e.g., H or Me.

In certain embodiments, Cy represents a substituted or unsubstituted non-aromatic carbocyclic or heterocyclic ring, i.e., including at least one sp³ hybridized atom, and preferably a plurality of sp³ hybridized atoms. In certain embodiments, Cy includes an amine within the atoms of the ring or on a substituent of the ring, e.g., Cy is pyridyl, imidazolyl, pyrrolyl piperidyl, pyrrolidyl, piperazyl, etc., and/or bears an amino substituent. In certain embodiments, Cy is a 5- to 7-membered ring. In certain embodiments, Cy is directly attached to N. In embodiments wherein Cy is a six-membered ring directly attached to N and bears an amino substituent at the 4 position of the ring relative to N, the N and amine substituents may be disposed trans on the ring.

In certain embodiments, substituents on Ar or Ar' are selected from halogen, lower alkyl, lower alkenyl, aryl, heteroaryl, carbonyl, thiocarbonyl, ketone, aldehyde, amino, acylamino, cyano, nitro, hydroxyl, azido, sulfonyl, sulfoxido, sulfate, sulfonate, sulfamoyl, sulfonamido, phosphoryl, phosphonate, phosphinate, —(CH₂)$_p$alkyl, (CH₂)$_p$alkenyl, —(CH₂)$_p$alkynyl, —(CH₂)$_p$aryl, —(CH₂)$_p$aralkyl, —(CH₂)$_p$OH, —(CH₂)$_p$O-lower alkyl, —(CH₂)$_p$O-lower alkenyl, —O(CH₂)$_n$R, —(CH₂)$_p$SH, —(CH₂)$_p$S-lower alkyl, —(CH₂)$_p$S-lower alkenyl, —S(CH₂)$_n$R, —(CH₂)$_p$N(R)₂, —(CH₂)$_p$NR-lower alkyl, —(CH₂)$_p$NR-lower alkenyl, —NR(CH₂)$_n$R, and protected forms of the above, wherein p and n, individually for each occurrence, represent integers from 0 to 10, preferably from 0 to 5.

In certain embodiments, compounds useful in the present invention may be represented by general formula (II):

Formula II

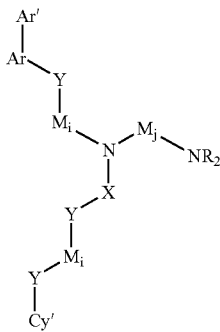

wherein, as valence and stability permit,

Ar and Ar' independently represent substituted or unsubstituted aryl or heteroaryl rings;

Y, independently for each occurrence, is absent or represents —N(R)—, —O—, —S—, or —Se—;

X is selected from —C(═O)—, —C(═S)—, —S(O₂)—, —S(O)—, —C(═NCN)—, —P(═O)(OR)—, and a methylene group optionally substituted with 1-2 groups such as lower alkyl, alkenyl, or alkynyl groups;

M represents, independently for each occurrence, a substituted or unsubstituted methylene group, such as —CH₂—, —CHF—, —CHOH—, —CH(Me)—, —C(═O)—, etc., or two M taken together represent substituted or unsubstituted ethene or ethyne, wherein some or all occurrences of M in M$_j$ form all or part of a cyclic structure;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

Cy' represents a substituted or unsubstituted aryl, heterocyclyl, heteroaryl, or cycloalkyl, including polycyclic groups;

j represents, independently for each occurrence, an integer from 0 to 10, preferably from 2 to 7; and i represents, independently for each occurrence, an integer from 0 to 5, preferably from 0 to 2.

In certain embodiments, M represents, independently for each occurrence, a substituted or unsubstituted methylene group, such as —CH₂—, —CHF—, —CHOH—, —CH(Me)-, —C(═O)—, etc.

In certain embodiments, Ar and Ar' represent phenyl rings, e.g., unsubstituted or substituted with one or more groups including heteroatoms such as O, N, and S. In certain embodiments, at least one of Ar and Ar' represents a phenyl ring. In certain embodiments, at least one of Ar and Ar' represents a heteroaryl ring, e.g., a pyridyl, thiazolyl, thienyl, pyrimidyl, etc. In certain embodiments, Y and Ar' are attached to Ar in a meta and/or 1,3-relationship.

In certain embodiments, Y is absent from all positions. In embodiments wherein Y is present in a position, i preferably represents an integer from 1-2 in an adjacent M$_i$ if i=0 would result in two occurrences of Y being directly attached, or an occurrence of Y being directly attached to N or NR₂.

In certain embodiments, Cy' is a substituted or unsubstituted aryl or heteroaryl. In certain embodiments, Cy' is directly attached to X. In certain embodiments, Cy' is a substituted or unsubstituted bicyclic or heteroaryl ring, preferably both bicyclic and heteroaryl, such as benzothiophene, benzofuran, benzopyrrole, benzopyridine, etc. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system. In certain embodiments, Cy' represents a benzo[b]thien-2-yl, preferably a 3-chloro-benzo[b]thien-2-yl, 3-fluoro-benzo[b]thien-2-yl, or 3-methyl-benzo[b]thien-2-yl, e.g., wherein the benzo ring is substituted with from 1-4 substituents selected from halogen, nitro, cyano, methyl (e.g., including halomethyl, such as CHCl₂ and CF₃), and ethyl (e.g., including haloethyl, such as CH₂CCl₃, C₂F₅, etc.), preferably from halogen and methyl (e.g., including halomethyl, such as CHCl₂ and CF₃). In certain such embodiments Cy' represents a 3-chloro-benzo[b]thien-2-yl, 3-fluoro-benzo[b]thien-2-yl, or 3-methyl-benzo[b]thien-2-yl wherein the benzo ring is substituted with fluoro at the 4-position (peri to the 3-substituent on the thienyl ring) and, optionally, at the 7-position ('peri' to the S of the thienyl ring).

In certain embodiments, X is selected from —C(═O)—, —C(═S)—, and —S(O₂)—.

In certain embodiments, R represents H or lower alkyl, e.g., H or Me.

In certain embodiments, NR₂ represents a primary amine or a secondary or tertiary amine substituted with one or two lower alkyl groups, aryl groups, or aralkyl groups, respectively, preferably a primary amine or secondary amine.

In certain embodiments, substituents on Ar or Ar' are selected from halogen, lower alkyl, lower alkenyl, aryl, heteroaryl, carbonyl, thiocarbonyl, ketone, aldehyde, amino, acylamino, cyano, nitro, hydroxyl, azido, sulfonyl, sulfoxido, sulfate, sulfonate, sulfamoyl, sulfonamido, phosphoryl, phosphonate, phosphinate, —(CH₂)$_p$alkyl, —(CH₂)$_p$alkenyl, —(CH$_2$)$_p$alkynyl, —(CH$_2$)$_p$aryl, —(CH$_2$)$_p$aralkyl, —(CH$_2$)$_p$OH, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$NR, lower alkenyl, —NR(CH$_2$)$_n$R, and protected forms of the above, wherein p and n, individually for each occurrence, represent integers from 0 to 10, preferably from 0 to 5.

In certain embodiments, compounds useful in the present invention may be represented by general formula (III):

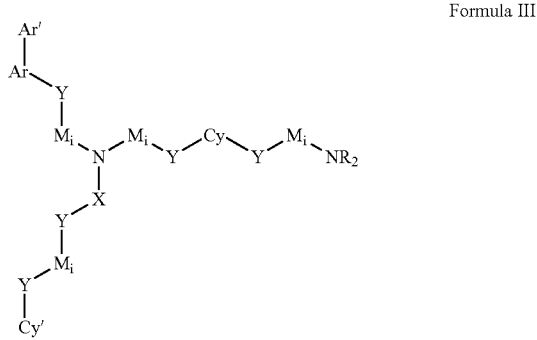

Formula III wherein, as valence and stability permit,

Ar and Ar' independently represent substituted or unsubstituted aryl or heteroaryl rings;

Y, independently for each occurrence, is absent or represents —N(R)—, —O—, —S—, or —Se—;

X is selected from —C(=O)—, —C(=S)—, —S(O$_2$)—, —S(O)—, —C(=NCN)—, —P(=O)(OR)—, and a methylene group optionally substituted with 1-2 groups such as lower alkyl, alkenyl, or alkynyl groups;

M represents, independently for each occurrence, a substituted or unsubstituted methylene group, such as —CH$_2$—, —CHF—, —CHOH—, —CH(Me)—, —C(=O)—, etc., or two M taken together represent substituted or unsubstituted ethene or ethyne;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

Cy and Cy' independently represent substituted or unsubstituted aryl, heterocyclyl, heteroaryl, or cycloalkyl, including polycyclic groups; and i represents, independently for each occurrence, an integer from 0 to 5, preferably from 0 to 2.

In certain embodiments, M represents, independently for each occurrence, a substituted or unsubstituted methylene group, such as —CH$_2$—, —CHF—, —CHOH—, —CH(Me)-, —C(=O)—, etc.

In certain embodiments, Ar and Ar' represent phenyl rings, e.g., unsubstituted or substituted with one or more groups including heteroatoms such as O, N, and S. In certain embodiments, at least one of Ar and Ar' represents a phenyl ring. In certain embodiments, at least one of Ar and Ar' represents a heteroaryl ring, e.g., a pyridyl, thiazolyl, thienyl, pyrimidyl, etc. In certain embodiments, Y and Ar' are attached to Ar in a meta and/or 1,3-relationship.

In certain embodiments, Y is absent from all positions. In embodiments wherein Y is present in a position, i preferably represents an integer from 1-2 in an adjacent M$_i$ if i=0 would result in two occurrences of Y being directly attached, or an occurrence of Y being directly attached to N or NR$_2$.

In certain embodiments, Cy' is a substituted or unsubstituted aryl or heteroaryl. In certain embodiments, Cy' is directly attached to X. In certain embodiments, Cy' is a substituted or unsubstituted bicyclic or heteroaryl ring, preferably both bicyclic and heteroaryl, such as benzothiophene, benzofuran, benzopyrrole, benzopyridine, etc. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system. In certain embodiments, Cy' represents a benzo[b]thien-2-yl, preferably a 3-chloro-benzo[b]thien-2-yl, 3-fluoro-benzo[b]thien-2-yl, or 3-methyl-benzo[b]thien-2-yl, e.g., wherein the benzo ring is substituted with from 1-4 substituents selected from halogen, nitro, cyano, methyl (e.g., including halomethyl, such as CHCl$_2$ and CF$_3$), and ethyl (e.g., including haloethyl, such as CH$_2$CCl$_3$, C$_2$F$_5$, etc.), preferably from halogen and methyl (e.g., including halomethyl, such as CHCl$_2$ and CF$_3$). In certain such embodiments Cy' represents a 3-chloro-benzo[b]thien-2-yl, 3-fluoro-benzo[b]thien-2-yl, or 3-methyl-benzo[b]thien-2-yl wherein the benzo ring is substituted with fluoro at the 4-position (peri to the 3-substituent on the thienyl ring) and, optionally, at the 7-position ('peri' to the S of the thienyl ring).

In certain embodiments, X is selected from —C(=O)—, —C(=S)—, and —S(O$_2$)—.

In certain embodiments, R represents H or lower alkyl, e.g., H or Me.

In certain embodiments, NR$_2$ represents a primary amine or a secondary or tertiary amine substituted with one or two lower alkyl groups, aryl groups, or aralkyl groups, respectively, preferably a primary amine or a secondary amine.

In certain embodiments, Cy represents a substituted or unsubstituted non-aromatic carbocyclic or heterocyclic ring, i.e., including at least one sp$^3$ hybridized atom, and preferably a plurality of sp$^3$ hybridized atoms. In certain embodiments, Cy is directly attached to N and/or to NR$_2$. In certain embodiments, Cy is a 5- to 7-membered ring. In embodiments wherein Cy is a six-membered ring directly attached to N and bears an amino substituent at the 4 position of the ring relative to N, the N and amine substituents may be disposed trans on the ring.

In certain embodiments, substituents on Ar or Ar' are selected from halogen, lower alkyl, lower alkenyl, aryl, heteroaryl, carbonyl, thiocarbonyl, ketone, aldehyde, amino, acylamino, cyano, nitro, hydroxyl, azido, sulfonyl, sulfoxido, sulfate, sulfonate, sulfamoyl, sulfonamido, phosphoryl, phosphonate, phosphinate, —(CH$_2$)$_p$alkyl, —(CH$_2$)$_p$alkenyl, —(CH$_2$)$_p$alkynyl, —(CH$_2$)$_p$aryl, —(CH$_2$)$_p$aralkyl, —(CH$_2$)$_p$O, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$R, —(CH$_2$)$_p$N(R)$_2$, CH$_2$)$_p$NR-lower alkyl, —(CH$_2$)$_p$NR-lower alkenyl, —NR(CH$_2$)$_n$R, and protected forms of the above, wherein n and p, individually for each occurrence, represent integers from 0 to 10, preferably from 0 to 5.

In certain embodiments, compounds useful in the subject methods include compounds represented by general formula (IV):

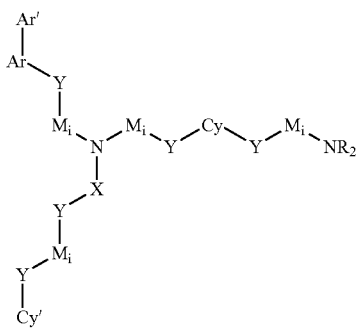

Formula IV wherein, as valence and stability permit,

Cy' represents a substituted or unsubstituted aryl or heteroaryl ring, including polycyclics;

Y, independently for each occurrence, is absent or represents —N(R)—, —O—, —S—, or —Se—;

X is selected from —C(=O)—, —C(=S)—, —S(O$_2$)—, —S(O)—, —C(=NCN)—, —P(=O)(OR)—, and a methylene group optionally substituted with 1-2 groups such as lower alkyl, alkenyl, or alkynyl groups;

M represents, independently for each occurrence, a substituted or unsubstituted methylene group, such as —CH$_2$—, —CHF—, —CHOH—, —CH(Me)—, —C(=O)—, etc., or two M taken together represent substituted or unsubstituted ethene or ethyne;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

R$_1$ and R$_2$ represent, independently and as valency permits, from 0-5 substituents on the ring to which it is attached, selected from halogen, lower alkyl, lower alkenyl, aryl, heteroaryl, carbonyl, thiocarbonyl, ketone, aldehyde, amino, acylamino, amido, amidino, cyano, nitro, hydroxyl, azido, sulfonyl, sulfoxido, sulfate, sulfonate, sulfamoyl, sulfonamido, phosphoryl, phosphonate, phosphinate, —(CH$_2$)$_p$alkyl, —(CH$_2$)$_p$alkenyl, —(CH$_2$)$_p$alkynyl, —(CH$_2$)$_p$aryl, —(CH$_2$)$_p$aralkyl, —(CH$_2$)$_p$OH, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$NR-lower alkenyl, —NR(CH$_2$)$_n$R, and protected forms of the above;

Cy represents substituted or unsubstituted aryl, heterocyclyl, heteroaryl, or cycloalkyl, including polycyclic groups;

i represents, independently for each occurrence, an integer from 0 to 5, preferably from 0 to 2; and p and n, individually for each occurrence, represent integers from 0 to 10, preferably from 0 to 5.

In certain embodiments, M represents, independently for each occurrence, a substituted or unsubstituted methylene group, such as —CH$_2$—, —CHF—, —CHOH—, —CH(Me)-, —C(=O)—, etc.

In certain embodiments, Cy' represents a substituted or unsubstituted bicyclic or heterocyclic ring system, preferably both bicyclic and heteroaryl, such as benzothiophene, benzofuran, benzopyrrole, benzopyridine, etc. In certain embodiments, Cy' is directly attached to X. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system. In certain embodiments, Cy' represents a benzo[b]thien-2-yl, preferably a 3-chloro-benzo[b]thien-2-yl, 3-fluoro-benzo[b]thien-2-yl, or 3-methyl-benzo[b]thien-2-yl, e.g., wherein the benzo ring is substituted with from 1-4 substituents selected from halogen, nitro, cyano, methyl (e.g., including halomethyl, such as CHCl$_2$ and CF$_3$), and ethyl (e.g., including haloethyl; such as CH$_2$CCl$_3$, C$_2$F$_5$, etc.), preferably from halogen and methyl (e.g., including halomethyl, such as CHCl$_2$ and CF$_3$). In certain such embodiments Cy' represents a 3-chloro-benzo[b]thien-2-yl, 3-fluoro-benzo[b]thien-2-yl, or 3-methyl-benzo[b]thien-2-yl wherein the benzo ring is substituted with fluoro at the 4-position (peri to the 3-substituent on the thienyl ring) and, optionally, at the 7-position ('peri' to the S of the thienyl ring).

In certain embodiments, Y is absent from all positions. In embodiments wherein Y is present in a position, i preferably represents an integer from 1-2 in an adjacent M$_i$ if i=0 would result in two occurrences of Y being directly attached, or an occurrence of Y being directly attached to N.

In certain embodiments, X is selected from —C(=O)—, —C(=S)—, and —S(O$_2$)—.

In certain embodiments, R represents H or lower alkyl, e.g., H or Me.

In certain embodiments, Cy represents a substituted or unsubstituted non-aromatic carbocyclic or heterocyclic ring, i.e., including at least one sp$^3$ hybridized atom, and preferably a plurality of sp$^3$ hybridized atoms. In certain embodiments, Cy is directly attached to N. In certain embodiments, Cy is a 5- to 7-membered ring. In embodiments wherein Cy is a six-membered ring directly attached to N and bears an amino substituent at the 4 position of the ring relative to N, the N and amine substituents may be disposed trans on the ring.

In certain embodiments, R$_1$ and R$_2$ represent, independently and as valency permits, from 0-5 substituents on the ring to which it is attached, selected from halogen, lower alkyl, lower alkenyl, carbonyl, thiocarbonyl, ketone, aldehyde, amino, acylamino, cyano, nitro, hydroxyl, sulfonyl, sulfoxido, sulfate, sulfonate, sulfamoyl, sulfonamido, —(CH$_2$)$_p$alkyl, —(CH$_2$)$_p$alkenyl, —(CH$_2$)$_p$alkynyl, —(CH$_2$)$_p$OH, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$NR-lower alkenyl, —NR(CH$_2$)$_n$R, and protected forms of the above.

In certain embodiments, compounds useful in the present invention may be represented by general formula (V):

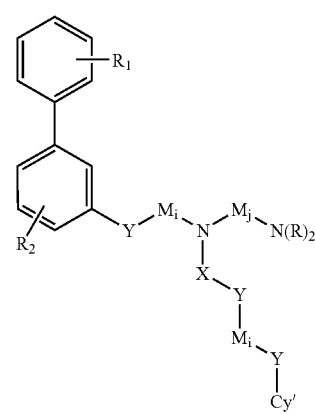

Formula V wherein, as valence and stability permit,

Cy' represents a substituted or unsubstituted aryl or heteroaryl ring, including polycyclics;

Y, independently for each occurrence, is absent or represents —N(R)—, —O—, —S—, or —Se—;

X is selected from —C(=O)—, —C(=S)—, —S(O$_2$)—, —S(O)—, —C(=NCN)—, —P(=O)(OR)—, and a methylene group optionally substituted with 1-2 groups such as lower alkyl, alkenyl, or alkynyl groups;

M represents, independently for each occurrence, a substituted or unsubstituted methylene group, such as —CH$_2$—, —CHF—, —CHOH—, —CH(Me)—, —C(=O)—, etc., or two M taken together represent substituted or unsubstituted ethene or ethyne;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

R$_1$ and R$_2$ represent, independently and as valency permits, from 0-5 substituents on the ring to which it is attached, selected from halogen, lower alkyl, lower alkenyl, aryl, heteroaryl, carbonyl, thiocarbonyl, ketone, aldehyde, amino, acylamino, amido, amidino, cyano, nitro, hydroxyl, azido, sulfonyl, sulfoxido, sulfate, sulfonate, sulfamoyl, sulfonamido, phosphoryl, phosphonate, phosphinate, —(CH$_2$)$_p$alkyl, —(CH$_2$)$_p$alkenyl, —(CH$_2$)$_p$alkyl, —(CH$_2$)$_p$aryl, —(CH$_2$)$_p$aralkyl, —(CH$_2$)$_p$OH, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$NR-lower alkenyl, —NR(CH$_2$)$_n$R, and protected forms of the above;

Cy' represents a substituted or unsubstituted aryl, heterocyclyl, heteroaryl, or cycloalkyl, including polycyclic groups;

j represents, independently for each occurrence, an integer from 0 to 10, preferably from 2 to 7;

i represents, independently for each occurrence, an integer from 0 to 5, preferably from 0 to 2; and p and n, individually for each occurrence, represent integers from 0 to 10, preferably from 0 to 5.

In certain embodiments, M represents, independently for each occurrence, a substituted or unsubstituted methylene group, such as —CH$_2$—, —CHF—, —CHOH—, —CH(Me)-, —C(=O)—, etc.

In certain embodiments, Cy' represents a substituted or unsubstituted bicyclic or heterocyclic ring system, preferably both bicyclic and heteroaryl, such as benzothiophene, benzofuran, benzopyrrole, benzopyridine, etc. In certain embodiments, Cy' is directly attached to X. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system. In certain embodiments, Cy' represents a benzo[b]thien-2-yl, preferably a 3-chloro-benzo[b]thien-2-yl, 3-fluoro-benzo(b) thien-2-yl, or 3-methyl-benzo[b]thien-2-yl, e.g., wherein the benzo ring is substituted with from 1-4 substituents selected from halogen, nitro, cyano, methyl (e.g., including halomethyl, such as CHCl$_2$ and CF$_3$), and ethyl (e.g., including haloethyl, such as CH$_2$CCl$_3$, C$_2$F$_5$, etc.), preferably from halogen and methyl (e.g., including halomethyl, such as CHCl$_2$ and CF$_3$). In certain such embodiments Cy' represents a 3-chloro-benzo(b)thien-2-yl, 3-fluoro-benzo[b]thien-2-yl, or 3-methyl-benzo[b]thien-2-yl wherein the benzo ring is substituted with fluoro at the 4-position (peri to the 3-substituent on the thienyl ring) and, optionally, at the 7-position ('peri' to the S of the thienyl ring).

In certain embodiments, Y is absent from all positions. In embodiments wherein Y is present in a position, i preferably represents an integer from 1-2 in an adjacent M$_i$ if i=0 would result in two occurrences of Y being directly attached, or an occurrence of Y being directly attached to N or NR$_2$.

In certain embodiments, X is selected from —C(=O)—, —C(=S)—, and —S(O$_2$)—.

In certain embodiments, NR$_2$ represents a primary amine or a secondary or tertiary amine substituted with one or two lower alkyl groups, aryl groups, or aralkyl groups, respectively, preferably a primary or secondary amine.

In certain embodiments, R represents H or lower alkyl, e.g., H or Me.

In certain embodiments, R$_1$ and R$_2$ represent, independently and as valency permits, from 0-5 substituents on the ring to which it is attached, selected from halogen, lower alkyl, lower alkenyl, carbonyl, thiocarbonyl, ketone, aldehyde, amino, acylamino, cyano, nitro, hydroxyl, sulfonyl, sulfoxido, sulfate, sulfonate, sulfamoyl, sulfonamido, —(CH$_2$)$_p$alkyl, —(CH$_2$)$_p$alkenyl, —(CH$_2$)$_p$alkynyl, —(CH$_2$)$_p$OH, —(CH$_2$)$_p$O-lower alkyl, —(CH$_2$)$_p$O-lower alkenyl, —O(CH$_2$)$_n$R, —(CH$_2$)$_p$SH, —(CH$_2$)$_p$S-lower alkyl, —(CH$_2$)$_p$S-lower alkenyl, —S(CH$_2$)$_n$R, —(CH$_2$)$_p$N(R)$_2$, —(CH$_2$)$_p$NR-lower alkyl, —(CH$_2$)$_p$NR-lower alkenyl, —NR(CH$_2$)$_n$R, and protected forms of the above.

In certain embodiments, compounds useful in the present invention may be represented by general formula (VI):

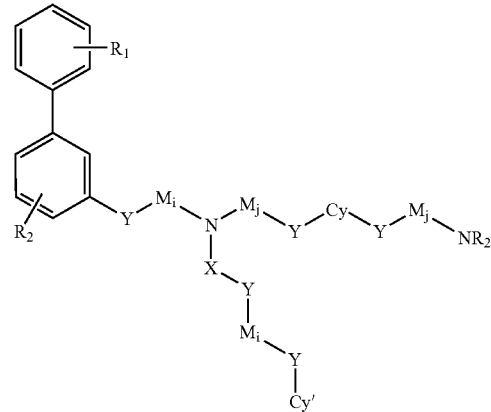

Formula VI wherein, as valence and stability permit,

Cy' represents a substituted or unsubstituted aryl or heteroaryl ring, including polycyclics;

Y, independently for each occurrence, is absent or represents —N(R)—, —O—, —S—, or —Se—;

X is selected from —C(=O)—, —C(=S)—, —S(O$_2$)—, —S(O)—, —C(=NCN)—, —P(=O)(OR)—, and a methylene group optionally substituted with 1-2 groups such as lower alkyl, alkenyl, or alkynyl groups;

M represents, independently for each occurrence, a substituted or unsubstituted methylene group, such as —CH$_2$—, —CHF—, —CHOH—, —CH(Me)—, —C(=O)—, etc., or two M taken together represent substituted or unsubstituted ethene or ethyne;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

Cy represents substituted or unsubstituted aryl, heterocyclyl, heteroaryl, or cycloalkyl, including polycyclic groups;

$R_1$ and $R_2$ represent, independently and as valency permits, from 0-5 substituents on the ring to which it is attached, selected from halogen, lower alkyl, lower alkenyl, aryl, heteroaryl, carbonyl, thiocarbonyl, ketone, aldehyde, amino, acylamino, amido, amidino, cyano, nitro, hydroxyl, azido, sulfonyl, sulfoxido, sulfate, sulfonate, sulfamoyl, sulfonamido, phosphoryl, phosphonate, phosphinate, —$(CH_2)_p$alkyl, —$(CH_2)_p$alkenyl, —$(CH_2)_p$alkynyl, —$(CH_2)_p$aryl, —$(CH_2)_p$aralkyl, —$(CH_2)_p$OH, —$(CH_2)_p$O-lower alkyl, —$(CH_2)_p$O-lower alkenyl, —$O(CH_2)_n$R, —$(CH_2)_p$SH, —$(CH_2)_p$S-lower alkyl, —$(CH_2)_p$S-lower alkenyl, —$S(CH_2)_n$R, —$(CH_2)_p$N(R)$_2$, —$(CH_2)_p$NR-lower alkyl, —$(CH_2)_p$NR-lower alkenyl, —$NR(CH_2)_n$R, and protected forms of the above;

i represents, independently for each occurrence, an integer from 0 to 5, preferably from 0 to 2; and n and p, individually for each occurrence, represent integers from 0 to 10, preferably from 0 to 5.

In certain embodiments, M represents, independently for each occurrence, a substituted or unsubstituted methylene group, such as —$CH_2$—, —CHF—, —CHOH—, —CH(Me)-, —C(=O)—, etc.

In certain embodiments, Cy' represents a substituted or unsubstituted bicyclic or heteroaryl ring system, preferably both bicyclic and heteroaryl, e.g., benzothiophene, benzofuran, benzopyrrole, benzopyridyl, etc. In certain embodiments, Cy' is directly attached to X. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system. In certain embodiments, Cy' represents a benzo[b]thien-2-yl, preferably a 3-chloro-benzo[b]thien-2-yl, 3-fluoro-benzo[b]thien-2-yl, or 3-methyl-benzo[b]thien-2-yl, e.g., wherein the benzo ring is substituted with from 1-4 substituents selected from halogen, nitro, cyano, methyl (e.g., including halomethyl, such as $CHCl_2$ and $CF_3$), and ethyl (e.g., including haloethyl, such as $CH_2CCl_3$, $C_2F_5$, etc.), preferably from halogen and methyl (e.g., including halomethyl, such as $CHCl_2$ and $CF_3$). In certain such embodiments Cy' represents a 3-chloro-benzo[b]thien-2-yl, 3-fluoro-benzo[b]thien-2-yl, or 3-methyl-benzo[b]thien-2-yl wherein the benzo ring is substituted with fluoro at the 4-position (peri to the 3-substituent on the thienyl ring) and, optionally, at the 7-position ('peri' to the S of the thienyl ring).

In certain embodiments, Y is absent from all positions. In embodiments wherein Y is present in a position, i preferably represents an integer from 1-2 in an adjacent $M_i$ if i=0 would result in two occurrences of Y being directly attached, or an occurrence of Y being directly attached to N or $NR_2$.

In certain embodiments, X is selected from —C(=O)—, —C(=S)—, and —$S(O_2)$—.

In certain embodiments, $NR_2$ represents a primary amine or a secondary or tertiary amine substituted with one or two lower alkyl groups, aryl groups, or aralkyl groups, respectively, preferably a primary amine.

In certain embodiments, R represents H or lower alkyl, e.g., H or Me.

In certain embodiments, Cy represents a substituted or unsubstituted non-aromatic carbocyclic or heterocyclic ring, i.e., including at least one $sp^3$ hybridized atom, and preferably a plurality of $sp^3$ hybridized atoms. In certain embodiments, Cy is directly attached to N and/or to $NR_2$. In certain embodiments, Cy is a 5- to 7-membered ring. In embodiments wherein Cy is a six-membered ring directly attached to N and bears an amino substituent at the 4 position of the ring relative to N, the N and amine substituents may be disposed trans on the ring.

In certain embodiments, $R_1$ and $R_2$ represent, independently and as valency permits, from 0-5 substituents on the ring to which it is attached, selected from halogen, lower alkyl, lower alkenyl, carbonyl, thiocarbonyl, ketone, aldehyde, amino, acylamino, cyano, nitro, hydroxyl, sulfonyl, sulfoxido, sulfate, sulfonate, sulfamoyl, sulfonamido, —$(CH_2)_p$alkyl, —$(CH_2)_p$alkenyl, —$(CH_2)_p$alkynyl, —$(CH_2)_p$OH, —$(CH_2)_p$O-lower alkyl, —$(CH_2)_p$O-lower alkenyl, —$O(CH_2)_n$R, —$(CH_2)_p$SH, —$(CH_2)_p$S-lower alkyl, —$(CH_2)_p$S-lower alkenyl, —$S(CH_2)_n$R, —$(CH_2)_p$N(R)$_2$, —$(CH_2)_p$NR-lower alkyl, —$(CH_2)_p$NR-lower alkenyl, —$NR(CH_2)_n$R, and protected forms of the above.

In certain embodiments, a subject compound has the structure of Formula VII:

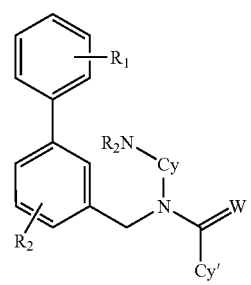

Formula VII wherein, as valence and stability permit,

Cy represents a substituted or unsubstituted heterocyclyl or cycloalkyl;

Cy' is a substituted or unsubstituted aryl or heteroaryl ring, including polycyclics;

W is O or S;

R represents, independently for each occurrence, H or substituted or unsubstituted aryl, heterocyclyl, heteroaryl, aralkyl, heteroaralkyl, alkynyl, alkenyl, or alkyl, or two R taken together may form a 4- to 8-membered ring, e.g., with N;

$R_1$ and $R_2$ represent, independently and as valency permits, from 0-5 substituents on the ring to which it is attached, selected from halogen, lower alkyl, lower alkenyl, aryl, heteroaryl, carbonyl, thiocarbonyl, ketone, aldehyde, amino, acylamino, amido, amidino, cyano, nitro, hydroxyl, azido, sulfonyl, sulfoxido, sulfate, sulfonate, sulfamoyl, sulfonamido, phosphoryl, phosphonate, phosphinate, —$(CH_2)_p$alkyl, —$(CH_2)_p$alkenyl, —$(CH_2)_p$alkynyl, —$(CH_2)_p$aryl, —$(CH_2)_p$aralkyl, —$(CH_2)_p$OH, —$(CH_2)_p$O-lower alkyl, —$(CH_2)_p$O-lower alkenyl, —$O(CH_2)_n$R, —$(CH_2)_p$SH, —$(CH_2)_p$S-lower alkyl, —$(CH_2)_p$S-lower alkenyl, —$S(CH_2)_n$R, —$(CH_2)_p$N(R)$_2$, —$(CH_2)_p$NR-lower alkyl, —$(CH_2)_p$NR-lower alkenyl, —$NR(CH_2)_n$R, and protected forms of the above;

n and p, individually for each occurrence, represent integers from 0 to 10, preferably from 0 to 5.

In certain embodiments, Cy' represents a substituted or unsubstituted bicyclic or heteroaryl ring system, preferably both bicyclic and heteroaryl, e.g., benzothiophene, benzofuran, benzopyrrole, benzopyridyl, etc. In certain other embodiments, Cy' represents an aryl or heteroaryl ring substituted at least with a substituted or unsubstituted aryl or heteroaryl ring, i.e., to form a biaryl ring system. In certain embodiments, Cy' represents a benzo[b]thien-2-yl, preferably a 3-chloro-benzo[b]thien-2-yl, 3-fluoro-benzo[b]thien-2-yl, or 3-methyl-benzo[b]thien-2-yl, e.g., wherein the benzo ring is substituted with from 1-4 substituents selected from halogen, nitro, cyano; methyl (e.g., including halomethyl, such as $CHCl_2$ and $CF_3$), and ethyl (e.g., including haloethyl, such as $CH_2CCl_3$, $C_2F_5$, etc.), preferably from halogen and methyl (e.g., including halomethyl, such as $CHCl_2$ and $CF_3$). In certain such embodiments Cy' represents a 3-chloro-benzo[b]thien-2-yl, 3-fluoro-benzo[b]thien-2-yl, or 3-methyl-benzo[b]thien-2-yl wherein the benzo ring is substituted with fluoro at the 4-position (peri to the 3-substituent on the thienyl ring) and, optionally, at the 7-position ('peri' to the S of the thienyl ring).

In certain embodiments, $NR_2$ represents a primary amine or a secondary or tertiary amine substituted with one or two lower alkyl groups, aryl groups, or aralkyl groups, respectively, preferably a primary or secondary amine.

In certain embodiments, Cy represents a substituted or unsubstituted saturated carbocyclic or heterocyclic ring, i.e., composed of a plurality of $sp^3$ hybridized atoms. In certain embodiments, Cy is a 5- to 7-membered ring. In embodiments wherein Cy is a six-membered ring directly attached to N and bears an amino substituent at the 4 position of the ring relative to N, the N and amine substituents may be disposed trans on the ring.

In certain embodiments, $R_1$ and $R_2$ represent, independently and as valency permits, from 0-5 substituents on the ring to which it is attached, selected from halogen, lower alkyl; lower alkenyl, carbonyl, thiocarbonyl, ketone, aldehyde, amino, acylamino, cyano, nitro, hydroxyl, sulfonyl, sulfoxido, sulfate, sulfonate, sulfamoyl, sulfonamido, —$(CH_2)_p$alkyl, —$(CH_2)_p$alkenyl, —$(CH_2)_p$alkynyl, —$(CH_2)_p$OH, —$(CH_2)_p$O-lower alkyl, —$(CH_2)_p$O-lower alkenyl, —$O(CH_2)_n$R, —$(CH_2)_p$SH, —$(CH_2)_p$S-lower alkyl, —$(CH_2)_p$S-lower alkenyl, —$S(CH_2)_n$R, —$(CH_2)_p$N(R)_2$, —$(CH_2)_p$NR-lower alkyl, —$(CH_2)_p$NR-lower alkenyl, —$NR(CH_2)_n$R, and protected forms of the above.

In certain embodiments, a subject compound has a structure of Formula VIII:

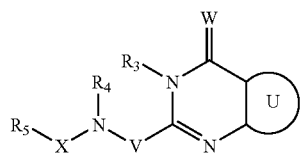

Formula VIII wherein, as valence and stability permit,

U represents a substituted or unsubstituted aryl or heteroaryl ring fused to the nitrogen-containing ring;

V represents a lower alkylene group, such as methylene, 1,2-ethylene, 1,1-ethylene, 1,1-propylene, 1,2-propylene, 1,3-propylene, etc.;

W represents S or O, preferably O;

X represents C=O, C=S, or $SO_2$;

$R_3$ represents substituted or unsubstituted aryl, heteroaryl, lower alkyl, lower alkenyl, lower alkynyl, carbocyclyl, carbocyclylalkyl, heterocyclyl, heterocyclylalkyl, aralkyl, or heteroaralkyl;

$R_4$ represents substituted or unsubstituted aralkyl or lower alkyl, such as phenethyl, benzyl, or aminoalkyl, etc.;

$R_5$ represents substituted or unsubstituted aryl, heteroaryl, aralkyl, or heteroaralkyl, including polycyclic aromatic or heteroaromatic groups.

In certain embodiments, U represents a phenyl ring fused to the nitrogen-containing ring.

In certain embodiments, $R_3$ is selected from substituted or unsubstituted aryl, heteroaryl, lower alkyl, lower alkenyl, aralkyl, and heteroaralkyl.

In certain embodiments, $R_4$ is an unsubstituted lower alkyl group, or is a lower alkyl group substituted with a secondary or tertiary amine.

In certain embodiments, $R_5$ is selected from substituted or unsubstituted phenyl or naphthyl, or is a diarylalkyl group, such as 2,2-diphenylethyl, diphenylmethyl, etc.

In certain embodiments, subject compounds include compounds represented by general formula (IX):

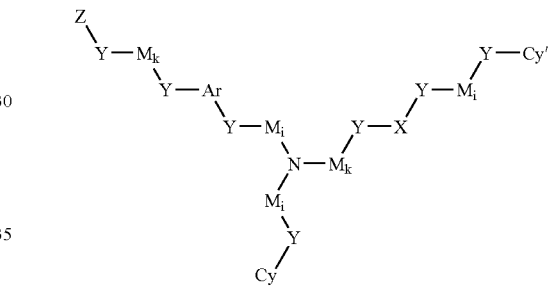

Formula IX wherein, as valence and stability permit,

Ar represents a substituted or unsubstituted aryl or heteroaryl ring;

Z is absent or represents a substituted or unsubstituted aryl, carbocyclyl, heterocyclyl, or heteroaryl ring, or a lower alkyl, nitro, cyano, or halogen substituent;

Y, independently for each occurrence, is absent or represents —N(R)—, —O—, —S—, or —Se—, provided that if Z is not a ring, then Y attached to Z is absent;

X is selected from —C(=O)—, —C(=S)—, —S(O_2)—, —S(O)—, —C(=NCN)—, —P(=O)(OR)—, and a methylene group optionally substituted with 1-2 groups such as lower alkyl, alkenyl, or alkynyl groups;

M represents, independently for each occurrence, a substituted or unsubstituted methylene group, such as —$CH_2$—, —CHF—, —CHOH—, —CH(Me)—, —C(=O)—, etc., or two M taken together represent substituted or unsubstituted ethene or ethyne;

R represents, independently for each occurrence, H or substituted or unsubstituted aryl, heterocyclyl, carbocyclyl, heteroaryl, aralkyl, heteroaralkyl, heterocyclylalkyl, carbocyclylalkyl, alkynyl, alkenyl, or alkyl, or two R taken together may form a 4- to 8-membered ring, e.g., with N;

Cy and Cy' independently represent substituted or unsubstituted aryl, heterocyclyl, heteroaryl, or cycloalkyl, including polycyclic groups;

i represents, independently for each occurrence, an integer from 0 to 5, preferably from 0 to 2; and k represents an integer from 0 to 3, preferably from 0 to 2.

In certain embodiments, M represents, independently for each occurrence, a substituted or unsubstituted methylene group, such as —$CH_2$—, —CHF—, —CHOH—, —CH(Me)-, —C(=O)—, etc. In certain embodiments, i represents 0 for all occurrences except in the sequence N-$M_i$-Y—Ar, where i represents 1.

In certain embodiments, Ar and X independently represent substituted or unsubstituted aryl or heteroaryl rings, e.g., unsubstituted or substituted with one or more groups optionally including heteroatoms such as O, N, and S. In certain embodiments, Ar represents a phenyl ring. In certain embodiments, at least one of Ar represents a heteroaryl ring, e.g., a pyridyl, thiazolyl, thienyl, pyrimidyl furanyl, etc. In certain embodiments, the occurrences of Y attached to Ar are disposed in a meta and/or 1,3-relationship.

In certain embodiments, Y is absent from all positions. In certain embodiments, the only present occurrence of Y is attached to $M_k$. In embodiments wherein Y is present in a position, i or k preferably represents 2 in an adjacent $M_{i/k}$ if i/k=0 would result in two occurrences of Y being directly attached to each other, or an occurrence of Y being directly attached to N. In certain embodiments, where two occurrences of Y are attached to M, at least one such occurrence of Y is absent. In certain embodiments, no more than two occurrences of Y are present.

In certain embodiments, Cy' is a substituted or unsubstituted aryl or heteroaryl. In certain embodiments, Cy' is directly attached to X. In certain embodiments, Cy' is a substituted or unsubstituted bicyclic or heteroaryl ring, preferably both bicyclic and heteroaryl, such as benzothiophene, benzofuran, benzopyrrole, benzopyridine, etc. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system. In certain embodiments, Cy' represents a benzo[b]thien-2-yl, preferably a 3-chloro-benzo[b]thien-2-yl, 3-fluoro-benzo[b]thien-2-yl, or 3-methyl-benzo[b]thien-2-yl, e.g., wherein the benzo ring is substituted with from 1-4 substituents selected from halogen, nitro, cyano, methyl (e.g., including halomethyl, such as $CHCl_2$ and $CF_3$), and ethyl (e.g., including haloethyl, such as $CH_2CCl_3$, $C_2F_5$, etc.), preferably from halogen and methyl (e.g., including halomethyl, such as $CHCl_2$ and $CF_3$). In certain such embodiments Cy' represents a 3-chloro-benzo[b]thien-2-yl, 3-fluoro-benzo[b]thien-2-yl, or 3-methyl-benzo[b]thien-2-yl wherein the benzo ring is substituted with fluoro at the 4-position (peri to the 3-substituent on the thienyl ring) and, optionally, at the 7-position ('peri' to the S of the thienyl ring).

In certain embodiments, X is selected from —C(=O)—, —C(=S)—, and —S($O_2$)—.

In certain embodiments, Cy represents a substituted or unsubstituted non-aromatic carbocyclic or heterocyclic ring, i.e., including at least one $sp^3$ hybridized atom, and preferably a plurality of $sp^3$ hybridized atoms. In certain embodiments, Cy includes an amine within the atoms of the ring or on a substituent of the ring, e.g., Cy is pyridyl, imidazolyl, pyrrolyl, piperidyl, pyrrolidyl, piperazyl, etc., and/or bears an amino substituent. In certain embodiments, Cy is a 5- to 7-membered ring. In certain embodiments, Cy is directly attached to N. In embodiments wherein Cy is a six-membered ring directly attached to N and bears an amino substituent at the 4 position of the ring relative to N, the N and amine substituents may be disposed trans on the ring.

In certain embodiments, substituents on Ar or Z, where Z is an aryl or heteroaryl ring, are selected from halogen, lower alkyl, lower alkenyl, aryl, heteroaryl, carbonyl, thiocarbonyl, ketone, aldehyde, amino, acylamino, cyano, nitro, hydroxyl, azido, sulfonyl, sulfoxido, sulfate, sulfonate, sulfamoyl, sulfonamido, phosphoryl, phosphonate, phosphinate, —$(CH_2)_p$alkyl, —$(CH_2)_p$alkenyl, —$(CH_2)_p$alkynyl, —$(CH_2)_p$aryl, —$(CH_2)_p$aralkyl, —$(CH_2)_p$OH, —$(CH_2)_p$O-lower alkyl, —$(CH_2)_p$O-lower alkenyl, —O$(CH_2)_n$R, —$(CH_2)_p$SH, —$(CH_2)_p$S-lower alkyl, —$(CH_2)_p$S-lower alkenyl, —S$(CH_2)_n$R, —$(CH_2)_p$N$(R)_2$, —$(CH_2)_p$NR-lower alkyl, —$(CH_2)_p$NR-lower alkenyl, —NR$(CH_2)_n$R, and protected forms of the above, wherein n and p, individually for each occurrence, represent integers from 0 to 10, preferably from 0 to 5.

In certain embodiments, Z is directly attached to Ar, or attached to Ar through a chain of one or two atoms. In certain embodiments, Z—Y-M, taken together, is absent.

In certain embodiments, compounds useful in the present invention may be represented by general formula (X):

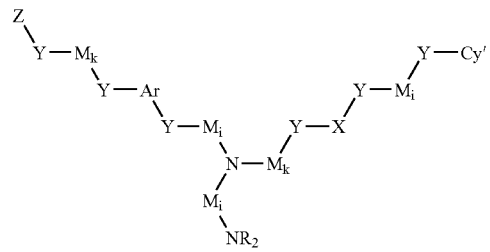

Formula X wherein, as valence and stability permit,

Ar represents a substituted or unsubstituted aryl or heteroaryl ring;

Z is absent or represents a substituted or unsubstituted aryl, carbocyclyl, heterocyclyl, or heteroaryl ring, or a lower alkyl, nitro, cyano, or halogen substituent;

Y, independently for each occurrence, is absent or represents —N(R)—, —O—, —S—, or —Se—, provided that if Z is not a ring, then Y attached to Z is absent;

X is selected from —C(=O)—, —C(=S)—, —S($O_2$)—, —S(O)—, —C(=NCN)—, —P(=O)(OR)—, and a methylene group optionally substituted with 1-2 groups such as lower alkyl, alkenyl, or alkynyl groups;

R represents, independently for each occurrence, H or substituted or unsubstituted aryl, heterocyclyl, carbocyclyl, heteroaryl, aralkyl, heteroaralkyl, heterocyclylalkyl, carbocyclylalkyl, alkynyl, alkenyl, or alkyl, or two R taken together may form a 4- to 8-membered ring, e.g., with N;

Cy' represents a substituted or unsubstituted aryl, heterocyclyl, heteroaryl, or cycloalkyl, including polycyclic groups;

M represents, independently for each occurrence, a substituted or unsubstituted methylene group, such as —$CH_2$—, —CHF—, —CHOH—, —CH(Me)—, —C(=O)—, etc., or two M taken together represent substituted or unsubstituted ethene or ethyne, wherein some or all occurrences of M in $M_j$ form all or part of a cyclic structure;

j represents, independently for each occurrence, an integer from 2 to 10, preferably from 2 to 7;

i represents, independently for each occurrence, an integer from 0 to 5, preferably from 0 to 2; and k represents an integer from 0 to 3, preferably from 0 to 2.

In certain embodiments, $NR_2$ represents a primary amine or a secondary or tertiary amine substituted with one or two lower alkyl groups, aryl groups, or aralkyl groups, respectively, preferably a primary or secondary amine.

In certain embodiments, M represents, independently for each occurrence, a substituted or unsubstituted methylene group, such as —$CH_2$—, —CHF—, —CHOH—, —CH(Me)-, —C(=O)—, etc. In certain embodiments, i represents 0 for all occurrences except in the sequence N-$M_i$-Y—Ar, where i represents 1.

In certain embodiments, Ar and X independently represent substituted or unsubstituted aryl or heteroaryl rings, e.g., unsubstituted or substituted with one or more groups optionally including heteroatoms such as O, N, and S. In certain embodiments, Ar represents a phenyl ring. In certain embodiments, Ar represents a heteroaryl ring, e.g., a pyridyl, thiazolyl, thienyl, pyrimidyl, furanyl, etc. In certain embodiments, the occurrences of Y attached to Ar are disposed in a meta and/or 1,3-relationship.

In certain embodiments, Y is absent from all positions. In certain embodiments, the only present occurrence of Y is attached to $M_k$. In embodiments wherein Y is present in a position, i or k preferably represents 2 in an adjacent $M_{i/k}$ if i/k=0 would result in two occurrences of Y being directly attached to each other, or an occurrence of Y being directly attached to N. In certain embodiments, where two occurrences of Y are attached to M, at least one such occurrence of Y is absent. In certain embodiments, no more than two occurrences of Y are present.

In certain embodiments, Cy' is a substituted or unsubstituted aryl or heteroaryl. In certain embodiments, Cy' is directly attached to X. In certain embodiments, Cy' is a substituted or unsubstituted bicyclic or heteroaryl ring, preferably both bicyclic and heteroaryl, such as benzothiophene, benzofuran, benzopyrrole, benzopyridine, etc. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system. In certain embodiments, Cy' represents a benzo[b]thien-2-yl, preferably a 3-chloro-benzo[b]thien-2-yl, 3-fluoro-benzo[b]thien-2-yl, or 3-methyl-benzo[b]thien-2-yl, e.g., wherein the benzo ring is substituted with from 1-4 substituents selected from halogen, nitro, cyano, methyl (e.g., including halomethyl, such as $CHCl_2$ and $CF_3$), and ethyl (e.g., including haloethyl, such as $CH_2CCl_3$, $C_2F_5$, etc.), preferably from halogen and methyl (e.g., including halomethyl, such as $CHCl_2$ and $CF_3$). In certain such embodiments Cy' represents a 3-chloro-benzo[b]thien-2-yl, 3-fluoro-benzo[b]thien-2-yl, or 3-methyl-benzo[b]thien-2-yl wherein the benzo ring is substituted with fluoro at the 4-position (peri to the 3-substituent on the thienyl ring) and, optionally, at the 7-position ('peri' to the S of the thienyl ring).

In certain embodiments, X is selected from —C(=O)—, —C(=S)—, and —$S(O_2)$—.

In certain embodiments, substituents on Ar or Z, where Z is an aryl or heteroaryl ring, are selected from halogen, lower alkyl, lower alkenyl, aryl, heteroaryl, carbonyl, thiocarbonyl, ketone, aldehyde, amino, acylamino, cyano, nitro, hydroxyl, azido, sulfonyl, sulfoxido, sulfate, sulfonate, sulfamoyl, sulfonamido, phosphoryl, phosphonate, phosphinate, —$(CH_2)_p$alkyl, —$(CH_2)_p$alkenyl, —$(CH_2)_p$alkynyl, —$(CH_2)_p$aryl, —$(CH_2)_p$aralkyl, —$(CH_2)_p$OH, —$(CH_2)_p$O-lower alkyl, —$(CH_2)_p$O-lower alkenyl, —O$(CH_2)_n$R, —$(CH_2)_p$SH, —$(CH_2)_p$S-lower alkyl, —$(CH_2)_p$S-lower alkenyl, —$S(CH_2)_n$R, —$(CH_2)_p$N$(R)_2$, —$(CH_2)_p$NR-lower alkyl, —$(CH_2)_p$NR-lower alkenyl, —NR$(CH_2)_n$R, and protected forms of the above, wherein n and p, individually for each occurrence, represent integers from 0 to 10, preferably from 0 to 5.

In certain embodiments, Z is directly attached to Ar, or attached to Ar through a chain of one or two atoms. In certain embodiments, Z—Y-M, taken together, is absent.

In certain embodiments, compounds useful in the present invention may be represented by general formula (XI):

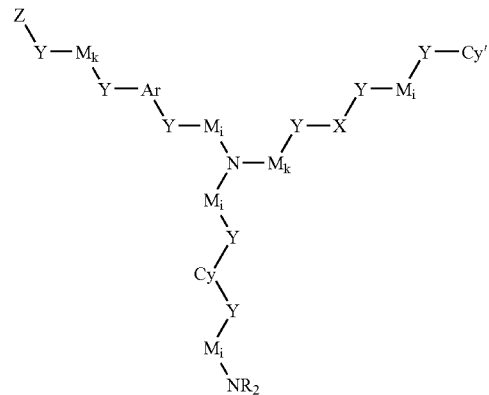

Formula XI wherein, as valence and stability permit,

Ar represents a substituted or unsubstituted aryl or heteroaryl ring;

Z is absent or represents a substituted or unsubstituted aryl, carbocyclyl, heterocyclyl, or heteroaryl ring, or a lower alkyl, nitro, cyano, or halogen substituent;

Y, independently for each occurrence, is absent or represents —N(R)—, —O—, —S—, or —Se—, provided that if Z is not a ring, then Y attached to Z is absent;

X is selected from —C(=O)—, —C(=S)—, —$S(O_2)$—, —S(O)—, —C(=NCN)—, —P(=O)(OR)—, and a methylene group optionally substituted with 1-2 groups such as lower alkyl, alkenyl, or alkynyl groups;

M represents, independently for each occurrence, a substituted or unsubstituted methylene group, such as —$CH_2$—, —CHF, —CHOH—, —CH(Me)—, —C(=O)—, etc., or two M taken together represent substituted or unsubstituted ethene or ethyne;

R represents, independently for each occurrence, H or substituted or unsubstituted aryl, heterocyclyl, carbocyclyl, heteroaryl, aralkyl, heteroaralkyl, heterocyclylalkyl, carbocyclylalkyl, alkynyl, alkenyl, or alkyl, or two R taken together may form a 4- to 8-membered ring, e.g., with N;

Cy and Cy' independently represent substituted or unsubstituted aryl, heterocyclyl, heteroaryl, or cycloalkyl, including polycyclic groups;

i represents, independently for each occurrence, an integer from 0 to 5, preferably from 0 to 2; and k represents an integer from 0 to 3, preferably from 0 to 2.

In certain embodiments, $NR_2$ represents a primary amine or a secondary or tertiary amine substituted with one or two lower alkyl groups, aryl groups, or aralkyl groups, respectively, preferably a primary or secondary amine.

In certain embodiments, M represents, independently for each occurrence, a substituted or unsubstituted methylene group, such as —$CH_2$—, —CHF—, —CHOH—, —CH(Me)-, —C(=O)—, etc.

In certain embodiments, Ar and Z independently represent substituted or unsubstituted aryl or heteroaryl rings, e.g., unsubstituted or substituted with one or more groups optionally including heteroatoms such as O, N, and S. In certain embodiments, at least one of Ar and Z represents a phenyl ring. In certain embodiments, at least one of Ar and Z represents a heteroaryl ring, e.g., a pyridyl, thiazolyl, thienyl, pyrimidyl, furanyl, etc. In certain embodiments, the occurrences of Y attached to Ar are disposed in a meta and/or 1,3-relationship.

In certain embodiments, Y is absent from all positions. In certain embodiments, the only present occurrence of Y is attached to $M_k$. In embodiments wherein Y is present in a position, i or k preferably represents 2 in an adjacent $M_{i/k}$ if i/k=0 would result in two occurrences of Y being directly attached to each other, or an occurrence of Y being directly attached to N. In certain embodiments, where two occurrences of Y are attached to M, at least one such occurrence of Y is absent. In certain embodiments, no more than two occurrences of Y are present.

In certain embodiments, Cy' is a substituted or unsubstituted aryl or heteroaryl. In certain embodiments, Cy' is directly attached to X. In certain embodiments, Cy' is a substituted or unsubstituted bicyclic or heteroaryl ring, preferably both bicyclic and heteroaryl, such as benzothiophene, benzofuran, benzopyrrole, benzopyridine, etc. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system. In certain embodiments, Cy' represents a benzo[b]thien-2-yl, preferably a 3-chloro-benzo[b]thien-2-yl, 3-fluoro-benzo[b]thien-2-yl, or 3-methyl-benzo(b)thien-2-yl, e.g., wherein the benzo ring is substituted with from 14 substituents selected from halogen, nitro, cyano, methyl (e.g., including halomethyl, such as $CHCl_2$ and $CF_3$), and ethyl (e.g., including haloethyl, such as $CH_2CCl_3$, $C_2F_5$, etc.), preferably from halogen and methyl (e.g., including halomethyl, such as $CHCl_2$ and $CF_3$). In certain such embodiments Cy' represents a 3-chloro-benzo[b]thien-2-yl, 3-fluoro-benzo[b]thien-2-yl, or 3-methyl-benzo[b]thien-2-yl wherein the benzo ring is substituted with fluoro at the 4-position (peri to the 3-substituent on the thienyl ring) and, optionally, at the 7-position ('peri' to the S of the thienyl ring).

In certain embodiments, Cy represents a substituted or unsubstituted non-aromatic carbocyclic or heterocyclic ring, i.e., including at least one $sp^3$ hybridized atom, and preferably a plurality of $sp^3$ hybridized atoms. In certain embodiments, Cy is a 5- to 7-membered ring. In certain embodiments, Cy is directly attached to N and/or to $NR_2$. In embodiments wherein Cy is a six-membered ring directly attached to N and bears an amino substituent at the 4 position of the ring relative to N, the N and amine substituents may be disposed trans on the ring.

In certain embodiments, X is selected from —C(=O)—, —C(=S)—, and —S(O_2)—.

In certain embodiments, substituents on Ar or Z, where Z is an aryl or heteroaryl ring, are selected from halogen, lower alkyl, lower alkenyl, aryl, heteroaryl, cabonyl, thiocarbonyl, ketone, aldehyde, amino, acylamino, cyano, nitro, hydroxyl, azido, sulfonyl, sulfoxido, sulfate, sulfonate, sulfamoyl, sulfonamido, phosphoryl, phosphonate, phosphinate, —$(CH_2)_p$alkyl, —$(CH_2)_p$alkenyl, —$(CH_2)_p$alkynyl, —$(CH_2)_p$aryl, —$(CH_2)_p$aralkyl, —$(CH_2)_p$OH, —$(CH_2)_p$O-lower alkyl, $(CH_2)_p$O-lower alkenyl, —O$(CH_2)_n$R, —$(CH_2)_p$SH, —$(CH_2)_p$S-lower alkyl, —$(CH_2)_p$S-lower alkenyl, —S$(CH_2)_n$R, —$(CH_2)_p$N(R)$_2$, —$(CH_2)_p$NR-lower alkyl, —$(CH_2)_p$NR-lower alkenyl, —NR$(CH_2)_n$R, and protected forms of the above, wherein n and p, individually for each occurrence, represent integers from 0 to 10, preferably from 0 to 5.

In certain embodiments, Z is directly attached to Ar, or attached to Ar through a chain of one or two atoms. In certain embodiments, Z—Y-M, taken together, is absent.

In certain embodiments, compounds useful in the present invention may be represented by general formula (XII):

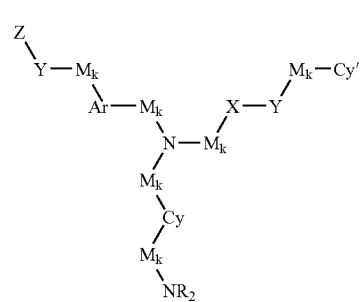

Formula XII wherein, as valence and stability permit,

Ar represents a substituted or unsubstituted aryl or heteroaryl ring;

Z is absent or represents a substituted or unsubstituted aryl, carbocyclyl, heterocyclyl, or heteroaryl ring, or a lower alkyl, nitro, cyano, or halogen substituent;

Y, independently for each occurrence, is absent or represents —N(R)—, —O—, —S—, or —Se—, provided that if Z is not a ring, then Y attached to Z is absent;

X is selected from —C(=O)—, —C(=S)—, —S(O$_2$)—, —S(O)—, —C(=NCN)—, —P(=O)(OR)—, and a methylene group optionally substituted with 1-2 groups such as lower alkyl, alkenyl, or alkynyl groups;

M represents, independently for each occurrence, a substituted or unsubstituted methylene group, such as —CH$_2$—, —CHF—, —CHOH—, —CH(Me)—, —C(=O)—, etc., or two M taken together represent substituted or unsubstituted ethene or ethyne;

R, independently for each occurrence, represents H or substituted or unsubstituted aryl, heterocyclyl, carbocyclyl, heteroaryl, aralkyl, heteroaralkyl, heterocyclylalkyl, carbocyclylalkyl, alkynyl, alkenyl, or alkyl;

Cy and Cy' independently represent substituted or unsubstituted aryl, heterocyclyl, heteroaryl, or cycloalkyl, including polycyclic groups; and represents an integer from 0 to 1.

In certain embodiments, NR$_2$ represents a primary amine or a secondary or tertiary amine substituted with one or two lower alkyl groups, respectively, preferably a primary or secondary amine, most preferably a secondary amine.

In certain embodiments, M represents, independently for each occurrence, a substituted or unsubstituted methylene group, such as —CH$_2$—, —CHF—, —CHOH—, —CH(Me)-, —C(=O)—, etc.

In certain embodiments, Y is absent from all positions. In certain embodiments, where Y is adjacent to $M_k$, either Y is absent or k=0. In certain embodiments, for at least one occurrence of $M_k$ attached to Cy, k=0, optionally for both occurrences. In certain embodiments, for $M_k$ attached to Ar and N, k=1.

In certain embodiments, Ar and Z independently represent substituted or unsubstituted aryl or heteroaryl rings, e.g., unsubstituted or substituted with one or more groups optionally including heteroatoms such as O, N, and S. In certain embodiments, at least one of Ar and Z represents a phenyl ring. In certain embodiments, at least one of Ar and Z represents a heteroaryl ring, e.g., a pyridyl, thiazolyl, thienyl, pyrimidyl, furanyl, etc. In certain embodiments, the occurrences of $M_k$ attached to Ar are disposed in a meta and/or 1,3-relationship.

In certain embodiments, Cy' is a substituted or unsubstituted aryl or heteroaryl. In certain embodiments, Cy' is directly attached to X. In certain embodiments, Cy' is a substituted or unsubstituted bicyclic or heteroaryl ring, preferably both bicyclic and heteroaryl, such as benzothiophene, benzofuran, benzopyrrole, benzopyridine, etc. In certain embodiments, Cy' is a monocyclic aryl or heteroaryl ring substituted at least with a substituted or unsubstituted aryl or heteroaryl ring, i.e., forming a biaryl system. In certain embodiments, Cy' includes two substituted or unsubstituted aryl or heteroaryl rings, e.g., the same or different, directly connected by one or more bonds, e.g., to form a biaryl or bicyclic ring system. In certain embodiments, Cy' represents a benzo[b]thien-2-yl, preferably a 3-chloro-benzo[b]thien-2-yl, 3-fluoro-benzo[b]thien-2-yl, or 3-methyl-benzo[b]thien-2-yl, e.g., wherein the benzo ring is substituted with from 1-4 substituents selected from halogen, nitro, cyano, methyl (e.g., including halomethyl, such as $CHCl_2$ and $CF_3$), and ethyl (e.g., including haloethyl, such as $CH_2CCl_3$, $C_2F_5$, etc.), preferably from halogen and methyl (e.g., including halomethyl, such as $CHCl_2$ and $CF_3$). In certain such embodiments Cy' represents a 3-chloro-benzo[b]thien-2-yl, 3-fluoro-benzo[b]thien-2-yl, or 3-methyl-benzo[b]thien-2-yl wherein the benzo ring is substituted with fluoro at the 4-position (peri to the 3-substituent on the thienyl ring) and, optionally, at the 7-position ('peri' to the S of the thienyl ring).

In certain embodiments, Cy represents a substituted or unsubstituted non-aromatic carbocyclic or heterocyclic ring, i.e., including at least one $sp^3$ hybridized atom, and preferably a plurality of $sp^3$ hybridized atoms. In certain embodiments, Cy is a 5- to 7-membered ring. In certain embodiments, Cy is directly attached to N and/or to $NR_2$. In embodiments wherein Cy is a six-membered ring directly attached to N and bears an amino substituent at the 4 position of the ring relative to N, the N and amino substituents may be disposed trans on the ring.

In certain embodiments, X is selected from —C(=O)—, —C(=S)—, and —S($O_2$)—.

In certain embodiments, substituents on Ar or Z, where Z is an aryl or heteroaryl ring, are selected from halogen, lower alkyl, lower alkenyl, aryl, heteroaryl, carbonyl, thiocarbonyl, ketone, aldehyde, amino, acylamino, cyano, nitro, hydroxyl, sulfonyl, sulfoxido, sulfate, sulfonate, sulfamoyl, sulfonamido, —$(CH_2)_p$alkyl, —$(CH_2)_p$alkenyl, —$(CH_2)_p$alkynyl, —$(CH_2)_p$OH, —$(CH_2)_p$O-lower alkyl, —$(CH_2)_p$O-lower alkenyl, —O$(CH_2)$nR, —$(CH_2)_p$SH, —$(CH_2)_p$S-lower alkyl, —$(CH_2)_p$S-lower alkenyl, —S$(CH_2)_n$R, —$(CH_2)_p$N(R)$_2$, —$(CH_2)_p$NR-lower alkyl, —$(CH_2)_p$NR-lower alkenyl, —NR$(CH_2)_n$R, and protected forms of the above, wherein n and p, individually for each occurrence, represent integers from 0 to 10, preferably from 0 to 5.

In certain embodiments, Z is directly attached to Ar, or attached to Ar through a chain of one or two atoms. In certain embodiments, Z—Y-M, taken together, is absent In certain embodiments, the subject agonists can be chosen on the basis of their selectively for the hedgehog pathway. This selectivity can be for the hedgehog pathway versus other pathways, or for selectivity between particular hedgehog pathways, e.g., ptc-1, ptc-2, etc.

In certain preferred embodiments, the subject agonists modulate ptc-smo mediated signal transduction with an $ED_{50}$ of 1 mM or less, more preferably of 1 μM or less, and even more preferably of 1 nM or less. For hedgehog-dependent agonists, the subject agonists increase the activity of hedgehog 10-fold, 100-fold, or even 1000-fold.

In particular embodiments, the small molecule is chosen for use because it is more selective for one patched isoform over the next, e.g., 10-fold, and more preferably at least 100- or even 1000-fold more selective for one patched pathway (ptc-1, ptc-2) over another.

In certain embodiments, a compound which is an agonist of the hedgehog pathway is chosen to selectively agonize hedgehog activity over protein kinases other than PKA, such as PKC, e.g., the compound modulates the activity of the PKA/hedgehog pathway at least an order of magnitude more strongly than it modulates the activity of another protein kinase, preferably at least two orders of magnitude more strongly, even more preferably at least three orders of magnitude more strongly. Thus, for example, a preferred activator of the hedgehog pathway may activate hedgehog activity with a $K_i$ at least an order of magnitude lower than its $K_i$ for activation of PKC, preferably at least two orders of magnitude lower, even more preferably at least three orders of magnitude lower. In certain embodiments, the $K_i$ for PKA/hedgehog activation is less than 10 nM, preferably less than 1 nM, even more preferably less than 0.1 μM.

Synthesis of Subject Compounds

Compounds of the present invention can be readily prepared by standard techniques of organic synthesis, e.g., according to examples set forth in the Exemplification below. For example, a subject compound may be prepared by reacting a compound or pair of compounds designated A with a compound or pair of compounds designated B and a compound designated C, as set forth below:

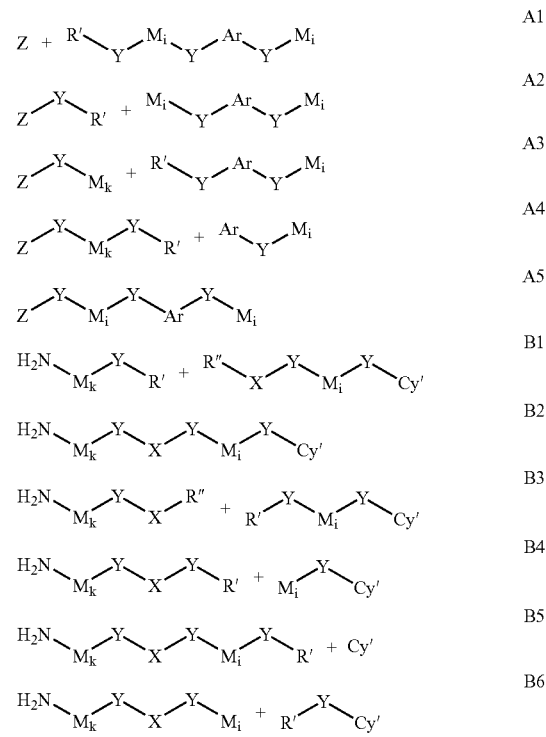

-continued

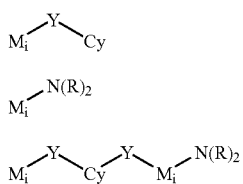

Similarly, a compound designated C above may be reacted with a compound or pair of compounds designated D and a compound or pair of compounds designated E:

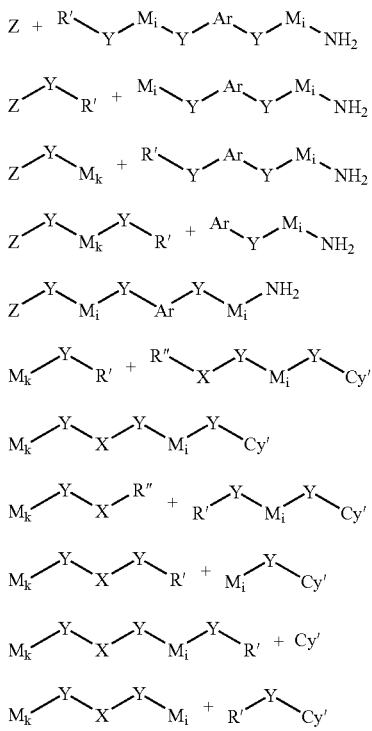

Alternatively, a compound or pair of compounds designated A above and a compound or pair of compounds designated E above may be reacted with a compound designated F:

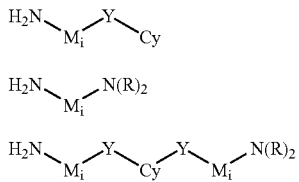

Combinations of compounds as indicated above are preferably reacted with each other in series, e.g., two compounds are reacted together, the product is reacted with a third compound, etc., and the compounds can generally be coupled in series in any order, as will be understood by one of skill in the art. In certain embodiments, functional groups on one or more compounds may require protection during one or more reactions, as is well understood in the art, and any suitable protecting groups can be employed for this purpose. One of skill in the art can readily select suitable protecting groups for a particular functional group and a particular reaction. Elaboration steps may be performed at any time to modify functional groups or moieties on the product of a reaction, for example, to convert $N(R)_2 = NH_2$ to $N(R)_2 = NHR$, e.g., by nucleophilic substitution, reductive alkylation, or any other suitable method.

In the compounds designated A-F above, the elements M, X, Y, Z, Cy, Cy', Ar, i, k, R, etc. are defined as above (as may be broadened by the description below), and R' independently for each occurrence represents H, a protecting group, or a labile reactive group, such as a trialkylsilyl (e.g., trimethylsilyl) group, and R" independently for each occurrence represents 1) a leaving group, such as a halogen (e.g., F, Cl, Br, or I), alkylthio, cyano, alkoxy, or any other group capable of being replaced by an amine nucleophile when attached to X, 2) an activatable group, such as OH, that can be activated by an activating agent, such as a carbodiimide (e.g., diisopropylcarbodiimide, dicyclohexylcarbodiimide, 1-(3-dimethylaminopropyl)-3-ethylcarbodiimide, etc.), phosphorous-based reagents (such as BOP—Cl, PyBROP, etc.), oxalyl chloride, phosgene, triphosgene, or any similar reagent, to result in a reactive intermediate having an increased susceptibility, relative to the compound wherein R"=OH, towards coupling with an amine, or 3) X and R" taken together represent an electrophilic group capable of reacting with an amine, such as an isocyanate, isothiocyanate, or other similar reactive moiety.

The various subunits designated A-F can be combined using any of a plethora of reactions well known to those of skill in the art, depending on the particular moieties to be coupled. For example, an amine, such as one of the $NH_2$ groups indicated on the subunits A-F, can be coupled with an alkyl group by reductive alkylation (e.g., the terminal occurrence of M is an aldehyde), by nucleophilic displacement of a leaving group (such as a halogen, sulfonate, or other suitable substituent), by nucleophilic opening of an epoxide, or by any other suitable reaction known to those of skill in the art. Similarly, amines can be coupled with activated carboxylic acid derivatives or thiocarboxylic acid derivatives, e.g., prepared in situ from a carboxylic acid or thiocarboxylic acid and an activating agent or prepared as isolated compounds such as isocyanates, carboxylic acid chlorides, etc., to provide amides, ureas, thioureas, thioamides, etc., with chloroformate esters, sulfonyl chlorides, or other such compounds to provide urethanes, sulfonamides, etc., or with other electrophilic reagents that form a covalent bond with an amine.

Aryl and/or heteroaryl rings can be readily coupled directly using Stille, Suzuki, or other related reactions, such as palladium-mediated cross-coupling reactions. Aryl and/or heteroaryl rings can be readily coupled through a heteroatom, e.g., using reactions such as the Ullman reaction, any of various palladium-mediated reactions developed by S. Buchwald and others, by nucleophilic aromatic substitution, or other such reactions. Similarly, amines, alcohols, thiols, and other such heteroatom-bearing compounds can be coupled to aryl and/or heteroaryl rings using palladium-mediated reactions developed by S. Buchwald and others, nucleophilic aromatic substitution, etc. Aryl and/or heteroaryl rings linked by substituted or unsubstituted hydrocarbon chains can be prepared by Stille, Suzuki, Heck, Friedel-Crafts, and other reactions as will be apparent to those of skill in the art.

A survey of a number of common synthetic reactions potentially useful for preparing compounds of the present invention are described in greater detail below and in FIGS.

1-31. The variable groups included in the subunits designated A-F above can be varied to correspond with any of the Formulae I-VIII and X-XII without departing from the general synthesis approaches outlined above.

Similarly, compounds of the present invention can be prepared by coupling a suitable moiety to a partially assembled structure. For example, a compound of Formula XI can be prepared by any of the steps I-VI shown in the scheme below.

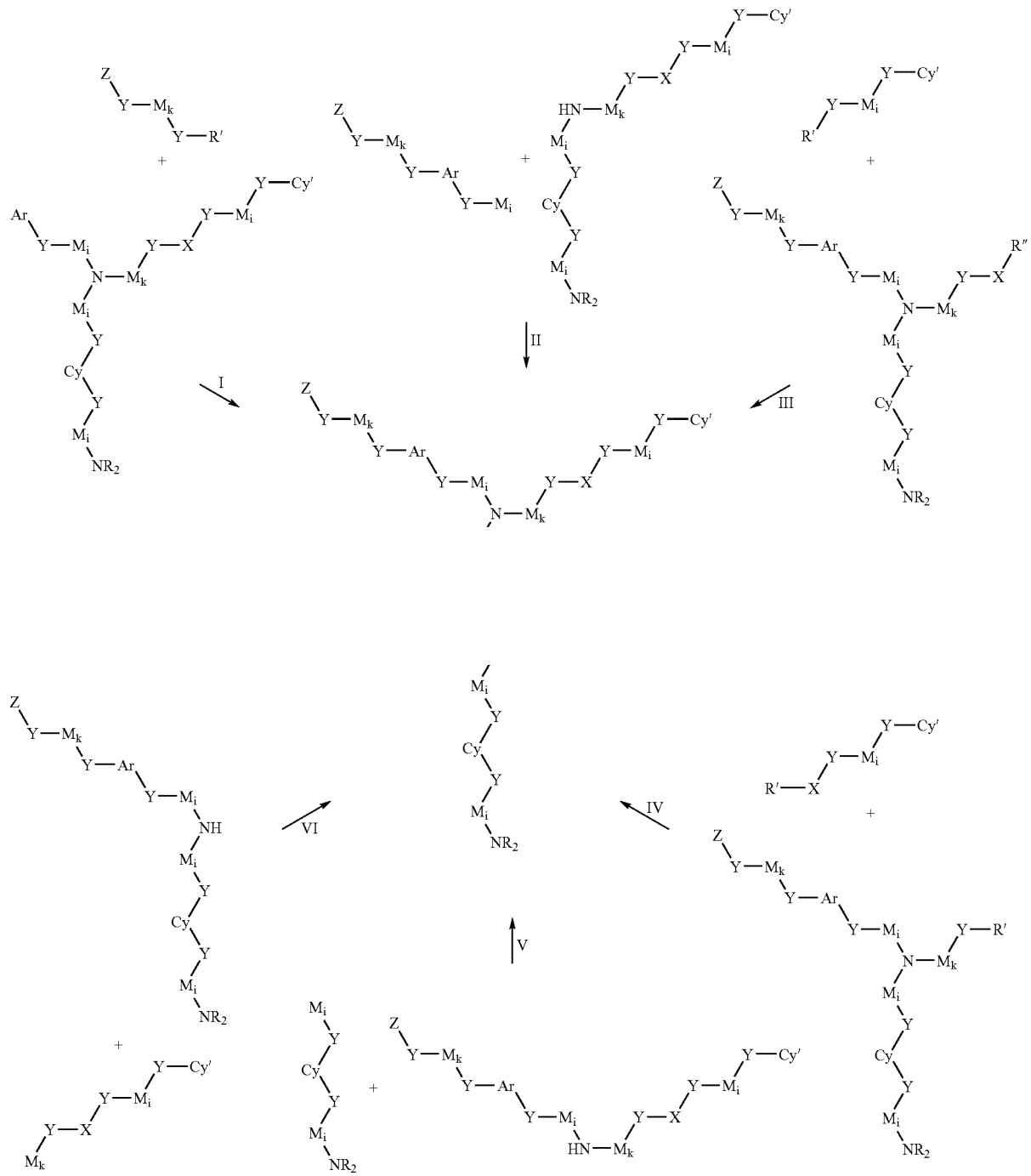

Similarly, a compound of Formula X may be prepared by any of the steps in the scheme below.
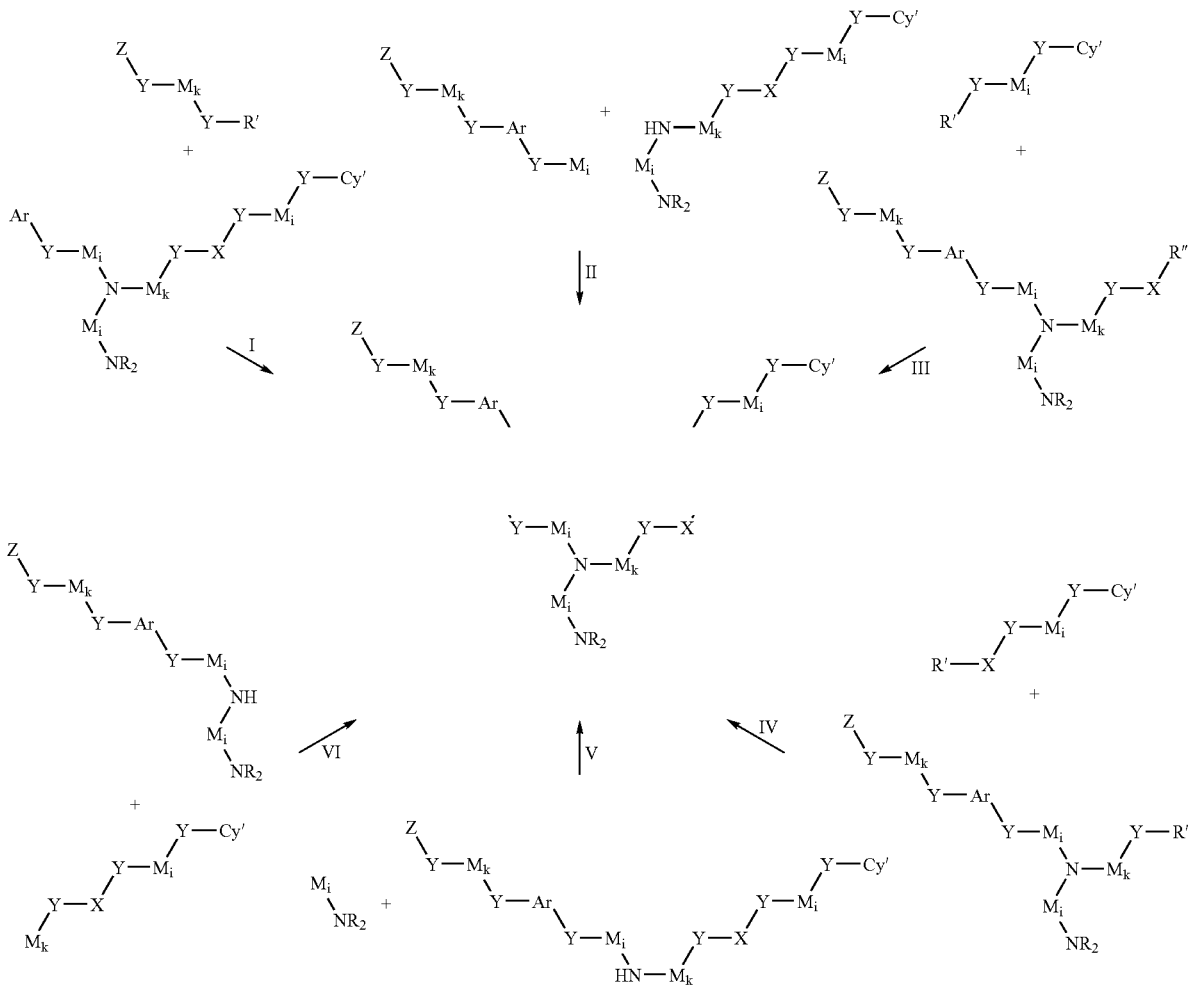
By analogy, a compound of Formula XII can be prepared by any of the steps set forth in the scheme below.
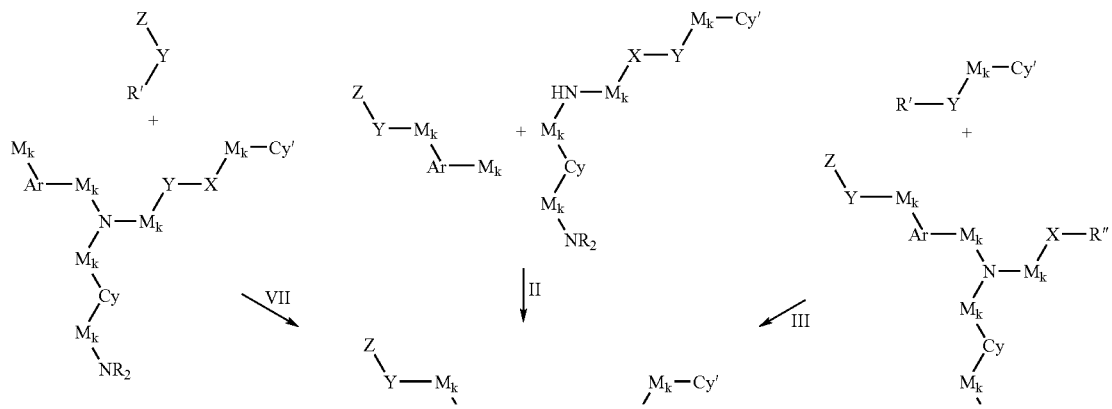

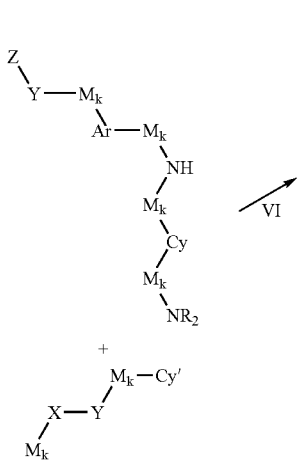
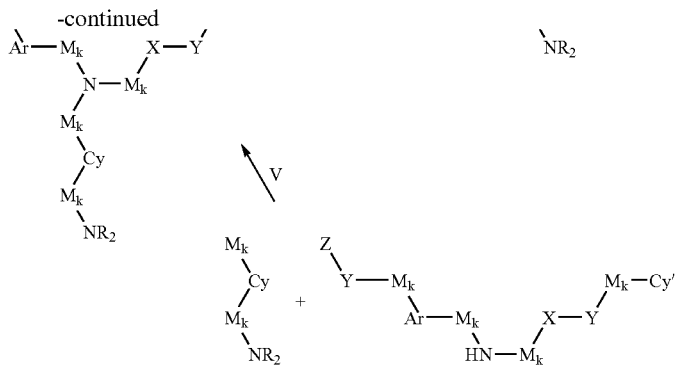

In the schemes above, M, Cy, Ar, X, Cy', Y, Z, R, i, k, R', and R" correspond to their use above, and can be more narrowly defined as set forth in the description of Formulae X-XII, or to correspond to elements of Formulae I-VIII, optionally as modified by the description accompanying Formulae I-VIII.

Reactions suitable for performing Step I include palladium-mediated reactions developed by S. Buchwald and others, nucleophilic aromatic substitution, oxidative coupling, etc.

Reactions suitable for performing Step II include nucleophilic displacement of a leaving group on M, reductive alkylation, reaction of the amine with an electrophilic carboxylic/thiocarboxylic acid derivative (acid chloride, isocyanate, isothiocyanate, or a carboxylic acid activated by BOP—Cl, PyBrOP, carbodiimide, or another activating reagent (such as are commonly used in the art of peptide coupling)), or other similar reactions, including those set forth in detail in certain of FIGS. 1-31 and the accompanying description below, or, where M and Y are absent, a palladium-mediated coupling as developed by Buchwald and others.

Reactions suitable for performing Steps III or IV include reaction of Y—R' with an electrophilic carbonyl or sulfonyl derivative (X—R"=acid chloride, isocyanate, isothiocyanate; chloroformate, sulfonyl chloride, or an acid activated by BOP—Cl, PyBrOP, carbodiimide, or another activating reagent (such as are commonly used in the art of peptide coupling)), or other similar reactions, such as those set forth in detail in certain of FIGS. 1-31 and the accompanying description below.

Reactions suitable for performing Step V include nucleophilic displacement of a leaving group, reductive alkylation, reaction of the amine with an electrophilic carboxylic/thiocarboxylic acid derivative (acid chloride, isocyanate, isothiocyanate, or a carboxylic acid activated by BOP—Cl, PyBrOP, carbodiimide, or another activating reagent (such as are commonly used in the art of peptide coupling)), or other similar reactions, including those set forth in detail in certain of FIGS. 1-31 and the accompanying description below.

Reactions suitable for performing Step VI include nucleophilic displacement of a leaving group, reductive alkylation, reaction of the amine with an electrophilic carboxylic/thiocarboxylic acid derivative (acid chloride, isothiocyanate, isocyanate, or a carboxylic acid activated by BOP—Cl, PyBrOP, carbodiimide, or another activating reagent (such as are commonly used in the art of peptide coupling)), or other similar reactions, including those set forth in detail in certain of FIGS. 1-31 and the accompanying description below.

Reactions suitable for performing Step VII where Y is coupled with a present occurrence of M include nucleophilic displacement of a leaving group, reductive alkylation, reaction of the amine with an electrophilic carboxylic/thiocarboxylic acid derivative (acid chloride, isocyanate, isothiocyanate, or a carboxylic acid activated by BOP—Cl, PyBrOP, carbodiimide, or another activating reagent (such as are commonly used in the art of peptide coupling)), or other similar reactions, including those set forth in detail in certain of FIGS. 1-31 and the accompanying description below. In embodiments where occurrences of M is absent, suitable coupling reactions include palladium-mediated reactions developed by S. Buchwald and others, nucleophilic aromatic substitution, oxidative coupling, etc. In embodiments where M and Y are absent and Z represents an aryl or heteroaryl ring, suitable reactions include Stille, Suzuki, and other reactions suitable for forming biaryl systems.

Methods of the invention further include reacting a compound of any of Formulae I-VII wherein at least one R of $NR_2$ represents H under conditions which convert that compound to a compound of the same formula wherein the corresponding occurrence of R represents a lower alkyl group. For example, reductive alkylations with an aldehyde and a reducing agent, nucleophilic alkylations with an alkyl halide such as MeI, or other similar reactions may be employed. In certain embodiments, such reactions may proceed through a silylated (e.g., $R=SiMe_3$) intermediate.

One of skill in the art will readily appreciate that compounds of the present invention are amenable to synthesis according to a wide array of protocols well known in the art in addition to those described herein, all of which are intended to fall within the scope of the present invention.

IV. Exemplary Applications of Method and Compositions

Another aspect of the present invention relates to a method of modulating a differentiated state, survival, and/or proliferation of a cell, by contacting the cell with a hedgehog agonist according to the subject method and as the circumstances may warrant.

For instance, it is contemplated by the invention that, in light of the findings of an apparently broad involvement of hedgehog, ptc, and smoothened in the formation of ordered spatial arrangements of differentiated tissues in vertebrates, the subject method could be used as part of a process for generating and/or maintaining an array of different vertebrate tissue both in vitro and in vivo. The hedgehog agonist, whether inductive or anti-inductive with respect proliferation or differentiation of a given tissue, can be, as appropriate, any of the preparations described above.

For example, the present method is applicable to cell culture techniques. In vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). One use of the present method may be in cultures of neuronal stem cells, such as in the use of such cultures for the generation of new neurons and glia. In such embodiments of the subject method, the cultured cells can be contacted with a hedgehog agonist of the present invention in order to alter the rate of proliferation of neuronal stem cells in the culture and/or alter the rate of differentiation, or to maintain the integrity of a culture of certain terminally differentiated neuronal cells. In an exemplary embodiment, the subject method can be used to culture, for example, sensory neurons or, alternatively, motor neurons. Such neuronal cultures can be used as convenient assay systems as well as sources of implantable cells for therapeutic treatments.

According to the present invention, large numbers of non-tumorigenic neural progenitor cells can be perpetuated in vitro and their rate of proliferation and/or differentiation can be affected by contact with hedgehog agonists of the present invention. Generally, a method is provided comprising the steps of isolating neural progenitor cells from an animal, perpetuating these cells in vitro or in vivo, preferably in the presence of growth factors, and regulating the differentiation of these cells into particular neural phenotypes, e.g., neurons and glia, by contacting the cells with a hedgehog agonist.

Progenitor cells are thought to be under a tonic inhibitory influence which maintains the progenitors in a suppressed state until their differentiation is required. However, recent techniques have been provided which permit these cells to proliferate, and unlike neurons which are terminally differentiated and therefore non-dividing, they can be produced in unlimited number and are highly suitable for transplantation into heterologous and autologous hosts with neurodegenerative diseases.

By "progenitor" it is meant an oligopotent or multipotent stem cell which is able to divide without limit and, under specific conditions, can produce daughter cells which terminally differentiate such as into neurons and glia. These cells can be used for transplantation into a heterologous or autologous host. By heterologous is meant a host other than the animal from which the progenitor cells were originally derived. By autologous is meant the identical host from which the cells were originally derived.

Cells can be obtained from embryonic, post-natal, juvenile or adult neural tissue from any animal. By any animal is meant any multicellular animal which contains nervous tissue. More particularly, is meant any fish, reptile, bird, amphibian or mammal and the like. The most preferable donors are mammals, especially mice and humans.

In the case of a heterologous donor animal, the animal may be euthanized, and the brain and specific area of interest removed using a sterile procedure. Brain areas of particular interest include any area from which progenitor cells can be obtained which will serve to restore function to a degenerated area of the host's brain. These regions include areas of the central nervous system (CNS) including the cerebral cortex, cerebellum, midbrain, brainstem, spinal cord and ventricular tissue, and areas of the peripheral nervous system (PNS) including the carotid body and the adrenal medulla. More particularly, these areas include regions in the basal ganglia, preferably the striatum which consists of the caudate and putamen, or various cell groups such as the globus pallidus, the subthalamic nucleus, the nucleus basalis which is found to be degenerated in Alzheimer's disease patients, or the substantia nigra pars compacta which is found to be degenerated in Parkinson's disease patients.

Human heterologous neural progenitor cells may be derived from fetal tissue obtained from elective abortion, or from a post-natal, juvenile or adult organ donor. Autologous neural tissue can be obtained by biopsy, or from patients undergoing neurosurgery in which neural tissue is removed, in particular during epilepsy surgery, and more particularly during temporal lobotomies and hippocampalectomies.

Cells can be obtained from donor tissue by dissociation of individual cells from the connecting extracellular matrix of the tissue. Dissociation can be obtained using any known procedure, including treatment with enzymes such as trypsin, collagenase and the like, or by using physical methods of dissociation such as with a blunt instrument or by mincing with a scalpel to a allow outgrowth of specific cell types from a tissue. Dissociation of fetal cells can be carried out in tissue culture medium, while a preferable medium for dissociation of juvenile and adult cells is artificial cerebral spinal fluid (aCSF). Regular aCSF contains 124 mM NaCl, 5 mM KCl, 1.3 mM $MgCl_2$, 2 mM $CaCl_2$, 26 mM $NaHCO_3$, and 10 mM D-glucose. Low $Ca^{2+}$ aCSF contains the same ingredients except for $MgCl_2$ at a concentration of 3.2 mM and $CaCl_2$ at a concentration of 0.1 mM.

Dissociated cells can be placed into any known culture medium capable of supporting cell growth, including MEM, DMEM, RPMI, F-12, and the like, containing supplements which are required for cellular metabolism such as glutamine and other amino acids, vitamins, minerals and useful proteins such as transferrin and the like. Medium may also contain antibiotics to prevent contamination with yeast, bacteria and fungi such as penicillin, streptomycin, gentamicin and the like. In some cases, the medium may contain serum derived from bovine, equine, chicken and the like. A particularly preferable medium for cells is a mixture of DMEM and F-12.

Conditions for culturing should be close to physiological conditions. The pH of the culture media should be close to physiological pH, preferably between pH 6-8, more preferably close to pH 7, even more particularly about pH 7.4. Cells should be cultured at a temperature close to physiological temperature, preferably between 30° C.-40° C., more preferably between 32° C.-38° C., and most preferably between 35° C.-37° C.

Cells can be grown in suspension or on a fixed substrate, but proliferation of the progenitors is preferably done in suspension to generate large numbers of cells by formation of "neurospheres" (see, for example, Reynolds et al. (1992) *Science* 255:1070-1709; and PCT Publications WO93101275, WO94/09119, WO94/10292, and WO94/16718). In the case of propagating (or splitting) suspension cells, flasks are shaken well and the neurospheres allowed to settle on the bottom corner of the flask. The spheres are then transferred to a 50 ml centrifuge tube and centrifuged at low speed. The medium is aspirated, the cells resuspended in a small amount of medium with growth factor, and the cells mechanically dissociated and resuspended in separate aliquots of media.

Cell suspensions in culture medium are supplemented with any growth factor which allows for the proliferation of progenitor cells and seeded in any receptacle capable of sustaining cells, though as set out above, preferably in culture flasks or roller bottles. Cells typically proliferate within 3-4 days in a 37° C. incubator, and proliferation can be reinitiated at any time after that by dissociation of the cells and resuspension in fresh medium containing growth factors.

In the absence of substrate, cells lift off the floor of the flask and continue to proliferate in suspension forming a hollow sphere of undifferentiated cells. After approximately 3-10 days in vitro, the proliferating clusters (neurospheres) are fed every 2-7 days, and more particularly every 24 days by gentle centrifugation and resuspension in medium containing growth factor.

After 6-7 days in vitro, individual cells in the neurospheres can be separated by physical dissociation of the neurospheres with a blunt instrument, more particularly by triturating the neurospheres with a pipette. Single cells from the dissociated neurospheres are suspended in culture medium containing growth factors, and differentiation of the cells can be control in culture by plating (or resuspending) the cells in the presence of a hedgehog agonist.

To further illustrate other uses of the subject hedgehog agonists, it is noted that intracerebral grafting has emerged as an additional approach to central nervous system therapies. For example, one approach to repairing damaged brain tissues involves the transplantation of cells from fetal or neonatal animals into the adult brain (Dunnett et al. (1987) *J Exp Biol* 123:265-289; and Freund et al. (1985) *J Neurosci* 5:603-616). Fetal neurons from a variety of brain regions can be successfully incorporated into the adult brain, and such grafts can alleviate behavioral defects. For example, movement disorder induced by lesions of dopaminergic projections to the basal ganglia can be prevented by grafts of embryonic dopaminergic neurons. Complex cognitive functions that are impaired after lesions of the neocortex can also be partially restored by grafts of embryonic cortical cells. The subject method can be used to regulate the growth state in the culture, or where fetal tissue is used, especially neuronal stem cells, can be used to regulate the rate of differentiation of the stem cells.

Stem cells useful in the present invention are generally known. For example, several neural crest cells have been identified, some of which are multipotent and likely represent uncommitted neural crest cells, and others of which can generate only one type of cell, such as sensory neurons, and likely represent committed progenitor cells. The role of hedgehog agonists employed in the present method to culture such stem cells can be to regulate differentiation of the uncommitted progenitor, or to regulate further restriction of the developmental fate of a committed progenitor cell towards becoming a terminally differentiated neuronal cell. For example, the present method can be used in vitro to regulate the differentiation of neural crest cells into glial cells, schwann cells, chromaffin cells, cholinergic sympathetic or parasympathetic neurons, as well as peptidergic and serotonergic neurons. The hedgehog agonists can be used alone, or can be used in combination with other neurotrophic factors which act to more particularly enhance a particular differentiation fate of the neuronal progenitor cell.

In addition to the implantation of cells cultured in the presence of the subject hedgehog agonists, yet another aspect of the present invention concerns the therapeutic application of a hedgehog agonist to regulate the growth state of neurons and other neuronal cells in both the central nervous system and the peripheral nervous system. The ability of ptc, hedgehog, and smoothened to regulate neuronal differentiation during development of the nervous system and also presumably in the adult state indicates that, in certain instances, the subject hedgehog agonists can be expected to facilitate control of adult neurons with regard to maintenance, functional performance, and aging of normal cells; repair and regeneration processes in chemically or mechanically lesioned cells; and treatment of degeneration in certain pathological conditions. In light of this understanding, the present invention specifically contemplates applications of the subject method to the treatment protocol of (prevention and/or reduction of the severity of) neurological conditions deriving from: (i) acute, subacute, or chronic injury to the nervous system, including traumatic injury, chemical injury, vascular injury and deficits (such as the ischemia resulting from stroke), together with infectious/inflammatory and tumor-induced injury (ii) aging of the nervous system including Alzheimer's disease; (iii) chronic neurodegenerative diseases of the nervous system, including Parkinson's disease, Huntington's chorea, amyotrophic lateral sclerosis and the like, as well as spinocerebellar degenerations; and (iv) chronic immunological diseases of the nervous system or affecting the nervous system, including multiple sclerosis. For example, in the specific case of Parkinson's disease, intervention by increasing the activity of hedgehog by a subject agonist can improve the in vivo survival of fetal and adult dopaminergic neurons, and thus can provide a more effective treatment of this disease. Thus, in one embodiment, the subject method comprises administering to an animal afflicted with Parkinson's disease, or at risk of developing Parkinson's disease, an amount of a hedgehog agonist effective for increasing the rate of survival of dopaminergic neurons in the animal.

The present method is applicable to cell culture techniques. In vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). Once a neuronal cell has become terminally differentiated it typically will not change to another terminally differentiated cell-type. However, neuronal cells can nevertheless readily lose their differentiated state. This is commonly observed when they are grown in culture from adult tissue, and when they form a blastema during regeneration. The present method provides a means for ensuring an adequately restrictive environment in order to maintain dopaminergic and GABAergic cells in differentiated states, and can be employed, for instance, in cell cultures designed to test the specific activities of other trophic factors.

In such embodiments of the subject method, a culture of differentiated cells including dopaminergic and/or GABAergic cells can be contacted with a hedgehog agonist in order to maintain the integrity of a culture of terminally differentiated neuronal cells by preventing loss of differentiation. The subject method can be used in conjunction with agents which induce the differentiation of neuronal precursors, e.g., progenitor or stem cells, into dopaminergic or GABAergic neurons.

Many neurological disorders are associated with degeneration of discrete populations of neuronal elements and may be treatable with a therapeutic regimen which includes a hedgehog agonist. For example, Alzheimer's disease is associated with deficits in several neurotransmitter systems, both those that project to the neocortex and those that reside with the cortex. For instance, the nucleus basalis in patients with Alzheimer's disease have been observed to have a profound (75%) loss of neurons compared to age-matched controls. Although Alzheimer's disease is by far the most common form of dementia, several other disorders can produce dementia. Several of these are degenerative diseases characterized by the death of neurons in various parts of the central nervous system, especially the cerebral cortex. However, some forms of dementia are associated with degeneration of the thalamus or the white matter underlying the cerebral cortex. Here, the cognitive dysfunction results from the isolation of cortical areas by the degeneration of efferents and afferents. Huntington's disease involves the degeneration of intrastriatal and cortical cholinergic neurons and GABAergic neurons. Pick's disease is a severe neuronal degeneration in the neocortex of the frontal and anterior temporal lobes, sometimes accompanied by death of neurons in the striatum. Treatment of patients suffering from such degenerative conditions can include the application of hedgehog agonists in order to control, for example, differentiation and apoptotic events which give rise to loss of neurons (e.g., to enhance survival of existing neurons) as well as promote differentiation and repopulation by progenitor cells in the area affected.

In addition to degenerative-induced dementias, a pharmaceutical preparation of one or more of the subject hedgehog agonists can be applied opportunely in the treatment of neurodegenerative disorders which have manifestations of tremors and involuntary movements. Parkinson's disease, for example, primarily affects subcortical structures and is characterized by degeneration of the nigrostriatal pathway, raphe nuclei, locus cereleus, and the motor nucleus of vagus. Ballism is typically associated with damage to the subthalamic nucleus, often due to acute vascular accident. Also included are neurogenic and myopathic diseases which ultimately affect the somatic division of the peripheral nervous system and are manifest as neuromuscular disorders. Examples include chronic atrophies such as amyotrophic lateral sclerosis, Guillain-Barre syndrome and chronic peripheral neuropathy, as well as other diseases which can be manifest as progressive bulbar palsies or spinal muscular atrophies. The present method is amenable to the treatment of disorders of the cerebellum which result in hypotonia or ataxia, such as those lesions in the cerebellum which produce disorders in the limbs ipsilateral to the lesion. For instance, a preparation of a hedgehog agonist, can used to treat a restricted form of cerebellar cortical degeneration involving the anterior lobes (vermis and leg areas) such as is common in alcoholic patients.

In an illustrative embodiment, the subject method is used to treat amyotrophic lateral sclerosis. ALS is a name given to a complex of disorders that comprise upper and lower motor neurons. Patients may present with progressive spinal muscular atrophy, progressive bulbar palsy, primary lateral sclerosis, or a combination of these conditions. The major pathological abnormality is characterized by a selective and progressive degeneration of the lower motor neurons in the spinal cord and the upper motor neurons in the cerebral cortex. The therapeutic application of a hedgehog agonist can be used alone, or in conjunction with other neurotrophic factors such as CNTF, BDNF or NGF to prevent and/or reverse motor neuron degeneration in ALS patients.

Hedgehog agonists of the present invention can also be used in the treatment of autonomic disorders of the peripheral nervous system, which include disorders affecting the enervation of smooth muscle and endocrine tissue (such as glandular tissue). For instance, the subject method can be used to treat tachycardia or atrial cardiac arrhythmias which may arise from a degenerative condition of the nerves innervating the striated muscle of the heart.

Furthermore, a potential role for certain of the hedgehog agonists derives from the role of hedgehog proteins in development and maintenance of dendritic processes of axonal neurons. Potential roles for hedgehog agonists consequently include guidance for axonal projections and the ability to promote differentiation and/or maintenance of the innervating cells to their axonal processes. Accordingly, compositions comprising hedgehog agonists may be employed to support the survival and reprojection of several types of ganglionic neurons sympathetic and sensory neurons as well as motor neurons. In particular, such therapeutic compositions may be useful in treatments designed to rescue, for example, various neurons from lesion-induced death as well as guiding reprojection of these neurons after such damage. Such diseases include, but are not limited to, CNS trauma infarction, infection (such as viral infection with varicella-zoster), metabolic, disease, nutritional deficiency, toxic agents (such as cisplatin treatment).

As appropriate, the subject method can also be used in generating nerve prostheses for the repair of central and peripheral nerve damage. In particular, where a crushed or severed axon is intubulated by use of a prosthetic device, hedgehog agonists can be added to the prosthetic device to regulate the rate of growth and regeneration of the dendritic processes. Exemplary nerve guidance channels are described in U.S. Pat. Nos. 5,092,871 and 4,955,892.

In another embodiment, the subject method can be used in the treatment of neoplastic or hyperplastic transformations such as may occur in the central nervous system. For instance, the hedgehog agonists can be utilized to cause such transformed cells to become either post-mitotic or apoptotic. The present method may, therefore, be used as part of a treatment for, e.g., malignant gliomas, meningioma, medulloblastomas, neuroectodermal tumors, and ependymomas.

The subject method has wide applicability to the treatment or prophylaxis of disorders affecting the regulation of peripheral nerves, including peripheral ganglionic neurons, sympathetic, sensory neurons, and motor neurons. In general, the method can be characterized as including a step of administering to an animal an amount of a hedgehog agonist effective to alter the proliferative and/or differentiation state of treated peripheral nerve cells. Such therapeutic compositions may be useful in treatments designed to rescue, for example, retinal ganglia, inner ear and acoustical nerves, and motor neurons, from lesion-induced death as well as guiding reprojection of these neurons after such damage. Such diseases and conditions include, but are not limited to, chemical or mechanical trauma, infection (such as viral infection with varicella-zoster), metabolic disease such as diabetes, nutritional deficiency, and toxic agents (such as cisplatin treatment). The goals of treatment in each case can be twofold: (1) eliminate the cause of the disease and (2) to relieve its symptoms.

Peripheral neuropathy is a condition involving nerve-ending damage in the hands and feet. Peripheral neuropathy generally refers to a disorder that affects the peripheral nerves, most often manifested as one or a combination of motor, sensory, sensorimotor, or autonomic neural dysfunction. The wide variety of morphologies exhibited by peripheral neuropathies can each be uniquely attributed to an equally wide variety of causes. For instance, peripheral neuropathies can be genetically acquired, can result from a systemic disease, or can be induced by a toxic agent. Some toxic agents that cause neurotoxicities are therapeutic drugs, antineoplastic agents, contaminants in foods or medicinals, and environmental and industrial pollutants.

In particular, chemotherapeutic agents known to cause sensory and/or motor neuropathies include vincristine, an antineoplastic drug used to treat hematological malignancies and sarcomas. The neurotoxicity is dose-related, and exhibits as reduced intestinal motility and peripheral neuropathy, especially in the distal muscles of the hands and feet, postural hypotension, and atone of the urinary bladder. Similar problems have been documented with taxol and cisplatin (Mollman, J. E., 1990, New Eng Jour Med. 322:126-127), although cisplatin-related neurotoxicity can be alleviated with nerve growth factor (NGF) (Apfel, S. C. et al, 1992, Annals of Neurology 31:76-80). Although the neurotoxicity is sometimes reversible after removal of the neurotoxic agent, recovery can be a very slow process (Legha, S., 1986, Medical Toxicology 1:421-427; Olesen, et al., 1991, Drug Safety 6:302-314).

There are a number of inherited peripheral neuropathies, including: Refsum's disease, abetalipoproteinemia, Tangier disease, Krabbe's disease, metachromatic leukodystrophy, Fabry's disease, Dejerine-Sottas syndrome, and others. Of all the inherited neuropathies, the most common by far is Charcot-Marie-Tooth disease.

Charcot-Marie-Tooth (CMT) Disease (also known as peroneal muscular atrophy, or hereditary motor sensory neuropathy (HMSN)) is the most common hereditary neurological disorder. It is characterized by weakness and atrophy, primarily of the peroneal muscles, due to segmental demyelination of peripheral nerves and associated degeneration of axons and anterior horn cells. Autosomal dominant inheritance is usual, and associated degenerative CNS disorders, such as Friedreich's ataxia, are common.

In one aspect, the method of the present invention can be used in the treatment and maintenance of hereditary neuropathies. This group of neuropathies is now becoming increasingly recognized due to the dramatic advances in molecular genetics. The symptoms of the various hereditary neuropathies are wide-ranging. A common denominator is usually the early onset of mild numbness and tingling in the feet that slowly progresses to involve the legs and the hands and later the rest of the upper extremities. Most of the hereditary neuropathies do have a motor component consisting of distal weakness in the lower and upper extremities. A majority of patients with hereditary neuropathies have high arches in their feet or other bony deformities. The symptoms are very slowly progressive and the majority of the patients are still walking two decades after the onset of their symptoms.

The diagnosis of a hereditary neuropathy is usually suggested with the early onset of neuropathic symptoms, especially when a positive family history is also present. Prior to the recent genetic advances, the diagnosis was supported by typical findings of marked slowing of the nerve conduction studies on electromyography and a nerve biopsy. Typical findings on a nerve biopsy include the presence of so-called onion-bulbs, indicating a recurring demyelinating and remyelinating of the nerve fibers. With the most recent genetic advances, two major hereditary neuropathies known as Charcot-Marie-Tooth disease and hereditary neuropathy with liability to pressure palsies can be diagnosed with a simple blood test that identifies the different mutations responsible for these two entities.

Hereditary neuropathies are caused by genetic abnormalities which are transmitted from generation to generation. For several of these, the genetic defect is known, and tests are available for diagnosis and prenatal counseling.

As set forth above, the subject method can be used as part of a therapeutic regimen in the treatment of Charcot-Marie Tooth Disease (CMT). This is a general term given to the hereditary sensorimotor neuropathies. CMT type 1 (CMT 1) is associated with demyelination or breakdown of the myelin sheaths. Several different abnormalities have been identified. CMT Type 1A is most commonly caused by duplication of a gene encoding a myelin protein called PMP-22, and CMT type 1B is caused by a mutation in a myelin protein called the Po glycoprotein. CMTX is a hereditary sensorimotor neuropathy which primarily affects men. It is caused by a mutation in a gene encoding a protein called Connexin 32 on the X-chromosome.

In another embodiment, the subject method can be used in the treatment of familial amyloidotic neuropathy and other related hereditary neuropathies. Amyloidotic neuropathy usually presents with pain, sensory loss and autonomic dysfunction. It is caused by a mutation in a protein called Transthyretin, resulting in deposition of the protein as amyloid in the peripheral nerves.

The subject method can be used in the treatment of hereditary porphyria, which can have components of peripheral neuropathy. Still another hereditary neuropathy for which the subject methods can be used for treatment is hereditary sensory neuropathy Type II (HSN II). The methods and compositions of the present invention can also be used in the treatment and maintenance of acquired neuropathies.

For example, hedgehog agonists can be used to prevent diabetic neuropathies. Diabetes is the most common known cause of neuropathy. It produces symptoms in approximately 10% of people with diabetes. In most cases, the neuropathy is predominantly sensory, with pain and sensory loss in the hands and feet. But some diabetics have mononeuritis or mononeuritis multiplex which causes weakness in one or more nerves, or lumbosacral plexopathy or amyotrophy which causes weakness in the legs.

The instant method can also be used in the treatment of immune-mediated neuropathies. The main function of the immune system is to protect the body against infectious organisms which enter from outside. In some cases, however the immune system turns against the body and causes autoimmune disease. The immune system consists of several types of white blood cells, including T-lymphocytes, which also regulate the immune response; and B-lymphocytes or plasma cells, which secrete specialized proteins called "antibodies" Sometimes, for unknown reasons, the immune system mistakenly attacks parts of the body such as the peripheral nenes. This is "autoimmune" Peripheral Neuropathy. There are several different types, depending on the part of the peripheral nerve which is attacked and the type of the immune reaction. The following are brief descriptions of the neuropathies which are mediated by the immune system.

For instance, a hedgehog agonist can be used to treat Guillain-Barre syndrome (GBS), an acute neuropathy that comes on suddenly or rapidly. Guillain-Barre syndrome can progress to paralysis and respiratory failure within days or weeks after onset. The neuropathy is caused when the immune system destroys the myelin sheaths of the motor and sensory nerves. It is often preceded by infection, vaccination or trauma, and that is thought to be what triggers the autoimmune reaction. The disease is self-limiting, with spontaneous recovery within six to eight weeks. But the recovery is often incomplete.

Other neuropathies which begin acutely, and which can be treated by the method of the present invention, include acute motor neuropathy, acute sensory neuropathy, and acute autonomic neuropathy, in which there is an immune attack against the motor, sensory or autonomic nerves, respectively. The Miller-Fisher syndrome is another variant in which there is paralysis of eye gaze, incoordination, and unsteady gait.

Still another acquired neuropathy which is may be treated by the subject method is chronic inflammatory demyelinating polyneuropathy (CIDP). CIDP is thought to be a chronic and more indolent form of the Guillain-Barre syndrome. The disease progresses either with repeated attacks, called relapses, or in a stepwise or steady fashion. As in GBS, there appears to be destruction of the myelin sheath by antibodies and T-lymphocytes. But since there is no specific test for CIDP, the diagnosis is based on the clinical and laboratory characteristics.

Chronic polyneuropathies with antibodies to peripheral nerves is still another peripheral neuropathy for which the subject methods can be employed to treat or prevent In some types of chronic neuropathies, antibodies to specific components of nerve have been identified. These include demyelinating neuropathy associated with antibodies to the myelin associated glycoprotein (MAG), motor neuropathy associated with antibodies to the gangliosides GM1 or GD1a, and sensory neuropathy associated with anti-sulfatide or GD1b ganglioside antibodies. The antibodies in these cases bind to oligosaccharide or sugar like molecules, which are linked to proteins (glycoproteins) or lipids (glycolipids or gangliosides) in the nerves. It is suspected that these antibodies may be responsible for the neuropathies.

The subject method can also be used as part of a therapeutic plan for treating neuropathies associated with vasculitis or inflammation of the blood vessels in peripheral nerves. Neuropathy can also be caused by vasculitis—an inflammation of the blood vessels in peripheral nerve. It produces small "strokes" along the course of the peripheral nerves, and may be restricted to the nerves or it may be generalized, include a skin rash, or involve other organs. Several rheumatological diseases like rheumatoid arthritis, lupus, periarteritis nodosa, or Sjogren's syndrome, are associated with generalized vasculitis, which can also involve the peripheral nerves. Vasculitis can cause polyneuritis, mononeuritis, or mononeuritis multiplex, depending on the distribution and severity of the lesions.

In still another embodiment, the method of the present invention can be used for treatment of brachial or lumbosacral plexitis. The brachial plexus, which lies under the armpit, contains the nerves to the arm and hand. Brachial plexitis is the result of inflammation of that nerve bundle, and produces weakness and pain in one or both arms. Umbosacral plexitis, which occurs in the pelvis, causes weakness and pain in the legs.

Hedgehog agonists may also be suitable for use in the treatment of neuropathies associated with monoclonal gammopathies. In monoclonal gammopathy, single clones of B-cells or plasma cells in the bone marrow or lymphoid organs expand to form benign or malignant tumors and secrete antibodies. "Monoclonal" is because there are single clones of antibodies, and "gammopathy" stands for gamma-globulins, which is another name for antibodies. In some cases, the antibodies react with nerve components; in others, fragments of the antibodies form amyloid deposits.

Yet another aspect of the present invention relates to the use of the subject method in the treatment of neuropathies associated with tumors or neoplasms. Neuropathy can be due to direct infiltration of nerves by tumor cells or to indirect effect of the tumor. The latter is called paraneoplastic neuropathy. Several types have been described. For instance, the subject methods can be used to manage sensory neuropathy associated with lung cancer. This neuropathy is associated with antibodies to a protein called Hu, which is present in the sensory neurons of the peripheral nerves. Likewise, the subject method can be used to treat neuropathies associated with multiple myeloma. Multiple myeloma is a bony tumor which is caused by antibody-secreting plasma cells in the bone marrow. The tumor is made up of a single clone of plasma cells, and the antibodies they produce are identical or monoclonal. Some people with multiple myeloma develop sensorimotor polyneuropathy with degeneration of axons in the peripheral nerves. In other embodiments, the subject method can be used to treat neuropathies associated with Waldenstron's macroglobulemia, chronic lymphocytic leukemia, or B-cell lymphoma. These are tumors caused by antibody-secreting B-lymphocytes in the spleen, bone marrow or lymph nodes. These antibodies are monoclonal and frequently react with peripheral nerve components such as MAG, GM1, or sulfatide. In still other embodiments, the hedgehog agonists of the present invention can be used as part of therapeutic protocol for the treatment of patients with cancers where neuropathy is a consequence of local irradiation or be caused by medications such as vincristine and cisplatin.

The present invention also contemplates the use of hedgehog agonists for the treatment of neuropathies associated with amyloidosis. Amyloid is a substance deposited in the peripheral nerves and interferes with their operation: the disorder is amyloidosis. There are two main types: primary amyloidosis, in which the deposits contain fragments of monoclonal antibodies (see monoclonal gammopathy above); and hereditary amyloidosis in which the deposits contain a mutated protein called Transthyretin. Primary amyloidosis is usually associated with monoclonal gammopathies or myeloma.

Still another aspect of the present invention provides the subject method as a means for treating neuropathies caused by infections. Peripheral neuropathies can be caused by infection of the peripheral nerves. Viruses that cause peripheral neuropathies include the AIDS virus, HIV-L which causes slowly progressive sensory neuropathy, Cytomegalovirus which causes a rapidly progressive paralytic neuropathy, Herpes zoster which cause shingles, and poliovirus which causes a motor neuropathy. Hepatitis B or C infections are sometimes associated with vasculitis neuropathy.

Bacterial infections that cause neuropathy include leprosy, which causes a patchy sensory neuropathy, and diphtheria which can cause a rapidly progressive paralytic neuropathy. Other infectious diseases that cause neuropathy include Lyme disease, which is caused by a spirochete, and trypanosomiasis which is caused by a parasite. Both commonly present with a multifocal neuropathy Neuropathies caused by nutritional imbalance are also candidate disorders for treatment by the subject method. Deficiencies of vitamins B12, B1 (thiamine), B6 (pyridoxine), or E, for example, can produce polyneuropathies with degeneration of peripheral nerve axons. This can be due to poor diet, or inability to absorb the nutrients from the stomach or gut. Moreover, megadoses of vitamin B6 can also cause a peripheral neuropathy, and the subject method can be used as part of a detoxification program in such cases.

Yet another use of the subject method is in the treatment of neuropathies arising in kidney diseases. Chronic renal failure can cause a predominantly sensory peripheral neuropathy with degeneration of peripheral nerve axons.

Another aspect of the present invention provides a method for treating hypothyroid neuropathies. Hypothyroidism is sometimes associated with a painful sensory polyneuropathy with axonal degeneration. Mononeuropathy or mononeuropathy multiplex can also occur due to compression of the peripheral nerves by swollen tissues.

The subject method can also be used in the treatment of neuropathies caused by alcohol and toxins. Certain toxins can cause peripheral neuropathy. Lead toxicity is associated with a motor neuropathy, arsenic or mercury cause a sensory neuropathy, and thallium can cause a sensory and autonomic neuropathy. Several organic solvents and insecticides can also cause polyneuropathy. Alcohol is directly toxic to nerves and alcohol abuse is a major cause of neuropathy. The subject method can be used, in certain embodiments, as part of a broader detoxification program.

In still another embodiment, the methods and compositions of the present invention can be used for the treatment of neuropathies caused by drugs. Several drugs are known to cause neuropathy. They include, among others, vincristine and cisplatin in cancer, nitrofurantoin, which is used in pyelonephritis, amiodarone in cardiac arrhythmias, disulfiram in alcoholism, ddC and ddI in AIDS, and dapsone which is used to treat leprosy. As above, the subject method can be used, in certain embodiments, as part of a broader detoxification program.

The method of the present invention can also be used in the treatment of neuropathies caused by trauma or compression. Localized neuropathies can result from compression of nerves by external pressure or overlying tendons and other tissues. The best known of these are the carpal tunnel syndrome which results from compression at the wrist, and cervical or lumbar radiculopathies (sciatica) which result from compression of nerve roots as they exit the spine. Other common areas of nerve compression include the elbows, armpits, and the back of the knees.

The subject method is also useful in variety of idiopathic neuropathies. The term "idiopathic" is used whenever the cause of the neuropathy cannot be found. In these cases, the neuropathy is classified according to its manifestations, i.e., sensory, motor, or sensorimotor idiopathic polyneuropathy.

The subject method has wide applicability to the treatment or prophylaxis of disorders afflicting muscle tissue. In general, the method can be characterized as including a step of administering to an animal an amount of a hedgehog agonist effective to alter the proliferative state of a treated muscle tissue. The mode of administration and dosage regimens will vary depending on the muscle tissue(s) which is to be treated.

In one aspect, the invention is directed to a muscle-trophic factor, and its use in stimulating muscle growth or differentiation in mammals. Such stimulation of muscle, growth is useful for treating atrophy, or wasting, in particular, skeletal muscle atrophy and cardiac muscle atrophy. In addition, certain diseases wherein the muscle tissue is damaged, is abnormal or has atrophied, are treatable using the invention, such as, for example, normal aging, disuse atrophy, wasting or cachexia, and various secondary disorders associated with age and the loss of muscle mass, such as hypertension, glucose intolerance and diabetes, dyslipidemia and atherosclerotic cardiovascular disease. The treatment of muscular myopathies such as muscular dystrophies is also embodied in the invention.

With denervation or disuse, skeletal muscles undergo rapid atrophy which leads to a profound decrease in size, protein content and contractile strength. This atrophy is an important component of many neuromuscular diseases in humans. In a clinical setting, compositions comprising the subject hedgehog agonists can be used for inhibiting muscle degeneration, e.g., for decreasing the loss of muscle mass, such as part of a treatment for such muscle wasting disorders.

In preferred embodiments pharmaceutical compositions according to the invention are administered to patients suffering from a disorder, i.e., an abnormal physical condition, a disease or pathophysiological condition associated with abnormal and/or aberrant regulation of muscle tissue. The disorders for which the compositions of the invention are administered are preferably those which directly or indirectly produce a wasting (i.e., loss) of muscle mass; that is, a muscle wasting disorder. These include muscular dystrophies, cardiac cachexia, emphysema, leprosy, malnutrition, osteomalacia, child acute leukemia, AIDS cachexia and cancer cachexia.

The muscular dystrophies are genetic diseases which are characterized by progressive weakness and degeneration of muscle fibers without evidence of neural degeneration. In Duchenne muscular dystrophy (DMD) patients display an average of a 67% reduction in muscle mass, and in myotonic dystrophy, fractional muscle protein synthesis has been shown to be decreased by an average of 28%, without any corresponding decrease in non-muscle protein synthesis (possibly due to impaired end-organ response to anabolic hormones or substrates). Accelerated protein degradation has been demonstrated in the muscles of DMD patients. The subject method can be used as part of a therapeutic strategy for preventing, and in some instance reversing, the muscle wasting conditions associated with such dystrophies.

Severe congestive heart failure (CHF) is characterized by a "cardiac cachexia," i.e., a muscle protein wasting of both the cardiac and skeletal muscles, with an average 19% body weight decrease. The cardiac cachexia is caused by an increased rate of myofibrillar protein breakdown. The subject method can be used as part of a treatment for cardiac cachexia.

Emphysema is a chronic obstructive pulmonary disease, defined by an enlargement of the air spaces distal to the terminal non-respiratory bronchioles, accompanied by destructive changes of the alveolar walls. Clinical manifestations of reduced pulmonary functioning include coughing, wheezing, recurrent respiratory infections, edema, and functional impairment and shortened lifespan. The efflux of tyrosine is increased by 47% in emphysematous patients. Also, whole body leucine flux remains normal, whole-body leucine oxidation is increased, and whole-body protein synthesis is decreased. The result is a decrease in muscle protein synthesis, accompanied by a decrease in whole body protein turnover and skeletal muscle mass. This decrease becomes increasingly evident with disease progression and long-term deterioration. The subject hedgehog agonists may be used to prevent and/or reverse, the muscle wasting conditions associated with such diseases.

In diabetes mellitus, there is a generalized wasting of small muscle of the hands, which is due to chronic partial denervation (neuropathy). This is most evident and worsens with long-term disease progression and severity. The subject method can be used as part of a therapeutic strategy for treatment of diabetes mellitus.

Leprosy is associated with a muscular wasting which occurs between the metacarpals of the thumb and index finger. Severe malnutrition is characterized by, inter alia, severe muscle wasting. The subject method can be used to treat muscle-wasting effects of leprosy.

Osteomalacia is a nutritional disorder caused by a deficiency of vitamin D and calcium. It is referred to as "rickets" in children, and "osteomalacia" in adults. It is marked by a softening of the bones (due to impaired mineralization, with excess accumulation of osteoid), pain, tenderness, muscle wasting and weakness, anorexia, and overall weight loss. It can result from malnutrition, repeated pregnancies and lactation (exhausting or depleting vitamin D and calcium stores), and vitamin D resistance. The subject method can be used as part of a therapeutic strategy for treatment of osteomalacia.

In childhood acute leukemia there is protein energy malnutrition which results in skeletal muscle wasting. Studies have shown that some children exhibit the muscle wasting even before diagnosis of the leukemia, with an average 27% decrease in muscle mass. There is also a simultaneous 33%-

37% increase in adipose tissue, resulting in no net change in relative body weight and limb circumference. Such patients may be amenable to treatment with a hedgehog agonist according to the method of the present invention Cancer cachexia is a complex syndrome which occurs with variable incidence in patients with solid tumors and hematological malignancies. Clinically, cancer cachexia is manifested as weight loss with massive depletion of both adipose tissue and lean muscle mass, and is one cause of death which results from cancer. Cancer cachexia patients have shorter survival times, and decreased response to chemotherapy. In addition to disorders which produce muscle wasting, other circumstances and conditions appear to be linked in some fashion with a decrease in muscle mass. Such afflictions include muscle wasting due to chronic back pain, advanced age, long-term hospitalization due to illness or injury, alcoholism and corticosteroid therapy. The subject method can be used as part of a therapeutic strategy for preventing, and in some instance reversing, the muscle wasting conditions associated with such cancers.

Studies have shown that in severe cases of chronic lower back pain, there is paraspinal muscle wasting. Decreasing paraspinal muscle wasting alleviates pain and improves function. A course of treatment for disorder can include administration of a therapeutic amount of a hedgehog agonist.

It is also believed that general weakness in old age is due to muscle wasting. As the body ages, an increasing proportion of skeletal muscle is replaced by fibrous tissue. The result is a significant reduction in muscle power, but only a marginal reduction in fat-free mass. The subject method can be used as part of a treatment and preventive strategies for preventing/reversing muscle wasting in elderly patients.

Studies have also shown that in patients suffering injuries or chronic illnesses and hospitalized for long periods of time, there is long-lasting unilateral muscle wasting, with an average 31% decrease in muscle mass. Studies have also shown that this can be corrected with intensive physiotherapy. However, it may be more effective for many patients to at least augment such therapies with treatment by the subject method In alcoholics there is wasting of the anterior tibial muscle. This proximal muscle damage is caused by neurogenic damage, namely, impaired glycolytic and phosphorylase enzyme activity. The damage becomes apparent and worsens the longer the duration of the alcohol abuse. Patients treated with corticosteroids experience loss of muscle mass. Such patients may also be amenable to treatment by the subject method.

The compounds of the invention can be used to alleviate the muscle mass loss resulting from the foregoing conditions, as well as others. Additionally, the hedgehog agonists of the present invention are useful in veterinary and animal husbandry applications to counter weight loss in animals, or to promote growth. For instance, the invention may also find use for increasing the efficiency of animal meat production. Specifically, animals may be fed or injected with a hedgehog agonist in order to increase overall skeletal muscle mass, e.g., to increase the weight of such farm animals as cows, pigs, sheep, chickens and salmon.

The maintenance of tissues and organs ex vivo is also highly desirable. Tissue replacement therapy is well established in the treatment of human disease. There are many situations where one may wish to transplant muscle cells, especially muscle stem cells, into a recipient host where the recipient's cells are missing, damaged or dysfunctional muscle cells in muscle wasting disease. For example, transplantation of normal myoblasts may be useful to treat Duchenne muscular dystrophy and other muscle degeneration and wasting diseases. See, for example, Partridge (1991) *Muscle & Nerve* 14:197-212. In the case of myoblasts, they may be injected at various sites to treat muscle-wasting diseases.

The subject method can be used to regulate the growth of muscle cells and tissue in vitro, as well as to accelerate the grafting of implanted muscle tissue to an animal host. In this regard, the present invention also concerns myoblast cultures which have been expanded by treatment with a hedgehog agonist. In an illustrative embodiment, such a method comprises obtaining a muscle sample, preferably one including myoblasts; optionally treating the cell sample enzymically to separate the cells; culturing, in the presence of a hedgehog agonist.

Yet another aspect of the present invention concerns the observation in the art that ptc, hedgehog, and/or smoothened are involved in morphogenic signals involved in other vertebrate organogenic pathways in addition to neuronal differentiation as described above, having apparent roles in other endodermal patterning, as well as both mesodermal and endodermal differentiation processes. Thus, it is contemplated by the invention that compositions comprising hedgehog agonists can also be utilized for both cell culture and therapeutic methods involving generation and maintenance of non-neuronal tissue.

In one embodiment, the present invention makes use of the discovery that ptc, hedgehog, and smoothened are apparently involved in controlling the development of stem cells responsible for formation of the digestive tract, liver, lungs, and other organs which derive from the primitive gut. Shh serves as an inductive signal from the endoderm to the mesoderm, which is critical to gut morphogenesis. Therefore, for example, hedgehog agonists of the instant method can be employed for regulating the development and maintenance of an artificial liver which can have multiple metabolic functions of a normal liver. In an exemplary embodiment, the subject method can be used to regulate the proliferation and differentiation of digestive tube stem cells to form hepatocyte cultures which can be used to populate extracellular matrices, or which can be encapsulated in biocompatible polymers, to form both implantable and extracorporeal artificial livers.

In another embodiment, therapeutic compositions of hedgehog agonists can be utilized in conjunction with transplantation of such artificial livers, as well as embryonic liver structures, to regulate uptake of intraperitoneal implantation, vascularization, and in vivo differentiation and maintenance of the engrafted liver tissue.

In yet another embodiment, the subject method can be employed therapeutically to regulate such organs after physical, chemical or pathological insult. For instance, therapeutic compositions comprising hedgehog agonists can be utilized in liver repair subsequent to a partial hepatectomy.

The generation of the pancreas and small intestine from the embryonic gut depends on intercellular signalling between the endodermal and mesodermal cells of the gut. In particular, the differentiation of intestinal mesoderm into smooth muscle has been suggested to depend on signals from adjacent endodermal cells. One candidate mediator of endodermally derived signals in the embryonic hindgut is Sonic hedgehog. See, for example, Apelqvist et al. (1997) *Curr Biol* 7:8014. The Shh gene is expressed throughout the embryonic gut endoderm with the exception of the pancreatic bud endoderm, which instead expresses high levels of the homeodomain protein Ipf1/Pdx1 (insulin promoter factor 1/pancreatic and duodenal homeobox 1), an essential regulator of early pancreatic development. Apelqvist et al., supra have examined whether the differential expression of Shh in the embryonic gut tube controls the differentiation of the surrounding mesoderm into specialized mesoderm derivatives of the small intestine and pancreas. To test this, they used the promoter of the Ipf1/Pdx1 gene to selectively express Shh in the developing pancreatic epithelium. In Ipf1/Pdx1-Shh transgenic mice, the pancreatic mesoderm developed into smooth muscle and interstitial cells of Cajal, characteristic of the intestine, rather than into pancreatic mesenchyme and spleen. Also, pancreatic explants exposed to Shh underwent a similar program of intestinal differentiation. These results provide evidence that the differential expression of endodermally derived Shh controls the fate of adjacent mesoderm at different regions of the gut tube.

In the context of the present invention, it is contemplated therefore that the subject hedgehog agonists can be used to control or regulate the proliferation and/or differentiation of pancreatic tissue both in vivo and in vitro.

There are a wide variety of pathological cell proliferative and differentiative conditions for which the agonists of the present invention may provide therapeutic benefits, with the general strategy being, for example, the correction of aberrant insulin expression, or modulation of differentiation. More generally, however, the present invention relates to a method of inducing and/or maintaining a differentiated state, enhancing survival and/or affecting proliferation of pancreatic cells, by contacting the cells with the subject agonists. For instance, it is contemplated by the invention that, in light of the apparent involvement of ptc, hedgehog, and smoothened in the formation of ordered spatial arrangements of pancreatic tissues, the subject method could be used as part of a technique to generate and/or maintain such tissue both in vitro and in vivo. For instance, modulation of the function of hedgehog can be employed in both cell culture and therapeutic methods involving generation and maintenance β-cells and possibly also for non-pancreatic tissue, such as in controlling the development and maintenance of tissue from the digestive tract, spleen, lungs, and other organs which derive from the primitive gut.

In an exemplary embodiment, the present method can be used in the treatment of hyperplastic and neoplastic disorders effecting pancreatic tissue, particularly those characterized by aberrant proliferation of pancreatic cells. For instance, pancreatic cancers are marked by abnormal proliferation of pancreatic cells which can result in alterations of insulin secretory capacity of the pancreas. For instance, certain pancreatic hyperplasias, such as pancreatic carcinomas, can result in hypoinsulinemia due to dysfunction of β-cells or decreased islet cell mass. To the extent that aberrant ptc, hedgehog, and smoothened signaling may be indicated in disease progression, the subject agonists can be used to enhance regeneration of the tissue after anti-tumor therapy.

Moreover, manipulation of hedgehog signaling properties at different points may be useful as part of a strategy for reshaping/repairing pancreatic tissue both in vivo and in vitro. In one embodiment, the present invention makes use of the apparent involvement of ptc, hedgehog, and smoothened in regulating the development of pancreatic tissue. In general, the subject method can be employed therapeutically to regulate the pancreas after physical, chemical or pathological insult. In yet another embodiment, the subject method can be applied to cell culture techniques, and in particular, may be employed to enhance the initial generation of prosthetic pancreatic tissue devices. Manipulation of proliferation and differentiation of pancreatic tissue, for example, by altering hedgehog activity, can provide a means for more carefully controlling the characteristics of a cultured tissue. In an exemplary embodiment, the subject method can be used to augment production of prosthetic devices which require β-islet cells, such as may be used in the encapsulation devices described in, for example, the Aebischer et al. U.S. Pat. No. 4,892,538, the Aebischer et al. U.S. Pat. No. 5,106,627, the Lim U.S. Pat. No. 4,391,909, and the Sefton U.S. Pat. No. 4,353,888. Early progenitor cells to the pancreatic islets are multipotential, and apparently coactivate all the islet-specific genes from the time they first appear. As development proceeds, expression of islet-specific hormones, such as insulin, becomes restricted to the pattern of expression characteristic of mature islet cells. The phenotype of mature islet cells, however, is not stable in culture, as reappearance of embryonic traits in mature β-cells can be observed. By utilizing the subject hedgehog agonists, the differentiation path or proliferative index of the cells can be regulated.

Furthermore, manipulation of the differentiative state of pancreatic tissue can be utilized in conjunction with transplantation of artificial pancreas so as to promote implantation, vascularization, and in vivo differentiation and maintenance of the engrafted tissue. For instance, manipulation of hedgehog function to affect tissue differentiation can be utilized as a means of maintaining graft viability.

Bellusci et al. (1997) *Development* 124:53 report that Sonic hedgehog regulates lung mesenchymal cell proliferation in vivo. Accordingly, the present method can be used to regulate regeneration of lung tissue, e.g., in the treatment of emphysema.

In still another embodiment of the present invention, compositions comprising hedgehog agonists can be used in the in vitro generation of skeletal tissue, such as from skeletogenic stem cells, as well as the in vivo treatment of skeletal tissue deficiencies. The present invention particularly contemplates the use of hedgehog agonists to regulate the rate of chondrogenesis and/or osteogenesis. By "skeletal tissue deficiency", it is meant a deficiency in bone or other skeletal connective tissue at any site where it is desired to restore the bone or connective tissue, no matter how the deficiency originated, e.g., whether as a result of surgical intervention, removal of tumor, ulceration, implant, fracture, or other traumatic or degenerative conditions.

For instance, the method of the present invention can be used as part of a regimen for restoring cartilage function to a connective tissue. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a Taxation of a joint by a torn ligament, misalignment of joints, bone fracture, or by hereditary disease. The present reparative method is also useful for remodeling cartilage matrix, such as in plastic or reconstructive surgery, as well as periodontal surgery. The present method may also be applied to improving a previous reparative procedure, for example, following surgical repair of a meniscus, ligament, or cartilage. Furthermore, it may prevent the onset or exacerbation of degenerative disease if applied early enough after trauma.

In one embodiment of the present invention, the subject method comprises treating the afflicted connective tissue with a therapeutically sufficient amount of a hedgehog agonist, particularly an agonist selective for Indian hedgehog signal transduction, to regulate a cartilage repair response in the connective tissue by managing the rate of differentiation and/or proliferation of chondrocytes embedded in the tissue. Such connective tissues as articular cartilage, interarticular cartilage (menisci), costal cartilage (connecting the true ribs and the sternum), ligaments, and tendons are particularly amenable to treatment in reconstructive and/or regenerative therapies using the subject method. As used herein, regenerative therapies include treatment of degenerative states which have progressed to the point of which impairment of the tissue is obviously manifest, as well as preventive treatments of tissue where degeneration is in its earliest stages or imminent.

In an illustrative embodiment, the subject method can be used as part of a therapeutic intervention in the treatment of cartilage of a diarthroidal joint, such as a knee, an ankle, an elbow, a hip, a wrist, a knuckle of either a finger or toe, or a tempomandibular joint. The treatment can be directed to the meniscus of the joint, to the articular cartilage of the joint, or both. To further illustrate, the subject method can be used to treat a degenerative disorder of a knee, such as which might be the result of traumatic injury (e.g., a sports injury or excessive wear) or osteoarthritis. The subject agonists may be administered as an injection into the joint with, for instance, an arthroscopic needle. In some instances, the injected agent can be in the form of a hydrogel or other slow release vehicle described above in order to permit a more extended and regular contact of the agent with the treated tissue.

The present invention further contemplates the use of the subject method in the field of cartilage transplantation and prosthetic device therapies. However, problems arise, for instance, because the characteristics of cartilage and fibrocartilage varies between different tissue: such as between articular, meniscal cartilage, ligaments, and tendons, between the two ends of the same ligament or tendon, and between the superficial and deep parts of the tissue. The zonal arrangement of these tissues may reflect a gradual change in mechanical properties, and failure occurs when implanted tissue, which has not differentiated under those conditions, lacks the ability to appropriately respond. For instance, when meniscal cartilage is used to repair anterior cruciate ligaments, the tissue undergoes a metaplasia to pure fibrous tissue. By regulating the rate of chondrogenesis, the subject method can be used to particularly address this problem, by helping to adaptively control the implanted cells in the new environment and effectively resemble hypertrophic chondrocytes of an earlier developmental stage of the tissue.

In similar fashion, the subject method can be applied to enhancing both the generation of prosthetic cartilage devices and to their implantation. The need for improved treatment has motivated research aimed at creating new cartilage that is based on collagen-glycosaminoglycan templates (Stone et al. (1990) *Clin Orthop Relat Red* 252:129), isolated chondrocytes (Grande et al. (1989) *J Orthop Res* 7:208; and Takigawa et al. (1987) *Bone Miner* 2:449), and chondrocytes attached to natural or synthetic polymers (Walitani et al. (1989) *J Bone Jt Surg* 71B:74; Vacanti et al. (1991) *Plast Reconstr Surg* 88:753; von Schroeder et al. (1991) *J Biomed Mater Res* 25:329; Freed et al. (1993) *J Biomed Mater Res* 27:11; and the Vacanti et al. U.S. Pat. No. 5,041,138). For example, chondrocytes can be grown in culture on biodegradable, biocompatible highly porous scaffolds formed from polymers such as polyglycolic acid, polylactic acid, agarose gel, or other polymers which degrade over time as function of hydrolysis of the polymer backbone into innocuous monomers. The matrices are designed to allow adequate nutrient and gas exchange to the cells until engraftment occurs. The cells can be cultured in vitro until adequate cell volume and density has developed for the cells to be implanted. One advantage of the matrices is that they can be cast or molded into a desired shape on an individual basis, so that the final product closely resembles the patient's own ear or nose (by way of example), or flexible matrices can be used which allow for manipulation at the time of implantation, as in a joint.

In one embodiment of the subject method, the implants are contacted with a hedgehog agonist during certain stages of the culturing process in order to manage the rate of differentiation of chondrocytes and the formation of hypertrophic chondrocytes in the culture.

In another embodiment, the implanted device is treated with a hedgehog agonist in order to actively remodel the implanted matrix and to make it more suitable for its intended function. As set forth above with respect to tissue transplants, the artificial transplants suffer from the same deficiency of not being derived in a setting which is comparable to the actual mechanical environment in which the matrix is implanted. The ability to regulate the chondrocytes in the matrix by the subject method can allow the implant to acquire characteristics similar to the tissue for which it is intended to replace.

In yet another embodiment, the subject method is used to enhance attachment of prosthetic devices. To illustrate, the subject method can be used in the implantation of a periodontal prosthesis, wherein the treatment of the surrounding connective tissue stimulates formation of periodontal ligament about the prosthesis.

In still further embodiments, the subject method can be employed as part of a regimen for the generation of bone (osteogenesis) at a site in the animal where such skeletal tissue is deficient. Indian hedgehog is particularly associated with the hypertrophic chondrocytes that are ultimately replaced by osteoblasts. For instance, administration of a hedgehog agonist of the present invention can be employed as part of a method for regulating the rate of bone loss in a subject. For example, preparations comprising hedgehog agonists can be employed, for example, to control endochondral ossification in the formation of a "model" for ossification.

In yet another embodiment of the present invention, a hedgehog agonist can be used to regulate spermatogenesis. The hedgehog proteins, particularly Dhh, have been shown to be involved in the differentiation and/or proliferation and maintenance of testicular germ cells. Dhh expression is initiated in Sertoli cell precursors shortly after the activation of Sry (testicular determining gene) and persists in the testis into the adult. Males are viable but infertile, owing to a complete absence of mature sperm. Examination of the developing testis in different genetic backgrounds suggests that Dhh regulates both early and late stages of spermatogenesis. Bitgood et al. (1996) *Curr Biol* 6:298. In a preferred embodiment, a hedgehog agonist can be used as a fertility agent. In similar fashion, hedgehog agonists of the subject method are potentially useful for modulating normal ovarian function.

The subject method also has wide applicability to the treatment or prophylaxis of disorders afflicting epithelial tissue, as well as in cosmetic uses. In general, the method can be characterized as including a step of administering to an animal an amount of a hedgehog agonist effective to alter the growth state of a treated epithelial tissue. The mode of administration and dosage regimens will vary depending on the epithelial tissue(s) which is to be treated. For example, topical formulations will be preferred where the treated tissue is epidermal tissue, such as dermal or mucosal tissues.

A method which "promotes the healing of a wound" results in the wound healing more quickly as a result of the treatment than a similar wound heals in the absence of the treatment. "Promotion of wound healing" can also mean that the method regulates the proliferation and/or growth of, inter alia keratinocytes, or that the wound heals with less scarring, less wound contraction, less collagen deposition and more superficial surface area. In certain instances, "promotion of wound healing" can also mean that certain methods of wound healing have improved success rates, (e.g., the take rates of skin grafts,) when used together with the method of the present invention.

Complications are a constant risk with wounds that have not fully healed and remain open. Although most wounds heal quickly without treatment, some types of wounds resist healing. Wounds which cover large surface areas also remain open for extended periods of time. In one embodiment of the present invention, the subject method can be used to accelerate the healing of wounds involving epithelial tissues, such as resulting from surgery, burns, inflammation or irritation. Certain of the hedgehog agonists of the present invention can also be applied prophylactically, such as in the form of a cosmetic preparation, to enhance tissue regeneration processes, e.g., of the skin, hair and/or fingernails.

Despite significant progress in reconstructive surgical techniques, scarring can be an important obstacle in regaining normal function and appearance of healed skin. This is particularly true when pathologic scarring such as keloids or hypertrophic scars of the hands or face causes functional disability or physical deformity. In the severest circumstances, such scarring may precipitate psychosocial distress and a life of economic deprivation. Wound repair includes the stages of hemostasis, inflammation, proliferation, and remodeling. The proliferative stage involves multiplication of fibroblasts and endothelial and epithelial cells. Through the use of the subject method, the rate of proliferation of epithelial cells in and proximal to the wound can be controlled in order to accelerate closure of the wound and/or minimize the formation of scar tissue:

Full and partial thickness burns are an example of a wound type which often covers large surface areas and therefore requires prolonged periods of time to heal. As a result, life-threatening complications such as infection and loss of bodily fluids often arise. In addition, healing in burns is often disorderly, resulting in scarring and disfigurement. In some cases wound contraction due to excessive collagen deposition results in reduced mobility of muscles in the vicinity of the wound. The compositions and method of the present invention can be used to accelerate the rate of healing of burns and to promote healing processes that result in more desirable cosmetic outcomes and less wound contraction and scarring.

Severe burns which cover large areas are often treated by skin autografts taken from undamaged areas of the patient's body. The subject method can also be used in conjunction with skin grafts to improve "take" rates of the graft by accelerating growth of both the grafted skin and the patient's skin that is proximal to the graft.

Dermal ulcers are yet another example of wounds that are amenable to treatment by the subject method, e.g., to cause healing of the ulcer and/or to prevent the ulcer from becoming a chronic wound. For example, one in seven individuals with diabetes develop dermal ulcers on their extremities, which are susceptible to infection. Individuals with infected diabetic ulcers often require hospitalization, intensive services, expensive antibiotics, and, in some cases, amputation. Dermal ulcers, such as those resulting from venous disease (venous stasis ulcers), excessive pressure (decubitus ulcers) and arterial ulcers also resist healing. The prior art treatments are generally limited to keeping the wound protected, free of infection and, in some cases, to restore blood flow by vascular surgery. According to the present method, the afflicted area of skin can be treated by a therapy which includes a hedgehog agonist which promotes epithelization of the wound, e.g., accelerates the rate of the healing of the skin ulcers.

The present treatment can also be effective as part of a therapeutic regimen for treating oral and paraoral ulcers, e.g., resulting from radiation and/or chemotherapy. Such ulcers commonly develop within days after chemotherapy or radiation therapy. These ulcers usually begin as small, painful irregularly shaped lesions usually covered by a delicate gray necrotic membrane and surrounded by inflammatory tissue. In many instances, lack of treatment results in proliferation of tissue around the periphery of the lesion on an inflammatory basis. For instance, the epithelium bordering the ulcer usually demonstrates proliferative activity, resulting in loss of continuity of surface epithelium. These lesions, because of their size and loss of epithelial integrity, lend the body to potential secondary infection. Routine ingestion of food and water becomes a very painful event and, if the ulcers proliferate throughout the alimentary canal, diarrhea usually is evident with all its complicating factors. According to the present invention, a treatment for such ulcers which includes application of a hedgehog agonist can reduce the abnormal proliferation and differentiation of the affected epithelium, helping to reduce the severity of subsequent inflammatory events.

In another exemplary embodiment, the subject method is provided for treating or preventing gastrointestinal diseases. Briefly, a wide variety of diseases are associated with disruption of the gastrointestinal epithelium or villi, including chemotherapy- and radiation-therapy-induced enteritis (i.e., gut toxicity) and mucositis, peptic ulcer disease, gastroenteritis and colitis, villus atrophic disorders, and the like. For example, chemotherapeutic agents and radiation therapy used in bone marrow transplantation and cancer therapy affect rapidly proliferating cells in both the hematopoietic tissues and small intestine, leading to severe and often dose-limiting toxicities. Damage to the small intestine mucosal barrier results in serious complications of bleeding and sepsis. The subject method can be used to promote proliferation of gastrointestinal epithelium and thereby increase the tolerated doses for radiation and chemotherapy agents. Effective treatment of gastrointestinal diseases may be determined by several criteria, including an enteritis score, other tests well known in the art.

Levine et al. (1997) *J Neurosci* 17:6277 show that hedgehog proteins can regulate mitogenesis and photoreceptor differentiation in the vertebrate retina, and Ihh is a candidate factor from the pigmented epithelium to promote retinal progenitor proliferation and photoreceptor differentiation. Likewise, Jensen et al. (1997) *Development* 124:363 demonstrated that treatment of cultures of perinatal mouse retinal cells with the amino-terminal fragment of Sonic hedgehog protein results in an increase in the proportion of cells that incorporate bromodeoxyuridine, in total cell numbers, and in rod photoreceptors, amsacrine cells and Muller glial cells, suggesting that Sonic hedgehog promotes the proliferation of retinal precursor cells. Thus, the subject method can be used in the treatment of degenerative diseases of retinal cells and regulate photoreceptor differentiation.

With age, the epidermis thins and the skin appendages atrophy. Hair becomes sparse and sebaceous secretions decrease, with consequent susceptibility to dryness, chapping, and fissuring. The dermis diminishes with loss of elastic and collagen fibers. Moreover, keratinocyte proliferation (which is indicative of skin thickness and skin proliferative capacity) decreases with age. An increase in keratinocyte proliferation is believed to counteract skin aging, i.e., wrinkles, thickness, elasticity and repair. According to the present invention, a proliferative form of a hedgehog agonist can be used either therapeutically or cosmetically to counteract, at least for a time, the effects of aging on skin.

Yet another aspect of the present invention relates to the use of the subject method to promote hair growth. Hair is basically composed of keratin, a tough and insoluble protein; its chief strength lies in its disulphide bond of cysteine. Each individual hair comprises a cylindrical shaft and a root, and is contained in a follicle, a flask-like depression in the skin. The bottom of the follicle contains a finger-like projection termed the papilla, which consists of connective tissue from which hair grows, and through which blood vessels supply the cells with nourishment. The shaft is the part that extends outwards from the skin surface, whilst the root has been described as the buried part of the hair. The base of the root expands into the hair bulb, which rests upon the papilla. Cells from which the hair is produced grow in the bulb of the follicle; they are extruded in the form of fibers as the cells proliferate in the follicle. Hair "growth" refers to the formation and elongation of the hair fiber by the dividing cells.

As is well known in the art, the common hair cycle is divided into three stages: anagen, catagen, and telogen. During the active phase (anagen), the epidermal stem cells of the dermal papilla divide rapidly. Daughter cells move upward and differentiate to form the concentric layers of the hair itself. The transitional stage, catagen, is marked by the cessation of mitosis of the stem cells in the follicle. The resting stage is known as telogen, where the hair is retained within the scalp for several weeks before an emerging new hair developing below it dislodges the telogen-phase shaft from its follicle. From this model it has become clear that the larger the pool of dividing stem cells that differentiate into hair cells, the more hair growth occurs. Accordingly, methods for increasing or reducing hair growth can be carried out by potentiating or inhibiting, respectively, the proliferation of these stem cells.

Thus, in certain embodiments, the subject method can be employed as a way of promoting the growth of human hair, e.g., to correct baldness, alopecia, or other diseases characterized by hair loss.

The subject method can also be used in treatment of a wound to eye tissue. Generally, damage to corneal tissue, whether by disease, surgery or injury, may affect epithelial and/or endothelial cells, depending on the nature of the wound. Corneal epithelial cells are the non-keratinized epithelial cells lining the external surface of the cornea and provide a protective barrier against the external environment. Corneal wound healing has been of concern to both clinicians and researchers. Ophthalmologists are frequently confronted with corneal dystrophies and problematic injuries that result in persistent and recurrent epithelial erosion, often leading to permanent endothelial loss. The use of proliferative forms of the subject hedgehog agonists can be used in these instances to promote epithelialization of the affected corneal tissue.

To further illustrate, specific disorders typically associated with epithelial cell damage in the eye, and for which the subject method can provide beneficial treatment, include persistent corneal epithelial defects, recurrent erosions, neurotrophic corneal ulcers, keratoconjunctivitis sicca, microbial corneal ulcers, viral cornea ulcers, and the like. Surgical procedures typically causing injury to the epithelial cell layers include laser procedures performed on the ocular surface, any refractive surgical procedures such as radial keratotomy and astigmatic keratotomy, conjunctival flaps, conjunctival transplants, epikeratoplasty, and corneal scraping. Moreover, superficial wounds such as scrapes, surface erosion, inflammation, etc. can cause lose of epithelial cells. According to the present invention, the corneal epithelium is contacted with an amount of a hedgehog agonist effective to cause proliferation of the corneal epithelial cells to appropriately heal the wound.

In another aspect of the invention, the subject method can be used to induce differentiation and/or promote proliferation of epithelially derived tissue. Such forms of these molecules can provide a basis for differentiation therapy for the treatment of hyperplastic and/or neoplastic conditions involving epithelial tissue. For example, such preparations can be used for the treatment of cutaneous diseases in which there is abnormal proliferation or growth of cells of the skin.

The present method can be used for improving the "take rate" of a skin graft. Grafts of epidermal tissue can, if the take rate of the graft is to long, blister and shear, decreasing the likelihood that the autograft will "take", i.e. adhere to the wound and form a basement membrane with the underlying granulation tissue. Take rates can be increased by the subject method by inducing proliferation of the keratinocytes. The method of increasing take rates comprises contacting the skin autograft with an effective wound healing amount of a hedgehog agonist described in the method of promoting wound healing and in the method of promoting the growth and proliferation of keratinocytes, as described above.

Skin equivalents have many uses not only as a replacement for human or animal skin for skin grafting, but also as test skin for determining the effects of pharmaceutical substances and cosmetics on skin. A major difficulty in pharmacological, chemical and cosmetic testing is the difficulties in determining the efficacy and safety of the products on skin. One advantage of the skin equivalents of the invention is their use as an indicator of the effects produced by such substances through in vitro testing on test skin.

Thus, in one embodiment of the subject method can be used as part of a protocol for skin grafting of, e.g., denuded areas; granulating wounds and burns. The use of hedgehog agonists can enhance such grafting techniques as split thickness autografts and epidermal autografts (cultured autogenic keratinocytes) and epidermal allografts (cultured allogenic keratinocytes). In the instance of the allograft, the use of the subject method to enhance the formation of skin equivalents in culture helps to provide/maintain a ready supply of such grafts (e.g., in tissue banks) so that the patients might be covered in a single procedure with a material which allows permanent healing to occur.

In this regard, the present invention also concerns composite living skin equivalents comprising an epidermal layer of cultured keratinocyte cells which have been expanded by treatment with a hedgehog agonist. The subject method can be used as part of a process for the preparation of composite living skin equivalents. In an illustrative embodiment, such a method comprises obtaining a skin sample, treating the skin sample enzymically to separate the epidermis from the dermis, treating the epidermis enzymically to release the keratinocyte cells, culturing, in the presence of a hedgehog agonist, the epidermal keratinocytes until confluence, in parallel, or separately, treating the dermis enzymatically to release the fibroblast cells, culturing the fibroblasts cells until sub-confluence, inoculating a porous, cross-linked collagen sponge membrane with the cultured fibroblast cells, incubating the inoculated collagen sponge on its surface to allow the growth of the fibroblast cells throughout the collagen sponge, and then inoculating it with cultured keratinocyte cells, and further incubating the composite skin equivalent complex in the presence of a hedgehog agonist to promote the growth of the cells.

In other embodiments, skin sheets containing both epithelial and mesenchymal layers can be isolated in culture and expanded with culture media supplemented with a proliferative form of a hedgehog agonist. Any skin sample amenable to cell culture techniques can be used in accordance with the present invention. The skin samples may be autogenic or allogenic.

In another aspect of the invention, the subject method can be used in conjunction with various periodontal procedures in which control of epithelial cell proliferation in and around periodontal tissue is desired. In one embodiment, hedgehog agonists can be used to enhance reepithelialization around natural and prosthetic teeth, e.g., to promote formation of gum tissue.

Hedgehog gene products are able to regulate maturation of T lymphocytes. Certain aspects of the invention are directed to hedgehog agonists and their uses as immunomodulatory agents against both acquired and hereditary immunological disorders.

For instance, such compositions can be used to increase the population of T-helper cells to optimum levels in the host, e.g., to stimulate the immune system of the animal. Such uses of the subject compositions can be used in the treatment of bacterial or viral infections, as well as to help the body fight against cancer cells. Alternatively, these substances also enable the host to adjust to diseases arising from disarrangement of self-recognition processes in which there is excessive attack by host T-cells against endogenous tissues. In such instances, the subject compositions can be used to reduce T-cell population so that the signs and symptoms of self-directed inflammatory (autoimmune) diseases such rheumatoid arthritis and multiple sclerosis are ameliorated.

As described herein, hedgehog proteins inhibit maturation of T lymphocytes. Based upon its inhibitory effect, the administration of hedgehog agonists is suggested herein as a treatment for several types of immunological disorders involving unwanted activation of cellular immunity, e.g., graft rejection, autoimmune disorders, and the like.

In general, the method of the present invention comprises administering to animal, or to cultured lymphocytes in vitro, an amount of a hedgehog agonist which produces a non-toxic response by the cell of inhibition of maturation. The subject method can be carried out on cells which may be either dispersed in culture or a part of an intact tissue or organ. Moreover, the method can be performed on cells which are provided in culture (in vitro), or on cells in a whole animal (in vivo). The invention also relates to methods of controlling the functional performance of T cells by use of the pharmaceutical preparations of the invention.

Without wishing to be bound by any particular theory, the inhibitory effect of hedgehog on T cell maturation may be due at least in part to the ability of hedgehog proteins to antagonize (directly or indirectly) patched-mediated regulation of gene expression and other physiological effects mediated by that protein. The patched gene product, a cell surface protein, is understood to signal through a pathway which causes transcriptional repression of members of the Wnt and Dpp/BMP families of morphogens, proteins which impart positional information. In other tissue, the introduction of hedgehog relieves (derepresses) this inhibition conferred by patched, allowing expression of particular gene programs.

In another aspect, the present invention provides pharmaceutical preparations comprising hedgehog agonists. The hedgehog agonists for use in the subject method may be conveniently formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art Except insofar as any conventional media or agent is incompatible with the activity of the hedgehog agonist, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations".

Pharmaceutical formulations of the present invention can also include veterinary compositions, e.g., pharmaceutical preparations of the hedgehog agonists suitable for veterinary uses, e.g., for the treatment of livestock or domestic animals, e.g., dogs.

Rechargeable or biodegradable devices may also provide methods of introduction. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a hedgehog agonist at a particular target site. The preparations of the present invention may be given orally, parenterally, topically, or rectally. They are of course given by forms suitable for each administration route. For example, they are administered in tablets or capsule form, by injection, inhalation, eye lotion, ointment, suppository, controlled release patch, etc., administration by injection, infusion or inhalation; topical by lotion or ointment; and rectal by suppositories. Oral and topical administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular hedgehog agonist employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular, and subcutaneous doses of the compounds of this invention for a patient will range from about 0.0001 to about 100 mg per kilogram of body weight per day, preferably from about 0.001 to about 10 mg per kilogram, even more preferably from about 0.01 to about 1 mg per kilogram.

If desired, the effective daily dose of the active compound may be administered as two, three, four, five, six or more sub-doses administered separately at appropriate intervals throughout the day, optionally, in unit dosage forms.

The term "treatment" is intended to encompass also prophylaxis, therapy, and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable and/or sterile carriers and can also be administered in conjunction with other antimicrobial agents such as penicillins, cephalosporins, aminoglycosides, and glycopeptides. Conjunctive therapy, thus includes sequential, simultaneous and separate administration of the active compound in a way that the therapeutic effects of the first administered one is not entirely disappeared when the subsequent is administered.

V. Pharmaceutical Compositions

While it is possible for a compound of the present invention to be administered alone, it is preferable to administer the compound as a pharmaceutical formulation (composition). The hedgehog agonists according to the invention may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

Thus, another aspect of the present invention provides pharmaceutically acceptable compositions comprising a therapeutically effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject compounds may be simply dissolved or suspended in sterile water. In certain embodiments, the pharmaceutical preparation is non-pyrogenic, i.e., does not elevate the body temperature of a patient.

The phrase "therapeutically effective amount" as used herein means that amount of a compound, material, or composition comprising a compound of the present invention which is effective for producing some desired therapeutic effect in at least a sub-population of cells in an animal and thereby blocking the biological consequences of that pathway in the treated cells, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agonists from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present hedgehog agonists may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate tartrate, naphthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay, (9) lubricants, such a talc, calcium stearate, magnesium stearate, solid polyethylene glycols, sodium lauryl sulfate, and mixtures thereof, and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in microencapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active hedgehog agonist.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the hedgehog agonists in the proper medium. Absorption enhancers can also be used to increase the flux of the hedgehog agonists across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" 0 and B books, Corvallis, Ore., U.S.A., 1977).

VI. Synthetic Schemes and Identification of Active Agonists

The subject inhibitors, and congeners thereof, can be prepared readily by employing the cross-coupling technologies of Suzuki, Stille, and the like. These coupling reactions are carried out under relatively mild conditions and tolerate a wide range of "spectator" functionality.

a. Combinatorial Libraries

The compounds of the present invention, particularly libraries of variants having various representative classes of substituents, are amenable to combinatorial chemistry and other parallel synthesis schemes (see, for example, PCT WO 94/08051). The result is that large libraries of related compounds, e.g., a variegated library of compounds represented above, can be screened rapidly in high throughput assays in order to identify potential hedgehog agonist lead compounds, as well as to refine the specificity, toxicity, and/or cytotoxic-kinetic profile of a lead compound. For instance, ptc, hedgehog, or smoothened bioactivity assays can be used to screen a library of the subject compounds for those having antagonist activity toward ptc or agonist activity towards hedgehog or smoothened.

Simply for illustration, a combinatorial library for the purposes of the present invention is a mixture of chemically related compounds which may be screened together for a desired property. The preparation of many related compounds in a single reaction greatly reduces and simplifies the number of screening processes which need to be carried out. Screening for the appropriate physical properties can be done by conventional methods.

Diversity in the library can be created at a variety of different levels. For instance, the substrate aryl groups used in the combinatorial reactions can be diverse in terms of the core aryl moiety, e.g., a variegation in terms of the ring structure, and/or can be varied with respect to the other substituents.

A variety of techniques are available in the art for generating combinatorial libraries of small organic molecules such as the subject hedgehog agonists. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; the ArQule U.S. Pat. Nos. 5,736,412 and 5,712,171; Chen et al. (1994) *JACS* 116:2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 100 to 1,000,000 or more diversomers of the subject hedgehog agonists can be synthesized and screened for particular activity or property.

In an exemplary embodiment, a library of candidate hedgehog agonists diversomers can be synthesized utilizing a scheme adapted to the techniques described in the Still et al. PCT publication WO 94/08051, e.g., being linked to a polymer bead by a hydrolyzable or photolyzable group, optionally located at one of the positions of the candidate agonists or a substituent of a synthetic intermediate. According to the Still et al. technique, the library is synthesized on a set of beads, each bead including a set of tags identifying the particular diversomer on that bead. The bead library can then be "plated" with hedgehog-responsive cells. The diversomers can be released from the bead, e.g., by hydrolysis.

The structures of the compounds useful in the present invention lend themselves readily to efficient synthesis. The nature of the structures of the subject compounds, as generally set forth above, allows the rapid combinatorial assembly of such compounds. For example, as in the scheme set forth below, an activated aryl group, such as an aryl triflate or bromide, attached to a bead or other solid support can be linked to another aryl group by performing a Stille or Suzuki coupling with an aryl stannane or an aryl boronic acid. If the second aryl group is functionalized with an aldehyde, an amine substituent can be added through a reductive amination. Alternatively, the second aryl group could be functionalized with a leaving group, such as a triflate, tosylate, or halide, capable of being displaced by an amine. Or, the second aryl group may be functionalized with an amine group capable of undergoing reductive amination with an amine, e.g., CyKNH$_2$. Other possible coupling techniques include transition metal-mediated amine arylation-reactions. The resultant secondary amine can then be further functionalized by an acylation, alkylation, or arylation to generate a tertiary amine or amide which can then be cleaved from the resin or support. These reactions generally are quite mild and have been successfully applied in combinatorial solid-phase synthesis schemes. Furthermore, the wide range of substrates and coupling partners suitable and available for these reactions permits the rapid assembly of large, diverse libraries of compounds for testing in assays as set forth herein. For certain schemes, and for certain substitutions on the various substituents of the subject compounds, one of skill in the art will recognize the need for masking certain functional groups with a suitable protecting group. Such techniques are well known in the art and are easily applied to combinatorial synthesis schemes.

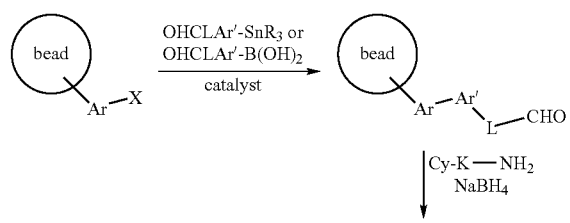

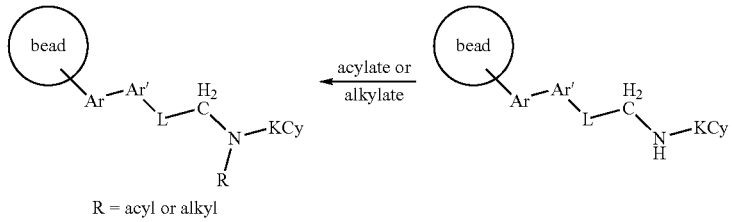

R = acyl or alkyl

Many variations on the above and related pathways permit the synthesis of widely diverse libraries of compounds which may be tested as agonists of hedgehog function.

b. Screening Assays

There are a variety of assays available for determining the ability of a compound to antagonize ptc function or agonize smoothened or hedgehog function, many of which can be disposed in high-throughput formats. In many drug-screening programs which test libraries of compounds and natural extracts, high throughput assays are desirable in order to maximize the number of compounds surveyed in a given period of time. Thus, libraries of synthetic and natural products can be sampled for other compounds which are hedgehog agonists.

In addition to cell-free assays, test compounds can also be tested in cell-based assays. In one embodiment, cell which are responsive to the addition of hedgehog protein can be contacted with a test agent of interest, with the assay scoring for, e.g., promotion of proliferation of the cell in the presence of the test agent.

A number of gene products have been implicated in patched-mediated signal transduction, including patched, transcription factors of the cubitus interruptus (ci) family, the serine/threonine kinase fused (fu) and the gene products of costal-2, smoothened and suppressor of fused.

The induction of cells by hedgehog proteins sets in motion a cascade involving the activation and inhibition of downstream effectors, the ultimate consequence of which is, in some instances, a detectable change in the transcription or translation of a gene. Potential transcriptional targets of hedgehog-mediated signaling are the patched gene (Hidalgo and Ingham, 1990 *Development* 110, 291-301; Marigo et al., 1996) and the vertebrate homologs of the *drosophila* cubitus interruptus gene, the Gli genes (Hui et al; (1994) *Dev Biol* 162:402-413). Patched gene expression has been shown to be induced in cells of the limb bud and the neural plate that are responsive to Shh. (Marigo et al.; (1996) *PNAS* 93:9346-51; Marigo et al. (1996) *Development* 122:1225-1233). The Gli genes encode putative transcription factors having zinc finger DNA binding domains (Orenic et al. (1990) *Genes & Dev* 4:1053-1067; Kinzler et al. (1990) *Mol Cell Biol* 10:634-642). Transcription of the Gi gene has been reported to be upregulated in response to hedgehog in limb buds, while transcription of the Gli3 gene is downregulated in response to hedgehog induction (Marigo et al. (1996) *Development* 122: 1225-1233). By selecting transcriptional regulatory sequences from such target genes, e.g., from patched or Gli genes, that are responsible for the up- or down-regulation of these genes in response to hedgehog signalling, and operatively linking such promoters to a reporter gene, one can derive a transcription based assay which is sensitive to the ability of a specific test compound to modify hedgehog-mediated signalling pathways. Expression of the reporter gene, thus, provides a valuable screening tool for the development of compounds that act as agonists of hedgehog.

Reporter gene based assays of this invention measure the end stage of the above-described cascade of events, e.g., transcriptional modulation. Accordingly, in practicing one embodiment of the assay, a reporter gene construct is inserted into the reagent cell in order to generate a detection signal dependent on activation of the hedgehog pathway, or stimulation by Shh itself. The amount of transcription from the reporter gene may be measured using any method known to those of skill in the art to be suitable. For example, mRNA expression from the reporter gene may be detected using RNAse protection or RNA-based PCR, or the protein product of the reporter gene may be identified by a characteristic stain or an intrinsic biological activity. The amount of expression from the reporter gene is then compared to the amount of expression in either the same cell in the absence of the test compound or it may be compared with the amount of transcription in a substantially identical cell that lacks the target receptor protein. Any statistically or otherwise significant increase in the amount of transcription indicates that the test compound has in some manner antagonized the normal ptc signal (or agonized the hedgehog or smoothened signal), e.g., the test compound is a potential hedgehog agonist.

EXEMPLIFICATION

The invention now being generally described, it will be more readily understood by reference to the following examples which are included merely for purposes of illustration of certain aspects and embodiments of the present invention, and are not intended to limit the invention.

In the experimental section below, the term 'Hh protein' is used to designate octyl-Shh-N, a lipophilic form of a bacterially derived fragment of human sonic hedgehog protein (amino acids 24-198, Shh-N). Specifically, Shh-N has been covalently linked in vitro via its amino terminal cysteine to an octyl maleimide group. This modified form, like others described recently (Pepinsky et al., *J. Biol. Chem.* 1998, 273, 1403745) exhibits higher specific potency than the corresponding unmodified fragment in several cell-based assays of hedgehog signalling.

Compound Screening

To measure the hedgehog agonist activity of compounds, we used [10T1/2(s12)] cells containing the hedgehog-responsive Gli-Luc reporter-construct. In each MTP (MicroTiter Plate; 96-well plate), 10,000-20,000 cells were plated per well, in full media (10% FBS). After about 2448 hr, plates were switched to low-serum media (=0.5% FBS). Subsequently, a test compound was added at 1-5 µM in the presence or absence of octyl-hedgehog (see below). After another 24 hr, the media from the MTs was discarded and replaced with luciferase assay-mix, containing lysis-buffer with luciferase substrate. The plates were incubated at RT for about 15-30 min and read in a luminometer.

Screen A

Plates were incubated for 48 hr before switching to low-serum. Compounds were screened at 1-2 µM in the presence of Hh protein (0.01 µg/ml; $EC_{30}$=about 30% of max-induced activity).

Screen B

Plates were incubated for 24 hr before switching to low-serum. Compounds were screened at 5 µM without adding Hh protein.

Compound Counter-Screen (SV-Luc)

For the counter-screen we used the [10T1/2(SV-Luc)] cells containing a SV40-luciferase expression cassette that allows for a constitutive level of luciferase-activity in the cells. This assay allows one to assess the specificity of the compounds selected in the Gli-Luc assay, i.e., whether the compounds specifically stimulate the hedgehog signalling pathway only, or reporter-constructs in general. Cell plating and cultivation as well as compound handling were performed as in the Gli-Luc assay. In this assay, no Hh protein was added because the reporter-construct is constitutively active already.

Figure 32A:
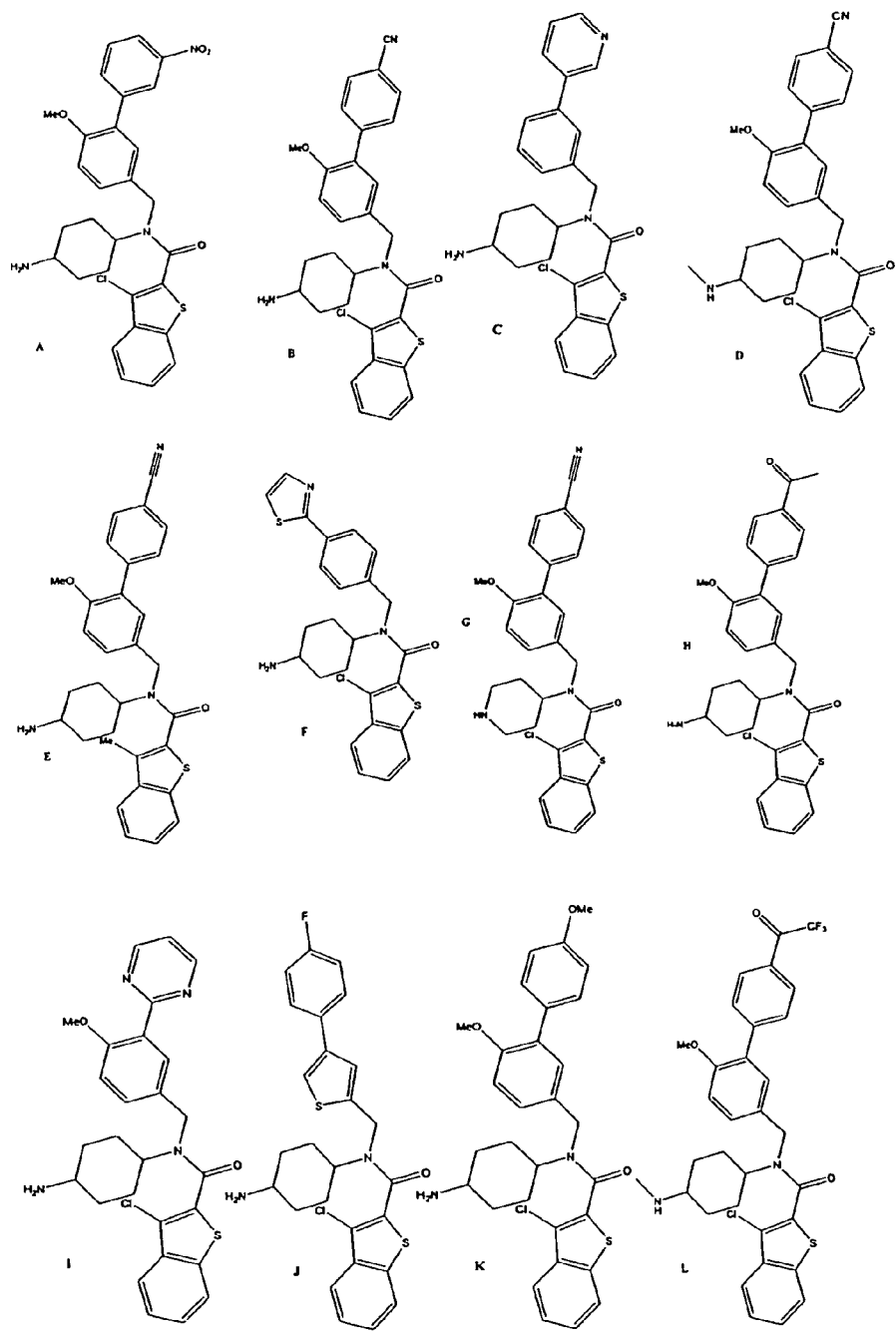
FIGS. 32 and 33 illustrate representative compounds according to the present invention.
Figure 32B:
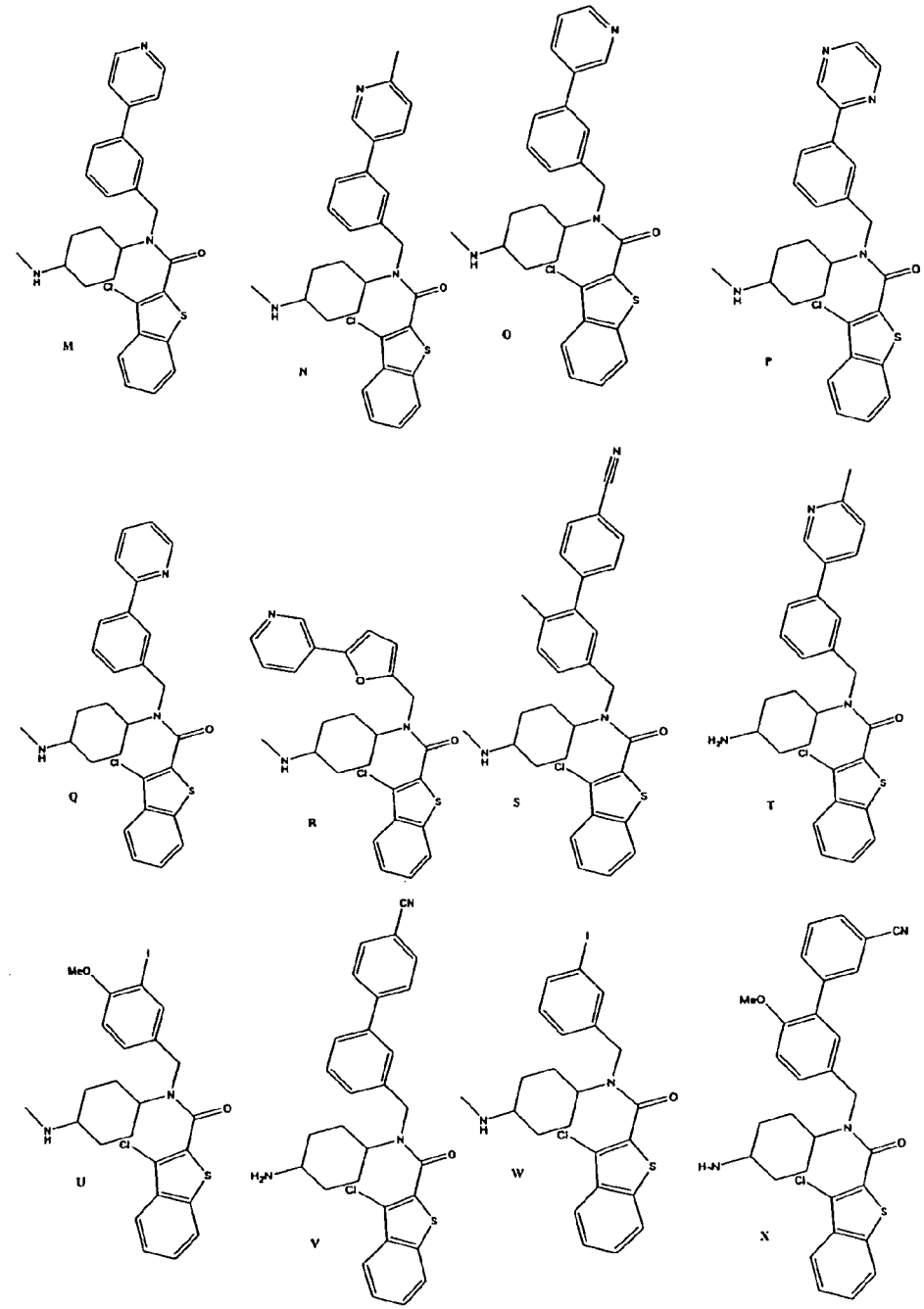
Figure 32:
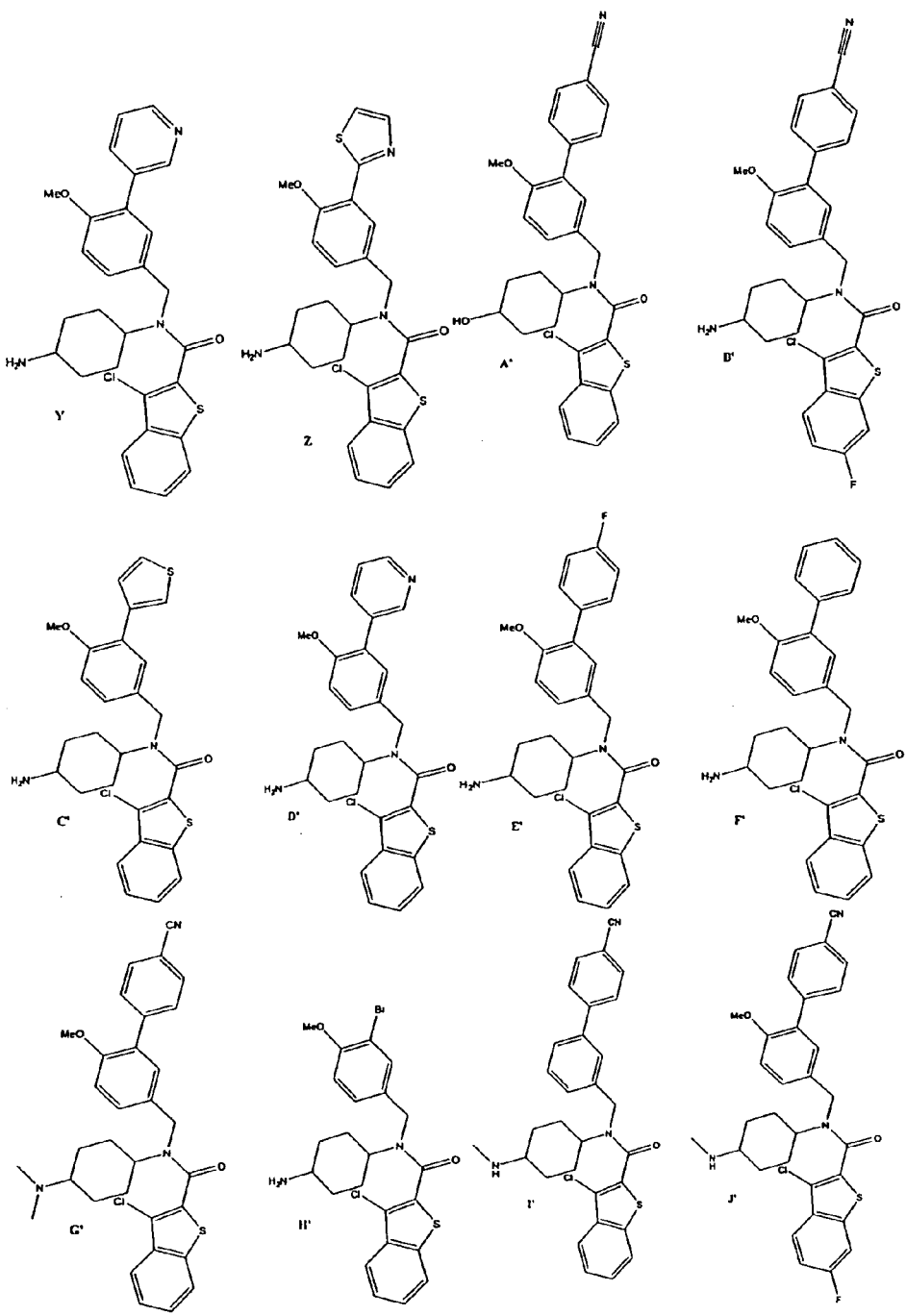
Figure 32D:
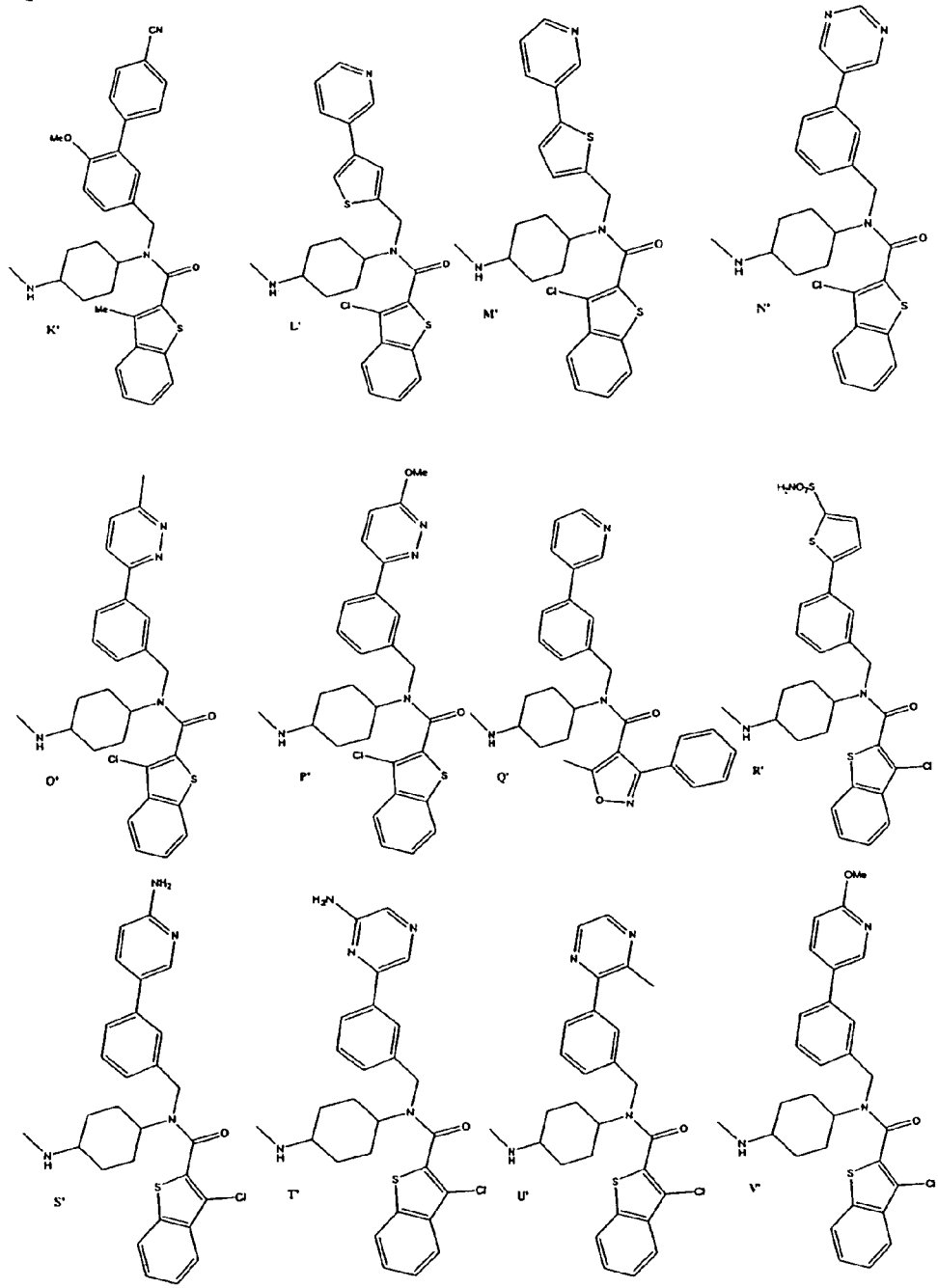
Figure 32E:
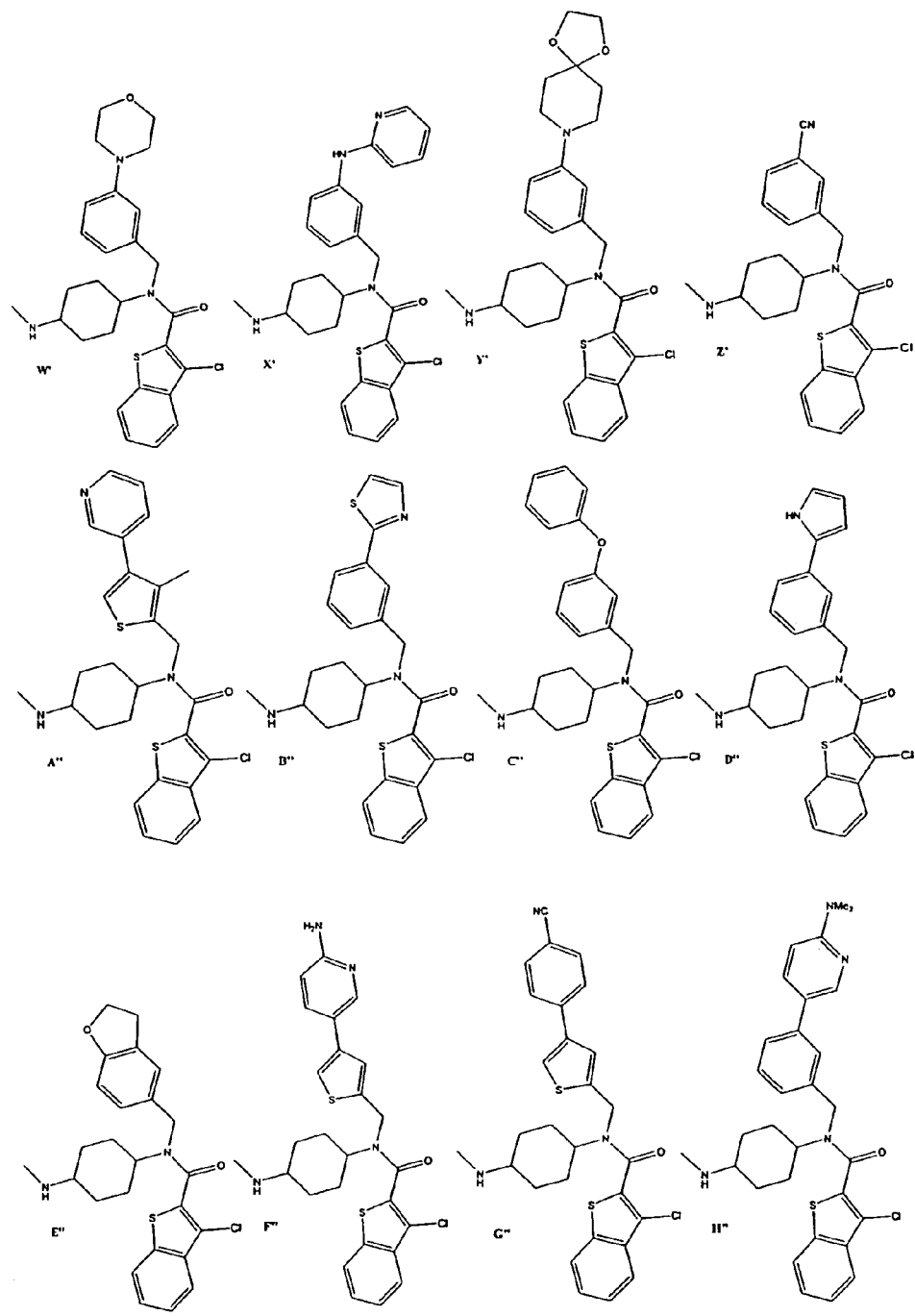
Figure 32F:
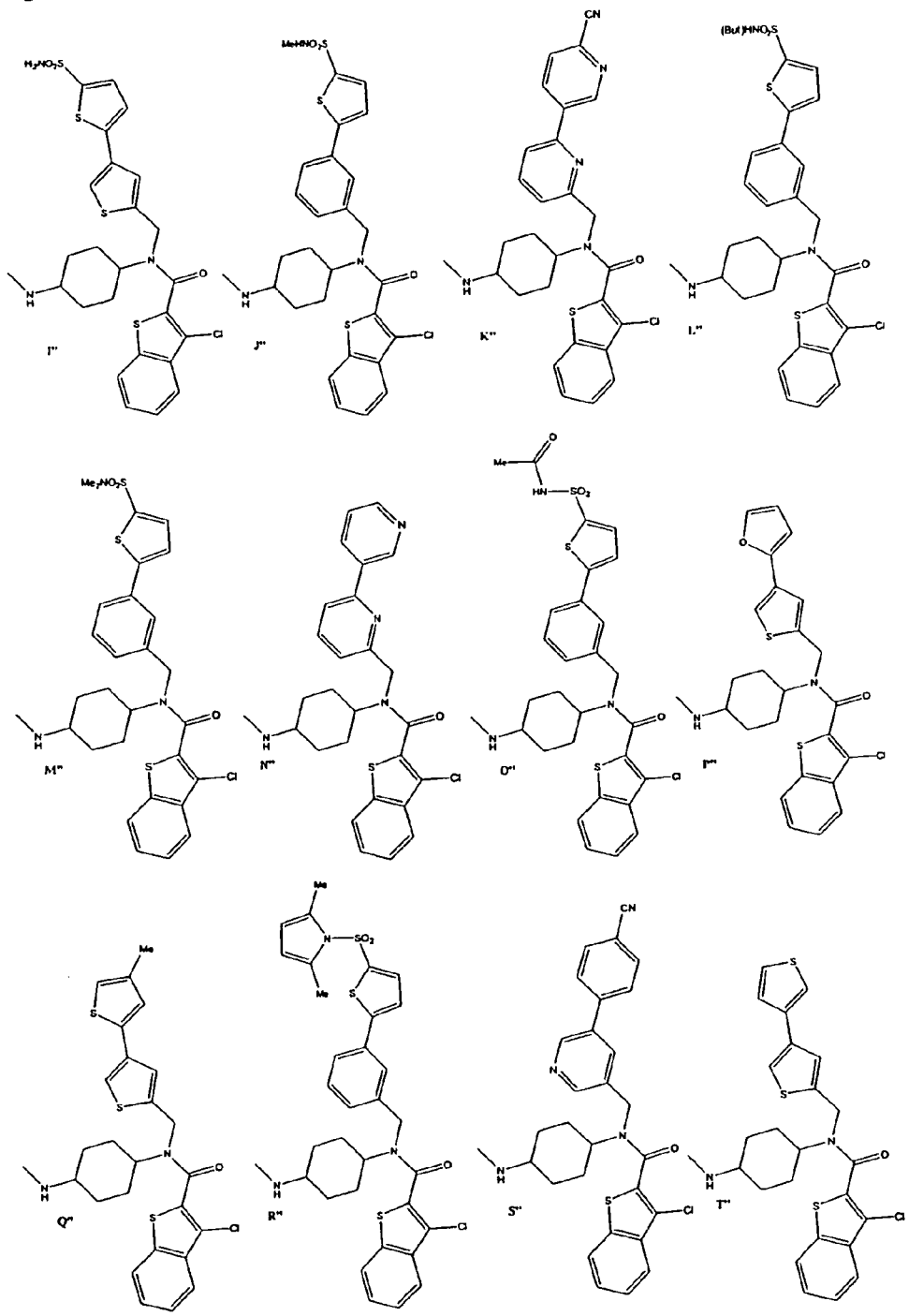
Figure 32G:
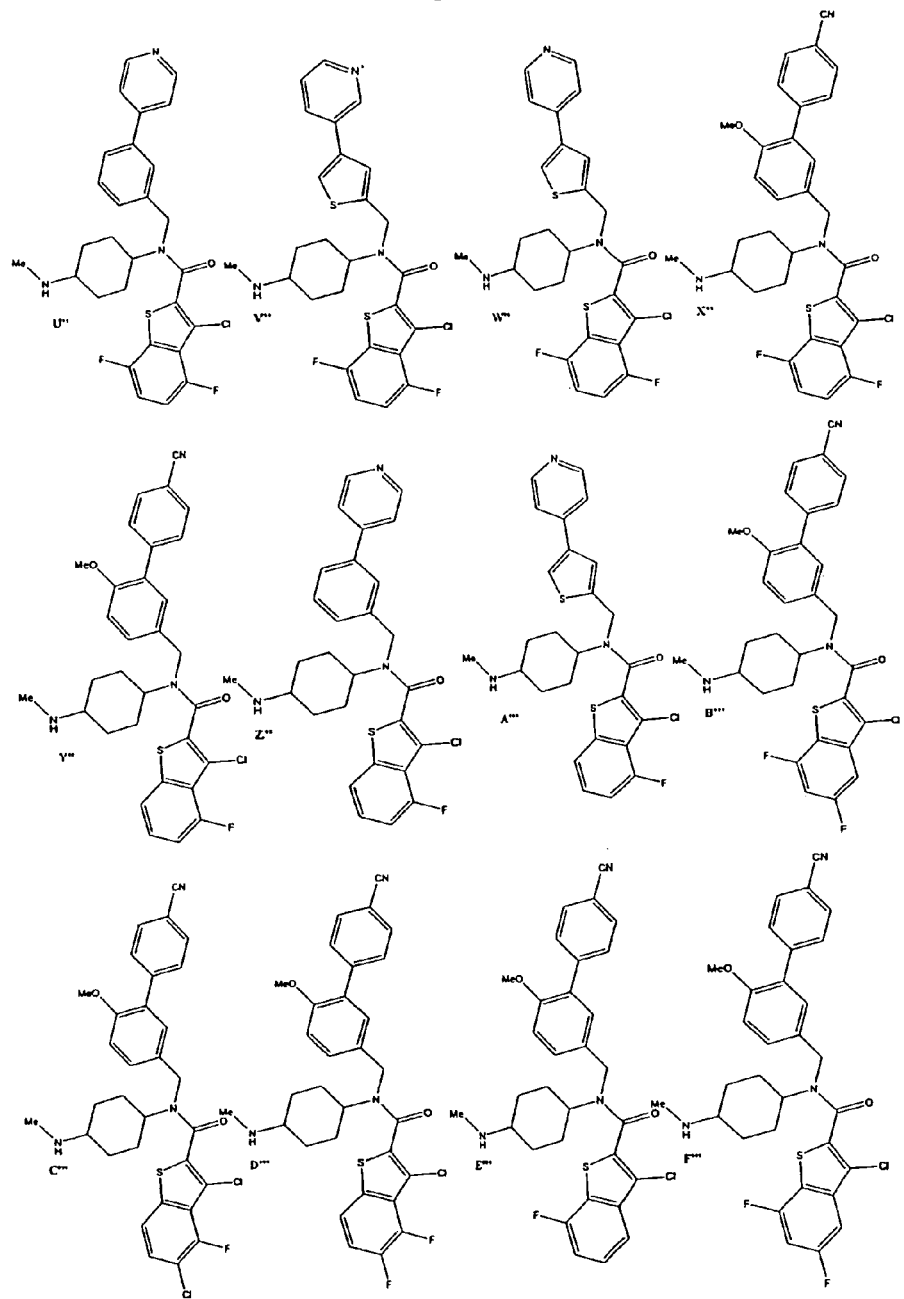
Figure 32H:
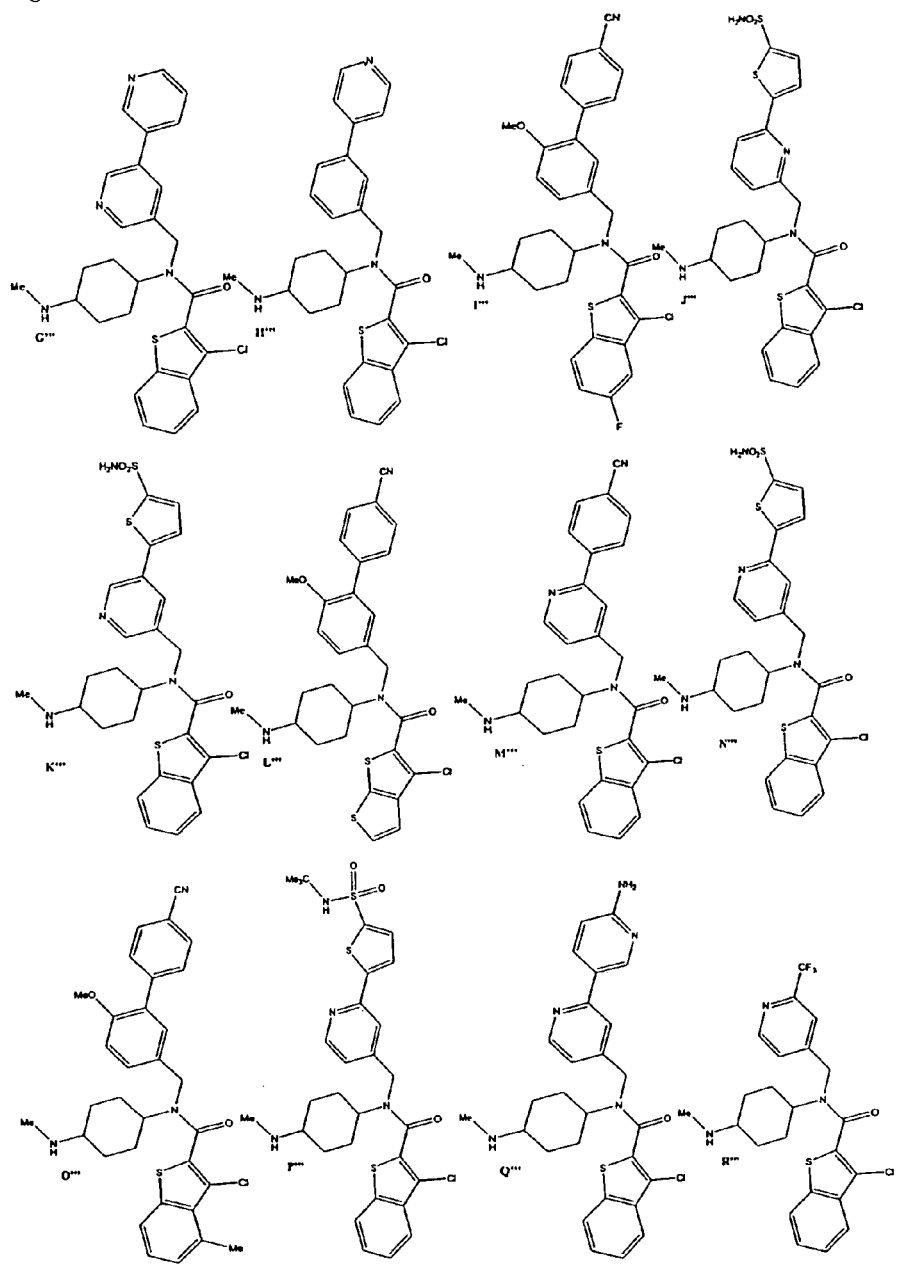
Figure 32I:
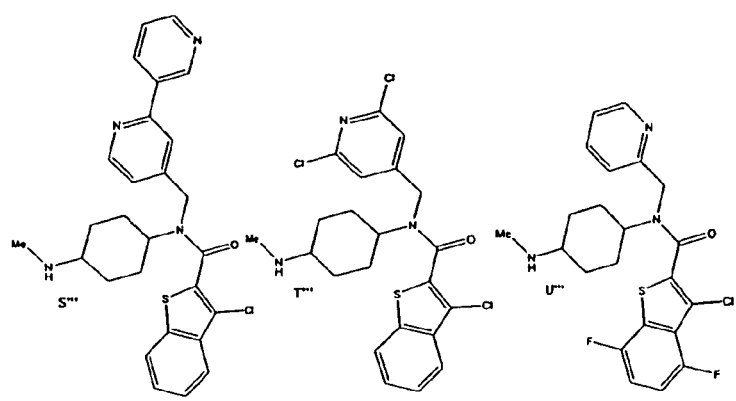
Figure 33A:
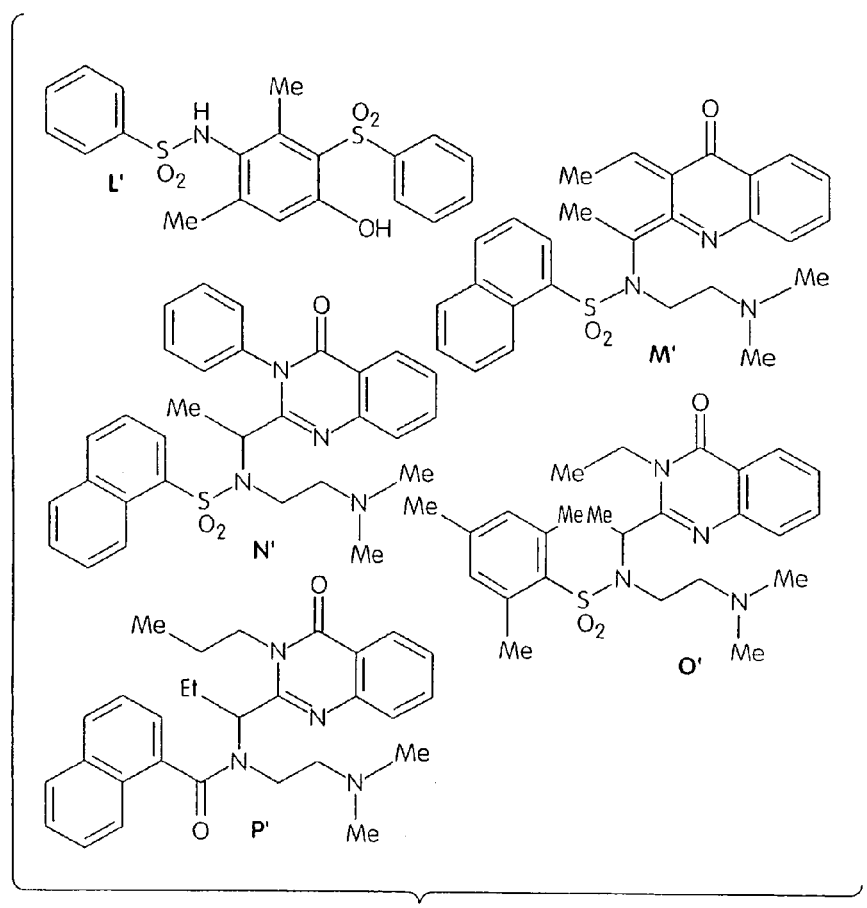
Figure 33B:
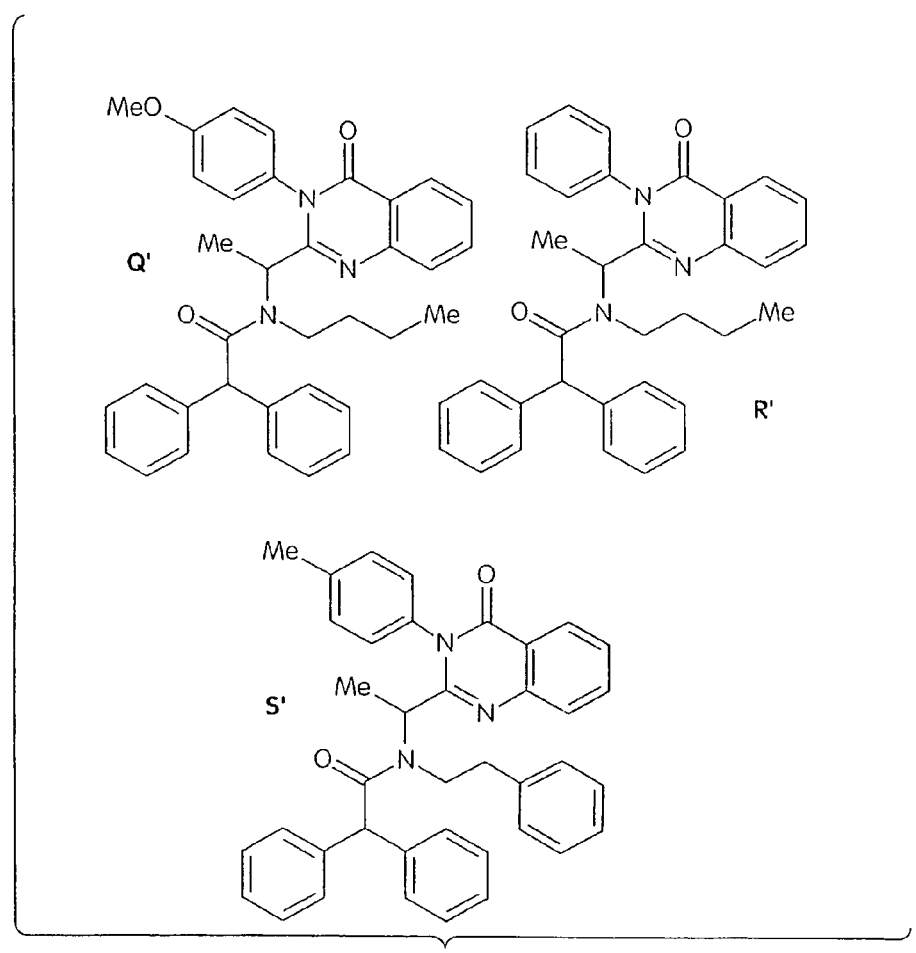
Figure 34A:
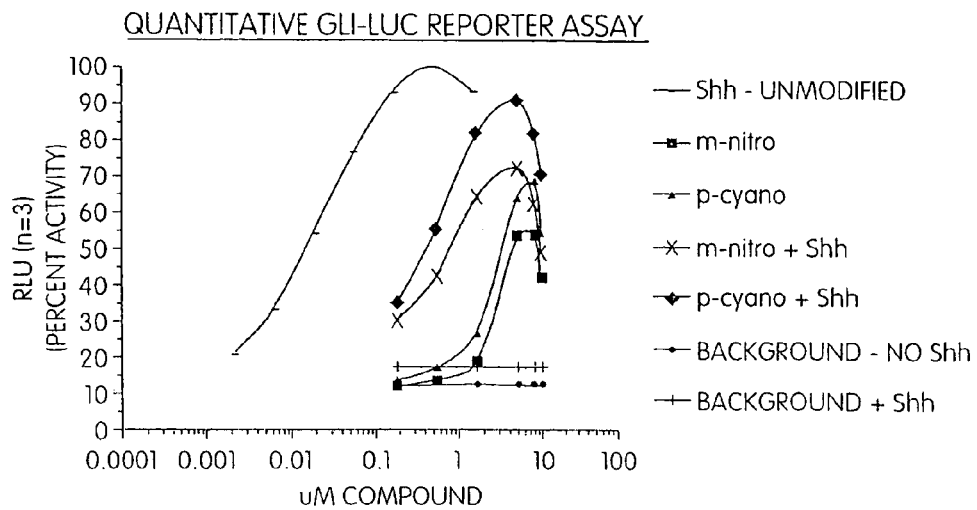
FIGS. 34a and 34b depict results from hedgehog pathway reporter assays using compounds of the present invention.
Figure 34B:
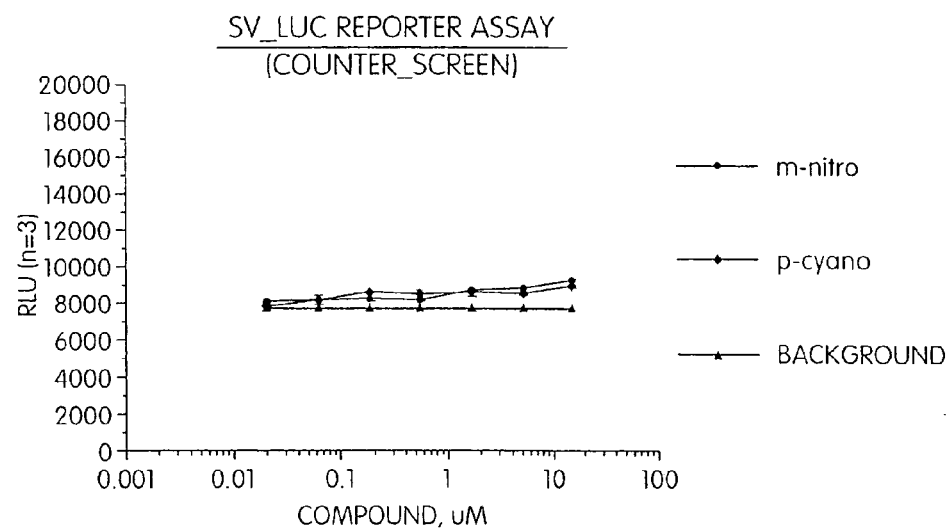

From Screen A, we identified hits identified in FIGS. 32 and 33. The 1,4-diaminocyclohexane subunit of the compounds of FIG. 32 which include this moiety have the two amino substituents disposed in a trans-relationship, e.g., both substituents equatorial on the cyclohexane subunit. These hits were confirmed in Screen B. The data shown in FIGS. 34a and 34b essentially involved dosing the two compounds in both assays (Gli-Luc & SV-Luc).

Figure 35:
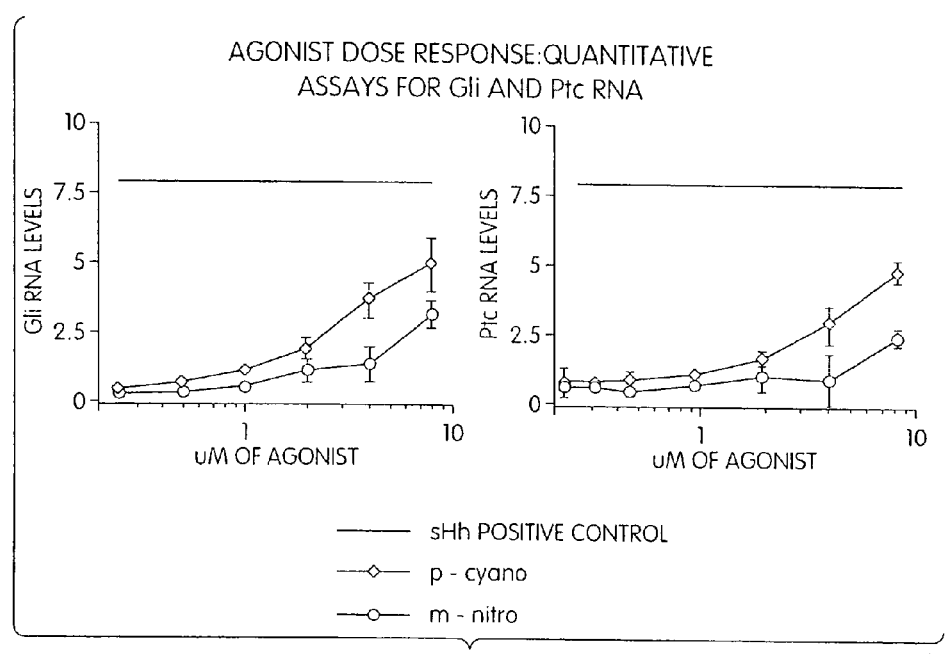
FIG. 35 presents assay results demonstrating upregulation of Ptc and Gli by hedgehog agonists of the present invention.

The data from the Gli-Luc assay is converted to percent activity where full activity with Hh protein is set at 100% (FIG. 35; Table 1). The data shows that the two compounds can significantly stimulate activity from the Gli-luc reporter construct (i.e., activate hedgehog signalling) even in the absence of Hh protein; concentration range 0.1-15 µM, EC50=2 µM, $EC_{max}$=50-70% of max-induced activity with Hh protein). Furthermore, the compounds show a more striking induction in the presence of hedgehog ($EC_{50}$=0.2-0.3 µM, $EC_{max}$=70-90% of max induced activity with Hh protein), indicating a synergy between the compounds and Hh protein, consistent with the compounds serving as agonists for the hedgehog pathway.

TABLE 1

| Compound | EC50 (µM) | Compound | EC50 (µM) |
|---|---|---|---|
| A |  | A' | <10 |
| B | <10 | B' | <10 |
| C | <1 | C' | <10 |
| D | <0.1 | D' | <10 |
| E | <10 | E' | <10 |
| F | <10 | F' | <10 |
| G | <10 | G' | <10 |
| H | <1 | H' | >10 |
| I | >10 | I' | <1 |
| J | <1 | J' | <1 |
| K | <1 | K' | <10 |
| L | <0.05 | L' | <0.05 |
| M | <1 | M' | <10 |
| N | <1 | N' | <1 |
| O | <1 | O' | <1 |
| P | <1 | P' | <1 |
| Q | <1 | Q' | <1 |
| R | <1 | R' | <0.05 |
| S | <1 | S' | <0.1 |
| T | <10 | T' | <0.5 |
| U | <10 | U' | <1 |
| V | <0 | V' | <1 |
| W | <10 | W' | <10 |
| X | <10 | X' | <10 |
| Y | <10 | Y' | <10 |
| Z | <10 | Z' | <10 |
| A" | <10 | B" | <10 |
| C" | <10 | D" | <10 |
| E" | <10 | F" | <0.1 |
| G" | <0.1 | H" | <0.1 |
| I" | <0.5 | J" | <0.5 |
| K" | <0.5 | L" | <1 |
| M" | <1 | N" | <1 |
| O" | <1 | P" | <10 |
| Q" | <1 | R" | <1 |
| S" | <10 | T" | <10 |
| U" | <0.005 | Y" | <0.005 |
| W" | <0.005 | X" | <0.005 |
| Y" | <0.05 | Z" | <0.05 |
| A'" | <0.05 | B'" | <0.05 |
| C'" | <0.05 | D'" | <0.05 |
| E'" | <0.05 | F'" | <0.05 |
| G'" | <5 | H'" | <0.05 |
| I'" | <0.05 | J'" | <0.5 |
| K'" | <5 | L'" | <5 |
| M'" | <0.5 | N'" | <5 |
| O'" | <1 | P'" | <5 |
| Q'" | <1 | R'" | <1 |
| S'" | <1 | T'" | <1 |
| U'" | <1 | | |

The data from the SV-Luc assay (FIG. 35) indicate that the two compounds do not affect the luciferase activity over the range of concentrations (up to 15 µM tested, suggesting that the compounds do not stimulate activity from a reporter-construct per se, but are probably specific to the hedgehog pathway. Also, the unaffected activity suggests that the compounds are not intrinsically toxic to the cells.

Hh Agonist: Quantitative RT-PCR Measurement of Gli Upregulation

The compounds of FIGS. 32 and 33 were tested for their ability to activate transcription of two well-studied targets of the Hedgehog pathway: the transcription factor Gli-1, and the putative Hedgehog receptor component Ptc-1. As depicted in FIG. 35, we found that, at a compound concentration of 8 µM, induction of both targets was approximately 60% for the p-cyanophenyl compound B and 40% for the m-nitrophenyl compound A of that obtained with the optimal concentration of Hh protein.

Assays were performed as follows:

Murine C3H 10T1/2 cells were seeded at approximately 200,000 cells per well in a 24-well plate in complete medium (10% FBS). After 24 hr, medium was removed and replaced with "starvation" medium (0.5% FBS) containing dilutions of compound or Hh protein. After 16-18 hr, total RNA was prepared using TriZol (Life Technologies, inc.).

One-microgram aliquots of total RNA were used to prepare random hexamer-primed cDNA with M-MTV Reverse transcriptase (Life Technologies, Inc.).

To measure the relative levels of Gli-1 and Ptc-1 transcripts, TaqMan assays (PE Biosystems) were performed with an ABI Prism 7700 Sequence Detection System. As an internal control, GAPDH transcript levels were simultaneously measured in each reaction. Data were analyzed using Sequence Detector v1.6.3 (Perkin Elmer).

Induction of Cerebellar Neuron Precursor Proliferation by Hedgehog Signaling Agonists.

Figure 36:
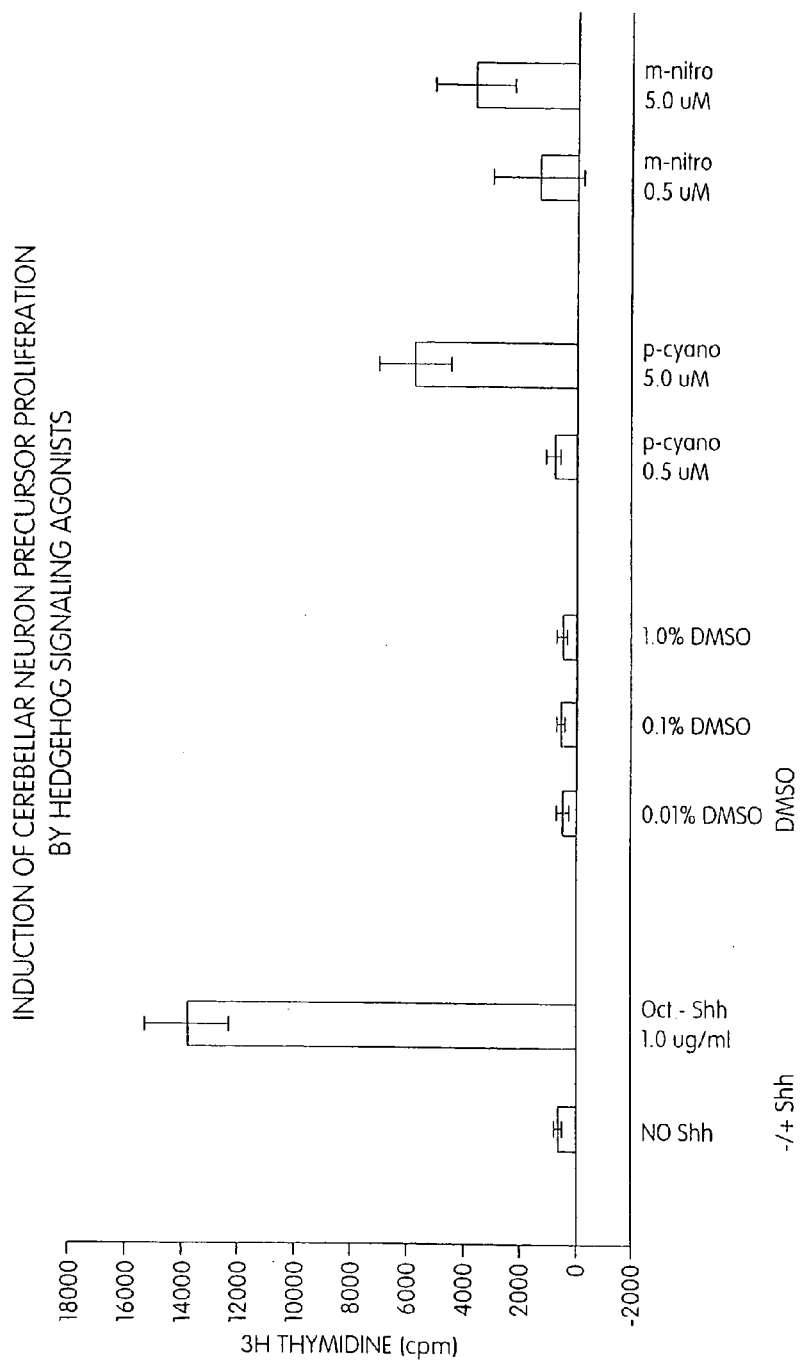

In order to test the efficacy of Hedgehog signaling agonists, the ability of the agonists to stimulate the proliferation of cerebellar neuron precursors was determined. Cerebellar granule neuron precursors are known to respond to Hh protein by proliferating. To test the agonists, cerebellar neurons were dissected out of postnatal (one week) rat brains, and placed into primary cell culture. Treatment agents were added once, on the first day of culture (0 DIV). Cells were left in culture until 2 DIV, when 3H-thymidine was added for 5 hours; the amount of incorporation by the cells of this 3H-thymidine provides a measure of the level of proliferation of the cells. Cells were then lysed, and the incorporation of 3H-thymidine was determined. The positive control was Hh protein, at 1.0 μg/ml final concentration. Hh protein alone caused approximately a 20-fold increase in 3H-thymidine incorporation, consistent with the known ability of Shh to stimulate proliferation of these cells. Non-Hh-protein-stimulated cells, including cells treated with control vehicle (DMSO), had very low levels of proliferation. However, the two of the Hh agonists in FIG. 32 that were tested, A and B, were found to significantly stimulate 3H-thymidine incorporation in the absence of Hh protein treatment, as depicted in FIG. 36. At 5.0 μM, the p-cyanophenyl compound B caused 10.2-fold induction of 3H-thymidine incorporation. FIG. 37 shows that agonist D also strongly stimulated 3H-thymidine incorporation in the absence of Shh. At 1.0, 0.3, or 0.1 μM, D caused 16-, 17-, or 13-fold induction, respectively, of 3H thymidine incorporation into the cells. These observations demonstrate that the hedgehog agonists can stimulate known hedgehog biological responses in target cells.

Nerve Crush Assay

CD-1 male mice were anesthetized with Avertin, 240 mg/kg IP. The area on the ventral side of the mouse leg around the knee was shaved and cleaned with 70% ethanol to remove the hair followed by swabbing with Betadine. The skin over the thigh was tented up with forceps and small scissors were used to make a ¼-inch cut in the skin. Fat was moved away to expose the femoral nerve, artery, and vein. With the tips of the curved #7 forceps pointing down, the muscle was spread apart just below the femoral artery/vein to reveal the sciatic nerve deep in the muscle. While using one pair of forceps to hold the muscle apart, a second pair was used to carefully lift up the nerve. Care was taken to not lift up the muscle fibers. The forceps were opened and closed 3 times to separate the nerve from the muscle. The nerve was held elevated from the muscle with the curved forceps and the hemostats were clamped down on the nerve to keep the nerve in the middle of the hemostats. The hemostats were held in place for 10 seconds. In this manner, both sciatic nerves were crushed approximately 1+ cm above the knee (and branches). The hemostats were unclipped and the nerve fell back into the muscle. A small pipette tip (P2) was used to apply a small amount of histological tissue marking dye to the crushed area. A surgical clip was used to close the incision. Care was taken not to clip the skin to the muscle. The clips were left in place throughout the entire experiment.

Control surgery was done to a group of mice. This involved lifting the nerve up with the forceps and letting it fall back into place without any crush. This site can also be marked with the histological dye.

Drug treatment began on the day of surgery. For Shh protein, a fusion protein of Shh and immunoglobin (as described in U.S. Provisional Application No. 60/164,025, incorporated herein by reference) administered at a dose of 1 mg/kg in a solution of PBS, a subcutaneous injection was given in the middle of the back of the animal with a 28 gauge, ½ cc insulin syringe and repeated every other day until day 12-13. (Recovery was complete by then.) For agonist administration, a solution of the agonist in 43% DMSO/PBS (FIGS. 38A and 39B), or in 10% DMSO/water (FIGS. 38B and 39D), was delivered by a minipump (1 μL/hour). Behavioral tests were initiated on day 4 post-surgery and continued until day 12 or 13.

Behavioral Testing—Grip Assay

A mouse was placed on an 8"×8" metal wire grid (like a test-tube rack) with 1 cm openings, and the grid was slowly inverted 10 times with a constant steady motion. The number of times the mouse failed to grip with its left and right hind limbs was recorded. The mouse was kept away from the edges of the grid by repositioning the mouse on the grid as necessary. If the mouse just hooked its leg around or through the grid it was considered a failure. An inversion was repeated if the mouse was walking, and failed to grip the grid.

Figure 38A:
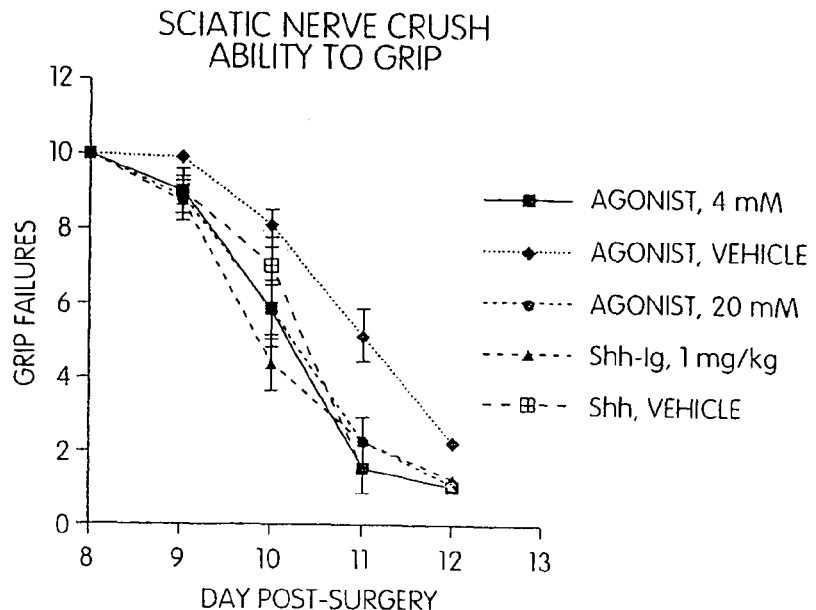
FIGS. 38A and B show the effect of subject agonists on healing of a crushed sciatic nerve as measured in a grip assay.
Figure 38B:
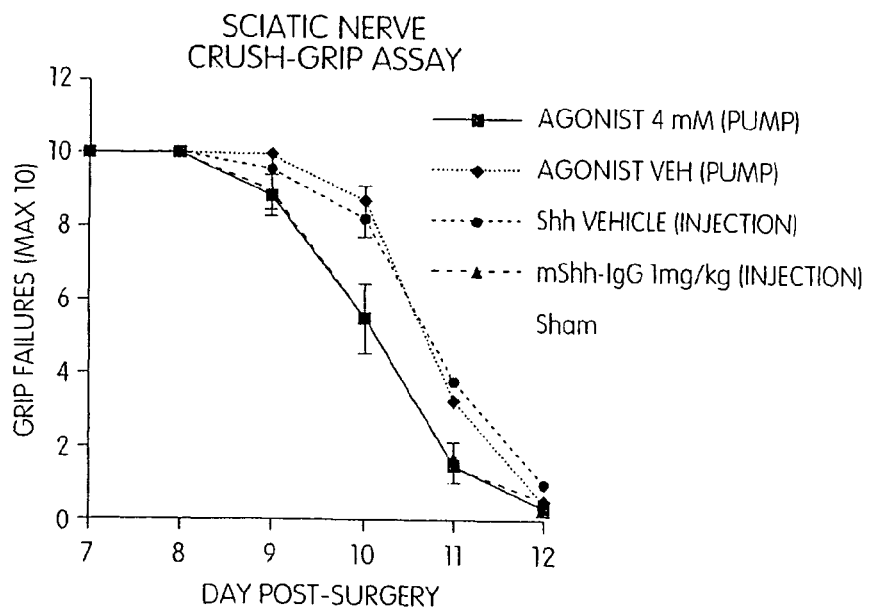

Failures of the left and right leg were pooled with other animals from that experimental group (6 animals/group×2 foot grip scores/animal=12 grip scores/group on any given time point). Results for agonist D are depicted in FIG. 38A. Animals treated with vehicle alone generally began to recover on their own by day 9 post-surgery. FIG. 38B depicts results obtained using agonist D dissolved in a vehicle of 10% DMSO/water in the treatment protocol.

Behavioral Testing—Toespread Measurements

Toespread measuring began at Day 4 post-surgery and was measured every other day. The mouse was held by the proximal part of the tail and permitted to hold onto the wire top of the cage with its front limbs. A small paintbrush or cotton applicator was used to paint the hind toes and footpads of the mouse. The mouse was allowed to walk across a clean sheet of paper, to leave at least two clean prints for each hind limb. Using a ruler, a line was drawn through the widest toe prints on each foot and the distance between them was measured. As the animals recovered, the distance increased to normal measurements.

Figure 39A:
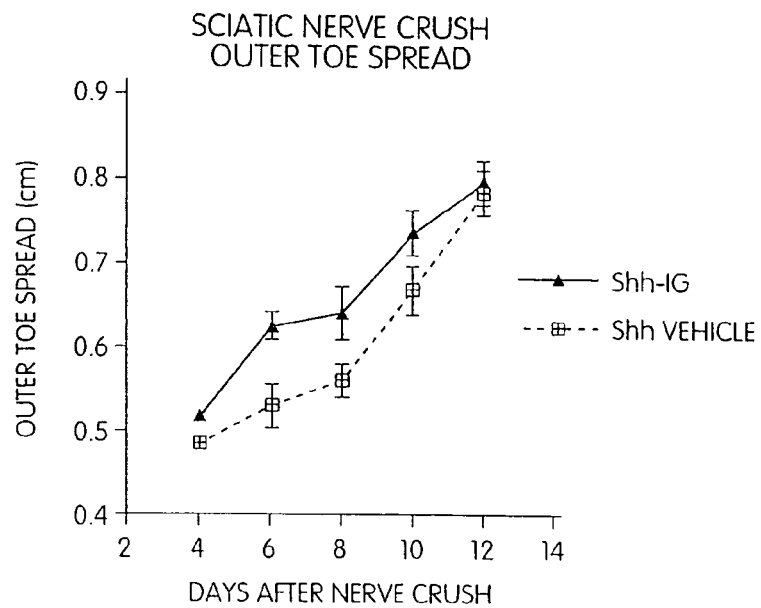
FIGS. 39A-D demonstrate the effect of subject agonists on healing of a crushed sciatic nerve as measured in a toe spread assay.
Figure 39B:
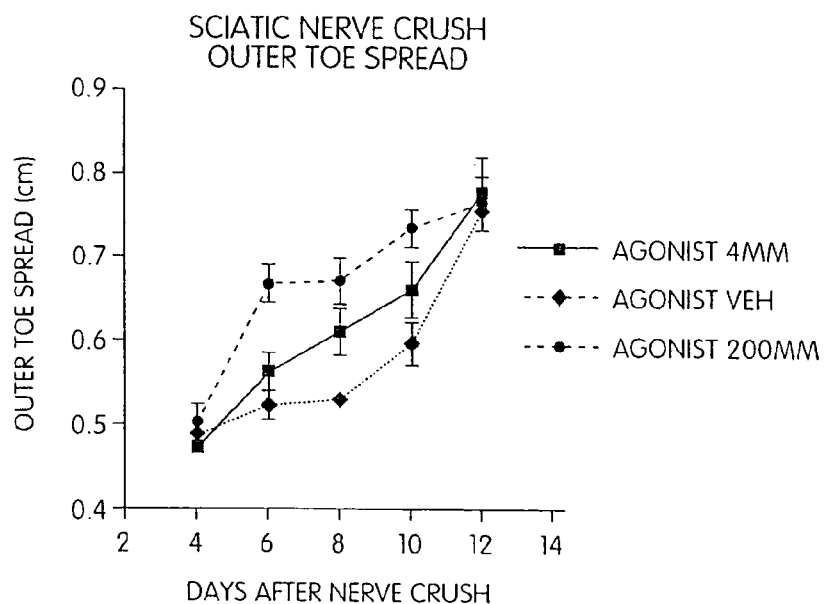
Figure 39C:
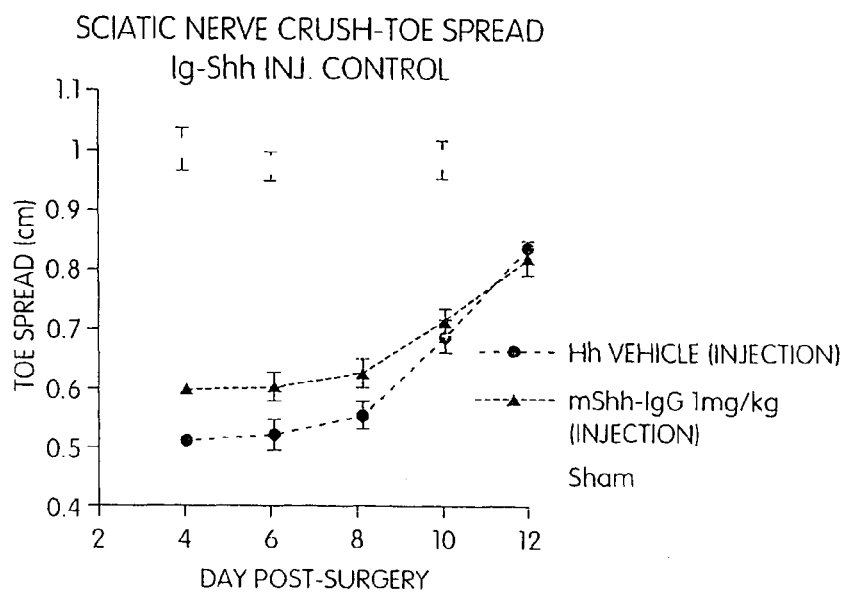
Figure 39D:
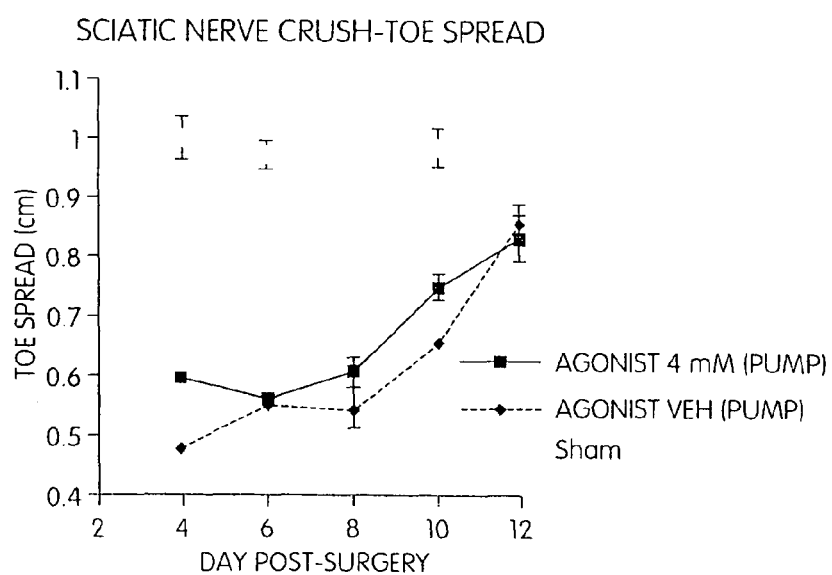

The left and right leg scores were averaged and pooled with the other animals from that experimental group (6 animals/group×2 foot grip scores/animal=12 toe spread scores/group on any given time point). Results using agonist D are depicted in FIGS. 39A and B. FIG. 39D depicts the effects of agonist D dissolved in a vehicle of 10% DMSO/water in this protocol.

Reporter Mice Assays

Mice with a β-galactosidase transgene (ptc-lacZ mice) under the regulatory control of the patched locus express the β-galactosidase protein in the same cells where the endogenous mouse patched gene is expressed. The β-galactosidase protein can thus be used as a faithful reporter of the expression of the endogenous patched gene. The patched gene is a known component of the hedgehog signalling pathway and is upregulated when the hedgehog pathway is activated. Hence, in the ptc-lacZ mice β-galactosidase protein is overexpressed in mice in which the hedgehog pathway has been activated, resulting in more intense blue staining (due to higher levels of the β-galactosidase enzyme) when tissues are stained for enzymatic activity with the X-gal substrate.

Ptc-lacZ mice were divided into four treatment groups and were treated with the following compounds or combinations of compounds for four days, beginning on the first day after birth (dipal-Shh=dipalmitoylated Sonic hedgehog):

| | | | |
|---|---|---|---|
| 1) | dipal-Shh | 10 mg/kg/injection | 2×/day |
| 2) | dipal-Shh | 1 mg/kg/injection | 2×/day |
| | vehicle | 10-15 μl/injection | 4× day |
| 3) | dipal-Shh | 1 mg/kg/injection | 2×/day |
| | agonist B | 15 mg/kg/injection | 4×/day |
| 4) | no treatment | | |

The vehicle for the agonist was 10% DMSO in PBS (pH 7.2). The agonist was injected from a 4.67 mM stock dissolved in the vehicle solution.

18 hours following the last injections, the mice were sacrificed and the following tissues were collected: skull, kidney, lung, scapula, skin and heart. All tissues were fixed in 0.2% glutaraldehyde, 5 mM EDTA (pH 8.0), 20 mM $MgCl_2$, 100 mM $Na_2HPO_4$ for 30 minutes before staining in 1 mg/ml X-gal, 12.5 mM potassium ferrocyanide, 12.5 mM potassium ferricyanide, 2 mM $MgCl_2$, 0.01% deoxycholate, 0.02% NP-40, and 100 mM $Na_2HPO_4$ for 30 hours. Tissues were judged for relative intensity and photographed.

Figure 40:
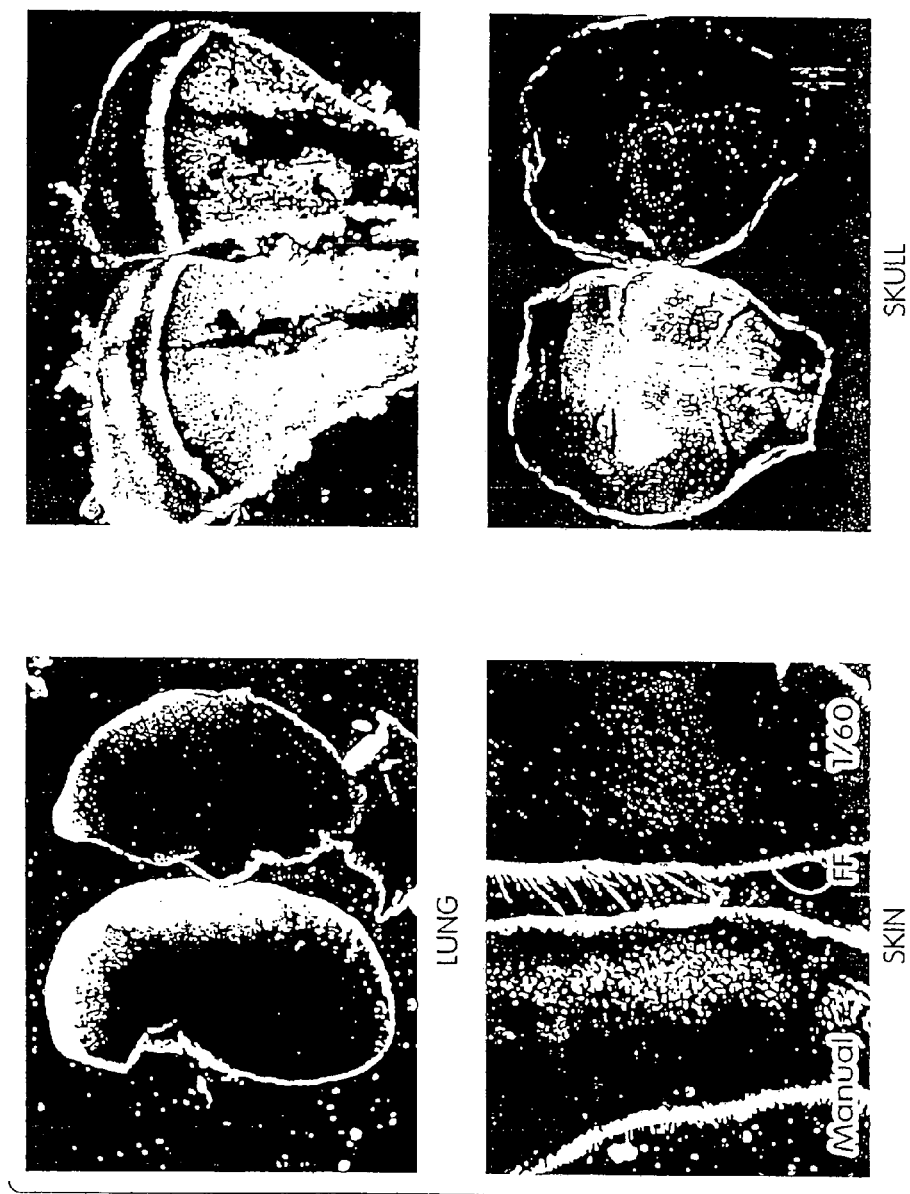
FIG. 40 shows the effect of subject agonists in combination with a low dose of hedgehog protein on lung, scapula, skin, and skull tissue of developing mice.
Figure 41:
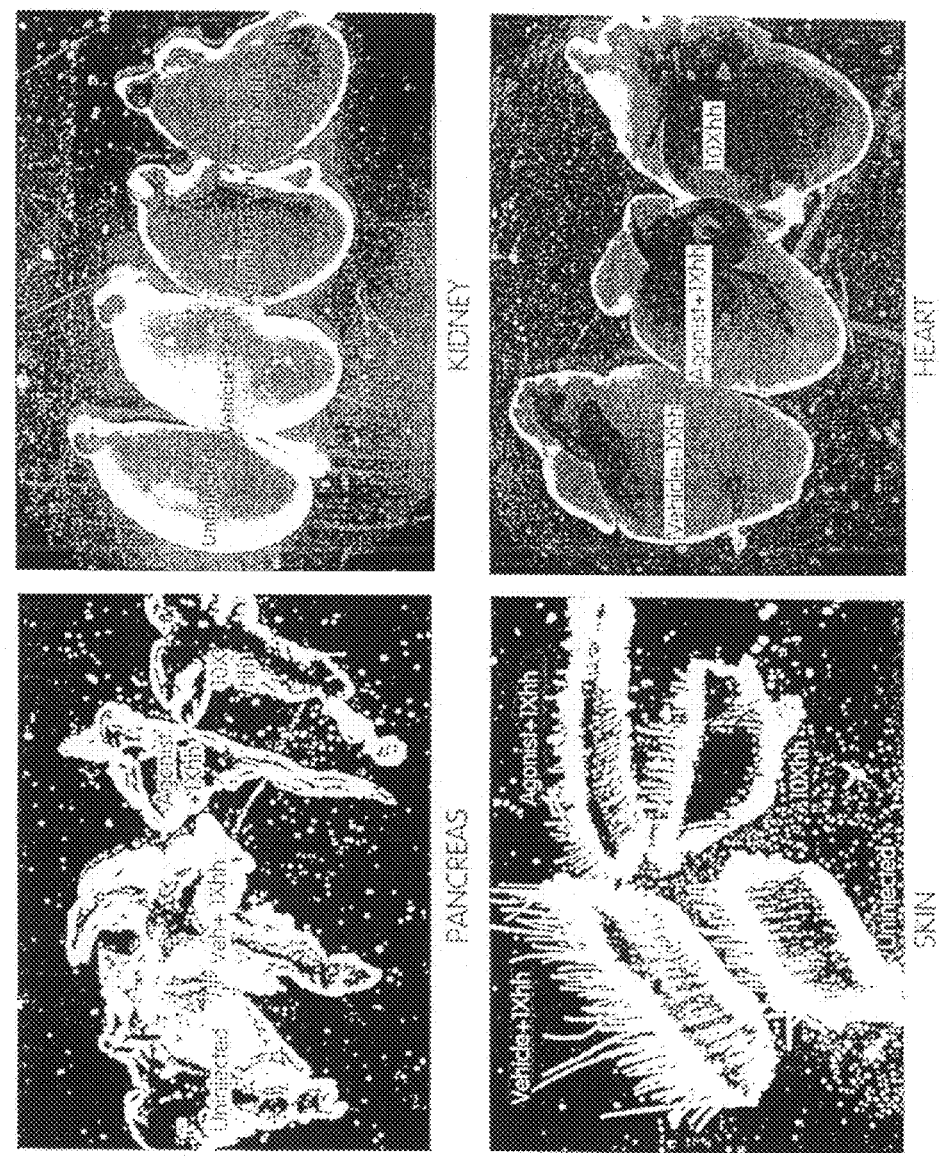
FIG. 41 depicts the effect of subject agonists in with and without added hedgehog protein on pancreas, kidney, skin, and heart tissue of developing mice.

All tissues from treatment group 3 (agonist+low dose dipal-Shh) showed significant upregulation of β-galactosidase (as visualized by more intense blue staining) compared to those from treatment group 2 (vehicle+low dose dipal-Shh), as seen in FIG. 40, wherein tissues from group 3 are depicted on the right side of each frame. The images in FIG. 41 show an example of tissue from each of the four treatment groups. The upregulation observed in group 3 was similar to that seen in treatment group 1 (high dose dipal-Shh). The level of β-galactosidase staining in treatment group 2 was similar to that seen in treatment group 4 (no treatment).

Agonist B was clearly capable of upregulating the hedgehog pathway in vivo in the presence of a low dose of dipal-shh which by itself is insufficient to produce detectable upregulation.

Figure 42:
FIG. 42 exhibits the effect of a subject agonist on the forelimb of a newborn mouse.

FIG. 42: Ptc-lacZ mice were divided into two treatment groups and were treated with the following compounds for three days, beginning on the first day after birth:

| 1) | vehicle | 8-15 µl/injection | 4×/day |
|---|---|---|---|
| 2) | agonist D | 4 mg/kg/injection | 4×/day |

The vehicle for the agonist was 10% DMSO in PBS (pH 7.2). The agonist was injected from a 1.0 mM stock dissolved in the vehicle solution.

Eighteen hours following the last injections, the mice were sacrificed and the forelimbs were collected and processed as described above. The forelimbs from the agonist-treated mice showed strong upregulation in the nerves, blood vessels, cartilage, and connective tissue.

Agonist D was clearly capable of upregulating the hedgehog pathway in vivo in the absence of dipal-Shh. The upregulation seen at this dose of agonist D is greater than that seen with injections of dipal-Shh at 10 mg/kg/injection, 2×/day.

In a third experiment, Ptc-lacZ mice were divided into five treatment groups and were treated with the following compounds for four days, beginning on the first day after birth:

| 1) | vehicle | 9-20 µl/injection | 4×/day |
|---|---|---|---|
| 2) | agonist D | 0.9 mg/kg/injection | 4×/day |
| 3) | agonist D | 0.3 mg/kg/injection | 4×/day |
| 4) | agonist D | 0.1 mg/kg/injection | 4×/day |
| 5) | octyl-shh | 10 mg/kg/injection | 2×/day |

The vehicle for the agonist was 10% DMSO in PBS (pH 7.2). The agonist was injected from stocks of 0.3, 0.1 and 0.03 mM dissolved in the vehicle solution.

Figure 43:
FIG. 43 presents the effect of a subject agonist on forelimbs of a newborn mouse at different concentrations.

Eighteen hours following the last injections, the mice were sacrificed and the forelimbs were collected and processed as described above. Results of this experiment are depicted in FIG. 43, in which the vehicle control is not shown. The forelimbs from the agonist-treated mice again showed strong upregulation in the nerves, blood vessels, cartilage, and connective tissue (compared to the vehicle group). The 0.9 mg/kg group showed the highest levels of upregulation in this experiment. Both the 0.9 mg/kg and the 03 mg/kg dose groups showed greater upregulation than the 10 mg/kg Hh protein group. The 0.1 mg/kg group showed very weak upregulation that was clearly less than that seen in the Hh protein group.

Agonist D was clearly capable of upregulating the hedgehog pathway in vivo in a dose-responsive manner. The upregulation seen at the 0.9 and 0.3 mg/kg doses of agonist D is greater than that seen with injections of Hh protein at 10 mg/kg/injection, 2×/day.

Lung Branching Assay

E12.5 old ptc-1 (d11) lacZ lungs were harvested and transgenic embryos identified by lacZ detection using tails. Explants were assembled on 1 µm polycarbonate filters (Costar) placed on top of plastic grids (histology embedding chamber) and placed in standard 12-well tissue culture plates filled with lung explant culture medium (DMEM based, additives optimized for the culture of mouse lungs) for 48 hrs, fixed in lacZ fixative, rinsed and stained for lacZ O/N at 37° C.

Results are depicted in FIG. 44. In the control panel on the left, LacZ expression can be observed in the mesenchyme immediately adjacent to distal branching tips, a pattern reflective of endogenous patched expression. Treatment with 5 µM of agonist B leads to significantly increased reporter gene expression and expansion of the expression domain of the transgene, indicative of hedgehog pathway upregulation. The rightmost panel shows the results of treatment with 5 µg/mL of Hh protein.

Kidney Branching Assay

E13.5 old ptc-1 (d11) lacZ lungs were harvested and transgenic embryos identified by lacZ detection using tails. Explants were assembled on 1 µm polycarbonate filters (Costar) placed on top of plastic grids (histology embedding chamber) and placed in standard 12-well tissue culture plates filled with kidney explant culture medium (DMEM based, additives optimized for the culture of mouse lungs) for 48 hrs, fixed in lacZ fixative, rinsed and stained for lacZ O/N at 37° C.

Results are depicted in FIG. 45. In the control panel on the left, LacZ expression can be observed in the mesenchyme immediately adjacent to proximal most ureteric epithelium, a pattern reflective of endogenous patched expression. Treatment with 5 µM of agonist B leads to significantly increased reporter gene expression and expansion of the expression domain of the transgene, indicative of hedgehog pathway upregulation. Note that the signal remains localized to the mesenchyme and does not expand into the more distally located ureteric and tubular epithelia, indicating that only the mesenchymal cell type(s) responding to hedgehog signaling in the endogenous situation respond to the agonist, while cell types which usually do not activate this pathway are unaffected by agonist treatment. The rightmost panel shows the results of treatment with 5 µg/mL of Hh protein.

Skin Explants

Figure 46B:
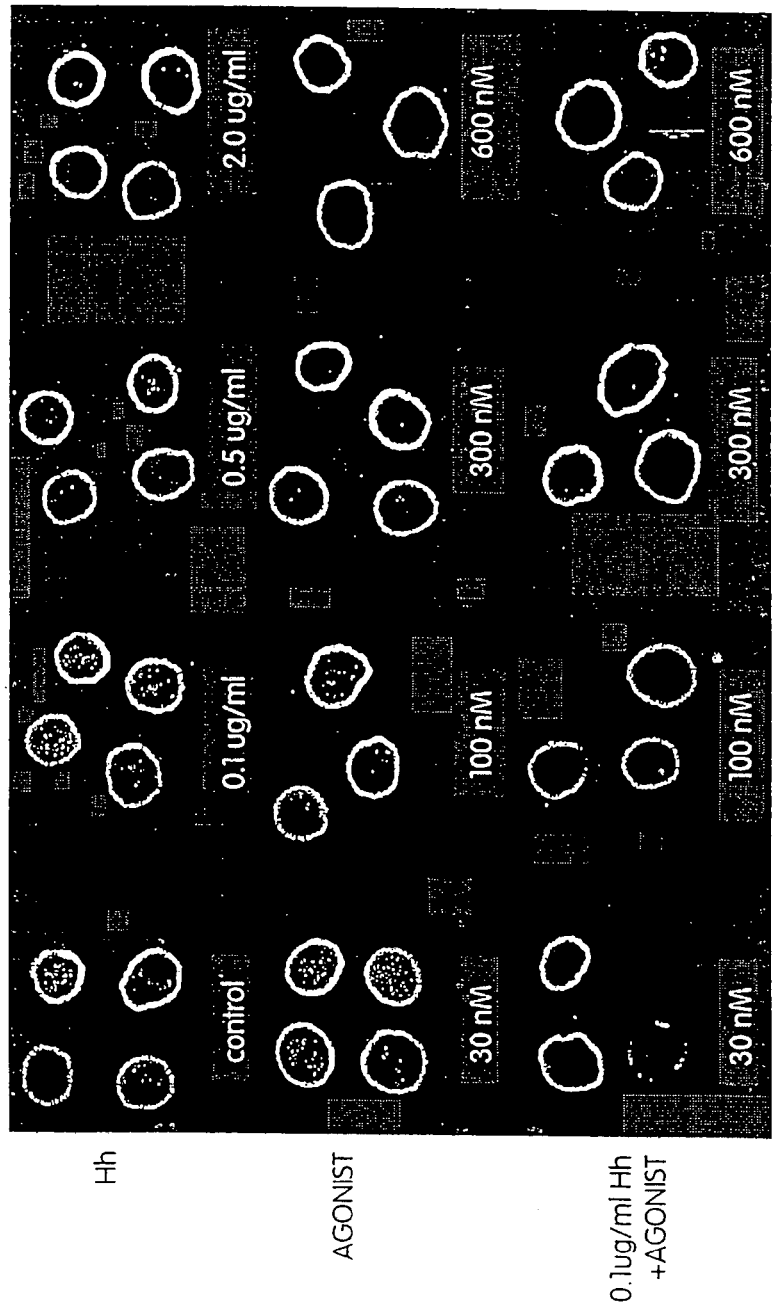
FIGS. 46A and B shows the effects of subject agonists on mouse skin tissue in the presence and absence of hedgehog protein.

Skin from ptc-lacZ E17.5 pups was excised with a 2 mm skin punch. Those skin punches were then cultured for 6 days in control media, or media including either agonist B or D or Hh protein, or media including both an agonist and Hh protein. The explants were then stained with X-Gal stain. FIG. 46A shows results for agonist B. Treatment with the agonist alone shows greater staining than culturing with a low dose of Hh protein alone, and treatment with agonist and a low dose of Hh protein shows staining similar to that of a substantially higher dose of Hh protein. Analogous results for agonist D are presented in FIG. 46B.

Activity in Human Cells

Figure 47A:
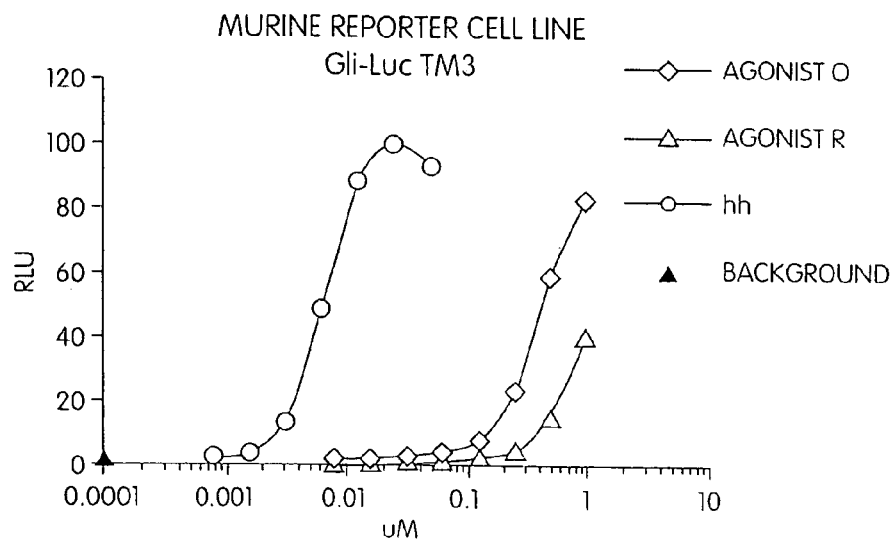
FIGS. 47A and B compare the activity of subject agonists in mouse and human reporter cells.
Figure 47B:
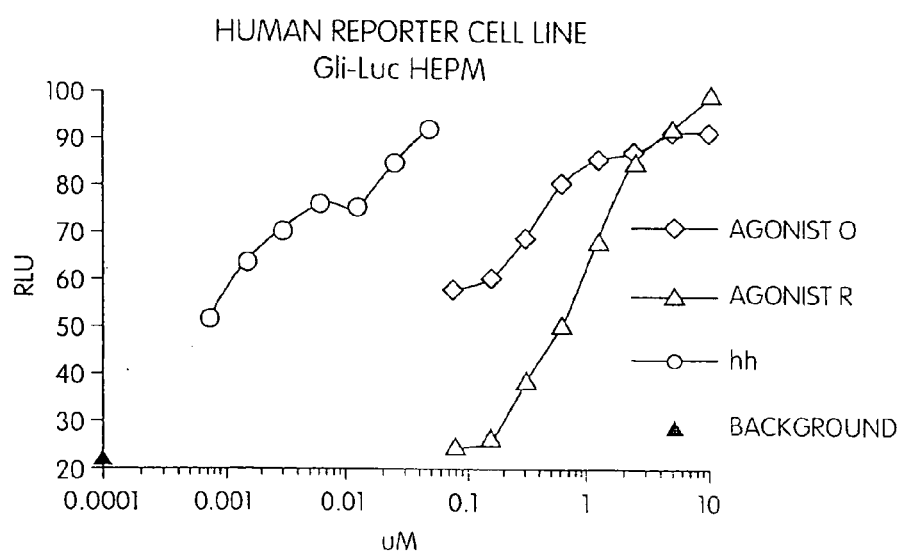
Figure 48:
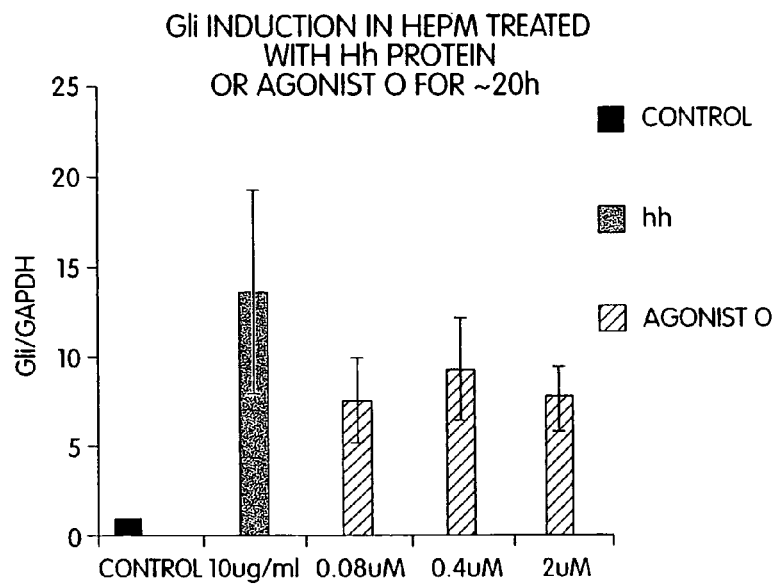
FIG. 48 depicts the upregulation of Gli in HEPM cells treated with a modified N-terminal fragment of Sonic hedgehog or with a subject agonist.

FIGS. 47A and B compare the activity of subject compounds O and R in mouse reporter cells (TM3 cells with a Gli-Luc reporter construct, as described above) and in human reporter cells (human embryonic palatal mesenchyme (HEPM) cells with a Gli-Luc construct). FIG. 48 shows a quantitative PCR analysis of RNA expressed from the hedgehog target gene Gli-1 in human cells treated with the vehicle, Hh protein, and agonist O. The activation of the reporter cell line and the elevated Gli-1 message in response to the compounds demonstrate that this agonist functions in human cells.

In Vivo Neurological Activity

The activation of the hedgehog (Hh) pathway has been shown to produce beneficial effects in animal models of neurodegenerative disease, including Parkinson's disease (PD). The subject small molecule agonists of the Hh pathway exhibit favorable pharmacokinetic properties and effectively activate the Hh pathway in adult rodent brain following oral administration, as demonstrated by a striatal induction of Gli-1 expression. Activation of the Hh pathway via these agonists exerts protective and/or regenerative effects in in vivo models of Huntington's disease (Malonate lesion), stroke (mouse middle cerebral artery occlusion, MCAO) and Parkinson's disease (mouse 1-methyl-4-phenyl-1,2,3,6-tetrahydropyridine, MPTP). These compounds can induce proliferation of neural precursors cells in the two brain regions where neurogenesis is known to continue throughout life, the subventricular zone (SVZ) of the lateral ventricles and the subgranular region of the hippocampal dentate gyrus.

Part 1: Hh Agonist is Neuroprotective in the Rat Malonate Model of Huntington's Disease Previous studies demonstrated that direct brain administration of Shh protein was neuroprotective in an animal model of Huntington's disease (HD), the malonate lesion model. Malonate is a mitochondrial toxin and defects in mitochondrial energy metabolism are thought to play a role in the pathology of neurodegenerative diseases such as HD. When malonate is injected into the rat striatum a lesion forms in this brain region. The experiments described below tested whether the Hh agonist would reduce the size of the malonate induced striatal lesion.

Hh agonist was administered directly into the brain ventricles of male SD rats via a cannula attached to an osmotic Alzet pump. The pumps were filled with either vehicle (5% 2-hydroxypropyl-B-cyclodextrin, 4.35% Mannitol, 0.2% DMSO) or Hh agonist (U" ranging from 1-600 mM) and the pump released compound into the ventricles at constant rate of 1 µl/hr for 6 days. After 6 days of pretreatment with compound, malonate was injected directly into the brain striatum and the Alzet pump was removed. Four days later rats were euthanized and the brains were sliced into 2 mm slabs. The slices were placed in a 2% solution (TTC) that stains living tissue red and the striatal infarct white. The size of the infarct (% infarct) was measured using image analysis software and the data were analyzed by one-way ANOVA followed by appropriate post-hoc tests ($p<0.05$).

Figure 49:
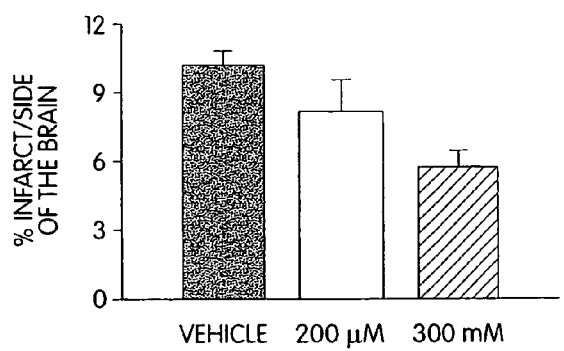
FIG. 49 illustrates the effects of compounds of the invention on malonate-induced lesions.

In the experiment shown in FIG. 49, rats were pretreated with either vehicle (n=8) or U" at 200 M (n=8) or 300 µM (n=7). These data show that direct brain administration of the Hh agonist at a concentration of 300 µM reduced the size of the malonate-induced infarct ($F(2,20)=5.12$, $p=0.0159$) as compared to vehicle treated animals.

These data demonstrate that the Hh agonist is neuroprotective in the malonate model of HD. In addition, this result shows that the Hh agonist can mimic the neuroprotective effects of the Hh protein since the protein was previously demonstrated to reduce striatal lesion size in this model system.

Part 2: Hh Agonist is Neuroprotective in the Mouse MCAO Model of Stroke

In this animal model, a small suture is inserted into the common carotid artery and threaded directly into the circulatory system of the brain. The suture is placed such that it blocks blood flow though the middle cerebral artery (MCA occlusion), which is the primary source of blood to the forebrain. After a set period of time, here 90 min, the suture is removed and blood flow to the forebrain is restored (reperfusion). The temporary blockage of blood flow to the forebrain results in behavioral symptoms and brain pathology that mimic those seen in human stroke patients. In the brain, within 24 hr post-MCA occlusion an infarct is visible using a stain (TTC) that stains living tissue red and the infracted area white. The infarct following a 90 min MCAO usually involves both cortical and subcortical brain regions.

Pre-MCAO Treatment with Hh Agonist

In this study, mice were treated for 3 days (1/day) prior to MCAO with either vehicle (0.5% methyl cellulose, 0.2% Tween-80/0.9% NaCl, n=12) or the Hh agonist X" (20 mg/kg, po, n=11). Animals were then subjected to 90 min MCAO followed by reperfusion. Approximately 24 hr after the start of occlusion (23.5 hr of reperfusion) mice were euthanized and the brain sectioned into 2 mm slabs. The brain slices were stained with TTC to show the infarcted area of the brain. The infarct area/total forebrain (% infarct) was analyzed by measured and statistically analyzed.

Figure 50:
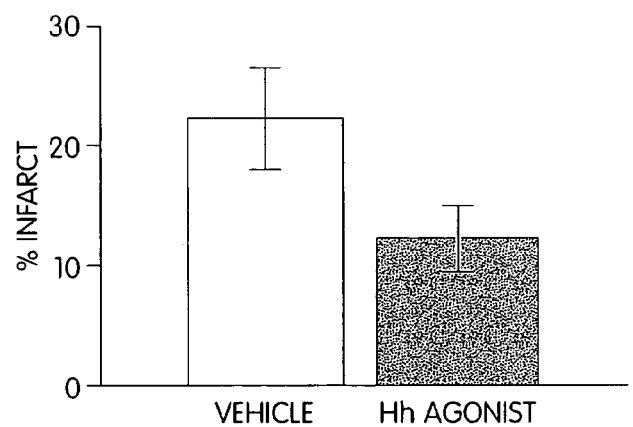
FIGS. 50 and 51 present results of experiments testing a compound of the invention for prevention of damage in a MCAO model of stroke.

FIG. 50 shows that the total infarct size was dramatically reduced in mice pretreated with the Hh agonist as compared to vehicle treated controls 0.057).

Figure 51:
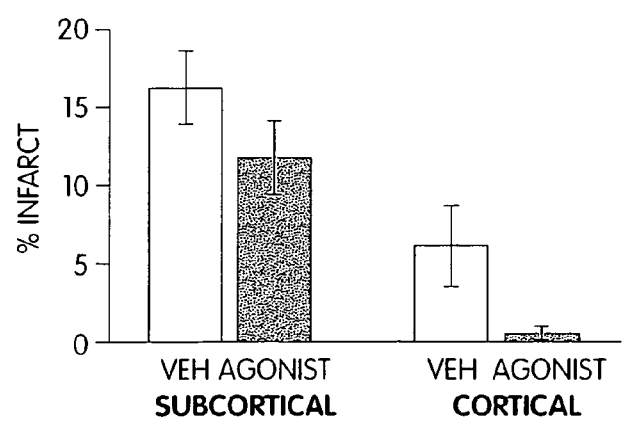

FIG. 51 shows the percentage of the infarct that was in the cortex and the percentage that was subcortical (including striatum, thalamus and hippocampus). These data show a marked reduction in cortical infarct size ($p=0.052$). Therefore, pretreatment with the Hh agonist was neuroprotective in this animal model of stroke.

Post-MCAO Treatment with Hh Agonist

Male mice (7-8 wks of age) were subjected to 90 min MCAO followed by reperfusion. Animals were then treated with either vehicle (n=11) or the Hh agonist X" (20 mg/kg, po, n=12) at the onset of reperfusion (90 min post-occlusion). Twenty-four hours after the onset of MCAO mice were euthanized, the brain sectioned into 2 mm slabs and slices stained with TTC for infarct size analysis.

Figure 52:
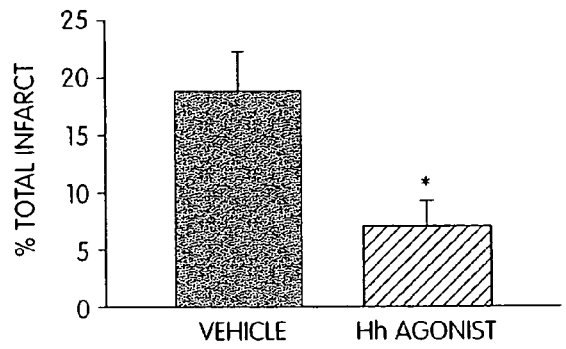
FIGS. 52 and 53 show the effects of post-MCAO treatment with a compound of the invention.

FIG. 52 shows that post-MCAO treatment with Hh agonist significantly decreased the size of the infarct in mice ($p<0.05$).

Figure 53:
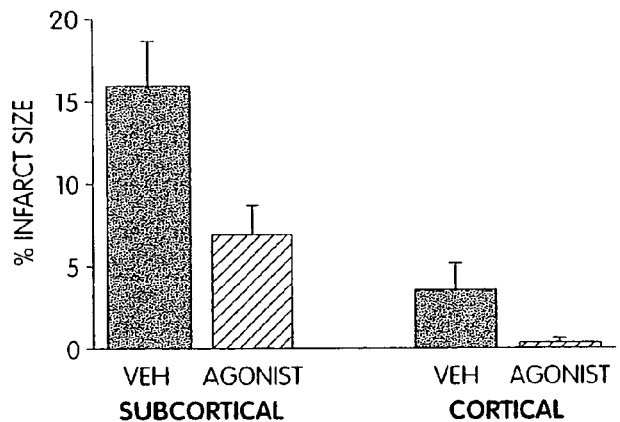

Similarly, FIG. 53 shows that post-MCAO agonist treatment dramatically reduced both cortical and subcortical lesion size.

Taken together these data show that oral administration of Hh agonist is neuroprotective and neurorestorative in the mouse MCAO model of stroke.

Part 3: Oral Treatment with Hh Agonists is Efficacious in the Mouse MPTP Model of Parkinson's Disease Previous studies demonstrated that SHh protein is efficacious in animal models of PD. 1-Methyl-4-phenyl-1,2,3,6-tetrahydropyridine, MPTP, is a dopaminergic neurotoxin and systemic injections of this compound into mice causes a reduction in dopamine levels similar to that seen in Parkinson's disease (PD) patients. The experiments described below were designed to test whether administration of Hh agonists to mice would reduce the loss of dopamine and tyrosine hydroxylase seen with MPTP treatment.

Pretreatment with Hh Agonist Attenuates Damage Caused by MPTP Lesioning

Figure 54:
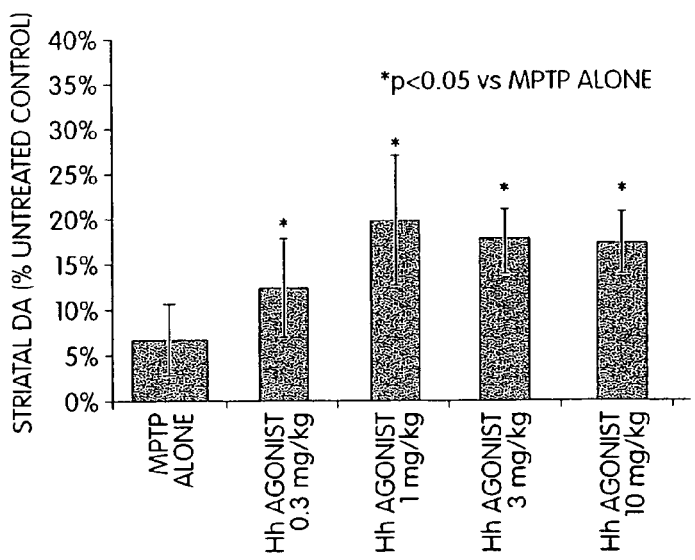
FIG. 54 portrays the effect of pretreatment with a compound of the invention in a model of Parkinson's disease.

The data shown in FIG. 54 are from an experiment in which mice were orally administered Hh agonist X" (0.3, 1, 3, and 10 mg/kg, po) for 3 days before treatment with MPTP. Seven days after MPTP treatment mice were euthanized and the levels of dopamine (DA) and tyrosine hydroxylase (1 were measure in the striatum.

FIG. 54 shows that pretreatment with the Hh agonist significantly attenuated (~↓260%) damage to the nigrostriatal pathway, as determined by striatal DA (FIG. 54) and TH activity, as compared to vehicle-treated mice seven days post-lesioning.

Post-MPTP Treatment with Hh Agonist is Efficacious

Figure 55:
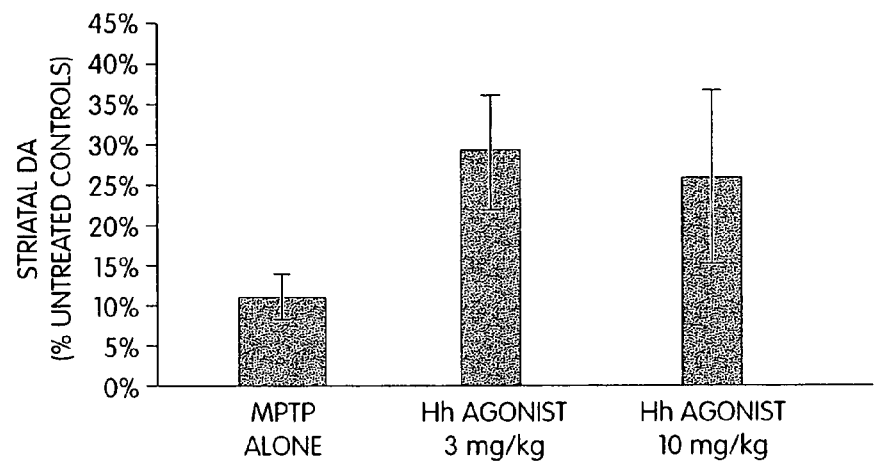
FIG. 55 exhibits the effect of using a compound of the invention as a therapeutic in a model of Parkinson's disease.

The data shown in FIG. 55 are from an experiment in which treatment with Hh Agonist started 3 days post-MPTP. Striatal DA (FIG. 55) and TH activity levels are significantly higher (~↑250%) as compared to vehicle-treated mice when agonist treatment is started three days after MPTP lesioning.

These findings clearly demonstrate that activation of the Hh pathway by small molecule Hh agonists exerts both protective and restorative effects on the nigrostriatal pathway. Collectively, these data have important implications towards the development of new therapeutic strategies for Parkinson's disease.

Part 4: Treatment with Hh Agonist Increases Proliferation of Neural Precursor Cells in Adult Rodents In the adult brain, generation of new neurons is known to continue in two brain regions, the subventricular zone of the lateral ventricles (SVZ) and the subgranular zone (SG) of the hippocampal dentate gyrus. It is known that Shh protein induces precursor cell proliferation in a number of in vitro systems, including cerebellar granular neurons. The experiments described below tested whether treatment with Hh agonists would affect proliferation of endogenous neural precursor cells in the adult rodent brain.

Direct Brain Administration of Hh Agonist to Adult Rats Increased Proliferation of SVZ Precursor Cells Hh agonist was administered directly into the brain ventricles of male SD rats via a cannula attached to an osmotic Alzet pump. The pumps were filled with either vehicle (5% 2-hydroxypropyl-B-cyclodextrin, 4.35% Mannitol, 0.2% DMSO) or Hh agonist (U" ranging from 10-600 µM and the pump released compound into the ventricles at constant rate of 0.5 µl/hr for 6 days. After 6 days of pretreatment with compound, animals were injected with Bromodeoxyuridine (BrdU, 50 mg/kg, ip) to label dividing cells. Two hours after BrdU treatment, rats were euthanized and perfused with fixative. Brains were collected and processed for BrdU immunohistochemistry. The number of BrdU-immunoreactive (BrdU-IR) cells was then counted in the SVZ on both the sides of the brain with the cannula (ipsilateral) and without (contralateral).

Figure 56:
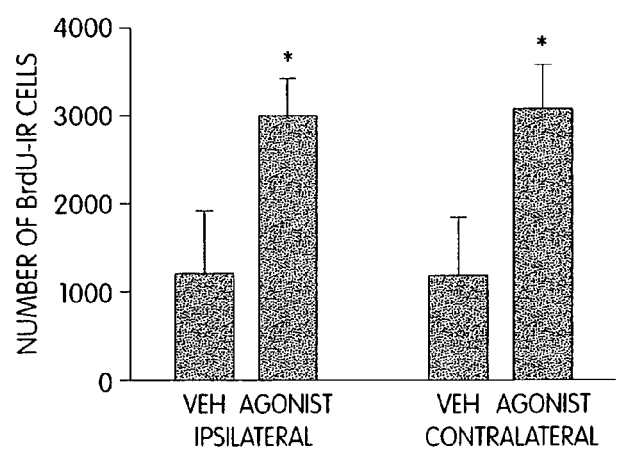
FIG. 56 depicts increased proliferation of neural cells in vivo after injection of a compound of the invention.

FIG. 56 shows data from an experiment in which animals were treated with either vehicle (n=3) or Hh agonist (200 µM, n=3). The number of BrdU-IR cells was dramatically increased on both sides of the brain following 6 days of agonist treatment (*p<0.05)

These data demonstrate that direct brain administration of Hh agonist increases the proliferation of endogenous precursor cells in the adult rat brain.

Oral Administration of Hh Agonist Increases Proliferation of Neural Precursor Cells in the Adult Mouse To test whether oral administration of the Hh agonist would affect proliferation of precursor cells, mice were dosed daily (once or twice/day, po) with either vehicle or the Hh agonist X" for 1-7 days. On the appropriate day, mice were injected with BrdU (ip) and 2 hours later euthanized, perfused with fixative and brains processed for BrdU immunohistochemistry. The number of BrdU-IR cells was counted in both the SVZ and subgranular zone of the hippocampal dentate gyrus (SG).

Figure 57:
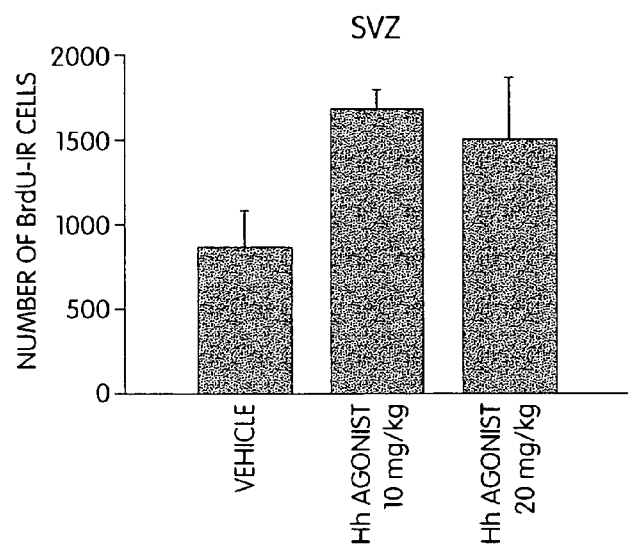
FIGS. 57 and 58 illustrate increased proliferation of neural cells in vivo after oral administration of a compound of the invention.
Figure 58:
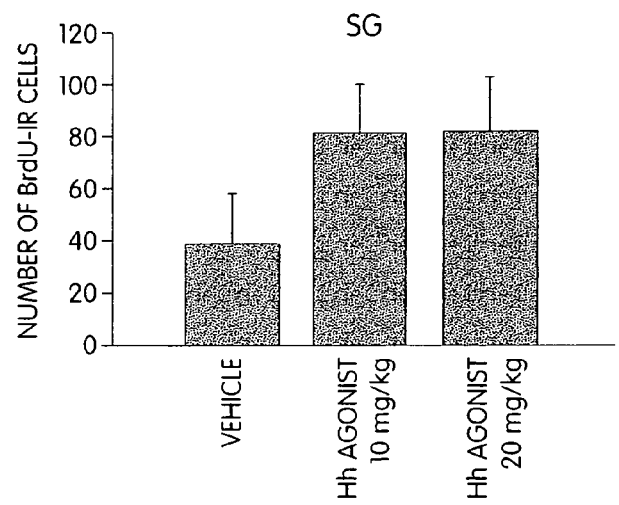

The data shown in FIGS. 57 and 58 are from a study in which mice were dosed orally for 7 days (BID) with either vehicle (n=4) or Hh agonist X" (10 mg/kg, n1=3 or 25 mg/kg, n=3). The day after the final dose, mice were injected with BrdU and 2 hrs. later brains were collected, processed, and analyzed as described above.

FIG. 57 shows that oral treatment with Hh agonist for 7 days increased the number of BrdU labeled cells in the SVZ as compared to vehicle treated controls (*p<0.05). The data in FIG. 58 shows that oral administration of Hh agonist also increased the number of proliferating cells in the SG of the dentate gyrus.

These data show that oral dosing with Hh agonist increases proliferation of neural precursor cells in both regions of the brain where neurogenesis is known to continue throughout life. Such an effect on proliferation of stem cells might be one of the mechanism by which the Hh agonists are neuroprotective/neuroregenerative in various models of neural disease and/or injury.

Part 5: Upregulation of Hh-Responsive Tissues by Orally Administered Agonist in Adult Animals The upregulation of Hh responsive transcription factor gli-1 was used as a marker to demonstrate the biological efficacy of orally delivered Hh agonists in vivo. Selected compounds representative of the invention were orally administered in adult animals as single doses, with the animals sacrificed and tissue collected 24 hours later. Gli-1 expression was measured using a standard quantitative real time PCR assay with GapDH as the reference gene. Gli-1 was demonstrated to be upregulated by agonist in brain, spinal cord, peripheral nerve, heart, and lung. Combined with data from therapeutic models of CNS and peripheral disease, these results demonstrate that Hh pathway-responsive tissues respond in the expected manner to orally delivered agonists to produce significant biological and therapeutic effects.

Figure 59:
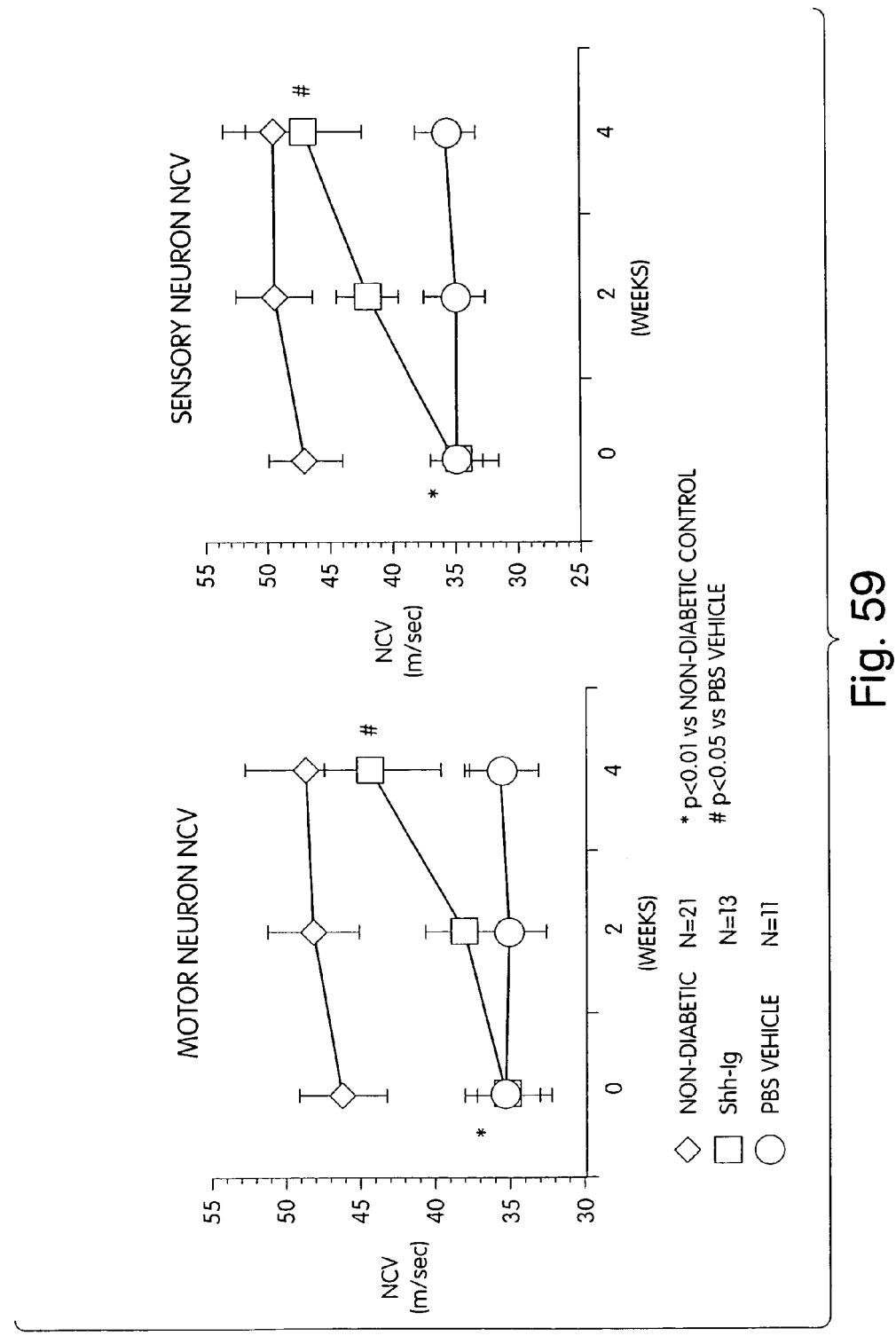
FIG. 59 shows the effect of Sonic hedgehog (Shh) protein in a model of diabetic neuropathy.
Figure 60:
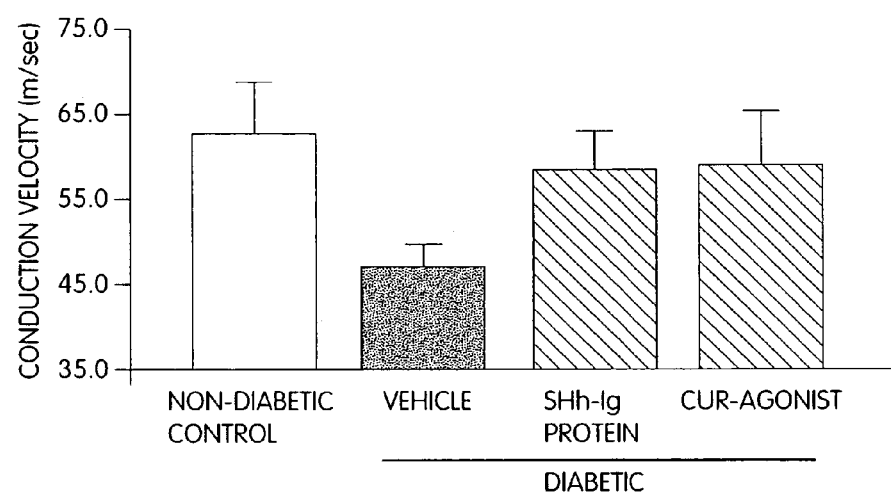
FIG. 60 demonstrates the effect of an agonist of the invention in a model of diabetic neuropathy.
Figure 61:
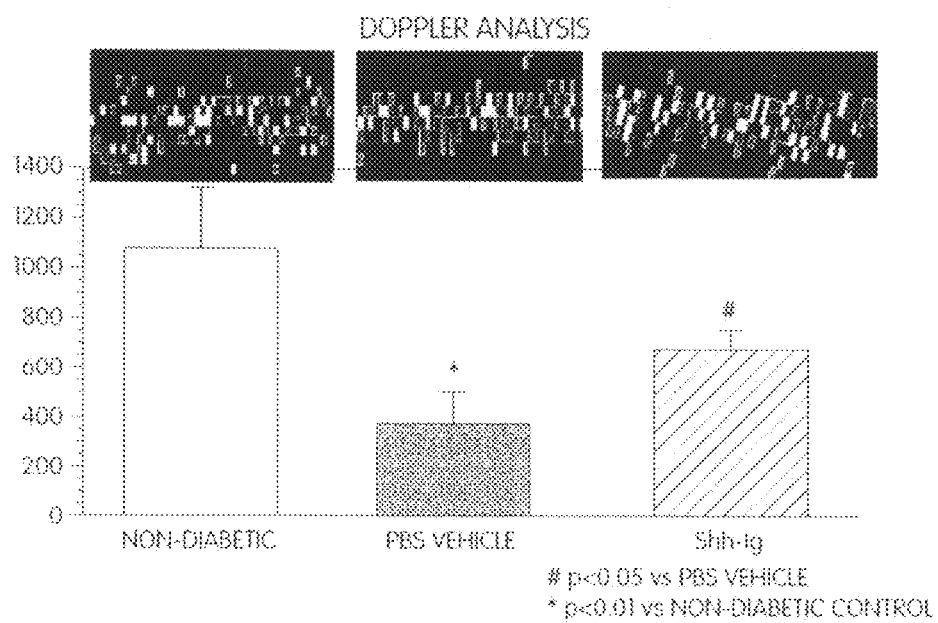
FIGS. 61 and 62 show images of the sciatic vasa nervorum after administration of an agonist of the invention in a model of diabetic neuropathy.
Figure 62:
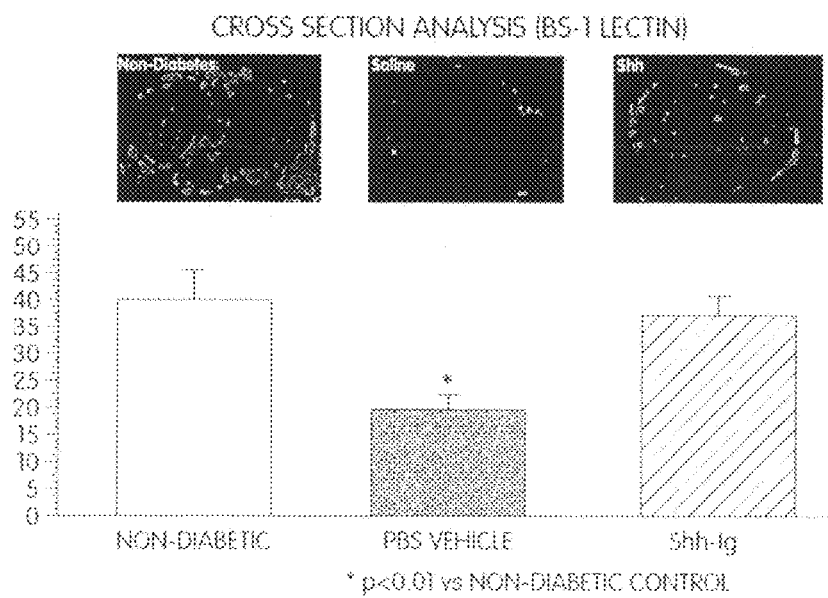
Figure 63:
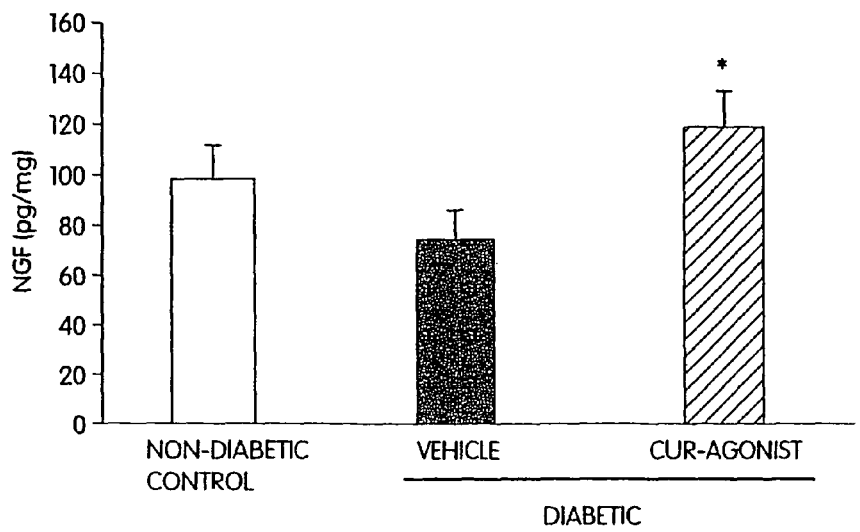
FIGS. 63-66 illustrate upregulation of various growth factors after administration of an agonist of the invention.

Part 6: Treatment of Diabetic Neuropathy in Streptozotocin (STZ) Diabetic Rat Model In rat STZ model of diabetic neuropathy, SHh-Ig protein was shown to normalize both motor and sensory nerve conduction velocity, a standard clinical trial endpoint (FIG. 59). Similar results were also shown for orally administered agonist D for motor NCV (FIG. 60). In addition, blood flow to the damaged nerves was improved as measured by laser Doppler perfusion imaging of the sciatic vasa nervorum (FIG. 61) and BS-1 lectin fluorescent imaging of the sciatic vasa nervorum (FIG. 62). In addition, both SHh-Ig and agonist D resulted in increased levels of nerve growth factor (NGF) in the sciatic nerve (FIG. 63), which is considered an indication of improved nerve health.

Figure 64:
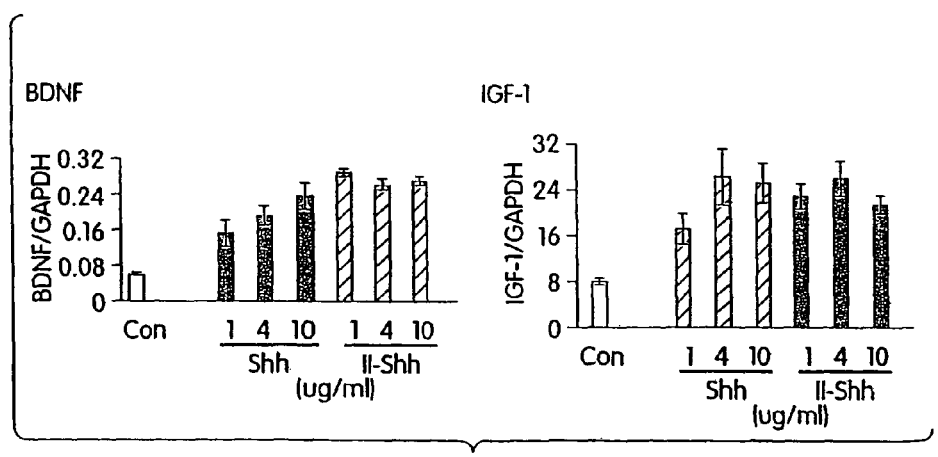
Figure 65:
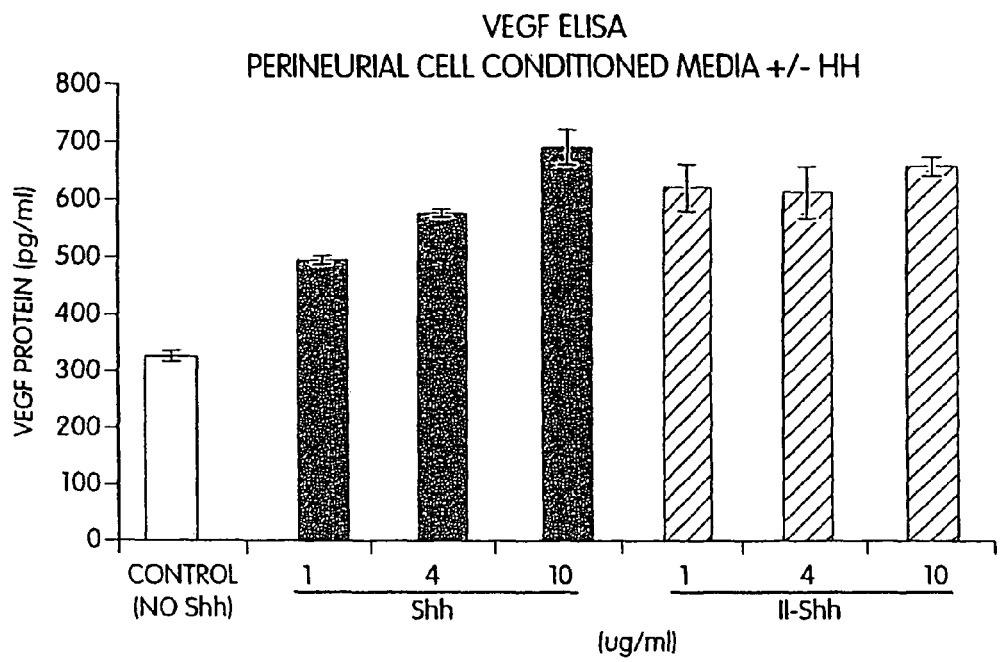
Figure 66:
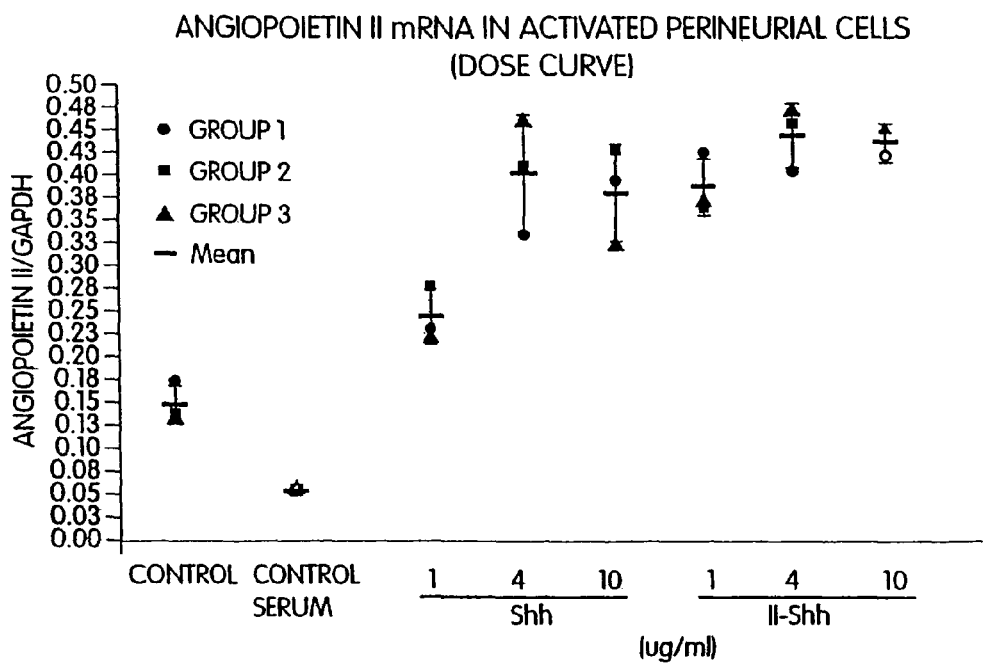

Studies were performed to assess whether factors implicated in nerve function and repair were upregulated following SHh treatment. Fibroblasts derived from nerve perineurim were cultured in vitro in the presence of SHh protein. The treated fibroblasts demonstrated upregulation of BDNF and IGF-1 (FIG. 64), which are thought to help mediate growth and repair of nerves as well as VEGF (FIG. 65) and angiopoietin-II (FIG. 66) which are angiogenic growth factors that mediate blood vessel repair and growth. VEGF has also been demonstrated to have direct trophic effects on cultured nerves. Taken together, these data demonstrate that activating the Hh pathway with SHh or agonist leads to upregulation of a number of key growth factors for nerve tissue and results in nerve repair.

In addition, these results demonstrate that treatment with SHh protein or agonist has potentially broad therapeutic utility in vascular diseases to promote blood vessel growth and improved blood flow.

Methods:

Induction, Monitoring and Maintenance of Diabetes

Diabetes was induced in male Wistar rats (Charles River, UK or Harlan, San Diego, USA) with an intraperitoneal injection (55 mg/kg) of streptozotocin (STZ; Sigma) given after an overnight fast. The drug was freshly dissolved in sterile saline immediately before injection. Three days later, tail vein blood glucose was measured by a strip-operated reflectance photometer and any STZ-treated rats with blood glucose<15 mmol/l were removed from the study. Rats were group-housed with free access to food and water in a 12 h light/dark cycle. At the end of each study, blood samples were collected from all rats, plasma extracted and plasma glucose levels measured by spectrophotometric assay using a commercial kit (Sigma, St. Louis, Mo.).

Drug Treatments

For in vitro assays, the SHh protein used was either unmodified (SHh) or modified by replacing the N-terminal cysteine with 2 isoleucine molecules (II-SHh) (F. R. Taylor et al., Enhanced potency of human sonic hedgehog by hydrophobic modification. 2001. *Biochemistry* 40:4359-4371). For in vivo studies, the modified SHh was additionally fused with IgG1 (SHh-IgG). The SHh-IgG was expressed in *Pichia pastorus* and purified using SP sepharose, protein A sepharose and CM poros chromatography. The intact fusion protein was pooled, filtered and dialyzed into 2×PBS for storage. Daily aliquots were prepared at the start of each study, coded so that the experimenters were unaware of the treatment group, and stored at −70° C. Injectates were thawed at room temperature immediately before use and diluted with water to achieve a final vehicle concentration of 1×PBS. Rats were given SHh-IgG thrice weekly (Mon, Wed, Fri) at doses of 0.3, 1.0 or 3.0 mg/kg s.c. to the scruff of the neck. All animals not receiving SHh-IgG were injected with vehicle. Treatments were initiated after 4-8 weeks of diabetes and maintained for a further 4 weeks so that the total duration of diabetes was 8-12 weeks, depending on the particular study.

Nerve Conduction Velocity Measurements

Rats were anesthetized with either halothane or isoflurane before assessing nerve conduction velocities (NCV). Motor nerve conduction velocity (MNCV) was measured from latencies of the compound M waves of the electromyogram in the hindlimb, and sensory nerve conduction velocity (SNCV) was measured from H reflex latencies in the same system. Preliminary studies involving selective transection of the dorsal but not ventral roots established the validity of our H wave measurements (APM, unpublished data). Stimulation of the nerve was performed at the sciatic notch and Achilles tendon and evoked electromyograms were recorded from the interosseus muscles of the foot. Mid-thigh nerve temperature was maintained at 36±0.5° C. throughout the procedure.

Laser Doppler Perfusion Imaging of the Sciatic Vasa Nervorum

The procedure was performed as described by P. Schratzberger et al. Reversal of experimental diabetic neuropathy by VEGF gene transfer. 2001. *J. Clin. Invest.* 107(9): 1083-92.

BS-1 Lectin Fluorescent Imaging of the Sciatic Vasa Nervorum

The procedure using BS-1 lectin was performed as described by P. Schratzberger et al. Reversal of experimental diabetic neuropathy by VEGF gene transfer. 2001. *J. Clin. Invest.* 107(9): 1083-92.

Nerve Growth Factor (NGF) and Vascular Endothelial Growth Factor (VEGF) Protein Assays NGF was measured in extracts from segments of sciatic nerve by ELISA as described by P. Fernyhough et al. Human recombinant nerve growth factor replaces deficient neurotrophic support in the diabetic rat. 1995. *Eur. J. Neurosci.* 7:1107-1110. VEGF was measured by a standard ELISA assay, VEGF, brain-derived neurotrophic factor (BDNF), insulin-like growth factor-1 (IGF-1) mRNA assays. All 3 growth factors were measured by standard quantitative real time PCR technology using GapDH as the reference gene.

PREPARATION OF COMPOUNDS OF THE PRESENT INVENTION a. Illustrative Synthetic Schemes Exemplary synthesis schemes for generating hedgehog agonists useful in the methods and compositions of the present invention are shown in FIGS. 1-31.

The reaction conditions in the illustrated schemes of FIGS. 1-31 are as follows:

1) $R_1CH_2CN$, $NaNH_2$, toluene
   (Arzneim-Forsch, 1990, 40, 11, 1242)
2) $H_2SO_4$, $H_2O$, reflux
   (Arzneim-Forsch, 1990, 40, 11, 1242)
3) $H_2SO_4$, EtOH, reflux
   (Arzneim-Forsch, 1990, 40, 11, 1242)
4) NaOH, EtOH, reflux
5) $(Boc)_2O$, 2 M NaOH, THF
6) LiHDMS, $R_1X$, THF
   (Merck Patent Applic # WO 96/06609)
7) Pd—C, $H_2$, MeOH
8) t-BuONO, CuBr, HBr, $H_2O$
   (J. Org. Chem. 1977, 42, 2426)
9) $ArB(OH)_2$, $Pd(PPh_3)_4$, Dioxane
   (J. Med. Chem. 1996, 39, 217-223)
10) $R_{12}(H)C{=}CR_{13}R_{14}$, $Pd(OAc)_2$, $Et_3N$, DMF
    (Org. React 1982, 27, 345)
11) $Tf_2O$, THF
    (J. Am. Chem. Soc. 1987, 109, 5478-5486)
12) $ArSnBu_3$, $Pd(PPh_3)_4$, Dioxane
    (J. Am. Chem. Soc. 1987, 109, 5478-5486)
13) $KMnO_4$, Py, $H_2O$
    (J. Med. Chem. 1996, 39, 217-223)
14) $NaOR_1$, THF
15) $NaSR_1$, THF
16) $HNR_1R_{13}$, THF
17) HONO, $NaBF_4$
    (Adv. Fluorine Chem. 1965, 4, 1-30)
18) $Pd(OAc)_2$, NaH, DPPF, $PhCH_3$, $R_1OH$
    (J. Org. Chem. 1997, 62, 5413-5418)
19) i. $R_1X$, $Et_3N$, $CH_2Cl_2$, ii. $R_{13}X$
20) $SOCl_2$, cat DMF
21) $CH_2N_2$, $Et_2O$
22) $Ag_2O$, $Na_2CO_3$, $Na_2S_2O_3$, $H_2O$
    (Tetrahedron Lett. 1979, 2667)
23) $AgO_2CPh$, $Et_3N$, MeOH
    (Org. Syn., 1970, 50, 77; J. Am. Chem. Soc. 1987, 109, 5432)
24) LiOH, THF-MeOH
25) $(EtO)_2P(O)CH_2CO_2R$, BuLi, THF
26) $MeO_2CCH(Br){=}P(Ph)_3$, benzene
27) KOH or KOtBu 28) Base, X(CH$_2$)$_n$CO$_2$R
29) DPPA, Et$_3$N, toluene
    (Synthesis 1985, 220)
30) HONO, H$_2$O
31) SO$_2$, CuCl, HCl, H$_2$O
    (Synthesis 1969, 1-10, 6)
32) Lawesson's reagent, toluene
    (Tetrahedron Asym. 1996, 7, 12, 3553)
33) R$_2$M, solvent
34) 30% H$_2$O$_2$, glacial CH$_3$CO$_2$H
    (Helv. Chim. Acta. 1968, 349, 323)
35) triphosgene, CH$_2$Cl$_2$
    (Tetrahedron Lett., 1996, 37, 8589)
36) i. (EtO)$_2$P(O)CHLiSO$_2$Oi-Pr, THF, ii. NaI
37) Ph$_3$PCH$_3$I, NaCH$_2$S(O)CH$_3$, DMSO
    (Synthesis 1987, 498)
38) Br$_2$, CHCl$_3$ or other solvent
    (Synthesis 1987, 498)
39) BuLi, Bu$_3$SnCl
40) ClSO$_2$OTMS, CCl$_4$
    (Chem. Ber. 1995, 128, 575-580)
41) MeOH—HCl, reflux
42) LAH, Et$_2$O or LiBH$_4$, EtOH or BH$_3$-THF
    (Tetrahedron Lett., 1996, 37, 8589)
43) MsCl, Et$_3$N, CH$_2$Cl$_2$
    (Tetrahedron Lett., 1996, 37, 8589)
44) Na$_2$SO$_3$, H$_2$O
    (Tetrahedron Lett., 1996, 37, 8589)
45) R$_2$R$_4$NH, Et$_3$N, CH$_2$Cl$_2$
46) R$_2$M, solvent
47) CH$_3$NH(OCH$_3$), EDC, HOBt, DIEA, CH$_2$Cl$_2$ or DMF
    (Tetrahedron Lett, 1981, 22, 3815)
48) MeLi, THF
49) mCPBA, CH$_2$Cl$_2$
50) HONO, Cu$_2$O, Cu(NO$_3$)$_2$, H$_2$O
    (J. Org. Chem. 1977, 42, 2053)
51) R$_1$M, solvent
52) HONO, NaS(S)COEt, H$_2$O
    (Org. Synth. 1947, 27, 81)
53) HSR$_2$ or HSR$_4$, CH$_2$Cl$_2$
54) i-BuOC(O)Cl, Et$_3$N, NH$_3$, THF
55) R$_2$R$_4$NH, CH$_2$Cl$_2$, NaBH(OAc)$_3$
56) R$_2$R$_4$NH, MeOH/CH$_3$CO$_2$H, NaBH$_3$CN
57) R$_2$OH, EDC, HOBt, DIEA, CH$_2$Cl$_2$ or DMF
58) R$_2$OH, HBTU, HOBt, DIEA, CH$_2$Cl$_2$ or DMF
59) R$_2$R$_4$NH, EDC, HOBt, DIEA, CH$_2$Cl$_2$ or DMF
60) R$_2$R$_4$NH, HBTU, HOBt, DIEA, CH$_2$Cl$_2$ or DMF
61) POCl$_3$, Py, CH$_2$Cl$_2$
62) R$_2$R$_4$NCO, solvent
63) R$_2$OC(O)Cl, Et$_3$N, solvent
64) R$_2$CO$_2$H, EDC or HBTU, HOBt, DIEA, CH$_2$Cl$_2$ or DMF
65) R$_2$X Et$_3$N, solvent
66) (CH$_3$S)$_2$C=N(CN), DMF, EtOH
    (J. Med. Chem. 1994, 37, 57-66)
67) R$_2$SO$_2$Cl, Et$_3$N, CH$_2$Cl$_2$
68) R$_2$— or R$_3$— or R$_4$CHO, MeOH/CH$_3$CO$_2$H, NaBH$_3$CN
    (Synthesis 1975, 135-146)
69) Boc(Tr)-D or L-CysOH, HBTU, HOBt, DIEA, CH$_2$Cl$_2$ or DMF
70) Boc(Tr)-D or L-CysH, NaBH$_3$CN, MeOH/CH$_3$CO$_2$H
    (Synthesis 1975, 135-146)
71) S-Tr-N-Boc cysteinal, ClCH$_2$CH$_2$Cl or THF, NaBH(OAc)$_3$
    (J. Org; Chem. 1996, 61, 3849-3862)
72) TFA, CH$_2$Cl$_2$, Et$_3$SiH or (3:1:1) thioanisole/ethanedithiol/DMS
73) TFA, CH$_2$Cl$_2$
74) DPPA, Et$_3$N, toluene, HOCH$_2$CH$_2$SiCH$_3$
    (Tetrahedron Lett 1984, 25, 3515)
75) TBAF, THF
76) Base, TrSH or BnSH
77) Base, R$_2$X or R$_4$X
78) R$_3$NH$_2$, MeOH/CH$_3$CO$_2$H, NaBH$_3$CN
79) N$_2$H$_4$, KOH
80) Pd$_2$(dba)$_3$, P(o-tol)$_3$, RNH$_2$, NaOtBu, Dioxane, R$_1$NH$_2$
    (Tetrahedron Lett. 1996, 37, 7181-7184).
81) Cyanamide.
82) Fmoc-Cl, sodium bicarbonate.
83) BnCOCl, sodium carbonate.
84) AllylOCOCl, pyridine.
85) Benzyl bromide, base.
86) Oxalyl chloride, DMSO.
87) RCONH$_2$.
88) Carbonyldiimidazole, neutral solvents (e.g., DCM, DMF, THF, toluene).
89) Thiocarbonyldiimidazole, neutral solvents (e.g., DCM, DMF, THF, toluene).
90) Cyanogen bromide, neutral solvents (e.g., DCM, DMF, THF, toluene).
91) RCOCl, Triethylamine
92) RNHNH$_2$, EDC.
93) RO$_2$CCOCl, Et$_3$N, DCM.
94) MsOH, Pyridine (J. Het. Chem., 1980, 607.)
95) Base, neutral solvents (e.g., DCM, toluene, THF).
96) H$_2$NOR, EDC.
97) RCSNH$_2$.
98) RCOCHBrR, neutral solvents (e.g., DCM, DMF, THF, toluene), (Org. Proc. Prep. Intl., 1992, 24, 127).
99) CH$_2$N$_2$, HCl. (Synthesis, 1993, 197).
100) NH$_2$NHR, neutral solvents (e.g., DCM, DMF, THF, toluene).
101) RSO$_2$Cl, DMAP. (Tetrahedron Lett., 1993, 34, 2749).
102) Et$_3$N, RX. (J. Org. Chem., 1990, 55, 6037).
103) NOCl or Cl$_2$ (J. Org. Chem., 1990, 55, 3916).
104) H$_2$NOH, neutral solvents (e.g., DCM, DMF, THF, toluene).
105) RCCR, neutral solvents (DCM, THF, Toluene).
106) RCHCHR, neutral solvents (DCM, THF, Toluene).
107) H$_2$NOH, HCl.
108) Thiocarbonyldiimidazole, SiO$_2$ or BF$_3$OEt$_2$. (J. Med. Chem., 1996, 39, 5228).
109) Thiocarbonyldiimidazole, DBU or DBN. (J. Med. Chem., 1996, 39, 5228).
110) HNO$_2$, HCl.
111) ClCH$_2$CO$_2$Et (Org. Reactions, 1959, 10, 143).
112) Morpholine enamine (Eur. J. Med. Chem., 1982, 17, 27).
113) RCOCHR'CN
114) RCOCHR'CO$_2$Et
115) Na$_2$SO$_3$
116) H$_2$NCHRCO$_2$Et
117) EtO$_2$CCHRNCO
118) RCNHNH$_2$.
119) RCOCO$_2$H, (J. Med. Chem., 1995, 38, 3741).
120) RCHO, KOAc.
121) 2-Fluoronitrobenzene.
122) SnCl$_2$, EtOH, DMF.
123) RCHO, NaBH$_3$CN, HOAc.
124) NH$_3$, MeOH.
125) 2,4,6-Me$_3$PhSO$_2$NH$_2$.
126) Et$_2$NH, CH$_2$Cl$_2$
127) MeOC(O)Cl, Et$_3$N, CH$_2$Cl$_2$
128) R$_2$NH$_2$, EDC, HOBT, Et$_3$N, CH$_2$Cl$_2$
129) DBU, PhCH$_3$ 130) BocNHCH(CH₂STr)CH₂NH₂, EDC, HOBT, Et₃N, CH₂Cl₂
131) R₂NHCH₂CO₂Me, HBTU, HOBT, Et₃N, CH₂Cl₂
132) BocNHCH(CH₂STr)CH₂OMs, LiHMDS, THF
133) R₂NHCH₂CO₂Me, NaBH(OAc)₃, ClCH₂CH₂Cl or THF
134) R₂NHCH₂CH(OEt)₂, HBTU, HOBT, Et₃N, CH₂Cl₂
135) NaBH(OAc)₃, ClCH₂CH₂Cl or THF, AcOH.
136) Piperidine, DMF.
137) Pd(Ph₃P)₄, Bu₃SnH.
138) RCO₂H, EDC, HOBT, Et₃N, DCM.
139) RNH₂, neutral solvents.
140) RCHO, NaBH₃CN, HOAc.
141) RNCO, solvent.
142) RCO₂H, EDC or HBTU, HOBt, DIEA, CH₂Cl₂ or DMF.
143) RCOCl, Triethylamine
144) RSO₂Cl₂, Et₃N, CH₂Cl₂.
145) SnCl₂, EtOH, DMF.
146) RNH₂, EDC, HOBt, DIEA, CH₂Cl₂ or DMF.
147) Dibromoethane, Et₃N, CH₂Cl₂
148) Oxalyl chloride, neutral solvents.
149) LiOH, THF-MeOH.
150) Carbonyldiimidazole, neutral solvents (e.g., DCM, DMF, THF, toluene).
151) RNH₂, Et₃N, CH₂Cl₂.
152) Base, RX.
153) DBU, PhCH₃
154) DPPA, Et₃N, toluene (Synthesis 1985, 220)
155) SOCl₂, cat DMF.
156) ArH, Lewis Acid (AlCl₃, SnCl₄, TiCl₄), CH₂Cl₂.
157) H₂NCHRCO₂Et, neutral solvents.
158) BocHNCHRCO₂H, EDC OR HBTU, HOBt, DIEA, CH₂Cl₂ or DMF.
159) TFA, CH₂Cl₂.

b. Illustrative Preparation of Aryl Subunits

Aryl subunits may be functionalized using a wide variety of reactions known to those in the art. The chemistry of aromatic and heteroaromatic rings is rich, and only a sampling of useful reactions can be presented here. A number of illustrative examples, particularly useful for generating the biaryl portion of the subject compounds, are shown below.

Suzuki Coupling No. 1:

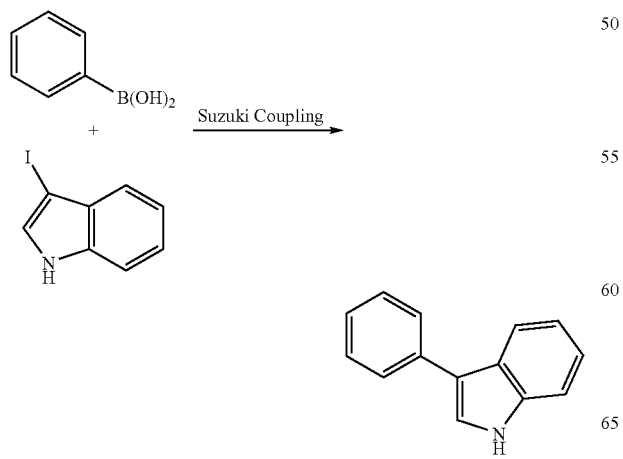

Suzuki Coupling No. 2:

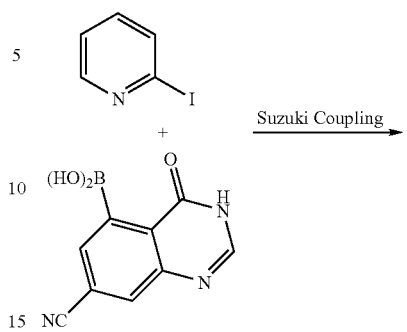

Stille Coupling No. 1:

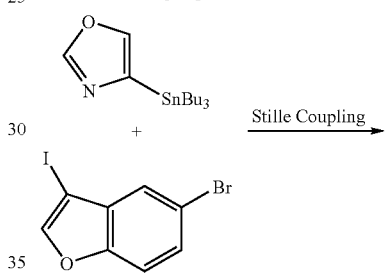

Stille Coupling No. 2:

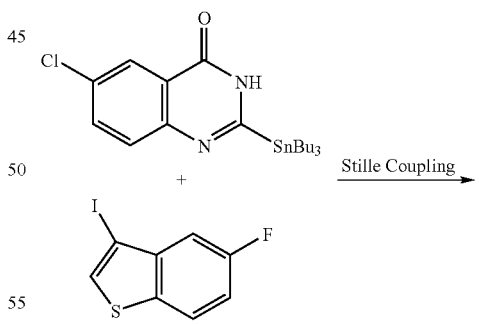

Stille Coupling No. 3:

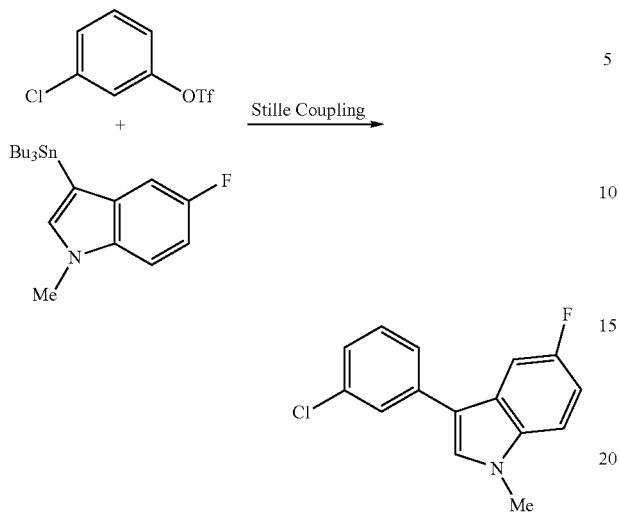

c. Illustrative Preparation of Coupling Substrates

Members of the general classes of coupling substrates outlined above—arylstannanes, arylboronic acids, aryl triflates and aryl halides—are available from the parent heterocycles. In general, the transformations required to prepare a coupling substrate are reliable and amenable to scale-up. Illustrative examples are shown below.

Preparation of an Aryl Iodide

Preparation of an Aryl Stannane

Preparation of an Aryl Triflate

Preparation of an Aryl Boronic Acid

Solid Phase Synthesis of Subject Compounds

General:

Washing Protocols

Method 1: water (3×), acetone (2×), N,N-dimethylformamide (3×), water (2×), acetone (1×), N,N-dimethylformamide (3×), water (2×), acetone (3×), methanol (3×), acetone (3×) and methanol (3×);

Method 2: dichloromethane, hexane, N,N-dimethylformamide, dichloromethane, hexane, dichloromethane and hexane;

Method 3: water, N,N-dimethylformamide, water, 1.0 M aqueous sodium hydroxide solution, (water, N—N dimethylformamide, water, 1.0 aqueous sodium hydroxide solution, water, N,N-dimethylformamide, dichloromethane, methanol, dichloromethane, and methanol.

Method 4: N,N-dimethylformamide, dichloromethane, N,N-dimethylformamide, dichloromethane, methanol, dichloromethane, methanol (2×) and ether (2×).

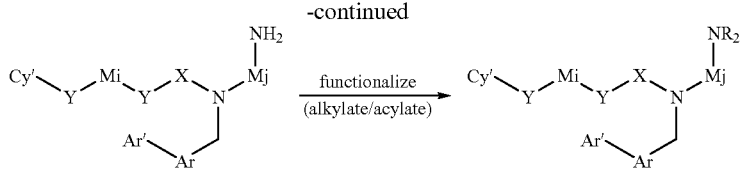

Step A-Preparation of (Nitrophen-4'-yloxycarboxy) benz-4-yloxmethyl Polystyrene-(Wang PNP carbonate polystyrene)

Hydroxybenz-4-yloxymethyl polystyrene (Wang resin)—

Sodium methoxide (233 g, 4.31 mol) was added slowly to a stirred mixture of chloromethyl polystyrene (2.4 kg, 3.6 mol functionalised loading) and 4-hydroxybenzyl alcohol (581 g, 4.68 mol) in N,N-dimethylacetamide (10 L) at room temperature under nitrogen. After dilution with N,N-dimethylacetamide (13 L), the mixture was heated at 50° C. for 5 h and then filtered via cannula through a P-ETFE mesh (70 μm). The crude product was washed extensively using the sequence of Method 1, then dried under vacuum at 60° C. to give 2630 g of the title resin.

(Nitrophen-4'-yloxycarboxy)benz-4-yloxmethyl polystyrene-(Wang PNP carbonate polystyrene)

4-Methylmorpholine (660 mL, 6.0 mol) was added dropwise over 2 h to a stirred mixture of hydroxybenz-4-yloxymethyl polystyrene (2000 g, 2.5 mol functionalised loading) and 4-nitrophenol chloroformate (1209 g, 6.0 mol) in dichloromethane (22 L) at (0° C. under nitrogen. The mixture was warmed gradually to room temperature, stirred overnight and filtered via cannula through a P-ETFE mesh (70 μm). The crude resin was washed extensively using the sequence of Method 2, then dried under vacuum at room temperature to give 2728 g of a mixture of the title resin and 4-methylmorpholine hydrochloride.

Step B-The Preparation of Wang Resin-Bound Diamines

General Method (for piperazine, homopiperazine and trans-1,4-diaminocyclohexane)

Crude (nitrophen-4'-yloxycarboxy)benz-4-yloxymethyl polystryrene (1002.5 g, ~0.9 mol functionalised loading) was swollen over 15 min in a 50% v/v mixture of anhydrous dichloromethane and N,N-dimethylformamide (9 L) under nitrogen. N,N-diisopropylamine (626 mL, 5 mol equivalents) and the appropriate diamine (5 mol equivalents) were added and the mixture was stirred vigorously overnight at room temperature. The mixture was filtered through a P-ETFE mesh (70 μm), washed extensively using the sequence of Method 3 and dried under vacuum at 60° C. to give the resin-bound diamine.

Ethylenediamine Bound to Wang Resin

Crude (nitrophen-4'-yloxycarboxy)benz-4-yloxymethyl polystyrene (1002.5 g, ~0.9 mol functionalised loading) was swollen over 15 min in dichloromethane (7 L) under nitrogen and treated with ethylenediamine (181 mL 2.7 mol). The resulting thick, yellow suspension was diluted with dichloromethane (2 L) and vigorously stirred overnight at room temperature. The mixture was filtered through a P-PETFE mesh (70 μm), washed extensively using the sequence of Method 3 and dried under vacuum at 60° C. to give the title resin-bound diamine.

m-Xylylenediamine Bound to Wang Resin

Crude (nitrophen-4'-yloxycarboxy)benz-4-yloxymethyl polystyrene (1002.5 g, ~0.9 mol functionalised loading) was swollen in tetrahydrofuran (7 L) over 15 min under nitrogen and treated with a solution of m-xylylenediamine (828 mL, 6.27 mol) in tetrahydrofuran (1 L). The resulting thick yellow suspension was diluted with dichloromethane (2 L) and vigorously stirred overnight at room temperature. The mixture was filtered through a P-ETFE mesh (70 μm), washed extensively using the sequence of Method 3 and dried under vacuum at 60° C. to give the resin-bound diamine.

Step C: Preparation of the Building Block Using a Suzuki Coupling Procedure

A suspension of the appropriate aryl bromide (1 equivalent) and potassium carbonate (2.2 equivalents) in toluene (13 volumes) was stirred and degassed at room temperature. Tetrakis(triphenylphosphine)palladium(0) (0.01 equivalent) was added and the reaction vessel evacuated and purged with nitrogen (three times). After 15 min, a degassed solution of 2-methoxy-5-formylphenylboronic acid (1.2 equivalents) in ethanol (6.3 volumes) was added via cannula, then the mixture was heated under reflux and stirred overnight under nitrogen. After cooling, the solid was filtered from solution and washed thoroughly with toluene. The filtrate was evaporated to dryness under reduced pressure to give the crude product. This was triturated with diethyl ether (5 volumes) and the resulting slurry was filtered, washed with diethyl ether and dried under vacuum. The biaryl aldehyde was obtained as a yellow powder.

Step D: Building Block Loading onto Wang Diamine

Reductive Alkylation

The appropriate resin (1 equivalent, ~0.75 mmol functionalised loading) was swollen in a mixture of tetrahydrofuran, triethylorthoformate and dichloromethane (1:1:1, v/v/v, 10 mL) over 15 min, then gently agitated and treated with the appropriate aldehyde (2 equivalents). After gentle agitation overnight at room temperature, the resin was filtered, washed thoroughly with tetrahydrofuran and dried under vacuum at 40° C. The dried resin was then swollen in tetrahydrofuran over 15 min and treated with acetic acid (0.12 equivalent) and sodium triacetoxyborohydride (5 equivalents). The resin suspension was gently agitated overnight at room temperature, then filtered, washed extensively using the sequence of Method 4 and dried under vacuum at 60° C.

Acid Chloride Capping

The appropriate resin (1 equivalent) was swollen in dichloromethane (10 volumes) over 10 min and treated with the appropriate acid chloride (3 equivalents) and N,N-diisopropylethylamine (3 equivalents). The resin suspension was gently agitated overnight at room temperature, filtered, and washed extensively using the sequence of Method 4 and dried under vacuum at 40° C.

Solution Phase Synthesis of Subject Compounds

The following exemplary scheme illustrates one route through which hedgehog agonists of the present invention may be prepared. Variations on this exemplary pathway will be readily comprehended and executed by those of ordinary skill in the art, permitting the preparation of a wide range of compounds that fall within the disclosed general formulae. The compound numbers used in this scheme are consistent with the procedures below, and are independent of the compound numbers used elsewhere in the application, such as the figures.

Synthesis of 3-Chloro-benzo[b]thiophene-2-carboxylic acid (4'-cyano-6-methoxy-biphenyl-3-ylmethyl)-(4-methylaminocyclohexyl)-amide hydrochloride (7)

(360 MHz: CDCl$_3$) 1.06-1.24 (m, 4H), 1.43 (s, 9H), 1.83 (d, 2H), 1.98 (d, 2H), 2.56-2.66 (m, 1H), 3.30-3.35 (m, 1H) and 4.31-4.38 (m, 1H).

N-Methyl-cyclohexane-1,4-diamine (2)

Amine 1 (15.0 g, 0.7 mol) was added slowly over 45 min to a 1N solution of lithium aluminium hydride in THF (450 mL, 0.36 mol) under nitrogen. The mixture was stirred for 30 min at room temperature, then heated at reflux for 5-6 hours under nitrogen. Water (13.2 mL) was added to the mixture followed by 15% aqueous sodium hydroxide (13.2 mL), and water (39.7 mL). The mixture was then stirred for 15-30 min. The solid was filtered off and washed with t-butylmethyl ether (200 mL), dichloromethane (200 mL), and t-butylmethyl ether (200 mL). The organic extracts were collected, dried (MgSO$_4$), and filtered. The drying agent was then washed with dichloromethane and the organic extracts combined and concentrated in vacuo to give the title compound 2 (7.52 g,

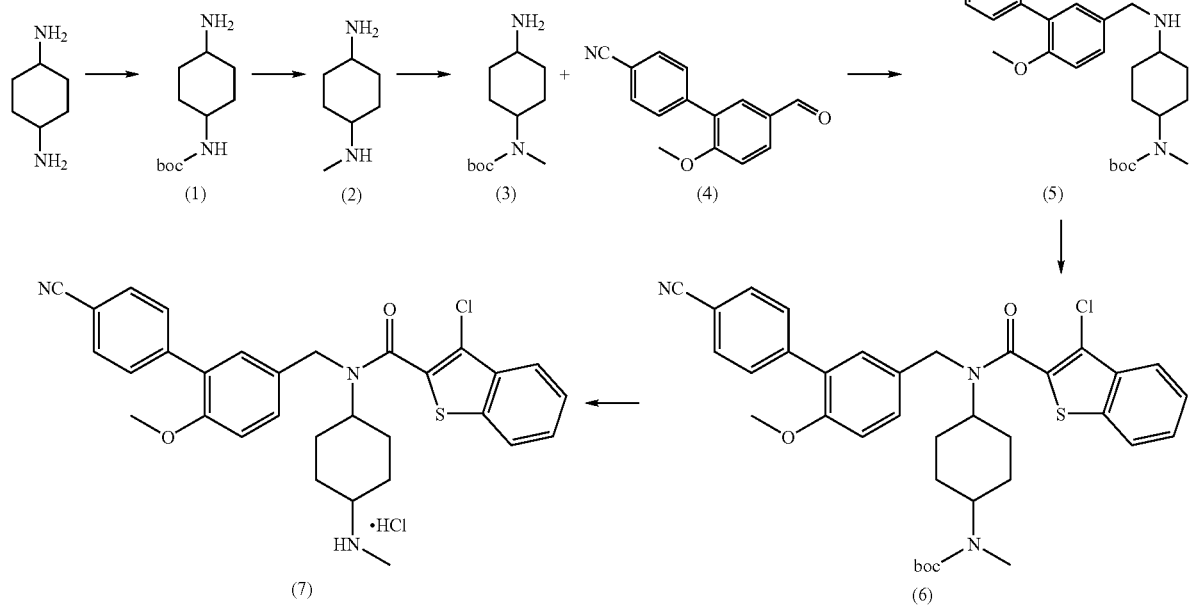

(4-Amino-cyclohexyl)-carbamic acid t-butyl ester (1)

A solution of di-t-butyl-dicarbonate (12.0 g, 54.7 mmol) and tetrahydrofuran (250 mL) was added slowly under nitrogen over 3 h to a suspension of 1,4-diaminocyclohexane (50.0 g, 0.44 mol) in tetrahydrofuran (250 mL) while maintaining the temperature below 10° C. The mixture was allowed to warm to room temperature and subsequently stirred for 16 hours, then filtered. The filtrate was concentrated in vacuo to give a residue. Water (500 mL) was added to the residue, followed by stirring for approximately 15 min, after which the mixture was filtered and the aqueous layer was extracted with dichloromethane (3×200 mL). The organic extracts were combined and concentrated to give a residue which was dissolved in t-butylmethyl ether (350 mL) and washed with water (3×50 mL). The t-butylmethyl ether was removed in vacuo to give the title compound 1 (8.1 g, 69%) as a solid: $\delta_H$ 84%) as a pale yellow solid: $\delta_H$ (360 MHz: CDCl$_3$) 1.04-1.20 (q, 4H), 1.51 (br s, 3H), 1.80-1.96 (m, 4H), 2.25-2.35 (m, 1H), 2.41 (s, 3H), 2.61-2.72 (m, 1H).

(4-Amino-cyclohexyl)-methyl-carbamic acid t-butyl ester (3)

Benzaldehyde (12.8 mL, 0.13 mol) was added in a single portion to a solution of N-methylamine 2 (16.2 g, 0.13 mol) and toluene (150 mL) under nitrogen The resulting mixture was heated to reflux using Dean-Stark apparatus for 4 h. After allowing the mixture to cool to room temperature, di-t-butyl dicarbonate (27.5 g, 0.13 mol) was added in portions and the mixture stirred for 16 h. The mixture was concentrated in vacuo to leave a yellow oil, to which 1N aqueous potassium hydrogen sulfate (90 mL) was added followed by vigorously stirring until TLC indicated the reaction was complete (~2.5 h) The mixture was extracted into ether (3×100 mL) and the aqueous layer made alkaline (pH~12) with aqueous sodium hydroxide. The aqueous layer was then saturated with sodium chloride and the product extracted into chloroform (3×40 mL). The combined extracts were concentrated in vacuo to give the title compound 3 (16.3 g, 59%) as a yellow oil: $\delta_H$ (360 MHz: CDCl$_3$) 1.11-1.34 (m, 5H), 1.45 (s, 9H), 1.66 (br d, 2H), 1.90 (br d, 2H), 2.56-2.66 (m, 1H), 2.71 (s, 3H) and 3.98 (br s, 2H).

{4-[(4'-Cyano-6-methoxy-biphenyl-3-ylmethyl)-amino]-cyclohexyl}-methyl-carbamic acid t-butyl ester (5)

A solution of amine 3 (5.0 g, 21.92 mmol), aldehyde 4 (5.19 g, 21.92 mmol) and trimethyl orthoformate (50 ml) were stirred at room temperature under nitrogen for 16 h. Sodium triacetoxyborohydride (6.5 g, 30.7 mmol) was then added portion wise and the mixture stirred at room temperature until the reaction was complete, as determined by LC-MS analysis. Water was added carefully and mixture stirred for a 5 min, followed by separation of the layers. The trimethyl orthoformate layer was poured onto 1N aqueous potassium hydrogen sulfate (100 mL) and stirred for 15 min. The precipitated solid was filtered, washed with water (50 mL), cold tributyl methyl ether (3×30 mL). The washed precipitate was then suspended in dichloromethane (150 mL) to which saturated aqueous sodium hydrogen carbonate (50 mL) was added and the pH made alkaline (pH~10) whilst maintaining vigorous stirring. The dichloromethane layer was washed with water, and brine, and the organic extract was dried (MgSO$_4$) and concentrated in vacuo to give the title compound 5 (6.9 g, 69%) as an off white solid: $\delta_H$ (360 MHz: CDCl$_3$) 1.18-1.31 (m, 4H), 1.43 (s, 9H), 1.68 (d, 2H), 2.01 (d, 2H), 2.4-2.56 (m, 1H), 2.69 (s, 3H), 3.76 (s, 2H), 3.80 (s, 3H), 6.92 (d, 1H), 7.24 (s, 1H), 7.29 (d, 1H), 7.61 (d, 2H) and 7.66 (d, 2H).

{4-[(3-Chloro-benzo[b]thiophene-2-carbonyl)-(4'-cyano-6-methoxy-biphenyl-ylmethyl)-amino]-cyclohexyl}-methyl-carbamic acid t-butyl ester (6)

N,N-Diisopropylethylamine (2.1 mL, 12.1 mmol) was added to a solution of amine 5 (2.2 g, 4.9 mmol), 3-chlorobenzo[b]thiophene-2-carbonyl chloride (1.3 g, 5.86 mmol) and anhydrous dichloromethane (22 mL), with stirring under argon. Once all of the starting material had been consumed as monitored by TLC (~2.5 hours), the mixture was washed with water, saturated aqueous sodium hydrogen carbonate, and brine. The organic layer was dried MgSO$_4$), and concentrated in vacuo. The yellow residue was then purified by silica-gel chromatography using hexane/ethyl acetate 3:1 to give the title compound 6 (2.93 g, 93%) as a pale yellow solid.

3-Chloro-benzo[b]thiophene-2-carboxylic acid (4'-cyano-6-methoxy-biphenyl-3-ylmethyl)-(4-methylamino-cyclohexyl)-amide hydrochloride (7)

Concentrated hydrochloric acid (27.5 mL) was added to a solution of compound 6 (11.0 g, 17.1 mmol) and ethanol (82.5 mL). The mixture was stirred until reaction was complete as monitored by TLC. The mixture was concentrated in vacuo and dichloromethane added and concentrated again, this was repeated until a solid was obtained. The solid was then slurried with t-butylmethyl ether (30 mL), filtered, and the organic layer dried (MgSO$_4$) and concentrated in vacuo to give the title compound 7 (10.0 g, 99%): $\delta_H$ (360 MHz: DMSO, 70° C.) 1.30-1.50 (m, 2H), 1.85 (br s, 4H), 2.12 (br d, 2H), 2.48 (s, 3H), 2.91 (br t, 1H), 3.81 (s, 3H), 3.87 (br s, 1H), 4.71 (s, 2H), 7.14 (d, 1H), 7.29 (s, 1H), 7.40 (d, 1H), 7.57-7.68 (m, 4H), 7.80-7.90 (m, 3H), 8.09 (d, 1H), 8.82 br s, 2H).

Synthesis of Selected Starting Materials

Synthesis of trans 4-(BOC methylamino)cyclohexylamine

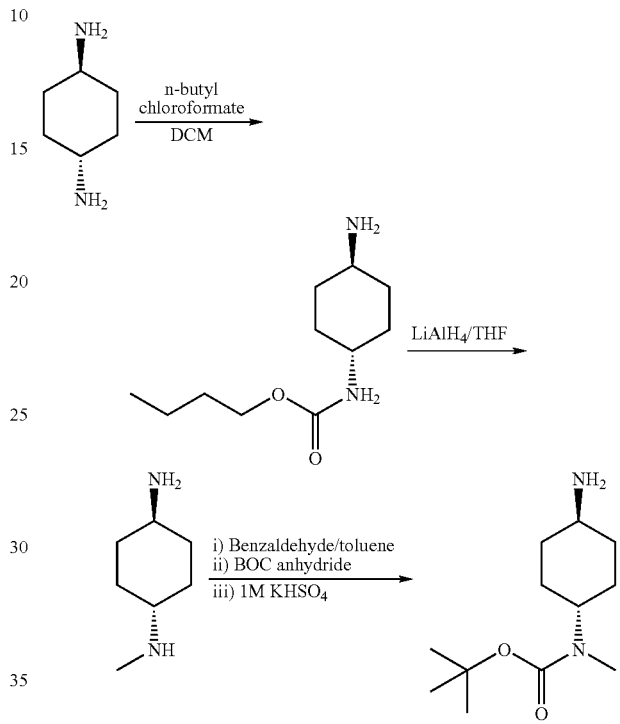

Trans 4-(Aminocyclohexyl) Carbamic Acid N-Butyl Ester

A solution of n-butylchloroformate (102 mL, 0.79 mol, 0.5 eq) in dichloromethane (1.8 L, 10 vol) was added to a solution of 1,4-trans-diaminocyclohexane (180 g, 1.58 mol, 1.0 eq) in dichloromethane (1.8 L, 10 vol) stirred under nitrogen while maintaining the temperature between 0 to 5° C. (ice/salt bath).

The resulting suspension was stirred for a further 60 to 70 minutes then allowed to warm to 5 to 10° C. A freshly prepared sodium carbonate solution (Na$_2$CO$_3$ 92.0 g, 0.8 mol, 0.5 eq in water 720 mL, 4 vol) was added and stirred for a further 5 minutes while warming to ambient temperature.

The phases were separated and the aqueous phase washed with dichloromethane (720 mL, 4 vol). The dichloromethane phases were combined and dried over sodium sulphate (360 g, 2 wt), filtered and concentrated to dryness on a rotary evaporator at 40° C. to give a crude mixture of diamine, bis, and mono carbamate.

The crude material (164 g, 1 wt) was suspended in water (410 mL, 2.5 vol) and stirred vigorously for 10 to 15 minutes at 20 to 25° C. The solid bis carbamate was removed by filtration and the filter cake washed with water (164 mL, 1 vol). The aqueous filtrate was extracted with 3×TBME (3×3.28 L, 20 vol). The TBME layers were combined and back-washed with water (246 mL, 1.5 vol), dried over sodium sulphate (492 g, 3 wt), filtered and concentrated on a rotary evaporator at 35 to 40° C. to afford solid mono carbamate product (87.5 g, 52%).

$^1$H-NMR (400 MHz)(CDCl$_3$): 4.47 (1H, bs); 3.97 (2H, m); 3.36 (1H, bs); 2.57 (1H, m); 1.94 (2H, m); 1.78 (2H, m); 1.51 (2H, m); 1.38 (2H, sextet); 1.13 (6H, m); 0.86 (3H, t).

Trans 4-(methylamino)cyclohexylamine

The carbamate (102 g) in THF (1 L: 10 vol) was added over 30 minutes to a suspension of lithium aluminium hydride (90.4 g: 5 equiv.) in THF (2 L: 20 vol) cooled on ice. Once the addition was complete, the reaction was heated to reflux for 2 hours (complete by tlc) then left to cool overnight. The reaction was cooled to 0-5° C. and quenched by adding water (90 ml), 15% sodium hydroxide (90 ml) and more water (270 ml). The suspension was then stirred at RT for an hour before filtering and washing the filter cake with TBME (2×2 L) and DCM (2×2 L). The solvents were removed by evaporation and residual water and n-butanol removed by azeotroping with toluene (2 L). Yield=62 g which contained 10.6 wt % toluene by NMR. This equals 55.4 g (91%)

Trans 4-(BOC methylamino)cyclohexylamine

The methylamine (55.4 g) and benzaldehyde (46 ml: 1.05 equiv) were dissolved in toluene (554 ml: 10 vol) and heated to reflux with a Dean-Stark apparatus for 6 hours. The calculated volume of water (7.5 ml) was removed. BOC anhydride (103.7 g: 1.1 equiv) was added portionwise to the cooled solution over 15 minutes and the reaction stirred for about 3 hours (shown to be complete by NMR). The solvent was removed to leave 160 g of an oily solid (8 wt % toluene means 147.2 g (107%) product). The solid was suspended in 1 M KHSO$_4$ (1.47 L: 10 vol). Further water (200 ml) and TBME (100 ml) was used to wash in residual starting material. After 4 hours, the reaction was extracted with TBME (600 ml then 3×300 ml). The aqueous was basified to pH 13 with 6 M sodium hydroxide (75 ml) and extracted with DCM (2×735 ml). The combined DCM layers were washed with brine (2×500 ml) before drying with Na$_2$SO$_4$. The solution was filtered and evaporated to leave an oil (69.5 g) containing DCM (2.4 wt %). Yield=67.8 g (69%).

Overall yield from carbamate=64% and 16.5% from trans 1,4-diaminocyclohexane.

Synthesis of 3-chloro-4,7-difluorobenzo[b]thiophene-2-carbonyl chloride

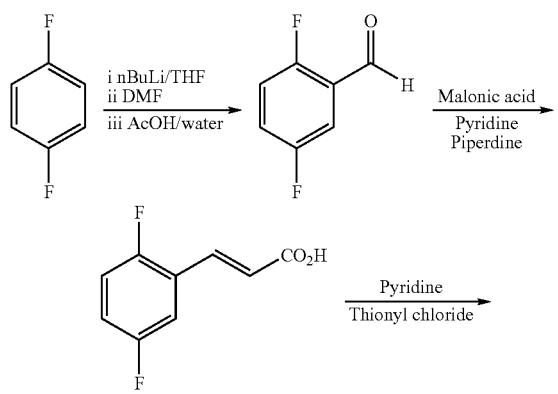

Preparation of 2,5-difluorobenzaldehyde

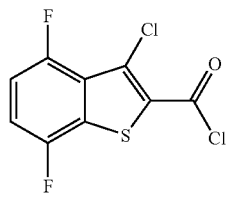

A solution of 1,4-difluorobenzene (10 g, 87.6 mmol, 1 wt) in THF (175 mL, 17.5 vol) was stirred under nitrogen and cooled to −75 to −78° C. n-Butyllithium (82 mL of 1.6 M solution in hexanes, 131.4 mmol, 1.5 eq) was added to the reaction mixture over approximately 20 minutes while maintaining the temperature at <−65° C. After a further hour, DMF (10.16 mL, 131.4 mmol, 1.5 eq) was added over approximately 10 minutes while maintaining the temperature<−65° C. The reaction mixture was quenched after 10 minutes by the addition of acetic acid (17.5 mL, 1.75 mL) directly followed by water (440 mL, 36.4 vol). This caused the reaction to exotherm to 5° C. The cold bath was then removed, TBME (220 mL, 22 vol) added and the reaction stirred for 5 minutes. The phases were separated and the aqueous phase extracted with TBME (2×220 mL, 22 vol). The organic phases were combined, washed with 0.2 M HCl (220 mL, 22 vol), 2 M Na$_2$CO$_3$ (220 mL, 22 vol) then saturated brine (220 mL, 22 vol), dried over magnesium sulphate (50 g, 5 wt) and concentrated on a rotary evaporator to afford the crude product (11.07 g). Purification by Kugelrohr distillation gave the product as a clear, colourless oil (7.52 g, 60%)

Preparation of 2,5-difluorocinnamic acid

Piperidine (2 mL, 20.2 mmol, 0.168 vol) was added to a stirred mixture of 2,5-difluorobenzaldehyde (12.07 g, 85.0 mmol, 1 wt) and malonic acid (18.28 g, 175.6 mmol, 1.51 wt) in pyridine (50 mL, 4.14 vol). The reaction mixture was heated under nitrogen and held at reflux (oil bath 100° C.) for 2 hours, effervescence was observed for about 90 minutes—initially vigorous then diminishing. The reaction mixture was then allowed to cool to 20 to 25° C. and poured into stirred 2 M hydrochloric acid (310 mL, 25.7 vol) (pH recorded as 1). The resulting precipitate was aged at 20 to 25° C. for 1 hour then filtered. The filter cake was washed with water (2×50 mL, 4.1 vol) then left to dry for a further 1 hour. The solid product was dried by dissolving it in TBME (250 mL, 20.7 vol), separating the phases and the water phase washed with TBME (100 mL, 8.3 vol). The TBME phases were combined, dried over magnesium sulphate (25 g, 2 wt), filtered and concentrated on a rotary evaporator to afford the product as a white solid (13.4 g, 85.7%).

Preparation of 3-chloro-4,7-difluorobenzo[b]thiophene-2-carbonyl chloride 2.5-difluorocinnamic acid (26 g, 0.14 mol) and thionyl chloride (36.1 ml; 0.49 mol) were mixed in a flask fitted with a gas-scrubbing train. The addition of pyridine (2.85 ml; 35 mmol) caused much gas evolution. The reaction mixture was heated (T$_{ext}$=140° C.) overnight. Heptane (260 ml; 10 vol) was heated to reflux and the reaction mixture added. The reaction flask was washed out with hot heptane (2×25 ml) and the combined solutions cooled to 0° C. The precipitate was filtered off, washed with heptane (2×25 ml) and dried under a stream of nitrogen. Yield=17.4 g (46%) All publications and patents cited herein are hereby incorporated by reference in their entirety.

Those skilled in the art will recognize, or be able to ascertain using no more than routine experimentation, many equivalents to the specific embodiments of the invention described herein. Such equivalents are intended to be encompassed by the following claims.

We claim:

1. A method for agonizing the hedgehog pathway in a cell, comprising contacting the cell with a hedgehog agonist in an amount sufficient to modulate proliferation or differentiation of the cell, wherein the hedgehog agonist is represented in general formula (XI):

Formula XI

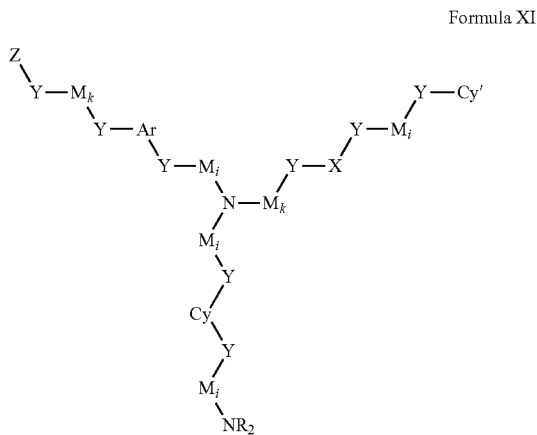

wherein, as valence and stability permit,

Ar represents a substituted or unsubstituted aryl or heteroaryl ring;

X is selected from —C(=O)—, —C(=S)—, —S(O$_2$)—, —S(O)—, and a methylene group optionally substituted with 1-2 lower alkyls;

Y is absent for each occurrence;

Z is absent or represents a substituted or unsubstituted aryl, carbocyclyl, heterocyclyl, or heteroaryl ring, or a lower alkyl, nitro, cyano, or halogen substituent;

R represents, independently for each occurrence, H or substituted or unsubstituted lower alkyl;

Cy' represents a substituted or unsubstituted aryl, heterocyclyl, heteroaryl, or cycloalkyl, including polycyclic groups;

M represents, independently for each occurrence, a substituted or unsubstituted methylene group, or two adjacent M taken together represent substituted or unsubstituted ethene or ethyne;

Cy represents a substituted or unsubstituted aryl, heterocyclyl, heteroaryl, or cycloalkyl, including polycyclic groups;

i represents 0 for all occurrences except in the sequence NM$_i$YAr, where i represents 1; and k represents 0.

2. The method of claim 1, wherein Cy is a cyclohexyl ring substituted with a primary or secondary amine.

3. The method of claim 2, wherein the amine is a methylamino group.

4. The method of claim 1, wherein Cy' is a 3-chloro-benzo(b)thien-2-yl, 3-fluoro-benzo(b)thien-2-yl, or 3-methyl-benzo(b)thien-2-yl group, wherein the benzo ring is substituted with from 1-4 substituents selected from halogen, nitro, cyano, methyl, and ethyl.

5. The method of claim 4, wherein the benzo ring is a 1,4-difluorobenzene ring.

6. The method of claim 1, wherein X is selected from —C(=O)—, —C(=S)—, and —S(O$_2$)—.

7. The method of claim 6, wherein Cy represents a substituted or unsubstituted cycloalkyl group.

8. The method of claim 6, wherein NR$_2$ represents a secondary amine.

9. The method of claim 7, wherein Cy' is a 3-chloro-benzo(b)thien-2-yl, 3-fluoro-benzo(b)thien-2-yl, or 3-methyl-benzo(b)thien-2-yl group, wherein the benzo ring is substituted with from 1-4 substituents selected from halogen, nitro, cyano, methyl, and ethyl.

10. The method of claim 9, wherein the benzo ring is substituted with from 1-4 substituents selected from halogen and methyl.

11. The method of claim 10, wherein each R independently represents H or a lower alkyl.

12. The method of claim 8, wherein Cy' is a 3-chloro-benzo(b)thien-2-yl, 3-fluoro-benzo(b)thien-2-yl, or 3-methyl-benzo(b)thien-2-yl group, wherein the benzo ring is substituted with from 1-4 substituents selected from halogen, nitro, cyano, methyl, and ethyl.

13. The method of claim 12, wherein the benzo ring is substituted with from 1-4 substituents selected from halogen and methyl.

14. The method of claim 13, wherein each R independently represents H or a lower alkyl.

15. The method of claim 1, wherein Cy represents a substituted or unsubstituted cycloalkyl group.

16. The method of claim 15, wherein NR$_2$ represents a secondary amine.

17. The method of claim 15, wherein Cy' is a 3-chloro-benzo(b)thien-2-yl, 3-fluoro-benzo(b)thien-2-yl, or 3-methyl-benzo(b)thien-2-yl group, wherein the benzo ring is substituted with from 1-4 substituents selected from halogen, nitro, cyano, methyl, and ethyl.

18. The method of claim 17, wherein the benzo ring is substituted with from 1-4 substituents selected from halogen and methyl.

19. The method of claim 16, wherein X is selected from —C(=O)—, —C(=S)—, and —S(O$_2$)—.

20. The method of claim 16, wherein each R independently represents H or a lower alkyl.

21. The method of claim 18, wherein each R independently represents H or a lower alkyl.

22. The method of claim 18, wherein X is selected from —C(=O)—, —C(=S)—, and —S(O$_2$)—.

23. The method of claim 1, wherein NR$_2$ represents a secondary amine.

24. The method of claim 23, wherein Cy' is a 3-chloro-benzo(b)thien-2-yl, 3-fluoro-benzo(b)thien-2-yl, or 3-methyl-benzo(b)thien-2-yl group, wherein the benzo ring is substituted with from 1-4 substituents selected from halogen, nitro, cyano, methyl, and ethyl.

25. The method of claim 24, wherein the benzo ring is substituted with from 1-4 substituents selected from halogen, and methyl.

26. The method of claim 23, wherein each R independently represents H or a lower alkyl.

27. The method of claim 25, wherein Cy represents a substituted or unsubstituted cycloalkyl group.

28. The method of claim 1, wherein the compound agonizes hedgehog mediated signal transduction with an $ED_{50}$ of 1 μM or less.

29. The method of claim 1, wherein the compound agonizes hedgehog mediated signal transduction with an $ED_{50}$ of 1 nM or less.

30. The method of claim 1, wherein the compound is administered to a patient as part of a therapeutic or cosmetic application.

31. The method of claim 30, wherein the therapeutic or cosmetic application is selected from regulation of neural tissues, bone and cartilage formation and repair, regulation of spermatogenesis, regulation of smooth muscle, regulation of lung, liver and other organs arising from the primitive gut, regulation of hematopoietic function, and regulation of skin and hair growth.

32. The method of claim 1, wherein the cells are contacted with the compound in vitro.

33. The method of claim 1, wherein the cells are contacted with an effective amount of the compound to promote the formation, proliferation, or both of hair follicles.

34. The method of claim 1, further comprising
a) culturing the cells ex vivo to produce hair follicles; and
b) implanting the hair follicles in a patient.

35. The method of claim 34, wherein the patient displays baldness.

36. The method of claim 34, wherein the patient has alopecia.

37. The method of claim 36, wherein the amount of hair implanted in step b) is suitable for treating alopecia in the patient.

38. The method of claim 1, wherein the hedgehog agonist interacts with smoothened.

39. The method of claim 1, wherein the hedgehog agonist disrupts interaction between patched and smoothened.

40. The method of claim 1, wherein the hedgehog agonist disrupts a patched-smoothened complex.

\* \* \* \* \*